(12) United States Patent
Boylan et al.

(10) Patent No.: US 10,576,085 B2
(45) Date of Patent: Mar. 3, 2020

(54) SUBSTITUTED AMINOPURINE COMPOUNDS, COMPOSITIONS THEREOF, AND METHODS OF TREATMENT THEREWITH

(71) Applicant: Signal Pharmaceuticals, LLC, San Diego, CA (US)

(72) Inventors: John F. Boylan, San Diego, CA (US); Gordon L. Bray, San Francisco, CA (US); Ellen Filvaroff, San Francisco, CA (US); Robert Hubbard, San Diego, CA (US); David Mikolon, San Diego, CA (US); Heather Raymon, San Diego, CA (US); Tao Shi, San Diego, CA (US); Tam M. Tran, San Diego, CA (US); Toshiya Tsuji, San Diego, CA (US); Lilly L. Wong, Solana Beach, CA (US); Shuichan Xu, San Diego, CA (US); Dan Zhu, San Diego, CA (US)

(73) Assignee: Signal Pharmaceuticals, LLC, San Diego, CA (US)

( * ) Notice: Subject to any disclaimer, the term of this patent is extended or adjusted under 35 U.S.C. 154(b) by 0 days.

(21) Appl. No.: 15/475,899

(22) Filed: Mar. 31, 2017

(65) Prior Publication Data
US 2017/0281633 A1   Oct. 5, 2017

Related U.S. Application Data

(60) Provisional application No. 62/317,412, filed on Apr. 1, 2016.

(51) Int. Cl.
*A61K 31/52* (2006.01)

(52) U.S. Cl.
CPC ........... *A61K 31/52* (2013.01); *Y10S 514/908* (2013.01)

(58) Field of Classification Search
CPC ..................................................... A61K 31/52
See application file for complete search history.

(56) References Cited

U.S. PATENT DOCUMENTS

| | | |
|---|---|---|
| 4,810,643 A | 3/1989 | Souza |
| 4,999,291 A | 3/1991 | Souza |
| 5,229,496 A | 7/1993 | Deeley et al. |
| 5,391,485 A | 2/1995 | Deeley et al. |
| 5,393,870 A | 2/1995 | Deeley et al. |
| 5,580,755 A | 12/1996 | Souza |
| 5,582,823 A | 12/1996 | Souza |
| 5,858,968 A | 1/1999 | Weiner et al. |
| 7,521,446 B2 | 4/2009 | Albers et al. |
| 7,723,340 B2 | 5/2010 | Albers et al. |
| 7,759,342 B2 | 7/2010 | Bennett et al. |
| 8,101,588 B2 | 1/2012 | Albers et al. |
| 8,158,635 B2 | 4/2012 | Beauchamps et al. |
| 8,324,225 B2 | 12/2012 | Brain et al. |
| 8,440,661 B2 | 5/2013 | Bennett et al. |
| 8,491,930 B2 | 7/2013 | Fernandez De Gatta Garcia et al. |
| 8,603,527 B2 | 12/2013 | Bhat et al. |
| 8,680,076 B2 | 3/2014 | Bennett et al. |
| 9,187,479 B2 | 11/2015 | Clareen et al. |
| 9,198,866 B2 | 12/2015 | Bhat et al. |
| 9,512,124 B2 | 12/2016 | Alexander et al. |
| 9,737,541 B2 * | 8/2017 | Alexander |
| 2007/0142405 A1 | 6/2007 | Dong et al. |
| 2009/0312320 A1 | 12/2009 | Albers et al. |
| 2010/0016586 A1 | 1/2010 | Bajji et al. |
| 2012/0115890 A1 | 5/2012 | Beauchamps et al. |
| 2013/0034495 A1 | 2/2013 | Beauchamps et al. |
| 2013/0191086 A1 | 7/2013 | Temple |
| 2014/0093566 A1 | 4/2014 | Bhat et al. |
| 2014/0206697 A1 | 7/2014 | Clareen et al. |

(Continued)

FOREIGN PATENT DOCUMENTS

| | | | |
|---|---|---|---|
| WO | WO 1999/015155 A1 | 4/1999 |
| WO | WO 2006/076595 A1 | 7/2006 |
| WO | WO 2007/062338 A2 | 5/2007 |

(Continued)

OTHER PUBLICATIONS

MedicineNet, "Definition of Cancer", http://www.MedicineNet.com, 2015, 1 page.*

(Continued)

*Primary Examiner* — Savitha M Rao
*Assistant Examiner* — Gregg Polansky
(74) *Attorney, Agent, or Firm* — Jones Day

(57) ABSTRACT

Provided herein are methods for treating or preventing a cancer, including solid tumors and hematological cancers, comprising administering an effective amount of aminopurine compounds of formula (I), and compositions comprising an effective amount of such compounds.

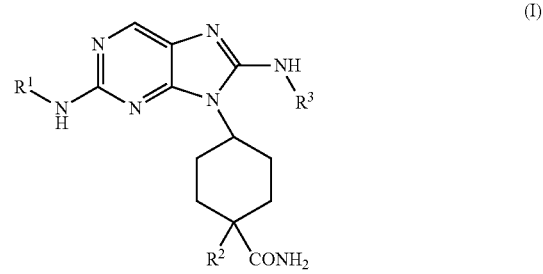

22 Claims, 39 Drawing Sheets

(56) References Cited

U.S. PATENT DOCUMENTS

| | | |
|---|---|---|
| 2016/0039822 A1 | 2/2016 | Clareen et al. |
| 2017/0042902 A1 | 2/2017 | Alexander et al. |

FOREIGN PATENT DOCUMENTS

| | | |
|---|---|---|
| WO | WO 2007/127382 A1 | 11/2007 |
| WO | WO 2008/057252 A2 | 5/2008 |
| WO | WO 2011/071491 A1 | 6/2011 |
| WO | WO 2014/172616 A2 | 10/2014 |
| WO | WO 2015/086505 A1 | 6/2015 |

OTHER PUBLICATIONS

Fuchs et al., "Oncogenic β-Catenin Signaling Networks in Colorectal Cancer", Cell Cycle, 2005, vol. 4(11), pp. 1522-1539.*

U.S. Appl. No. 15/475,836, filed Mar. 31, 2017, Chen et al.

Alcorn et al., "c-Jun N-Terminal Kinase 1 is Required for the Development of Pulmonary Fibrosis," *Am. J. Respir. Cell Mol. Biol.*, 40:422-432 (2009).

Aljaberi et al., "Functional performance of silicified microcrystalline cellulose versus microcrystalline cellulose: a case study," Drug Development and Industrial Pharmacy 35(9): 1066-1071 (2009).

Davis, "Signal transduction by the JNK group of MAP kinases," Cell, 203:239-252 (2000).

Edge et al., "Polysaccharide engineering: Silicified microcrystalline cellulose as a novel high-functionality pharmaceutical material" in: *Polysaccharide Applications: Cosmetics and Pharmaceuticals*, American Chemical Society Symposium Series 737, Chapter 7, pp. 98-112 (1999).

Kluwe et al., "Modulation of hepatic fibrosis by c-Jun-N-terminal kinase inhibition," *Gastroenterology*, 138:347-359 (2010).

Lee et al., "Bleomycin induces alveolar epithelial cell death through JNK-dependent activation of the mitochondrial death pathway," *Am. J. Physiol. Lung Cell Mol. Physiol.*, 289:L521-L528 (2005).

Lin et al., "Connective tissue growth factor induces collagen I expression in human lung fibroblasts through the Rac1/MLK3/JNK/AP-1 pathway," *Biochim. Biophys. Acta*, 1833:2823-2833 (2013).

Tobyn et al., "Physiochemical comparison between microcrystalline cellulose and silicified microcrystalline cellulose," International Journal of Pharmaceutics 169(2):183-194 (1998).

Yoshida et al., "MAP kinase activation and apoptosis in lung tissues from patients with idiopathic pulmonary fibrosis," J. Pathol., 198:388-396 (2002).

Bollag et al., "Vemurafenib: the first drug approved for BRAF-mutant cancer," *Nat. Rev. Drug Discov.*, 11(11):873-866 (2012).

Cheson et al., "Revised response criteria for malignant lymphoma," *J. Clin. Oncol.*, 25(9):579-586 (2007).

Corcoran et al., "EGFR-mediated re-activation of MAPK signaling contributes to insensitivity of BRAF mutant colorectal cancers to RAF inhibition with vemurafenib," *Cancer Discov.*, 2(3):227-235 (2012).

Durie et al, "International uniform response criteria for multiple myeloma," *Leukemia*, 20:1467-1473 (2006).

Eisenhauer et al., "New response evaluation criteria in solid tumours: revised RECIST guideline (version 1.1)," *Eur. J. Cancer*, 45(2):228-247 (2009).

Emens et al., "Chemotherapy: friend of foe to cancer vaccines," Curr. Opin. Mol. Ther., 3(1):77-84 (2001).

Hallek et al., "Guidelines for the diagnosis and treatment of chronic lymphocytic leukemia: a report from the International Workshop on Chronic Lymphocytic Leukemia updating the National Cancer Institute—Working Group 1996 guidelines," *Blood*, 111(12):5446-5456 (2008).

Penichet et al., "Antibody-cytokine fusion proteins for the therapy of cancer," J. Immunol. Methods, 284:91-101 (2001).

Roitt et al., Immunology, Third Edition, Mosby, St. Louis, MO, 17.1-17.12 (1993).

Therasse et al., "New guidelines to evaluate the response to treatment in solid tumors," J. Natl. Cancer Inst., 92(3):205-216 (2000).

Wen et al., "Updated response assessment criteria for high-grade gliomas: response assessment in neuro-oncology working group," *J. Clin. Oncol.*, 28(11):1963-1972 (2010).

Wilen et al., "Strategies in optical resolutions," *Tetrahedron*, 33:2725-2736 (1977).

Wilen, Tables of Resolving Agents and Optical Resolutions, (E.L. Eliel, Ed.), University of Notre Dame Press, Notre Dame, IN, p. 268 (1972).

* cited by examiner

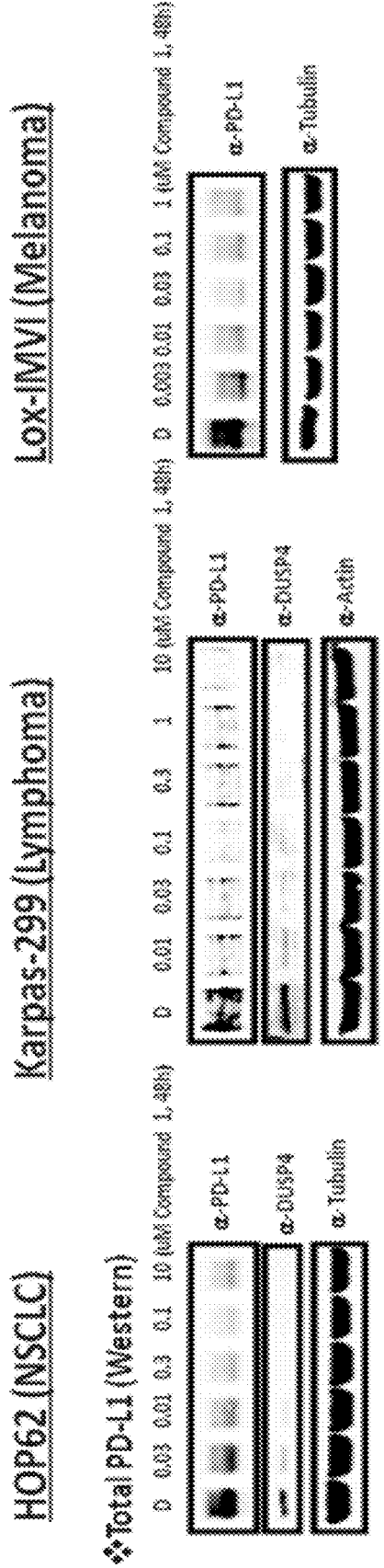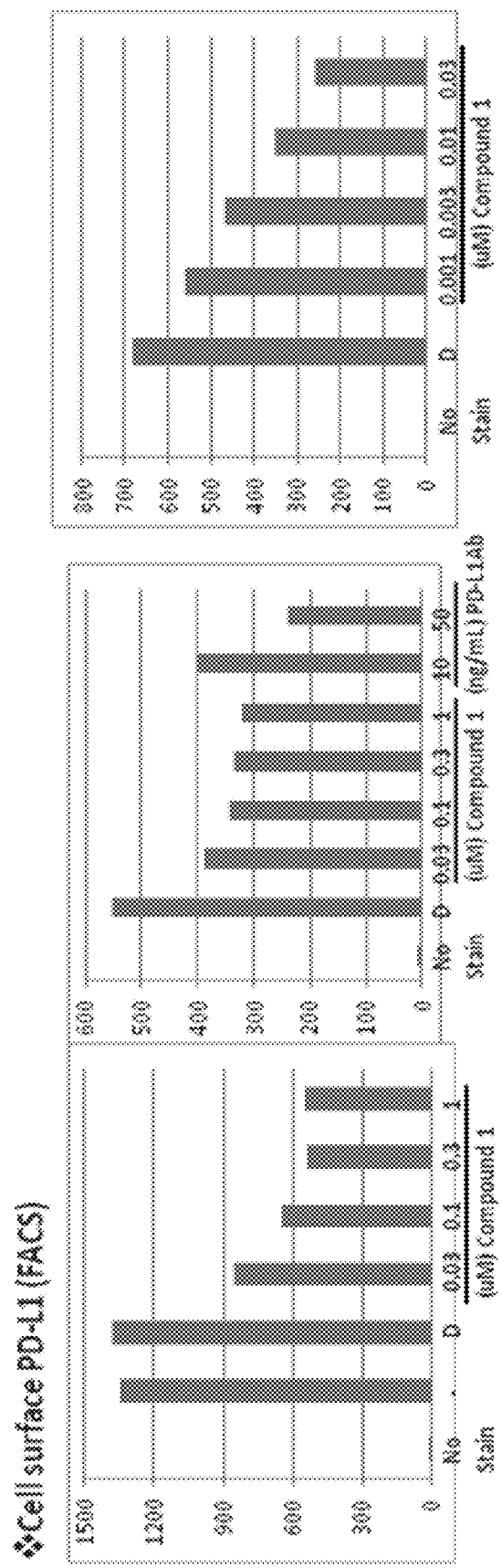
FIG. 4A
FIG. 4B

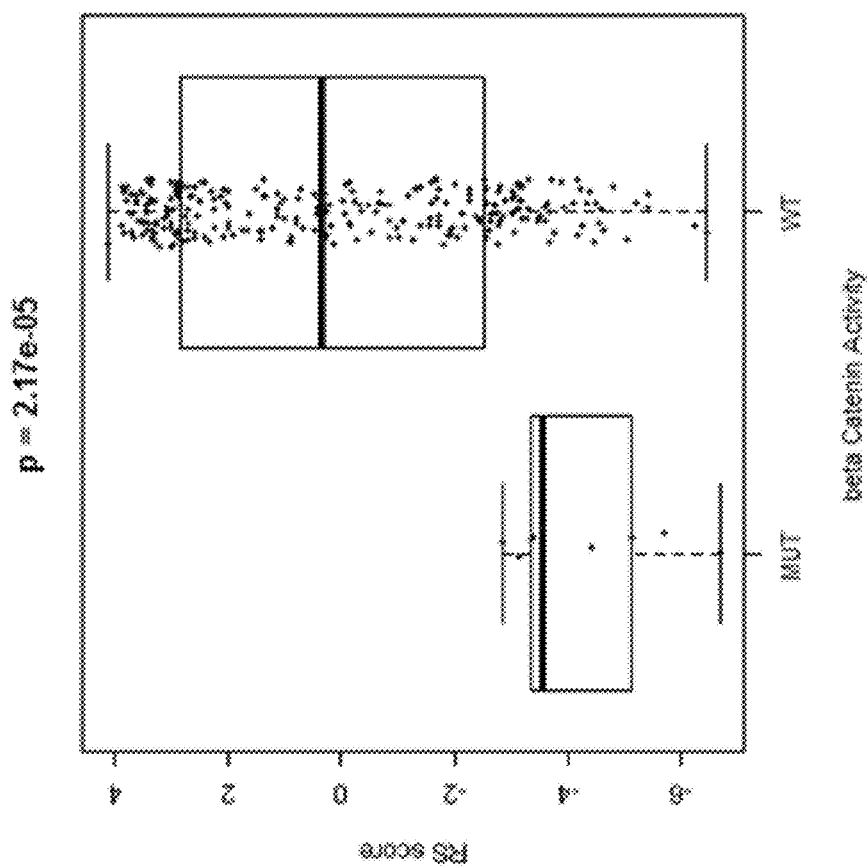
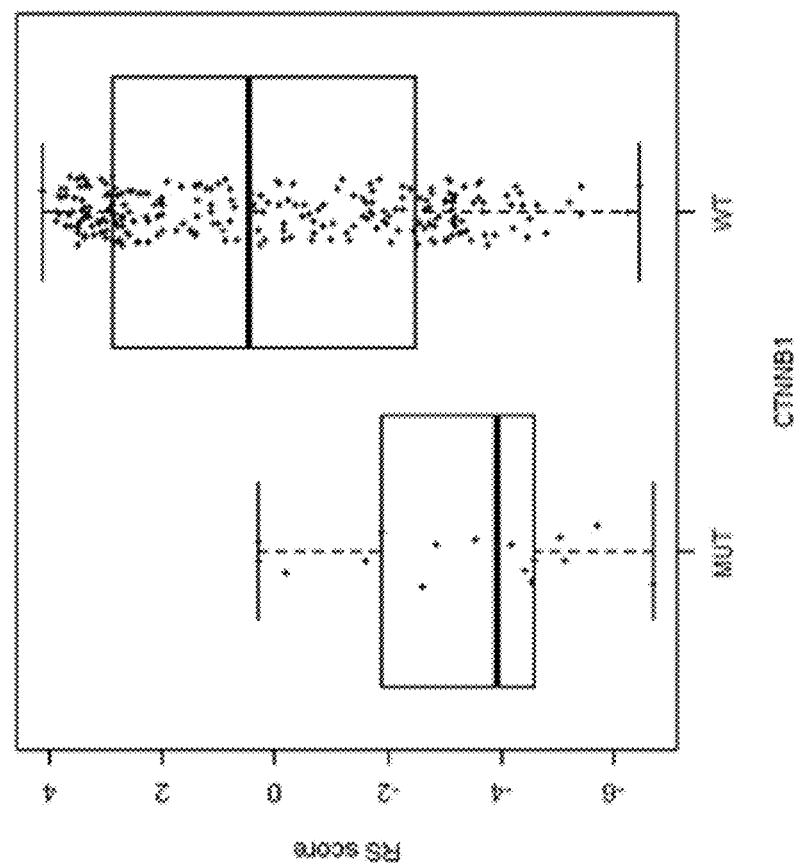
FIG. 19A
FIG. 19B

Human Bronchial Epithelial cell gene expression at 24hrs

SUBSTITUTED AMINOPURINE COMPOUNDS, COMPOSITIONS THEREOF, AND METHODS OF TREATMENT THEREWITH

CROSS-REFERENCE TO RELATED APPLICATIONS

This application claims priority to U.S. Provisional Patent Application No. 62/317,412, filed Apr. 1, 2016, which is incorporated herein by reference in its entirety and for all purposes.

FIELD

Provided herein are methods for treating or preventing a cancer, including solid tumors and hematological cancers, comprising administering an effective amount of certain aminopurine compounds described herein, and compositions comprising an effective amount of such compounds.

BACKGROUND

Cancer is characterized primarily by an increase in the number of abnormal cells derived from a given normal tissue, invasion of adjacent tissues by these abnormal cells, or lymphatic or blood-borne spread of malignant cells to regional lymph nodes and to distant sites (metastasis). Clinical data and molecular biologic studies indicate that cancer is a multistep process that begins with minor pre-neoplastic changes, which may under certain conditions progress to neoplasia. The neoplastic lesion may evolve clonally and develop an increasing capacity for invasion, growth, metastasis, and heterogeneity, especially under conditions in which the neoplastic cells escape the host's immune surveillance (Roitt, I., Brostoff, J and Kale, D., Immunology, 17.1-17.12 (3rd ed., Mosby, St. Louis, Mo., 1993)).

Cancers figure among the leading causes of death worldwide, accounting for 8.2 million deaths in 2012. It is expected that annual cancer cases will rise from 14 million in 2012 to 22 million within the next two decades (See Cancer Fact sheet No 297, World Health Organization, February 2014, retrieved 10 Jun. 2014 and Globocan 2012, IARC).

The current drugs used in cancer treatment are highly toxic and often non-specific. Current anticancer therapy strategies are typically focused on rapid proliferating cells, which can shrink primary and metastatic tumors, but such effects are usually transient and tumor relapse of most metastatic cancers frequently occur. One possible reason for failure is the existence of cancer stem cells. Unlike most cells within the tumor, cancer stem cells are resistant to well-defined chemotherapy, and after treatment, they can regenerate all the cell types in the tumor through their stem cell-like behavior of largely quiescent nature and their abundant expression of drug transporters.

There is an enormous variety of cancers which are described in detail in the medical literature. The incidence of cancer continues to climb as the general population ages, as new cancers develop, and as susceptible populations (e.g., people infected with AIDS or excessively exposed to sunlight) grow. However, options for the treatment of cancer are limited. A tremendous demand therefore exists for new methods and compositions that can be used to treat patients with cancer Citation or identification of any reference in Section of this application is not to be construed as an admission that the reference is prior art to the present application.

SUMMARY

Provided herein are Aminopurine Compounds, including compositions (e.g. pharmaceutical compositions) comprising such Aminopurine Compounds, that can be used in the methods provided herein.

Provided herein are methods of treating a cancer, in particular a solid tumor or a hematological cancer. The Aminopurine Compound provided herein can be used in the methods for treating or preventing a cancer, in particular a solid tumor or a hematological cancer, as described herein. The methods comprise administering to a subject in need thereof an effective amount of Aminopurine Compound 1. Also provided herein are methods for treating and preventing cancer metastasis, comprising administering to a subject in need thereof an effective amount of an Aminopurine Compound as provided herein. The Aminopurine Compound provided herein can be used in the methods for treating and preventing cancer metastasis. Additionally, provided herein are methods of eradicating cancer stem cells in a subject, comprising administering to a subject in need thereof an effective amount of an Aminopurine Compound as provided herein. The Aminopurine Compound provided herein can be used in the methods of eradicating cancer stem cells in a subject. Also provided are methods of inducing differentiation in cancer stem cells in a subject, comprising administering to a subject in need thereof an effective amount of an Aminopurine Compound as provided herein. The Aminopurine Compound provided herein can be used in the methods of inducing differentiation in cancer stem cells in a subject. In another aspect, provided are methods of inducing cancer stem cell death in a subject, comprising administering to a subject in need thereof an effective amount of an Aminopurine Compound as provided herein. The Aminopurine Compound provided herein can be used in the methods of inducing cancer stem cell death in a subject.

Provided herein are methods of treating a cancer, in particular a solid tumor or a hematological cancer using a pharmaceutical composition that includes an Aminopurine Compound described herein. The Aminopurine Compound pharmaceutical composition provided herein can be used in the methods for treating or preventing a cancer, in particular a solid tumor or a hematological cancer, as described herein. The methods comprise administering to a subject in need thereof an effective amount of a pharmaceutical composition that includes Aminopurine Compound 1. Also provided herein are methods for treating and preventing cancer metastasis, comprising administering to a subject in need thereof an effective amount of a pharmaceutical composition that includes an Aminopurine Compound as provided herein. The Aminopurine Compound pharmaceutical composition provided herein can be used in the methods for treating and preventing cancer metastasis. Additionally, provided herein are methods of eradicating cancer stem cells in a subject, comprising administering to a subject in need thereof an effective amount of a pharmaceutical composition that includes an Aminopurine Compound as provided herein. The Aminopurine Compound pharmaceutical composition provided herein can be used in the methods of eradicating cancer stem cells in a subject. Also provided are methods of inducing differentiation in cancer stem cells in a subject, comprising administering to a subject in need thereof an effective amount of a pharmaceutical composition that includes an Aminopurine Compound as provided herein. The Aminopurine Compound pharmaceutical composition provided herein can be used in the methods of inducing differentiation in cancer stem cells in a subject. In another aspect, provided are methods of inducing cancer stem cell death in a subject, comprising administering to a subject in need thereof an effective amount of a pharmaceutical composition that includes an Aminopurine Compound as provided herein. The Aminopurine Compound pharmaceutical composition provided herein can be used in the methods of inducing cancer stem cell death in a subject.

Compounds useful in the methods disclosed herein are Aminopurine Compounds as described herein, such as, for example, in Table 1, or a pharmaceutically acceptable salt, tautomer, stereoisomer, enantiomer, or isotopologue thereof and pharmaceutical compositions of Aminopurine Compounds.

The present embodiments can be understood more fully by reference to the detailed description and examples, which are intended to exemplify non-limiting embodiments.

BRIEF DESCRIPTION OF THE DRAWINGS

FIG. 2A illustrates proteins extracted from treated cells and analyzed by Western blot using antibodies against DUSP4, DUSP6, cyclin D1, c-Myc, YAP or β-actin. FIGS. 2B-2C illustrate RNAs extracted using Cell-To-CT kit and quantitative PCR was performed with probes specific for DUSP4, DUSP6, SPRY2, c-Myc and cyclin D1. Specific probes for β-actin were used for normalization. FIGS. 2D-2I illustrate Compound 1 Treatment modulates MAPK-driven mRNA levels in Colo 205 (mut BRAFV600E) and HT-29 (mut BRAFV600E) Cells. Colo 205 or HT-29 cells were treated with DMSO or 0.3 or 1 µM Compound 1 for 6 h. mRNA was extracted using MagMAX Total RNA Isolation kit and quantitative PCR was performed.

FIGS. 4A-4B illustrate Compound 1 down-regulates PD-L1 level in multiple cancer cell lines. FIG. 4A illustrates Western blotting of total PD-L1 in Hop66, Karpas-299, and LOX-IMVI. Cells were cultured in presence or absence of Compound 1 for indicated time before expression levels of PD-L1, DUSP4 and α-tubulin or α-actin were measured by Western blot.

FIG. 4B illustrates surface staining of PD-L1 with the Fluorescence-Activated Cell Sorter (FACS). Cells were treated with DMSO or Compound 1 at indicated concentrations for 48 h and cell surface expression of PD-L1 was detected using the FACS analysis with an APC-labeled antibody to PD-L1 (clone 29E.1A3; BioLegend, San Diego, Calif.). Geometric mean of PD-L1 positive cells was determined by FlowJo 10 (Treestar, Ashland, Oreg.).

Figures 10A, 10B:
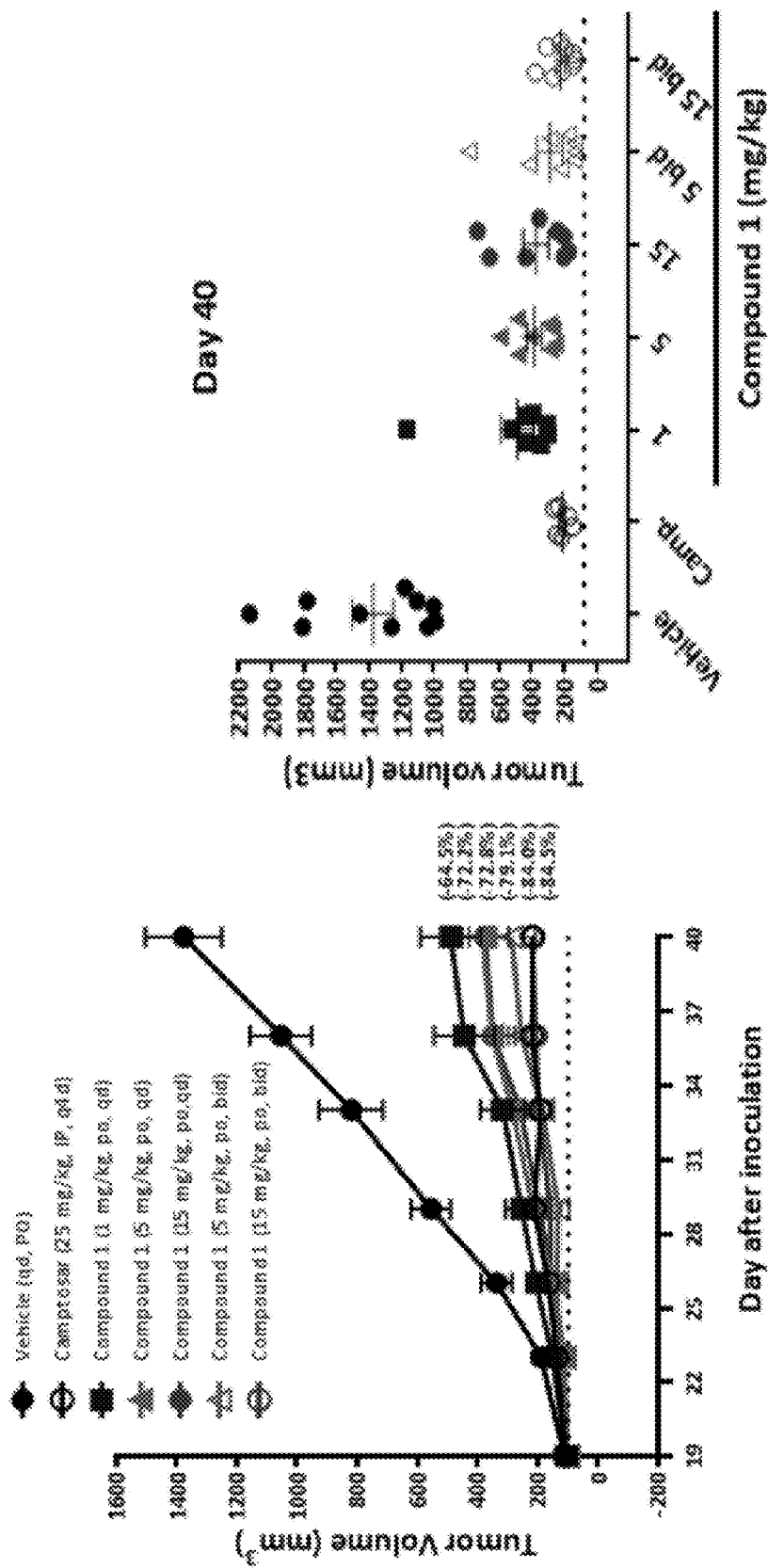

FIGS. 10A-10B illustrates antitumor activity of Compound 1 in the PDX146 Xenograft Model. Female NSG mice were inoculated with 25 µg of PDX146 tumor in a cell slurry into the right flank. Mice were randomized into treatment groups (n=8-10/group) at the time of treatment initiation. Test article treatment started on Day 19 when the tumors were approximately 100-110 mm³. FIG. 10A illustrates tumor volume as a function of time. FIG. 10B illustrates individual tumor volume on the last study day, day 40. Percent inhibition is calculated relative to the vehicle control on the last study day and is in parentheses next to the respective tumor volume for the treatment groups. Dotted line is the tumor volume at the initiation of dosing. Camp=camptosar.

Figure 11:
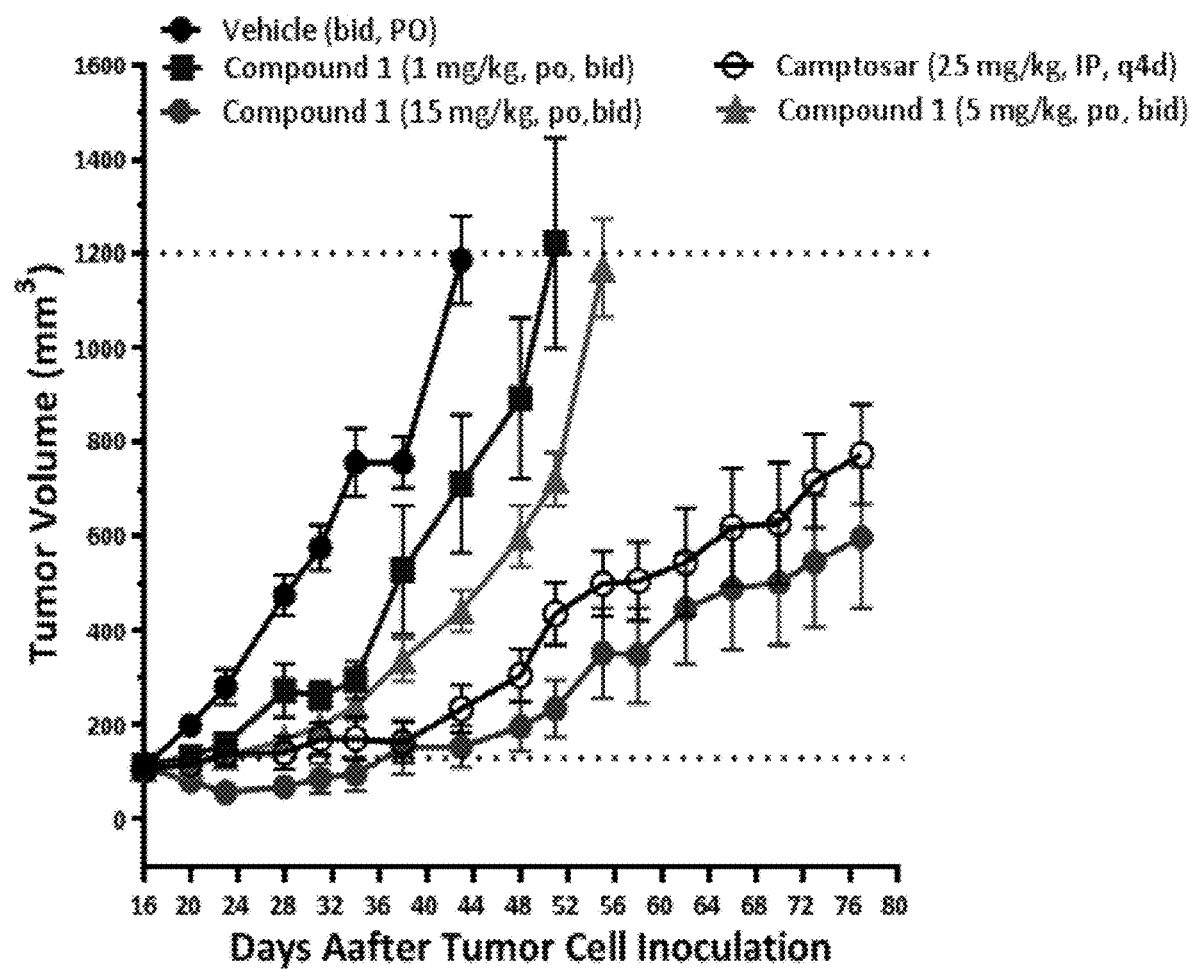

FIG. 11 illustrates tumor Growth Delay with Continuous Compound 1 Treatment in the PDX146 Xenograft Model. Female NSG mice were inoculated with 25 µg of PDX146 tumor in a cell slurry into the right flank. Mice were randomized into treatment groups (n=8-10/group) at the time of treatment initiation. Test article treatment started on Day 16 when the tumors were approximately 100-110 mm³. Black dotted line is the tumor volume at the initiation of dosing and the red dotted line is the tumor volume on Day 43 when the vehicle control group was terminated.

FIGS. 12A-12D illustrates Single doses of Compound 1 inhibit biomarkers in the MAPK, Wnt and Hippo signaling pathways in the PDX146 Xenograft Model: Modulation of MAPK, Wnt and Hippo pathways in PDX146 tumors treated with Compound 1. qRT-PCR assays were performed on RNA extracted from PDX146 tumors at the indicated timepoint post-dose. Data are expressed as mean±SEM. P values are derived from a one-way ANOVA with a Dunnet's post-hoc analysis.

FIGS. 13A-13D illustrate Compound 1 inhibits biomarkers in the MAPK, Wnt and Hippo signaling pathways from PDX146 tumors following a single dose administration: Modulation of MAPK, Wnt and Hippo pathways in PDX146 tumors treated with Compound 1. qRT-PCR assays were performed on RNA extracted from PDX146 tumors at the indicated time point post-dose. YAP data is generated from western blot analysis of tumors from the 5 mg/kg treatment group and is expressed as a ratio of YAP to β-actin protein expression. Data are expressed as mean±SEM. P values are derived from a one-way ANOVA with a Dunnet's post-hoc analysis.

FIGS. 14A-14D illustrate phospho-RSK (pRSK) and phospho-ERK (pERK) protein levels, biomarkers of the MAPK signaling pathway, were modulated by a single dose administration of Compound 1. Western blot (pRSK) or Mesoscale (pERK) assays were performed on protein extracted from PDX146 tumors at the indicated time point post-dose. Phospho-RSK data is expressed as a % of the vehicle control. Phospho-ERK data is expressed as mean±SEM.

Figure 15A:
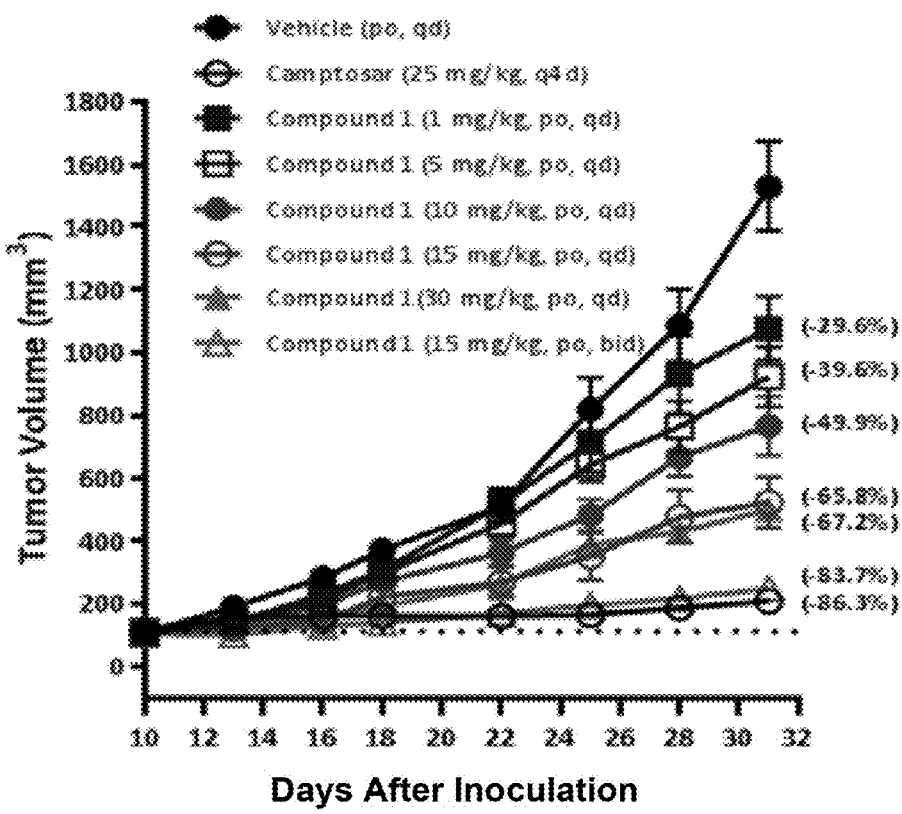
Figure 15B:
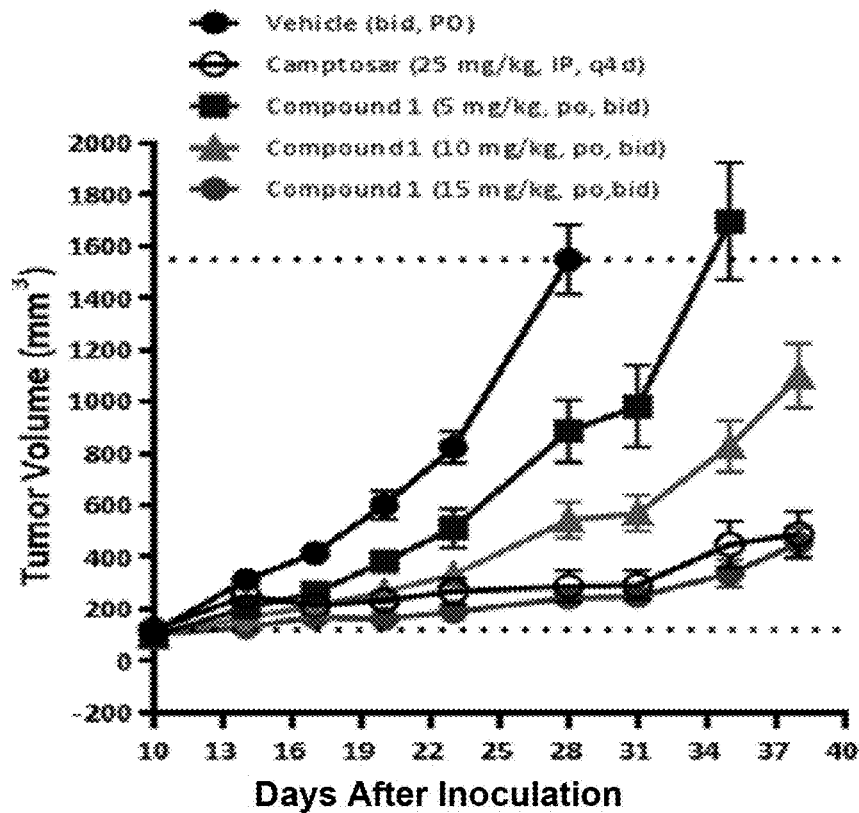

FIGS. 15A-15B illustrate antitumor activity of Compound 1 in the β-catenin mutant SW48 colorectal xenograft model. Female SCID mice were inoculated with 2×10⁶ SW48 tumor cells into the right flank. Mice were randomized into treatment groups (n=10/group) at the time of treatment initiation. Test article treatment started on Day 10 when the tumors were approximately 110 and 105 mm³ (FIG. 15A and FIG. 15B, respectively). Black dotted line is the tumor volume at the initiation of dosing. Graph on the left is a dose-response study (graph A). FIG. 15B illustrates a time to progression study where animals were maintained on drug during the course of the study (graph B). Dotted line is the tumor volume on Day 28 when the vehicle control group was terminated.

Figure 16:
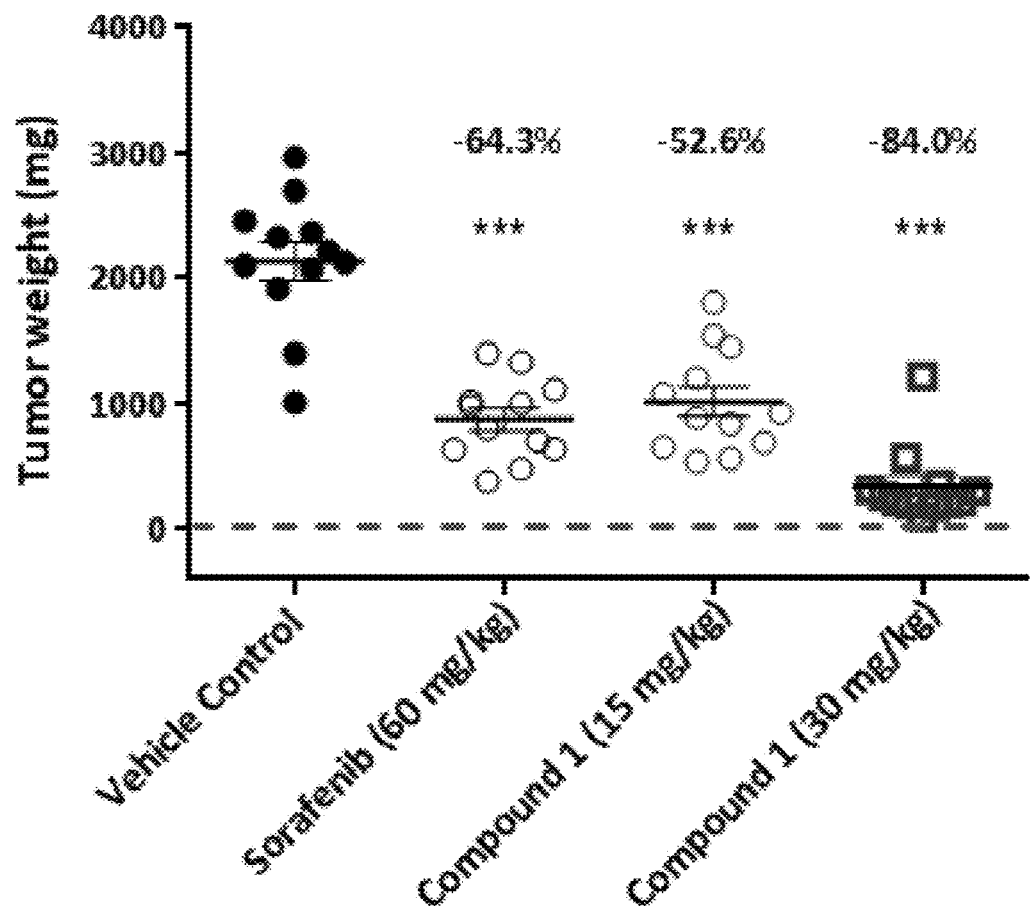

FIG. 16. illustrates antitumor activity in the orthotopic Hep3B2.1-7 hepatocellular carcinoma xenograft. Female SCID mice were orthotopically inoculated with 2×10⁶ Hep3B2.1-7 tumor cells per animal. Seven days post-inoculation animals were randomized into treatment groups based on body weight and treatment commenced (Study day 0). Take rate assessment of a satellite group confirmed the presence of tumor in the liver in 100% of the animals. Compound 1 was dosed orally, QD for 21 days. On the day of study termination, tumors were removed and weighed. Individual tumor weights and the mean tumor weight±SEM of each group are plotted. Percent inhibition is calculated relative to the vehicle control and is above the respective tumor weight for the treatment groups. P values are derived from a one-way ANOVA with a Dunnet's post-hoc analysis. ***=p<0.001. Compound 1 showed a statistically significant reduction in tumor weight compared to vehicle controls.

Figure 17:
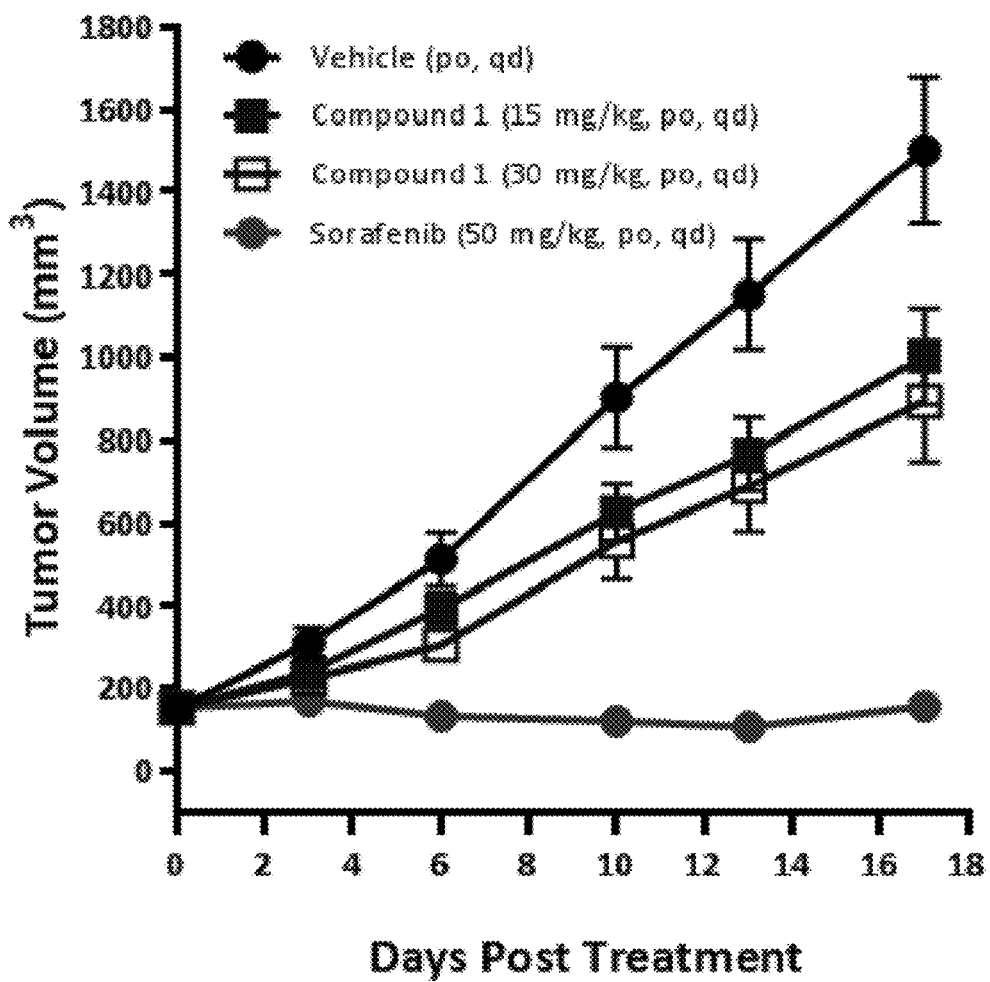

FIG. 17. illustrates antitumor activity of Compound 1 in the C-Met amplified hepatocellular carcinoma patient-derived xenograft model, LI0612. Female SCID mice were inoculated with hepatocellular carcinoma PDX model LI0612 tumor fragments (2-4 mm in diameter) into the right flank. Mice were randomized into treatment groups (n=10/group) at the time of treatment initiation. Test article treatment started on Day 18 when the tumors were approximately 150 mm³. Tumor growth progressed in the vehicle control and Compound 1 treatment groups over the dosing period. A change in the growth kinetics was noted with Compound 1 administration resulting in significant tumor growth inhibition (TGI) with 30 mg/kg treatment (p=0.038, compared to the vehicle control).

Figure 18:
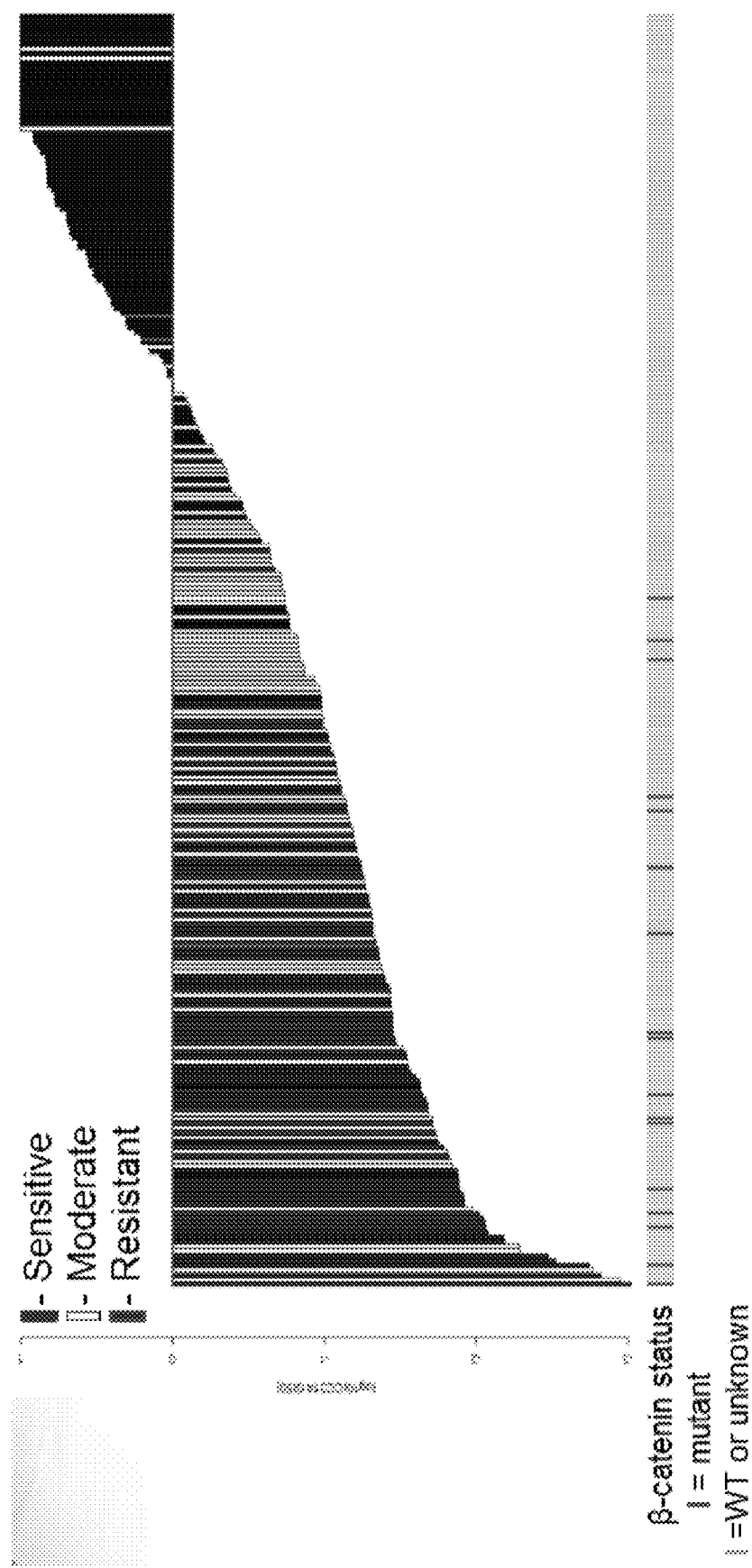

FIG. 18. illustrates sensitivity of cell lines having β-catenin mutations to Compound 1 treatment and shows that cell lines with mutated β-catenin are generally more sensitive to Compound 1 treatment.

Figure 19D:
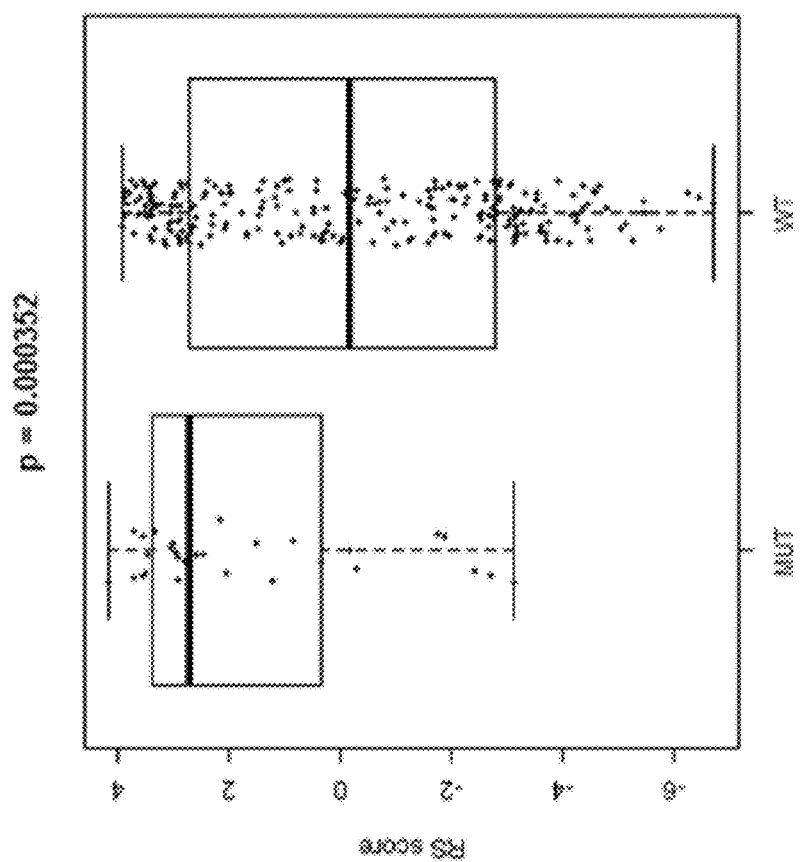
Figure 19C:
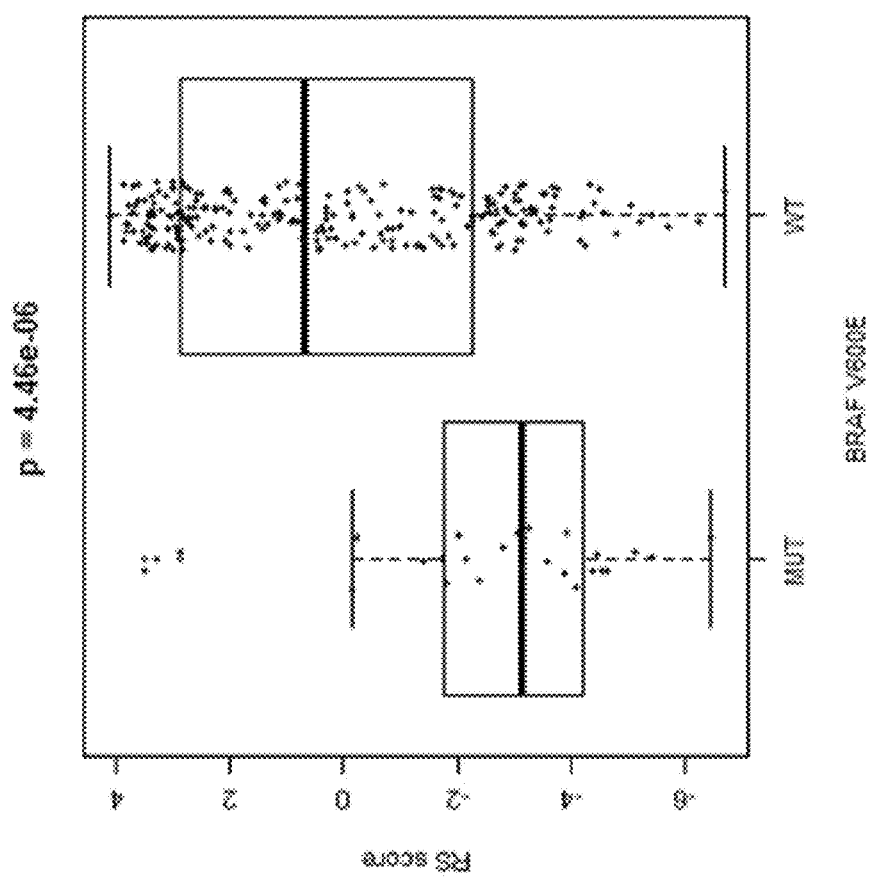
Figure 19E:
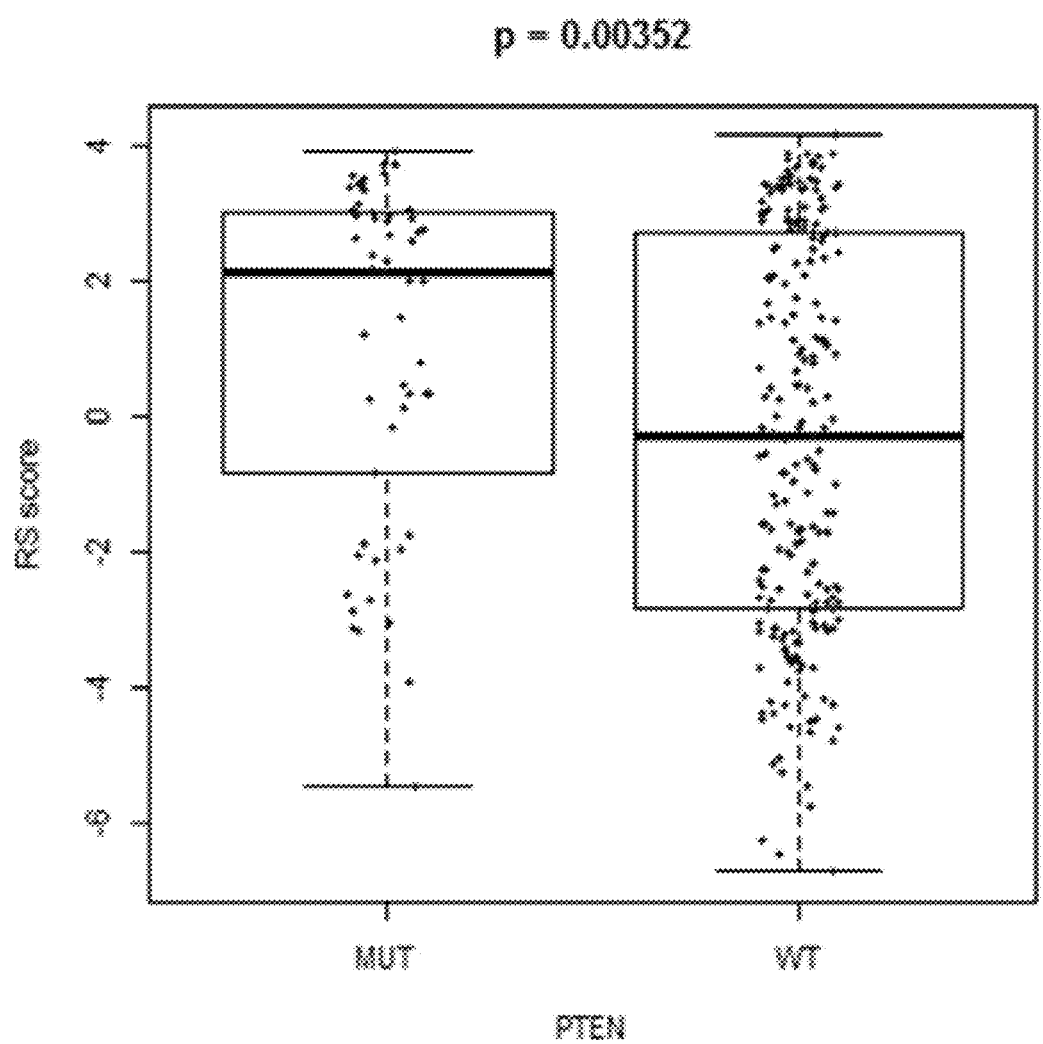

FIGS. 19A-19E. illustrate cell line sensitivity and resistance to treatment with Compound 1. FIGS. 19A-19C show that cell lines containing BRAF and CTNNB1 mutations are more sensitive to treatment with Compound 1 than cell lines with wild type BRAF and CTNNB1. FIG. 19D and FIG. 19E show that cell lines with mutations in RB and the PI3K/PTEN pathway are associated with resistance to Compound 1 treatment in vitro.

Figure 20:
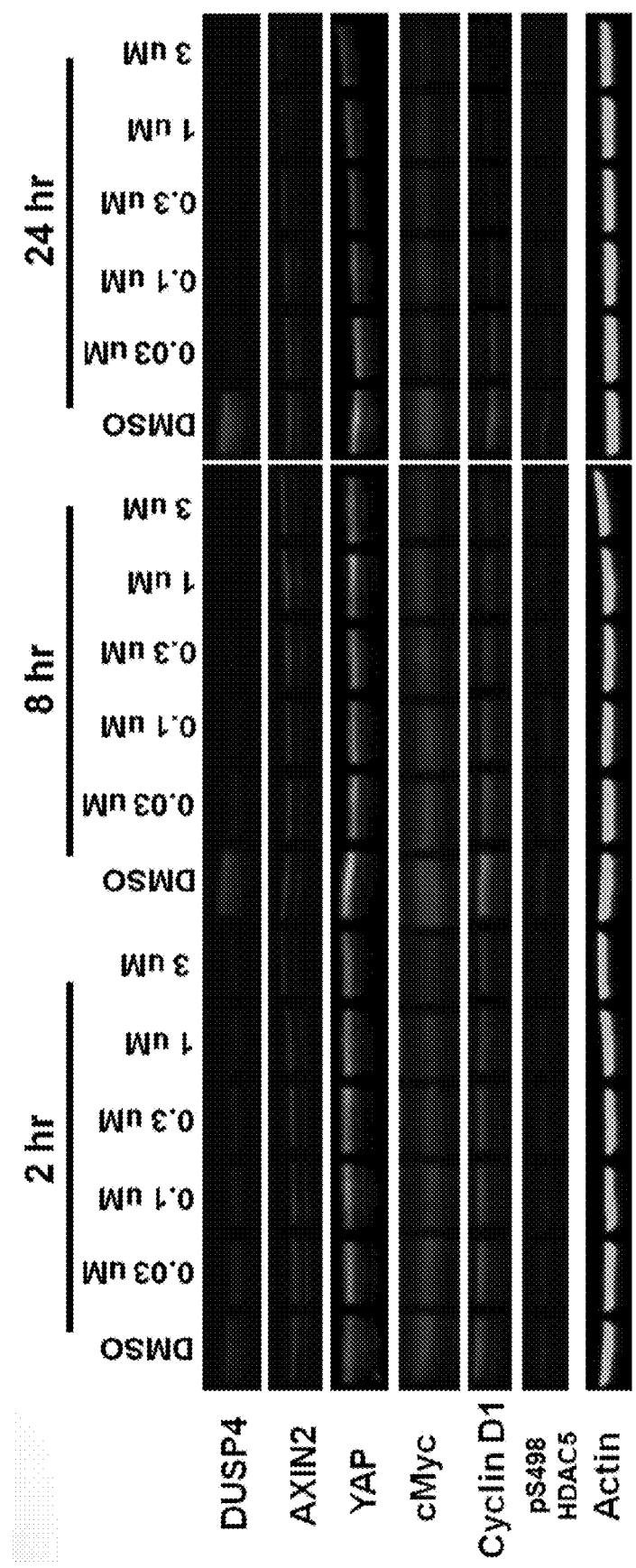

FIG. 20. illustrates Compound 1 modulates MAPK, β-catenin, and YAP in the BRAF and CTNNB1 mutant cell line SW48.

Figure 21A:
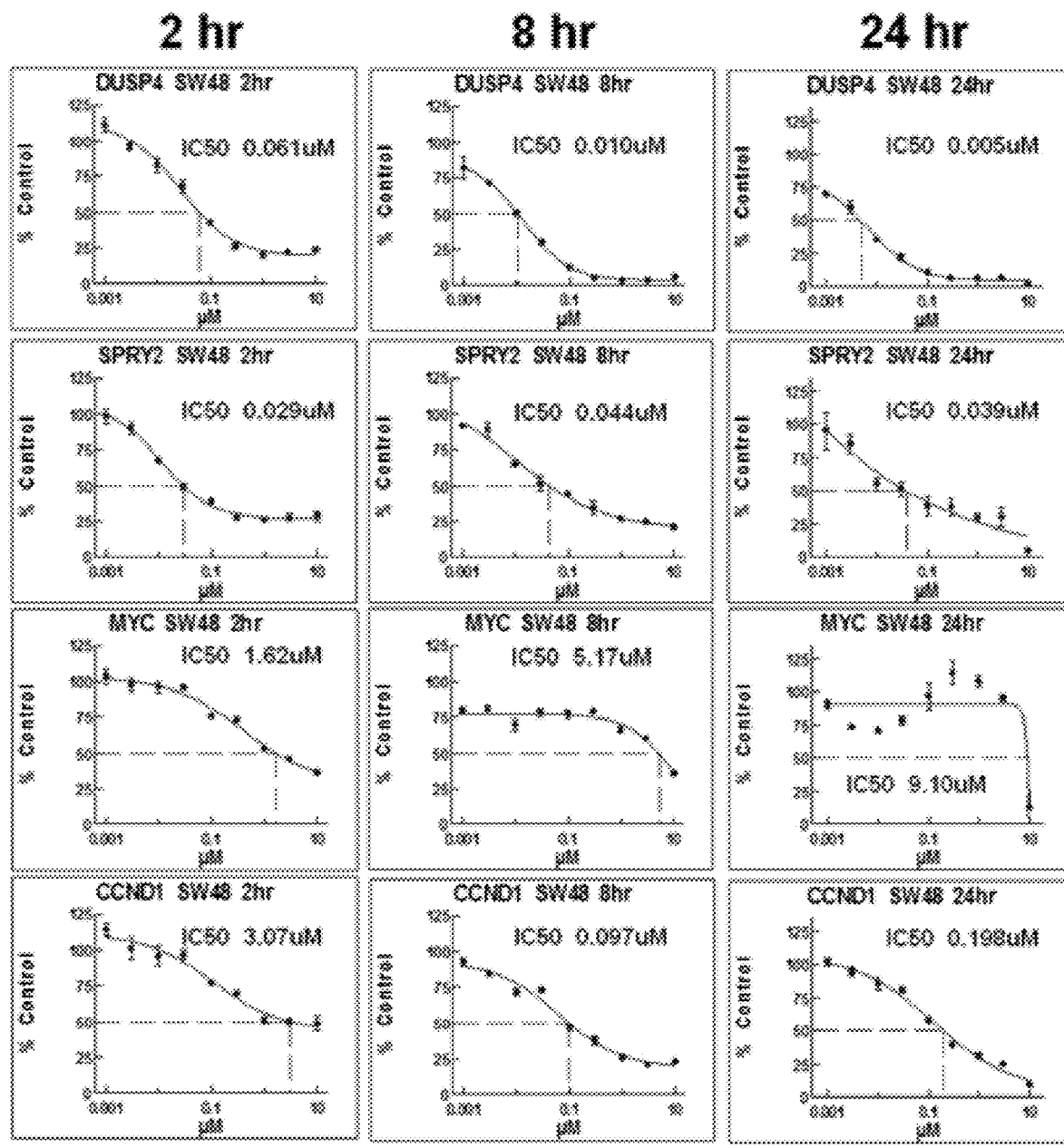
Figure 21B:
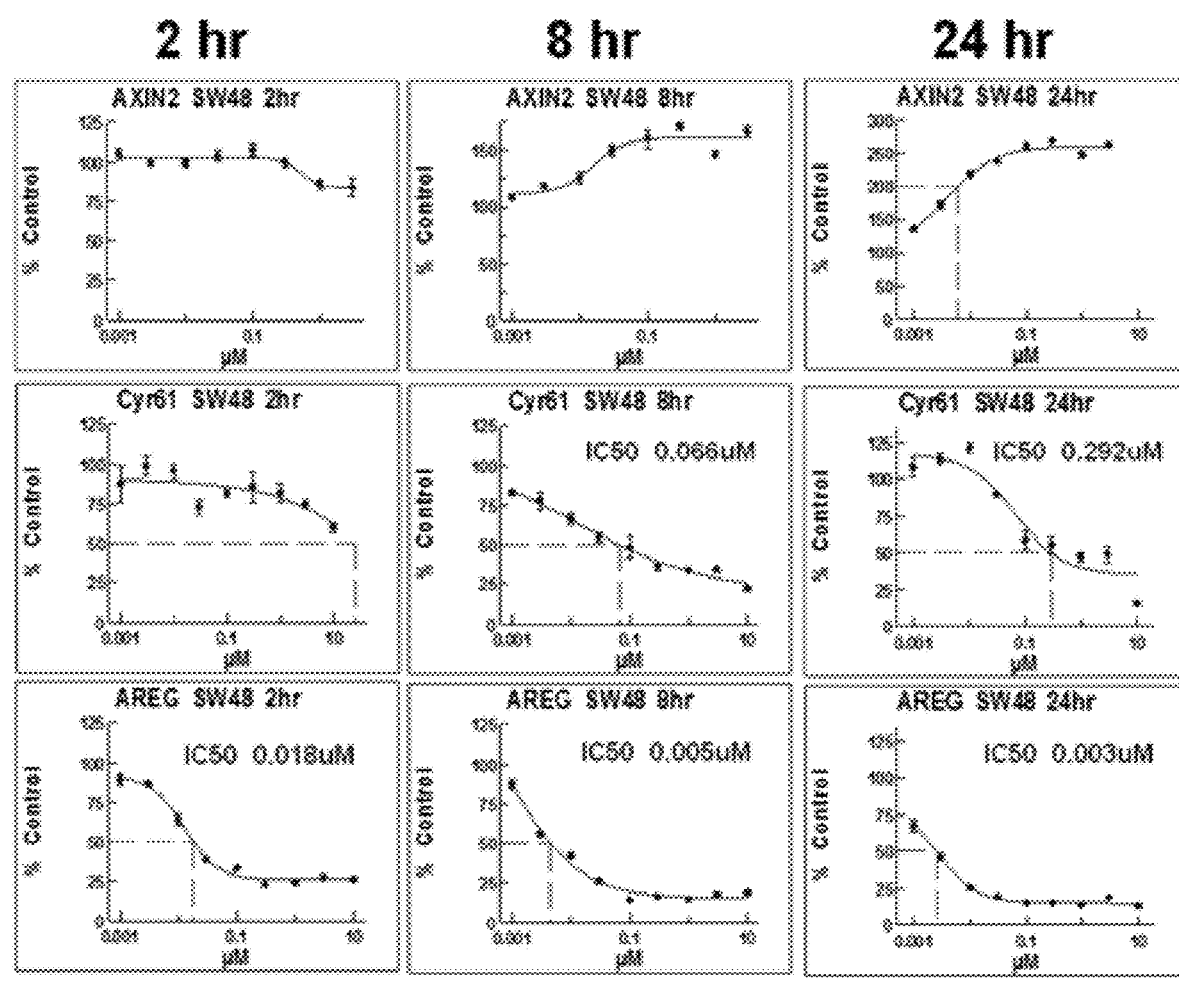

FIGS. 21A-21B. illustrate Compound 1 modulates target gene expression controlled by MAPK, β-catenin, and YAP in the BRAF and CTNNB1 mutant cell line SW48.

Figure 22:
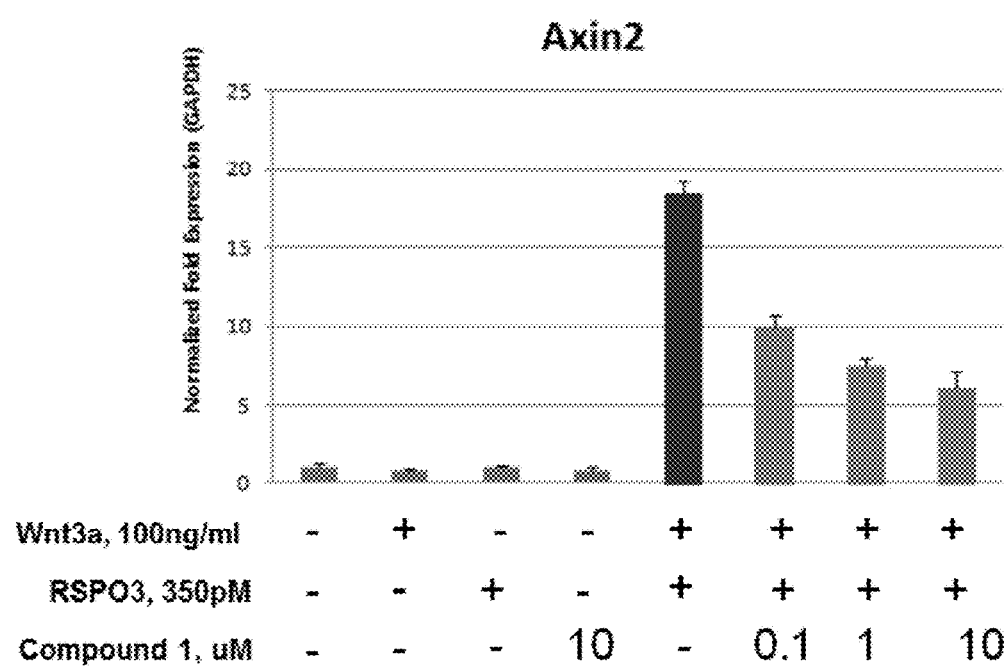

FIG. 22. illustrates that Compound 1 inhibits Axin2 expression in human bronchial epithelial cells. Gene expression was measured at 24 hours.

FIGS. 23A-23D. illustrate that Compound 1 inhibits colony formation of β-catenin mutant cells at a level greater than MEK inhibitors (trametinib) and ERK inhibitors (GDC0994).

Figure 23A:
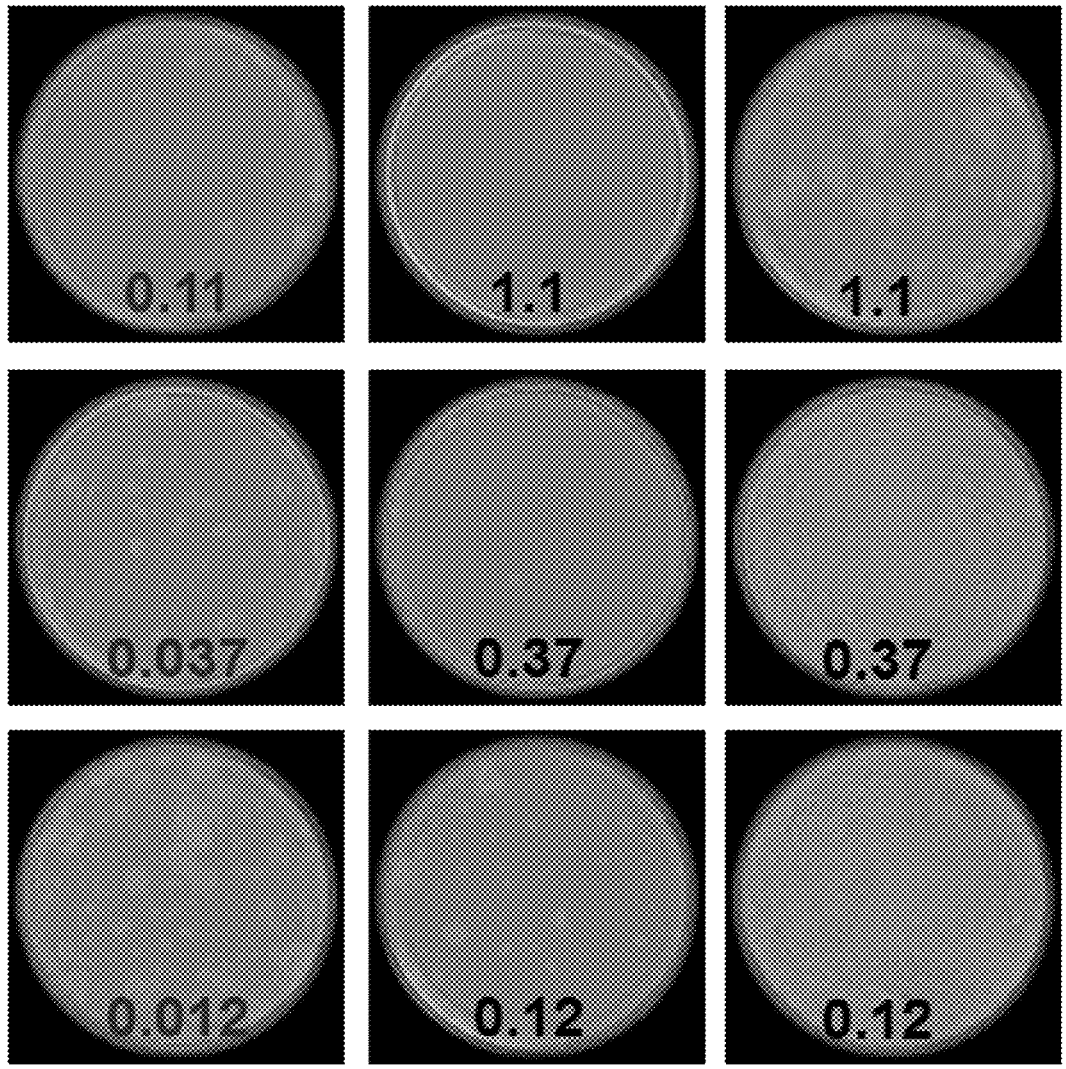
Figure 23B:
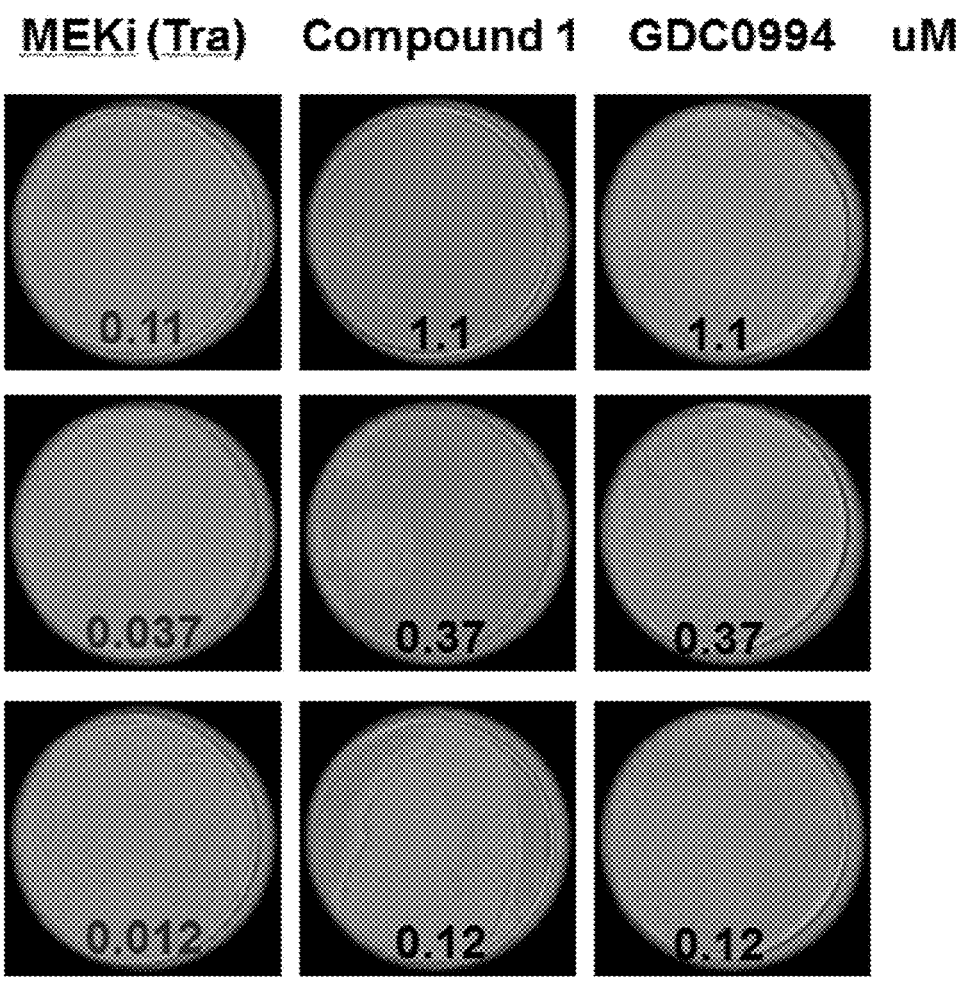
Figure 23C:
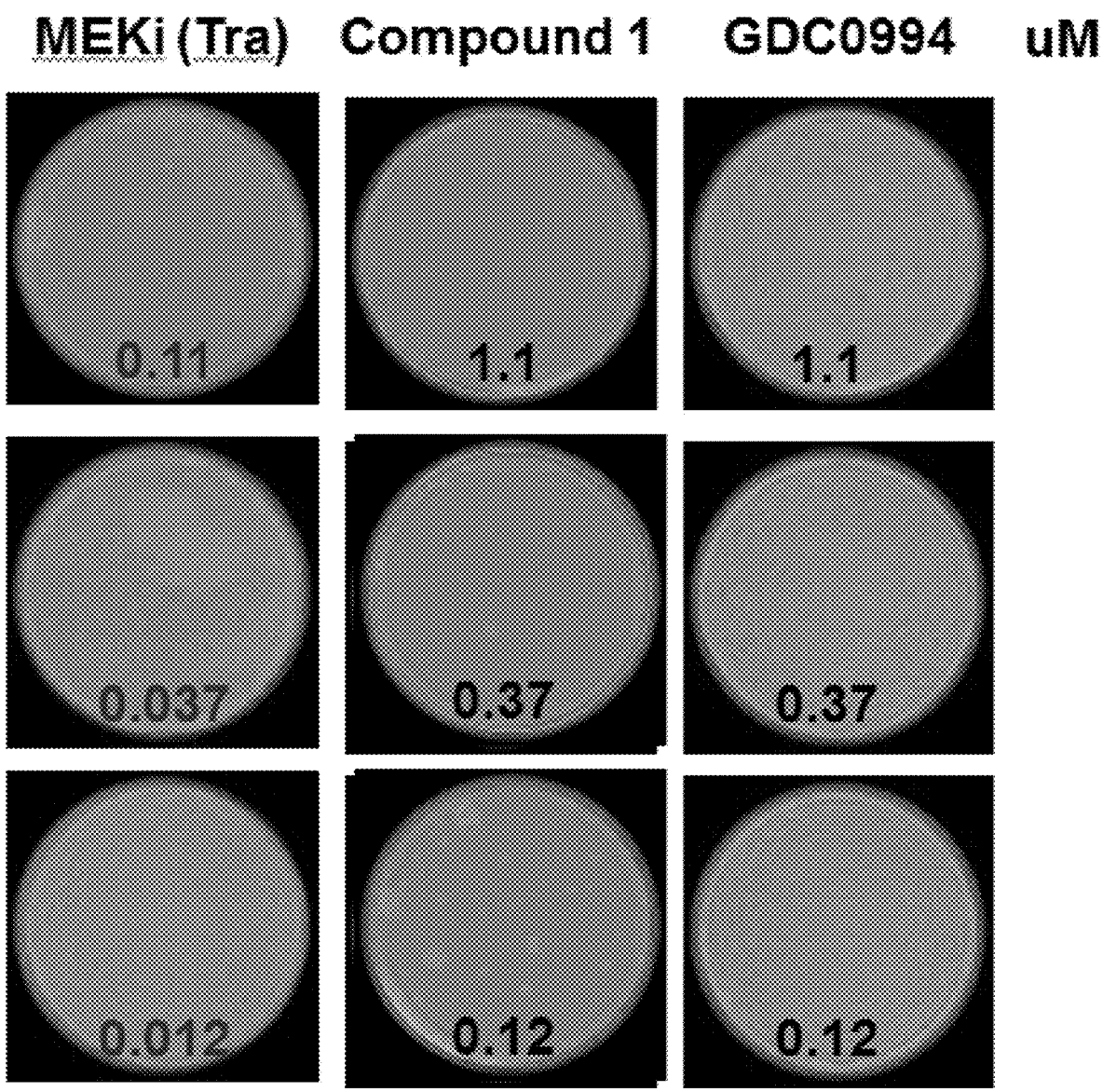
Figure 23D:
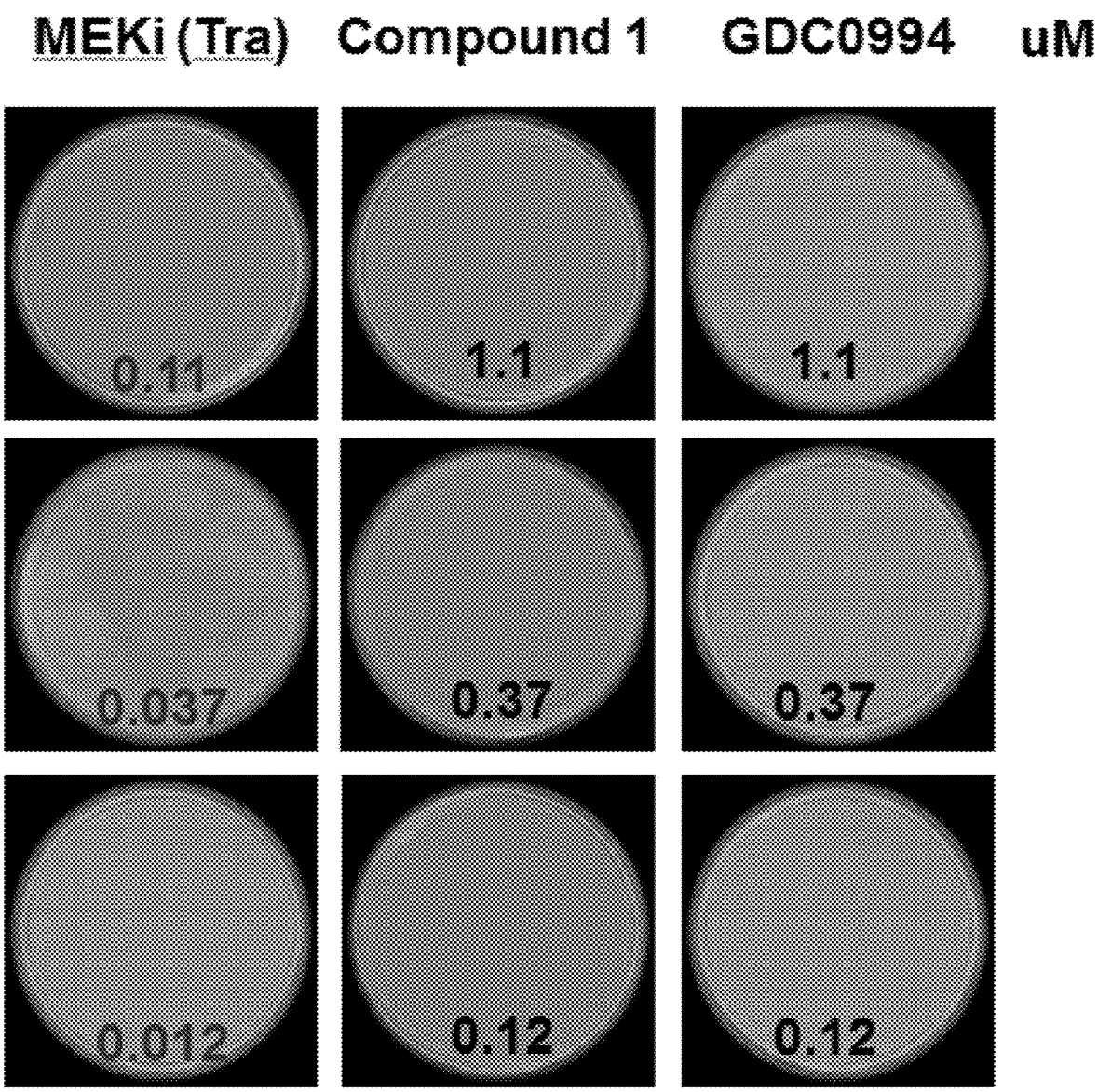

FIG. 23A shows inhibition of colony formation of SW48 (colo) cells. FIG. 23B shows inhibition of colony formation of HCT-116 (colo) cells. FIG. 23C shows inhibition of colony formation of AGS (gastric) cells. FIG. 23D shows inhibition of colony formation of Hep3B (HCC) cells.

Figure 24:
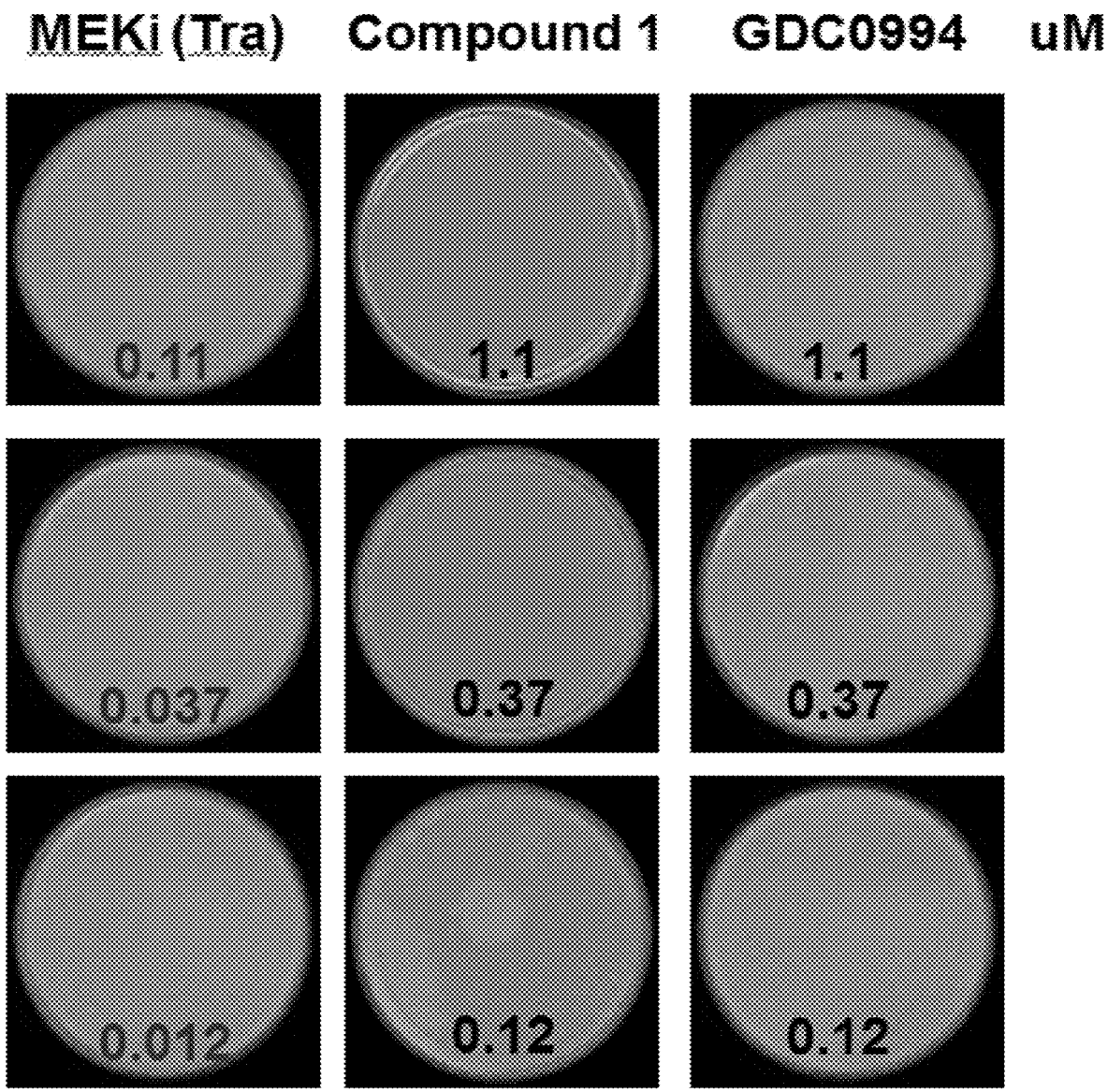

FIG. 24 illustrates that AGS cells resistant to the MEK inhibitor trametinib are sensitive to Compound 1 in a colony formation assay.

Figure 25:
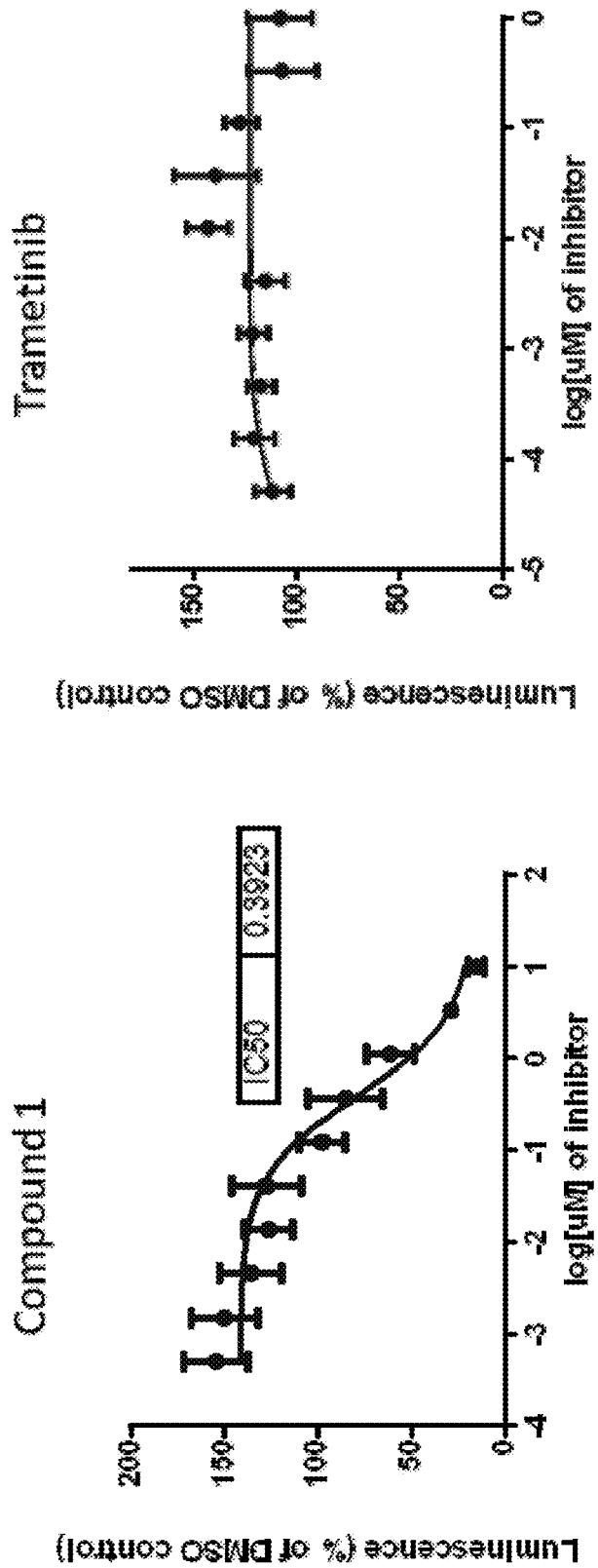

FIG. 25 illustrates TEAD reporter activity in 8×GTIIC-luciferase WI38 VA13 cells treated with Compound 1 and trametinib for 72 hours. Luciferase activity was analyzed using the Bright Glo luciferase assay (Promega). Compound 1 inhibited TEAD reporter activity, with an average $IC_{50}$ of >10 μM in the 24 hour assay and an average $IC_{50}$ of 1.85 μM in the 72 hour assay (cumulative data of three experiments). Viability was not reproducibly affected by Compound 1 across the three assays. Trametinib did not inhibit TEAD reporter activity at 24 or 72 hours.

DETAILED DESCRIPTION

Definitions

An "alkyl" group is a saturated, partially saturated, or unsaturated straight chain or branched non-cyclic hydrocarbon having from 1 to 10 carbon atoms, typically from 1 to 8 carbons or, in some embodiments, from 1 to 6, 1 to 4, or 2 to 6 or carbon atoms. Representative alkyl groups include -methyl, -ethyl, -n-propyl, -n-butyl, -n-pentyl and -n-hexyl; while saturated branched alkyls include -isopropyl, -sec-butyl, -isobutyl, -tert-butyl, -isopentyl, -neopentyl, tert-pentyl, -2-methylpentyl, -3-methylpentyl, -4-methylpentyl, -2,3-dimethylbutyl and the like. Examples of unsaturated alkyl groups include, but are not limited to, vinyl, allyl, —CH═CH(CH₃), —CH═C(CH₃)₂, —C(CH₃)═CH₂, —C(CH₃)═CH(CH₃), —C(CH₂CH₃)═CH₂, —C≡C(CH₃), —C≡C(CH₂CH₃), —CH₂C≡CH, —CH₂C≡C(CH₃) and —CH₂C≡C(CH₂CH₃), among others. An alkyl group can be substituted or unsubstituted. When the alkyl groups described herein are said to be "substituted," they may be substituted with any substituent or substituents as those found in the exemplary compounds and embodiments disclosed herein, as well as halogen (chloro, iodo, bromo, or fluoro); alkyl; hydroxyl; alkoxy; alkoxyalkyl; amino; alkylamino; carboxy; nitro; cyano; thiol; thioether; imine; imide; amidine; guanidine; enamine; aminocarbonyl; acylamino; phosphonate; phosphine; thiocarbonyl; sulfinyl; sulfone; sulfonamide; ketone; aldehyde; ester; urea; urethane; oxime; hydroxyl amine; alkoxyamine; aryloxyamine, aralkoxyamine; N-oxide; hydrazine; hydrazide; hydrazone; azide; isocyanate; isothiocyanate; cyanate; thiocyanate; B(OH)₂, or O(alkyl)aminocarbonyl.

A "cycloalkyl" group is a saturated, or partially saturated cyclic alkyl group of from 3 to 10 carbon atoms having a single cyclic ring or multiple condensed or bridged rings which can be optionally substituted with from 1 to 3 alkyl groups. In some embodiments, the cycloalkyl group has 3 to 8 ring members, whereas in other embodiments the number of ring carbon atoms ranges from 3 to 5, 3 to 6, or 3 to 7. Such cycloalkyl groups include, by way of example, single ring structures such as cyclopropyl, cyclobutyl, cyclopentyl, cyclohexyl, cycloheptyl, cyclooctyl, 1-methylcyclopropyl, 2-methylcyclopentyl, 2-methylcyclooctyl, and the like, or multiple or bridged ring structures such as 1-bicyclo[1.1.1] pentyl, bicyclo[2.1.1]hexyl, bicyclo[2.2.1]heptyl, bicyclo [2.2.2]octyl, adamantyl and the like. Examples of unsaturated cycloalkyl groups include cyclohexenyl, cyclopentenyl, cyclohexadienyl, butadienyl, pentadienyl, hexadienyl, among others. A cycloalkyl group can be substituted or unsubstituted. Such substituted cycloalkyl groups include, by way of example, cyclohexanol and the like.

An "aryl" group is an aromatic carbocyclic group of from 6 to 14 carbon atoms having a single ring (e.g., phenyl) or multiple condensed rings (e.g., naphthyl or anthryl). In some embodiments, aryl groups contain 6-14 carbons, and in others from 6 to 12 or even 6 to 10 carbon atoms in the ring portions of the groups. Particular aryls include phenyl, biphenyl, naphthyl and the like. An aryl group can be substituted or unsubstituted. The phrase "aryl groups" also includes groups containing fused rings, such as fused aromatic-aliphatic ring systems (e.g., indanyl, tetrahydronaphthyl, and the like).

A "heteroaryl" group is an aryl ring system having one to four heteroatoms as ring atoms in a heteroaromatic ring system, wherein the remainder of the atoms are carbon atoms. In some embodiments, heteroaryl groups contain 3 to 6 ring atoms, and in others from 6 to 9 or even 6 to 10 atoms in the ring portions of the groups. Suitable heteroatoms include oxygen, sulfur and nitrogen. In certain embodiments, the heteroaryl ring system is monocyclic or bicyclic. Non-limiting examples include but are not limited to, groups such as pyrrolyl, pyrazolyl, imidazolyl, triazolyl, tetrazolyl, oxazolyl, isoxazolyl, benzisoxazolyl (e.g., benzo[d]isoxazolyl), thiazolyl, pyrolyl, pyridazinyl, pyrimidyl, pyrazinyl, thiophenyl, benzothiophenyl, furanyl, benzofuranyl, indolyl (e.g., indolyl-2-onyl or isoindolin-1-onyl), azaindolyl (pyrrolopyridyl or 1H-pyrrolo[2,3-b]pyridyl), indazolyl, benzimidazolyl (e.g., 1H-benzo[d]imidazolyl), imidazopyridyl (e.g., azabenzimidazolyl or 1H-imidazo[4,5-b]pyridyl), pyrazolopyridyl, triazolopyridyl, benzotriazolyl (e.g., 1H-benzo[d][1,2,3]triazolyl), benzoxazolyl (e.g., benzo[d] oxazolyl), benzothiazolyl, benzothiadiazolyl, isoxazolopyridyl, thianaphthalenyl, purinyl, xanthinyl, adeninyl, guaninyl, quinolinyl, isoquinolinyl (e.g., 3,4-dihydroisoquinolin-1(2H)-onyl), tetrahydroquinolinyl, quinoxalinyl, and quinazolinyl groups.

A "heterocyclyl" is an aromatic (also referred to as heteroaryl) or non-aromatic cycloalkyl in which one to four of the ring carbon atoms are independently replaced with a heteroatom from the group consisting of O, S and N. In some embodiments, heterocyclyl groups include 3 to 10 ring members, whereas other such groups have 3 to 5, 3 to 6, or 3 to 8 ring members. Heterocyclyls can also be bonded to other groups at any ring atom (i.e., at any carbon atom or heteroatom of the heterocyclic ring). A heterocycloalkyl group can be substituted or unsubstituted. Heterocyclyl groups encompass unsaturated, partially saturated and saturated ring systems, such as, for example, imidazolyl, imidazolinyl and imidazolidinyl (e.g., imidazolidin-4-one or imidazolidin-2,4-dionyl) groups. The phrase heterocyclyl includes fused ring species, including those comprising fused aromatic and non-aromatic groups, such as, for example, 1- and 2-aminotetraline, benzotriazolyl (e.g., 1H-benzo[d][1,2,3]triazolyl), benzimidazolyl (e.g., 1H-benzo[d]imidazolyl), 2,3-dihydrobenzo[1,4]dioxinyl, and benzo[1,3]dioxolyl. The phrase also includes bridged polycyclic ring systems containing a heteroatom such as, but not limited to, quinuclidyl. Representative examples of a heterocyclyl group include, but are not limited to, aziridinyl, azetidinyl, azepanyl, oxetanyl, pyrrolidyl, imidazolidinyl (e.g., imidazolidin-4-onyl or imidazolidin-2,4-dionyl), pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, benzisoxazolyl (e.g., benzo [d]isoxazolyl), thiazolyl, thiazolinyl, isothiazolyl, thiadiazolyl, oxadiazolyl, piperidyl, piperazinyl (e.g., piperazin-2-onyl), morpholinyl, thiomorpholinyl, tetrahydropyranyl (e.g., tetrahydro-2H-pyranyl), tetrahydrothiopyranyl, oxathianyl, dioxyl, dithianyl, pyranyl, pyridyl, pyrimidyl, pyridazinyl, pyrazinyl, triazinyl, dihydropyridyl, dihydrodithiinyl, dihydrodithionyl, 1,4-dioxaspiro[4.5]decanyl, homopiperazinyl, quinuclidyl, indolyl (e.g., indolyl-2-onyl or isoindolin-1-onyl), indolinyl, isoindolyl, isoindolinyl, azaindolyl (pyrrolopyridyl or 1H-pyrrolo[2,3-b]pyridyl), indazolyl, indolizinyl, benzotriazolyl (e.g. 1H-benzo[d][1,2,3]triazolyl), benzimidazolyl (e.g., 1H-benzo[d]imidazolyl or 1H-benzo[d]imidazol-2(3H)-onyl), benzofuranyl, benzothiophenyl, benzothiazolyl, benzoxadiazolyl, benzoxazinyl, benzodithiinyl, benzoxathiinyl, benzothiazinyl, benzoxazolyl (i.e., benzo[d]oxazolyl), benzothiazolyl, benzothiadiazolyl, benzo[1,3]dioxolyl, pyrazolopyridyl (for example, 1H-pyrazolo[3,4-b]pyridyl, 1H-pyrazolo[4,3-b]pyridyl), imidazopyridyl (e.g., azabenzimidazolyl or 1H-imidazo[4,5-b]pyridyl), triazolopyridyl, isoxazolopyridyl, purinyl, xanthinyl, adeninyl, guaninyl, quinolinyl, isoquinolinyl (e.g., 3,4-dihydroisoquinolin-1(2H)-onyl), quinolizinyl, quinoxalinyl, quinazolinyl, cinnolinyl, phthalazinyl, naphthyridinyl, pteridinyl, thianaphthalenyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, tetrahydropyrimidin-2(1H)-one and tetrahydroquinolinyl groups. Representative non-aromatic heterocyclyl groups do not include fused ring species that comprise a fused aromatic group. Examples of non-aromatic heterocyclyl groups include aziridinyl, azetidinyl, azepanyl, pyrrolidyl, imidazolidinyl (e.g., imidazolidin-4-onyl or imidazolidin-2,4-dionyl), pyrazolidinyl, thiazolidinyl, tetrahydrothiophenyl, tetrahydrofuranyl, piperidyl, piperazinyl (e.g., piperazin-2-onyl), morpholinyl, thiomorpholinyl, tetrahydropyranyl (e.g., tetrahydro-2H-pyranyl), tetrahydrothiopyranyl, oxathianyl, dithianyl, 1,4-dioxaspiro[4.5]decanyl, homopiperazinyl, quinuclidyl, or tetrahydropyrimidin-2(1H)-one. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed below.

A "cycloalkylalkyl" group is a radical of the formula: -alkyl-cycloalkyl, wherein alkyl and cycloalkyl are as defined above. Substituted cycloalkylalkyl groups may be substituted at the alkyl, the cycloalkyl, or both the alkyl and the cycloalkyl portions of the group. Representative cycloalkylalkyl groups include but are not limited to methylcyclopropyl, methylcyclobutyl, methylcyclopentyl, methylcyclohexyl, ethylcyclopropyl, ethylcyclobutyl, ethylcyclopentyl, ethylcyclohexyl, propylcyclopentyl, propylcyclohexyl and the like.

An "aralkyl" group is a radical of the formula: -alkyl-aryl, wherein alkyl and aryl are defined above. Substituted aralkyl groups may be substituted at the alkyl, the aryl, or both the alkyl and the aryl portions of the group. Representative aralkyl groups include but are not limited to benzyl and phenethyl groups and fused (cycloalkylaryl)alkyl groups such as 4-ethyl-indanyl.

An "heterocyclylalkyl" group is a radical of the formula: -alkyl-heterocyclyl, wherein alkyl and heterocyclyl are defined above. Substituted heterocyclylalkyl groups may be substituted at the alkyl, the heterocyclyl, or both the alkyl and the heterocyclyl portions of the group. Representative heterocylylalkyl groups include but are not limited to 4-ethyl-morpholinyl, 4-propylmorpholinyl, furan-2-yl methyl, furan-3-yl methyl, pyridin-3-yl methyl, tetrahydrofuran-2-yl ethyl, and indol-2-yl propyl.

A "halogen" is chloro, iodo, bromo, or fluoro.

A "hydroxyalkyl" group is an alkyl group as described herein substituted with one or more hydroxy groups.

An "alkoxy" group is —O-(alkyl), wherein alkyl is defined herein.

An "alkoxyalkyl" group is -(alkyl)-O-(alkyl), wherein alkyl is defined herein.

An "amine" group is a radical of the formula: —NH$_2$.

A "hydroxyl amine" group is a radical of the formula: —N(R$^\#$)OH or —NHOH, wherein R$^\#$ is a substituted or unsubstituted alkyl, cycloalkyl, cycloalkylalkyl, aryl, aralkyl, heterocyclyl or heterocyclylalkyl group as defined herein.

An "alkoxyamine" group is a radical of the formula: —N(R$^\#$)O-alkyl or —NHO-alkyl, wherein R$^\#$ and alkyl are as defined herein.

An "aryloxyamine" group is a radical of the formula: —N(R$^\#$)O-aryl or —NHO-aryl, wherein R$^\#$ and aryl are as defined herein.

An "aralkoxyamine" group is a radical of the formula: —N(R$^\#$)O-aralkyl or —NHO-aralkyl, wherein R$^\#$ and aralkyl as defined herein.

An "alkylamine" group is a radical of the formula: —NH-alkyl or —N(alkyl)$_2$, wherein each alkyl is independently as defined herein.

An "aminocarbonyl" group is a radical of the formula: —C(=O)N(R$^\#$)$_2$, —C(=O)NH(R$^\#$) or —C(=O)NH$_2$, wherein each R$^\#$ is as defined herein.

An "acylamino" group is a radical of the formula: —NHC(=O)(R$^\#$) or —N(alkyl)C(=O)(R$^\#$), wherein each alkyl and R$^\#$ are independently as defined herein.

An "O(alkyl)aminocarbonyl" group is a radical of the formula: —O(alkyl)C(=O)N(R$^\#$)$_2$, —O(alkyl)C(=O)NH(R$^\#$) or —O(alkyl)C(=O)NH$_2$, wherein each R$^\#$ and alkyl are independently as defined herein.

An "N-oxide" group is a radical of the formula: —N$^+$—O$^-$.

A "carboxy" group is a radical of the formula: —C(=O)OH.

A "ketone" group is a radical of the formula: —C(=O)(R$^\#$), wherein R$^\#$ is as defined herein.

An "aldehyde" group is a radical of the formula: —CH(=O).

An "ester" group is a radical of the formula: —C(=O)O(R$^\#$) or —OC(=O)(R$^\#$), wherein R$^\#$ is as defined herein.

A "urea" group is a radical of the formula: —N(alkyl)C(=O)N(R$^\#$)$_2$, —N(alkyl)C(=O)NH(R$^\#$), —N(alkyl)C(=O)NH$_2$, —NHC(=O)N(R$^\#$)$_2$, —NHC(=O)NH(R$^\#$), or —NHC(=O)NH$_2^\#$, wherein each alkyl and R$^\#$ are independently as defined herein.

An "imine" group is a radical of the formula: —N=C(R$^\#$)$_2$ or —C(R$^\#$)=N(R$^\#$), wherein each R$^\#$ is independently as defined herein.

An "imide" group is a radical of the formula: —C(=O)N(R#)C(=O)(R$^\#$) or —N((C=O)(R$^\#$))$_2$, wherein each R$^\#$ is independently as defined herein.

A "urethane" group is a radical of the formula: —OC(=O)N(R$^\#$)$_2$, —OC(=O)NH(R$^\#$), —N(R$^\#$)C(=O)O(R$^\#$), or —NHC(=O)O(R$^\#$), wherein each R$^\#$ is independently as defined herein.

An "amidine" group is a radical of the formula: —C(=N(R$^\#$))N(R$^\#$)$_2$, —C(=N(R$^\#$))NH(R$^\#$), —C(=N(R$^\#$))NH$_2$, —C(=NH)N(R$^\#$)$_2$, —C(=NH)NH(R$^\#$), —C(=NH)NH$_2$, —N=C(R$^\#$)N(R$^\#$)$_2$, —N=C(R$^\#$)NH(R$^\#$), —N=C(R$^\#$)NH$_2$, —N(R$^\#$)C(R$^\#$)=N(R$^\#$), —NHC(R$^\#$)=N(R$^\#$), —N(R#)C(R#)=NH, or —NHC(R#)=NH, wherein each R# is independently as defined herein.

A "guanidine" group is a radical of the formula: —N(R#)C(=N(R#))N(R#)₂, —NHC(=N(R#))N(R#)₂, —N(R#)C(=NH)N(R#)₂, —N(R#)C(=N(R#))NH(R#), —N(R#)C(=N(R#))NH₂, —NHC(=NH)N(R#)₂, —NHC(=N(R#))NH(R#), —NHC(=N(R#))NH₂, —NHC(=NH)NH(R#), —NHC(=NH)NH₂, —N=C(N(R#)₂)₂, —N=C(NH(R#))₂, or —N=C(NH₂)₂, wherein each R# is independently as defined herein.

An "enamine" group is a radical of the formula: —N(R#)C(R#)=C(R#)₂, —NHC(R#)=C(R#)₂, —C(N(R#)₂)=C(R#)₂, —C(NH(R#))=C(R#)₂, —C(NH₂)=C(R#)₂, —C(R#)=C(R#)(N(R#)₂), —C(R#)=C(R#)(NH(R#)) or —C(R#)=C(R#)(NH₂), wherein each R# is independently as defined herein.

An "oxime" group is a radical of the formula: —C(=NO(R#))(R#), —C(=NOH)(R#), —CH(=NO(R#)), or —CH(=NOH), wherein each R# is independently as defined herein.

A "hydrazide" group is a radical of the formula: —C(=O)N(R#)N(R#)₂, —C(=O)NHN(R#)₂, —C(=O)N(R#)NH(R#), —C(=O)N(R#)NH₂, —C(=O)NHNH(R#)₂, or —C(=O)NHNH₂, wherein each R# is independently as defined herein.

A "hydrazine" group is a radical of the formula: —N(R#)N(R#)₂, —NHN(R#)₂, —N(R#)NH(R#), —N(R#)NH₂, —NHNH(R#), or —NHNH₂, wherein each R# is independently as defined herein.

A "hydrazone" group is a radical of the formula: —C(=N—N(R#)₂)(R#)₂, —C(=N—NH(R#))(R#)₂, —C(=N—NH₂)(R#)₂, —N(R#)(N=C(R#)₂), or —NH(N=C(R#)₂), wherein each R# is independently as defined herein.

An "azide" group is a radical of the formula: —N₃.

An "isocyanate" group is a radical of the formula: —N=C=O.

An "isothiocyanate" group is a radical of the formula: —N=C=S.

A "cyanate" group is a radical of the formula: —OCN.

A "thiocyanate" group is a radical of the formula: —SCN.

A "thioether" group is a radical of the formula; —S(R#), wherein R# is as defined herein.

A "thiocarbonyl" group is a radical of the formula: —C(=S)(R#), wherein R# is as defined herein.

A "sulfinyl" group is a radical of the formula: —S(=O)(R#), wherein R# is as defined herein.

A "sulfone" group is a radical of the formula: —S(=O)₂(R#), wherein R# is as defined herein.

A "sulfonylamino" group is a radical of the formula: —NHSO₂(R#) or —N(alkyl)SO₂(R#), wherein each alkyl and R# are defined herein.

A "sulfonamide" group is a radical of the formula: —S(=O)₂N(R#)₂, or —S(=O)₂NH(R#), or —S(=O)₂NH₂, wherein each R# is independently as defined herein.

A "phosphonate" group is a radical of the formula: —P(=O)(O(R#))₂, —P(=O)(OH)₂, —OP(=O)(O(R#))(R#), or —OP(=O)(OH)(R#), wherein each R# is independently as defined herein.

A "phosphine" group is a radical of the formula: —P(R#)₂, wherein each R# is independently as defined herein.

When the groups described herein, with the exception of alkyl group, are said to be "substituted," they may be substituted with any appropriate substituent or substituents. Illustrative examples of substituents are those found in the exemplary compounds and embodiments disclosed herein, as well as halogen (chloro, iodo, bromo, or fluoro); alkyl; hydroxyl; alkoxy; alkoxyalkyl; amino; alkylamino; carboxy; nitro; cyano; thiol; thioether; imine; imide; amidine; guanidine; enamine; aminocarbonyl; acylamino; phosphonate; phosphine; thiocarbonyl; sulfinyl; sulfone; sulfonamide; ketone; aldehyde; ester; urea; urethane; oxime; hydroxyl amine; alkoxyamine; aryloxyamine, aralkoxyamine; N-oxide; hydrazine; hydrazide; hydrazone; azide; isocyanate; isothiocyanate; cyanate; thiocyanate; oxygen (=O); B(OH)₂, O(alkyl)aminocarbonyl; cycloalkyl, which may be monocyclic or fused or non-fused polycyclic (e.g., cyclopropyl, cyclobutyl, cyclopentyl, or cyclohexyl), or a heterocyclyl, which may be monocyclic or fused or non-fused polycyclic (e.g., pyrrolidyl, piperidyl, piperazinyl, morpholinyl, or thiazinyl); monocyclic or fused or non-fused polycyclic aryl or heteroaryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl) aryloxy; aralkyloxy; heterocyclyloxy; and heterocyclyl alkoxy.

As used herein, the term "Aminopurine Compound" refers to compounds of formula (I) as well as to further embodiments provided herein. In one embodiment, an "Aminopurine Compound" is a compound set forth in Table 1. In one embodiment, an "Aminopurine Compound" is a compound having the formula of Compound 1. The term "Aminopurine Compound" includes pharmaceutically acceptable salts, tautomers, isotopologues, and stereoisomers of the compounds provided herein.

"Compound 1" refers to a compound (including pharmaceutically acceptable salts, tautomers, isotopologues, and stereoisomers thereof) having the name: cis-4-[2-{[(3S,4R)-3-fluorooxan-4-yl]amino}-8-(2,4,6-trichloroanilino)-9H-purin-9-yl]-1-methyl cyclohexane-1-carboxamide and having an alternative name of; (1s,4s)-4-(2-(((3S,4R)-3-fluorotetrahydro-2H-pyran-4-yl)amino)-8-((2,4,6-trichlorophenyl)amino)-9H-purin-9-yl)-1-methylcyclohexanecarboxamide; and as provided below:

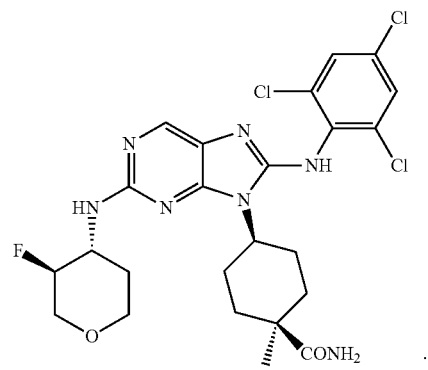 [SMILES: C[C@]1(C(N)=O)CC[C@@H](n2c(Nc3c(Cl)cc(Cl)cc3Cl)nc3cnc(N[C@@H]4CCOC[C@H]4F)nc32)CC1]

As used herein, the term "pharmaceutically acceptable salt(s)" refers to a salt prepared from a pharmaceutically acceptable non-toxic acid or base including an inorganic acid and base and an organic acid and base. Suitable pharmaceutically acceptable base addition salts of the compounds of formula (I) include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methyl-glucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, maleic, phosphoric, sulfuric, and methanesulfonic acids. Examples of specific salts thus include hydrochloride and mesylate salts. Others are well-known in the art, see for example, *Remington's Pharmaceutical Sciences*, 18$^{th}$ eds., Mack Publishing, Easton Pa. (1990) or *Remington: The Science and Practice of Pharmacy*, 19$^{th}$ eds., Mack Publishing, Easton Pa. (1995).

As used herein and unless otherwise indicated, the term "stereoisomer" or "stereomerically pure" means one stereoisomer of an Aminopurine Compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. The Aminopurine Compounds can have chiral centers and can occur as racemates, individual enantiomers or diastereomers, and mixtures thereof. All such isomeric forms are included within the embodiments disclosed herein, including mixtures thereof.

The use of stereomerically pure forms of such Aminopurine Compounds, as well as the use of mixtures of those forms, is encompassed by the embodiments disclosed herein. For example, mixtures comprising equal or unequal amounts of the enantiomers of a particular Aminopurine Compound may be used in methods and compositions disclosed herein. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, NY, 1962); and Wilen, S. H., *Tables of Resolving Agents and Optical Resolutions* p. 268 (E. L. Eliel, Ed., Univ. of Notre Dame Press, Notre Dame, Ind., 1972).

It should also be noted the Aminopurine Compounds can include E and Z isomers, or a mixture thereof, and cis and trans isomers or a mixture thereof. In certain embodiments, the Aminopurine Compounds are isolated as either the E or Z isomer. In other embodiments, the Aminopurine Compounds are a mixture of the E and Z isomers.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

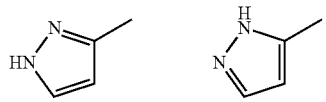

As readily understood by one skilled in the art, a wide variety of functional groups and other structures may exhibit tautomerism and all tautomers of compounds of formula (I) are within the scope of the present invention.

It should also be noted the Aminopurine Compounds can contain unnatural proportions of atomic isotopes at one or more of the atoms. For example, the compounds may be radiolabeled with radioactive isotopes, such as for example tritium ($^{3}$H), iodine-125 ($^{125}$I), sulfur-35 ($^{35}$S), or carbon-14 ($^{14}$C), or may be isotopically enriched, such as with deuterium ($^{2}$H), carbon-13 ($^{13}$C), or nitrogen-15 ($^{15}$N). As used herein, an "isotopologue" is an isotopically enriched compound. The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. The term "isotopic composition" refers to the amount of each isotope present for a given atom. Radiolabeled and isotopically enriched compounds are useful as therapeutic agents, e.g., cancer and inflammation therapeutic agents, research reagents, e.g., binding assay reagents, and diagnostic agents, e.g., in vivo imaging agents. All isotopic variations of the Aminopurine Compounds as described herein, whether radioactive or not, are intended to be encompassed within the scope of the embodiments provided herein. In some embodiments, there are provided isotopologues of the Aminopurine Compounds, for example, the isotopologues are deuterium, carbon-13, or nitrogen-15 enriched Aminopurine Compounds.

"Treating" as used herein, means an alleviation, in whole or in part, of a disorder, disease or condition, or one or more of the symptoms associated with a disorder, disease, or condition, or slowing or halting of further progression or worsening of those symptoms, or alleviating or eradicating the cause(s) of the disorder, disease, or condition itself. In one embodiment, the disorder is a cancer, in particular, a solid tumor or hematological cancer. In some embodiments, "treating" means an alleviation, in whole or in part, of a cancer, or symptoms associated with a cancer, in particular, a solid tumor or hematological cancer, or a slowing, or halting of further progression or worsening of those symptoms.

"Preventing" as used herein, means a method of delaying and/or precluding the onset, recurrence or spread, in whole or in part, of a cancer, in particular, a solid tumor or hematological cancer; barring a subject from acquiring a cancer, in particular, a solid tumor or hematological cancer; or reducing a subject's risk of acquiring a cancer, in particular, a solid tumor or hematological cancer.

The term "effective amount" in connection with an Aminopurine Compound means an amount capable of treating or preventing a cancer, in particular, a solid tumor or hematological cancer, or symptoms thereof, as disclosed herein. The effective amount of Aminopurine Compound, for example in a pharmaceutical composition, may be at a level that will exercise the desired effect; for example, about 0.005 mg/kg of a subject's body weight to about 100 mg/kg of a patient's body weight in unit dosage for parenteral administration. As will be apparent to those skilled in the art, it is to be expected that the effective amount of an Aminopurine Compound disclosed herein may vary depending on the severity of the indication being treated.

The terms "patient" and "subject" as used herein include an animal, including, but not limited to, an animal such a cow, monkey, horse, sheep, pig, chicken, turkey, quail, cat, dog, mouse, rat, rabbit or guinea pig, in one embodiment a mammal, in another embodiment a human. In one embodiment, a subject is a human having or at risk for having cancer, in particular, a solid tumor or hematological cancer, or symptoms thereof. In one embodiment, a patient is a human having histologically or cytologically-confirmed solid tumor or hematological cancer, including subjects who have progressed on (or not been able to tolerate) standard anticancer therapy or for whom no standard anticancer therapy exists.

As used herein, and unless otherwise specified, the terms "cancer" refers to or describes the physiological condition in mammals that is typically characterized by unregulated cell growth. Examples of cancer include solid tumors and hematological cancer. In some embodiments, the cancer is a primary cancer, in others, the cancer is metastasized.

As used herein "solid tumors" includes, but is not limited to, bladder cancer (including, but not limited to, superficial bladder cancer), breast cancer (including, but not limited to, luminal B type, ER+, PR+ and Her2+ breast cancer), central nervous system cancer (including, but not limited to, glioblastoma multiforme (GBM), glioma, medulloblastoma, and astrocytoma), colorectal cancer, gastrointestinal cancer (including, but not limited to, stomach cancer, esophageal cancer, and rectum cancer), endocrine cancer (including, but not limited to, thyroid cancer, and adrenal gland cancer), eye cancer (including, but not limited to, retinoblastoma), female genitourinary cancer (including, but not limited to, cancer of the placenta, uterus, vulva, ovary, cervix), head and neck cancer (including, but not limited to, cancer of the pharynx, esophageal, and tongue), liver cancer, lung cancer (including, but not limited to, non-small cell lung cancer (NSCLC), small cell lung cancer (SCLC), mucoepidermoid, bronchogenic, squamous cell carcinoma (SQCC), and analplastic/NSCLC), skin cancer (including, but not limited to, melanoma, and SQCC), soft tissue cancer (including but not limited to, sarcoma, Ewing's sarcoma, and rhabdomyosarcoma), bone cancer (including, but not limited to, sarcoma, Ewing's sarcoma, and osteosarcoma), squamous cell cancer (including, but not limited to, lung, esophageal, cervical, and head and neck cancer), pancreas cancer, kidney cancer (including, but not limited to, renal Wilm's tumor and renal cell carcinoma), and prostate cancer. In one embodiment, the solid tumor is not triple negative breast cancer (TNBC). In some embodiments, the solid tumor is breast cancer, colon cancer, lung cancer or bladder cancer. In one such embodiment, the solid tumor is superficial bladder cancer. In another, the solid tumor is lung squamous cell carcinoma. In yet another embodiment, the solid tumor is luminal B type breast cancer.

As used herein "hematological cancer" includes, but is not limited to, leukemia (including, but not limited to, acute lymphocytic leukemia (ALL), chronic myeloid leukemia (CML), acute T-cell leukemia, B cell precursor leukemia, acute promyelocytic leukemia (APML), plasma cell leukemia, myelomonoblastic/T-ALL, B myelomonocytic leukemia, erythroleukemia, and acute myeloid leukemia (AML)), lymphoma (including but not limited to Hodgkin's lymphoma, non-Hodgkin's lymphoma (NHL), Burkitt's lymphoma (BL), B cell lymphoma, lymphoblastic lymphoma, follicular lymphoma (FL), diffuse large B-cell lymphoma (DLBCL), large cell immunoblastic lymphoma), and multiple myeloma.

In the context of a cancer, inhibition may be assessed by inhibition of disease progression, inhibition of tumor growth, reduction of primary tumor, relief of tumor-related symptoms, inhibition of tumor secreted factors (including tumor secreted hormones, such as those that contribute to carcinoid syndrome), delayed appearance of primary or secondary tumors, slowed development of primary or secondary tumors, decreased occurrence of primary or secondary tumors, slowed or decreased severity of secondary effects of disease, arrested tumor growth and regression of tumors, increased Time To Progression (TTP), increased Progression Free Survival (PFS), increased Overall Survival (OS), among others. OS as used herein means the time from treatment onset until death from any cause. TTP as used herein means the time from treatment onset until tumor progression; TTP does not include deaths. As used herein, PFS means the time from treatment onset until tumor progression or death. In one embodiment, PFS rates will be computed using the Kaplan-Meier estimates. In the extreme, complete inhibition, is referred to herein as prevention or chemoprevention. In this context, the term "prevention" includes either preventing the onset of clinically evident cancer altogether or preventing the onset of a preclinically evident stage of a cancer. Also intended to be encompassed by this definition is the prevention of transformation into malignant cells or to arrest or reverse the progression of premalignant cells to malignant cells. This includes prophylactic treatment of those at risk of developing a cancer.

In certain embodiments, the treatment of lymphoma may be assessed by the International Workshop Criteria (IWC) for non-Hodgkin lymphoma (NHL) (see Cheson B D, Pfistner B, Juweid, M E, et. al. Revised Response Criteria for Malignant Lymphoma. J. Clin. Oncol: 2007: (25) 579-586), using the response and endpoint definitions shown below:

| Response | Definition | Nodal Masses | Spleen, liver | Bone Marrow |
|---|---|---|---|---|
| CR | Disappearance of all evidence of disease | (a) FDG-avid or PET positive prior to therapy; mass of any size permitted if PET negative<br>(b) Variably FDG-avid or PET negative; regression to normal size on CT | Not palpable, nodules disappeared | Infiltrate cleared on repeat biopsy; if indeterminate by morphology, immunohistochemistry should be negative |
| PR | Regression of measurable disease and no new sites | ≥50% decrease in SPD of up to 6 largest dominant masses; no increase in size of other nodes | ≥50% decrease in SPD of nodules (for single nodule in greatest | Irrelevant if positive prior to therapy; cell type should be specified |

| Response | Definition | Nodal Masses | Spleen, liver | Bone Marrow |
| --- | --- | --- | --- | --- |
| | | (a) FDG-avid or PET positive prior to therapy; one or more PET positive at previously involved site<br>(b) Variably FDG-avid or PET negative; regression on CT | transverse diameter); no increase in size of liver or spleen | |
| SD | Failure to attain CR/PR or PD | (a) FDG-avid or PET positive prior to therapy; PET positive at prior sites of disease and no new sites on CT or PET<br>(b) Variably FDG-avid or PET negative; no change in size of previous lesions on CT | | |
| PD or relapsed disease | Any new lesion or increase by ≥50% of previously involved sites from nadir | Appearance of a new lesion(s) ≥1.5 cm in any axis, ≥50% increase in SPD of more than one node, or ≥50% increase in longest diameter of a previously identified node ≥1 cm in short axis Lesions PET positive if FDG-avid lymphoma or PET positive prior to therapy | ≥50% increase from nadir in the SPD of any previous lesions | New or recurrent involvement |

Abbreviations:
CR, complete remission;
FDG, [$^{18}$F]fluorodeoxyglucose;
PET, positron emission tomography;
CT, computed tomography;
PR, partial remission;
SPD, sum of the product of the diameters;
SD, stable disease;
PD, progressive disease.

| End point | Patients | Definition | Measured from |
| --- | --- | --- | --- |
| Primary | | | |
| Overall survival | All | Death as a result of any cause | Entry onto study |
| Progression-free survival | All | Disease progression or death as a result of any cause | Entry onto study |
| Secondary | | | |
| Event-free survival | All | Failure of treatment or death as result of any cause | Entry onto study |
| Time to progression | All | Time to progression or death as a result of lymphoma | Entry onto study |
| Disease-free survival | In CR | Time to relapse or death as a result of lymphoma or acute toxicity of treatment | Documentation of response |
| Response duration | In CR or PR | Time to relapse or progression | Documentation of response |
| Lymphoma-specific survival | All | Time to death as a result of lymphoma | Entry onto study |
| Time to next treatment | All | Time to new treatment | End of primary treatment |

Abbreviations:
CR: complete remission;
PR: partial remission.

In one embodiment, the end point for lymphoma is evidence of clinical benefit. Clinical benefit may reflect improvement in quality of life, or reduction in patient symptoms, transfusion requirements, frequent infections, or other parameters. Time to reappearance or progression of lymphoma-related symptoms can also be used in this end point.

In certain embodiments, the treatment of lymphoma may be assessed by the International Workshop Criteria (IWC) for non-Hodgkin lymphoma (NHL) (see Cheson B D, Pfistner B, Juweid, M E, et. al. Revised Response Criteria for Malignant Lymphoma. J. Clin. Oncol: 2007: (25) 579-586), using the response and endpoint definitions shown below:

| Response | Definition | Nodal Masses | Spleen, liver | Bone Marrow |
| --- | --- | --- | --- | --- |
| CR | Disappearance of all evidence of disease | (a) FDG-avid or PET positive prior to therapy; mass of any size permitted if PET negative (b) Variably FDG-avid or PET negative; regression to normal size on CT | Not palpable, nodules disappeared | Infiltrate cleared on repeat biopsy; if indeterminate by morphology, immunohistochemistry should be negative |
| PR | Regression of measurable disease and no new sites | ≥50% decrease in SPD of up to 6 largest dominant masses; no increase in size of other nodes (a) FDG-avid or PET positive prior to therapy; one or more PET positive at previously involved site (b) Variably FDG-avid or PET negative; regression on CT | ≥50% decrease in SPD of nodules (for single nodule in greatest transverse diameter); no increase in size of liver or spleen | Irrelevant if positive prior to therapy; cell type should be specified |
| SD | Failure to attain CR/PR or PD | (a) FDG-avid or PET positive prior to therapy; PET positive at prior sites of disease and no new sites on CT or PET (b) Variably FDG-avid or PET negative; no change in size of previous lesions on CT | | |
| PD or relapsed disease | Any new lesion or increase by ≥50% of previously involved sites from nadir | Appearance of a new lesion(s) ≥1.5 cm in any axis, ≥50% increase in SPD of more than one node, or ≥50% increase in longest diameter of a previously identifed node ≥1 cm in short axis Lesions PET positive if FDG-avid lymphoma or PET positive prior to therapy | ≥50% increase from nadir in the SPD of any previous lesions | New or recurrent involvement |

Abbreviations:
CR, complete remission;
FDG, [$^{18}$F]fluorodeoxyglucose;
PET, positron emission tomography;
CT, computed tomography;
PR, partial remission;
SPD, sum of the product of the diameters;
SD, stable disease;
PD, progressive disease.

| End point | Patients | Definition | Measured from |
| --- | --- | --- | --- |
| Primary | | | |
| Overall survival | All | Death as a result of any cause | Entry onto study |
| Progression-free survival | All | Disease progression or death as a result of any cause | Entry onto study |
| Secondary | | | |
| Event-free survival | All | Failure of treatment or death as result of any cause | Entry onto study |

| End point | Patients | Definition | Measured from |
| --- | --- | --- | --- |
| Time to progression | All | Time to progression or death as a result of lymphoma | Entry onto study |
| Disease-free survival | In CR | Time to relapse or death as a result of lymphoma or acute toxicity of treatment | Documentation of response |
| Response duration | In CR or PR | Time to relapse or progression | Documentation of response |
| Lymphoma-specific survival | All | Time to death as a result of lymphoma | Entry onto study |
| Time to next treatment | All | Time to new treatment | End of primary treatment |

Abbreviations:
CR: complete remission;
PR: partial remission.

In one embodiment, the end point for lymphoma is evidence of clinical benefit. Clinical benefit may reflect improvement in quality of life, or reduction in patient symptoms, transfusion requirements, frequent infections, or other parameters. Time to reappearance or progression of lymphoma-related symptoms can also be used in this end point.

In certain embodiments, the treatment of CLL may be assessed by the International Workshop Guidelines for CLL (see Hallek M, Cheson B D, Catovsky D, et al. Guidelines for the diagnosis and treatment of chronic lymphocytic leukemia: a report from the International Workshop on Chronic Lymphocytic Leukemia updating the National Cancer Institute-Working Group 1996 guidelines. Blood, 2008; (111) 12: 5446-5456) using the response and endpoint definitions shown therein and in particular:

| Parameter | CR | PR | PD |
| --- | --- | --- | --- |
| Group A | | | |
| Lymphadenopathy[†] | None >1.5 cm | Decrease ≥50% | Increase ≥50% |
| Hepatomegaly | None | Decrease ≥50% | Increase ≥50% |
| Splenomegaly | None | Decrease ≥50% | Increase ≥50% |
| Blood lymphocytes | <4000/μL | Decrease ≥50% from baseline | Increase ≥50% over baseline |
| Marrow[‡] | Normocellular, <30% lymphocytes, no B-lymphoid nodules. Hypocellular marrow defines CRi (5.1.6). | 50% reduction in marrow infiltrate, or B-lymphoid nodules | |
| Group B | | | |
| Platelet count | >100 000/μL | >100 000/μL or increase ≥50% over baseline | Decrease of ≥50% from baseline secondary to CLL |
| Hemoglobin | >11.0 g/dL | >11 g/dL or increase ≥50% over baseline | Decrease of >2 g/dL from baseline secondary to CLL |
| Neutrophils[‡] | >1500/μL | >1500/μL or >50% improvement over baseline | |

Group A criteria define the tumor load;
Group B criteria define the function of the hematopoietic system (or marrow).
CR (complete remission): all of the criteria have to be met, and patients have to lack disease-related constitutional symptoms;
PR (partial remission): at least two of the criteria of group A plus one of the criteria of group B have to be met;
SD is absence of progressive disease (PD) and failure to achieve at least a PR;
PD: at least one of the above criteria of group A or group B has to be met.
Sum of the products of multiple lymph nodes (as evaluated by CT scans in clinical trials, or by physical examination in general practice). These parameters are irrelevant for some response categories.

In certain embodiments, the treatment of multiple myeloma may be assessed by the International Uniform Response Criteria for Multiple Myeloma (IURC) (see Durie B G M, Harousseau J-L, Miguel J S, et al. International uniform response criteria for multiple myeloma. Leukemia, 2006; (10) 10: 1-7), using the response and endpoint definitions shown below:

| Target lesions | Non-target lesions | New lesions | Overall response |
| --- | --- | --- | --- |
| PR | Non-PD | No | PR |
| SD | Non-PD | No | SD |
| PD | Any | Yes or no | PD |

| Response Subcategory | Response Criteria[a] |
| --- | --- |
| sCR | CR as defined below plus<br>Normal FLC ratio and<br>Absence of clonal cells in bone marrow[b] by immunohistochemistry or immunofluorescence[c] |
| CR | Negative immunofixation on the serum and urine and<br>Disappearance of any soft tissue plasmacytomas and<br><5% plasma cells in bone marrow[b] |
| VGPR | Serum and urine M-protein detectable by immunofixation but not on electrophoresis or 90% or greater reduction in serum M-protein plus urine M-protein level <100 mg per 24 h |
| PR | ≥50% reduction of serum M-protein and reduction in 24-h urinary M-protein by≥90% or to <200 mg per 24 h<br>If the serum and urine M-protein are unmeasurable,[d] a ≥50% decrease in the difference between involved and uninvolved FLC levels is required in place of the M-protein criteria<br>If serum and urine M-protein are unmeasurable, and serum free light assay is also unmeasurable, ≥50% reduction in plasma cells is required in place of M-protein, provided baseline bone marrow plasma cell percentage was ≥30%<br>In addition to the above listed criteria, if present at baseline, a ≥50% reduction in the size of soft tissue plasmacytomas is also required |
| SD (not recommended for use as an indicator of response; stability of disease is best described by providing the time to progression estimates) | Not meeting criteria for CR, VGPR, PR or progressive disease |

Abbreviations:
CR, complete response;
FLC, free light chain;
PR, partial response;
SD, stable disease;
sCR, stringent complete response;
VGPR, very good partial response;

[a]All response categories require two consecutive assessments made at anytime before the institution of any new therapy; all categories also require no known evidence of progressive or new bone lesions if radiographic studies were performed. Radiographic studies are not required to satisfy these response requirements;
[b]Confirmation with repeat bone marrow biopsy not needed;
[c]Presence/absence of clonal cells is based upon the κ/λ ratio. An abnormal κ/λ ratio by immunohistochemistry and/or immunofluorescence requires a minimum of 100 plasma cells for analysis. An abnormal ratio reflecting presence of an abnormal clone is κ/λ of >4:1 or <1:2.
[d]Measurable disease defined by at least one of the following measurements: Bone marrow plasma cells ≥30%; Serum M-protein ≥1 g/dl (≥10 gm/l)[10 g/l]; Urine M-protein ≥200 mg/24 h; Serum FLC assay: Involved FLC level ≥10 mg/dl (≥100 mg/l); provided serum FLC ratio is abnormal.

In certain embodiments, the treatment of a cancer may be assessed by Response Evaluation Criteria in Solid Tumors (RECIST 1.1) (see Therasse P., et al. New Guidelines to Evaluate the Response to Treatment in Solid Tumors. J. of the National Cancer Institute; 2000; (92) 205-216 and Eisenhauer E. A., Therasse P., Bogaerts J., et al. New response evaluation criteria in solid tumours: Revised RECIST guideline (version 1.1). European J. Cancer; 2009; (45) 228-247). Overall responses for all possible combinations of tumor responses in target and non-target lesions with our without the appearance of new lesions are as follows:

| Target lesions | Non-target lesions | New lesions | Overall response |
| --- | --- | --- | --- |
| CR | CR | No | CR |
| CR | Incomplete response/SD | No | PR |
| PR | Non-PD | No | PR |
| SD | Non-PD | No | SD |
| PD | Any | Yes or no | PD |
| Any | PD | Yes or no | PD |
| Any | Any | Yes | PD |

CR = complete response;
PR = partial response;
SD = stable disease; and
PD = progressive disease.

With respect to the evaluation of target lesions, complete response (CR) is the disappearance of all target lesions, partial response (PR) is at least a 30% decrease in the sum of the longest diameter of target lesions, taking as reference the baseline sum longest diameter, progressive disease (PD) is at least a 20% increase in the sum of the longest diameter of target lesions, taking as reference the smallest sum longest diameter recorded since the treatment started or the appearance of one or more new lesions and stable disease (SD) is neither sufficient shrinkage to qualify for partial response nor sufficient increase to qualify for progressive disease, taking as reference the smallest sum longest diameter since the treatment started.

With respect to the evaluation of non-target lesions, complete response (CR) is the disappearance of all non-target lesions and normalization of tumor marker level; incomplete response/stable disease (SD) is the persistence of one or more non-target lesion(s) and/or the maintenance of tumor marker level above the normal limits, and progressive disease (PD) is the appearance of one or more new lesions and/or unequivocal progression of existing non-target lesions.

The procedures, conventions, and definitions described below provide guidance for implementing the recommendations from the Response Assessment for Neuro-Oncology (RANO) Working Group regarding response criteria for high-grade gliomas (Wen P., Macdonald, D R., Reardon, D A., et al. Updated response assessment criteria for high-grade gliomas: Response assessment in neuro-oncology working group. J Clin Oncol 2010; 28: 1963-1972). Primary modifications to the RANO criteria for Criteria for Time Point Responses (TPR) can include the addition of operational conventions for defining changes in glucocorticoid dose, and the removal of subjects' clinical deterioration component to focus on objective radiologic assessments. The baseline MM scan is defined as the assessment performed at the end of the post-surgery rest period, prior to initiating or re-initiating compound treatment. The baseline MRI is used as the reference for assessing complete response (CR) and partial response (PR). Whereas, the smallest SPD (sum of the products of perpendicular diameters) obtained either at baseline or at subsequent assessments will be designated the nadir assessment and utilized as the reference for determining progression. For the 5 days preceding any protocol-defined MRI scan, subjects receive either no glucocorticoids or are on a stable dose of glucocorticoids. A stable dose is defined as the same daily dose for the 5 consecutive days preceding the MRI scan. If the prescribed glucocorticoid dose is changed in the 5 days before the baseline scan, a new baseline scan is required with glucocorticoid use meeting the criteria described above. The following definitions will be used.

Measurable Lesions: Measurable lesions are contrast-enhancing lesions that can be measured bi-dimensionally. A measurement is made of the maximal enhancing tumor diameter (also known as the longest diameter, LD). The greatest perpendicular diameter is measured on the same image. The cross hairs of bi-dimensional measurements should cross and the product of these diameters will be calculated.

Minimal Diameter: T1-weighted image in which the sections are 5 mm with 1 mm skip. The minimal LD of a measurable lesion is set as 5 mm by 5 mm. Larger diameters may be required for inclusion and/or designation as target lesions. After baseline, target lesions that become smaller than the minimum requirement for measurement or become no longer amenable to bi-dimensional measurement will be recorded at the default value of 5 mm for each diameter below 5 mm. Lesions that disappear will be recorded as 0 mm by 0 mm.

Multicentric Lesions: Lesions that are considered multicentric (as opposed to continuous) are lesions where there is normal intervening brain tissue between the two (or more) lesions. For multicentric lesions that are discrete foci of enhancement, the approach is to separately measure each enhancing lesion that meets the inclusion criteria. If there is no normal brain tissue between two (or more) lesions, they will be considered the same lesion.

Nonmeasurable Lesions: All lesions that do not meet the criteria for measurable disease as defined above will be considered non-measurable lesions, as well as all nonenhancing and other truly nonmeasurable lesions. Nonmeasurable lesions include foci of enhancement that are less than the specified smallest diameter (i.e., less than 5 mm by 5 mm), nonenhancing lesions (e.g., as seen on T1-weighted post-contrast, T2-weighted, or fluid-attenuated inversion recovery (FLAIR) images), hemorrhagic or predominantly cystic or necrotic lesions, and leptomeningeal tumor. Hemorrhagic lesions often have intrinsic T1-weighted hyperintensity that could be misinterpreted as enhancing tumor, and for this reason, the pre-contrast T1-weighted image may be examined to exclude baseline or interval sub-acute hemorrhage.

At baseline, lesions will be classified as follows: Target lesions: Up to 5 measurable lesions can be selected as target lesions with each measuring at least 10 mm by 5 mm, representative of the subject's disease; Non-target lesions: All other lesions, including all nonmeasurable lesions (including mass effects and T2/FLAIR findings) and any measurable lesion not selected as a target lesion. At baseline, target lesions are to be measured as described in the definition for measurable lesions and the SPD of all target lesions is to be determined. The presence of all other lesions is to be documented. At all post-treatment evaluations, the baseline classification of lesions as target and non-target lesions will be maintained and lesions will be documented and described in a consistent fashion over time (e.g., recorded in the same order on source documents and eCRFs). All measurable and nonmeasurable lesions must be assessed using the same technique as at baseline (e.g., subjects should be imaged on the same MM scanner or at least with the same magnet strength) for the duration of the study to reduce difficulties in interpreting changes. At each evaluation, target lesions will be measured and the SPD calculated. Non-target lesions will be assessed qualitatively and new lesions, if any, will be documented separately. At each evaluation, a time point response will be determined for target lesions, non-target lesions, and new lesion. Tumor progression can be established even if only a subset of lesions is assessed. However, unless progression is observed, objective status (stable disease, PR or CR) can only be determined when all lesions are assessed.

Confirmation assessments for overall time point responses of CR and PR will be performed at the next scheduled assessment, but confirmation may not occur if scans have an interval of <28 days. Best response, incorporating confirmation requirements, will be derived from the series of time points.

Aminopurine Compounds

Provided herein are compounds having the following formula (I):

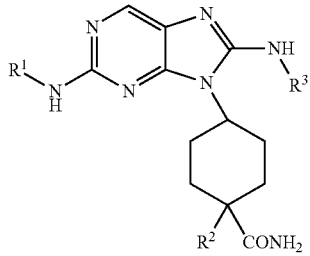

(I)

and pharmaceutically acceptable salts, tautomers, stereoisomers, enantiomers, and isotopologues thereof, wherein:

$R^1$ is substituted or unsubstituted $C_{1-8}$ alkyl, substituted or unsubstituted cycloalkyl, substituted or unsubstituted cycloalkylalkyl, or substituted or unsubstituted non-aromatic heterocyclyl;

$R^2$ is H or substituted or unsubstituted $C_{1-3}$ alkyl; and $R^3$ is phenyl, substituted with one or more halogen, optionally further substituted with one or more substituents independently selected from substituted or unsubstituted $C_{1-3}$ alkyl, CN, and —OR', wherein each R' is independently substituted or unsubstituted $C_{1-3}$ alkyl.

In some embodiments, the compound is not 4-[2-[(1-methylethyl)amino]-8-[(2,4,6-trifluorophenyl)amino]-9H-purin-9-yl]-cis-cyclohexanecarboxamide

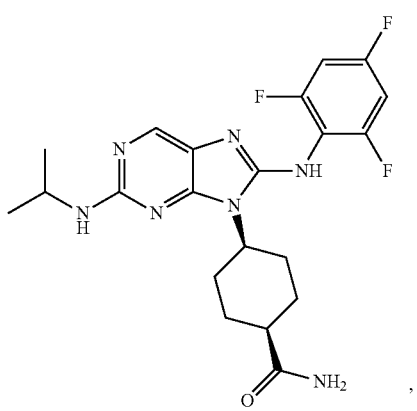

or 4-[8-[(2,4-difluorophenyl)amino]-2-[(trans-4-hydroxycyclohexyl)amino]-9H-purin-9-yl]-cis-cyclohexanecarboxamide

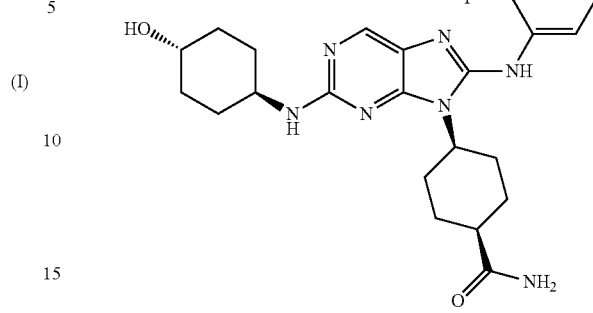

In one embodiment, the compound is a compound of formula (II):

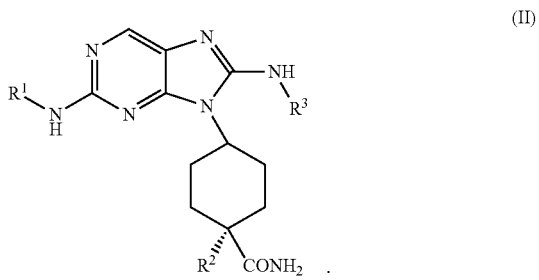

(II)

In some embodiments or compounds of formula (I), $R^1$ is substituted or unsubstituted $C_{1-8}$ alkyl. In some embodiments, $R^1$ is substituted or unsubstituted methyl, ethyl, n-propyl, isopropyl, n-butyl, sec-butyl, isobutyl, tert-butyl, n-pentyl, 2-methylpentyl, 3-methylpentyl, isopentyl, or neopentyl. In some embodiments, $R^1$ is substituted with one or more substituents independently selected from halogen and OR, wherein each R is independently H or substituted or unsubstituted $C_{1-3}$ alkyl. For example, $R^1$ is substituted with one or more substituents independently selected from F, OH, and $OCH_3$. In some embodiments, $R^1$ is ethyl, isopropyl, isobutyl, tert-butyl, $CH_2CH_2F$, $CH_2CHF_2$, $CH_2CF_3$, $CH_2CH(CH_3)OH$, $CH_2CH(CH_3)OCH_3$, $CH(CH_3)CH_2OH$, $CH(CH_3)CH_2OCH_3$, $CH_2C(F_2)CH_2OH$, $CH_2C(F_2)CH_2OCH_3$, $CH(CF_3)CH_2OH$, $CH(CF_3)CH_2OCH_3$, $CH(CH_2OH)CH_2CH_3$, $CH(CH_2OCH_3)CH_2CH_3$, $CH_2C(CH_3)_2CH_2OH$, or $CH_2C(CH_3)_2CH_2OCH_3$. For example, $R^1$ is isopropyl, isobutyl, tert-butyl, $CH_2CF_3$, $CH_2CH(CH_3)OH$, $CH(CH_3)CH_2OH$, $CH(CH_3)CH_2OCH_3$, $CH_2C(F_2)CH_2OH$, $CH(CF_3)CH_2OH$, $CH(CH_2OH)CH_2CH_3$, or $CH_2C(CH_3)_2CH_2OH$.

In one embodiment, $R^1$ is isopropyl, $CH(CH_3)CH_2OH$, or $CH(CH_2OH)CH_2CH_3$. In some embodiments, $R^1$ is (S)-2-propan-1-ol:

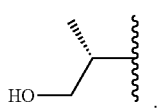

In some embodiments, $R^1$ is substituted or unsubstituted cycloalkyl. In some embodiments, $R^1$ is substituted or unsubstituted cyclopropyl, cyclobutyl, cyclopentyl, cyclohexyl, or cycloheptyl. In some embodiments, $R^1$ is substituted with one or more substituents independently selected from halogen, OR, $SO_2R'$, substituted or unsubstituted $C_{1-3}$ alkyl, and substituted or unsubstituted heterocyclyl, wherein each R is independently H or substituted or unsubstituted $C_{1-3}$ alkyl, and each R' is independently substituted or unsubstituted $C_{1-3}$ alkyl. In some embodiments, $R^1$ is substituted with one or more substituents independently selected from F, OH, $OCH_3$, $SO_2CH_3$, methyl, and substituted or unsubstituted 5-membered heterocyclyl, for example, pyrrolidinedionyl, or oxadiazolyl. In some other embodiments, $R^1$ is cyclobutyl, cyclopentyl, cyclohexyl, or cycloheptyl, optionally substituted with one or more substituents independently selected from F, OH, $OCH_3$, $SO_2CH_3$, methyl, pyrrolidinedionyl, and oxadiazolyl. In some embodiments, $R^1$ is

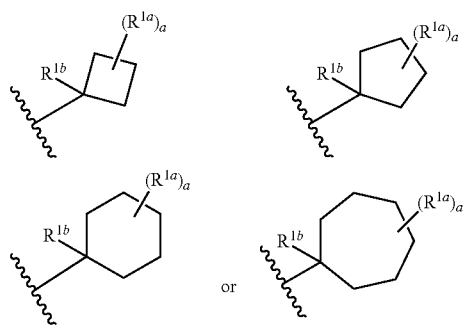

wherein
each $R^{1a}$ is independently F, OH, $OCH_3$, $SO_2CH_3$, or methyl;
$R^{1b}$ is H or $CH_3$;
and a is 0-4.

In some embodiments, $R^1$ is substituted or unsubstituted cycloalkylalkyl. In some embodiments, $R^1$ is substituted or unsubstituted ($C_{1-3}$ alkyl)-($C_{1-8}$ cycloalkyl), for example, $R^1$ is substituted or unsubstituted $CH_2$-cyclopropyl, $CH_2$-cyclobutyl, $CH_2$-cyclopentyl, $CH_2$-cyclohexyl, or $CH_2$-cycloheptyl. In some embodiments, $R^1$ is substituted with one or more substituents independently selected from ($C_{1-3}$ alkyl) OR or OR, wherein each R is independently H or substituted or unsubstituted $C_{1-3}$ alkyl. For example, $R^1$ is $CH_2$-cyclopropyl, $CH_2$-cyclobutyl, $CH_2$-cyclopentyl, or $CH_2$-cyclohexyl, optionally substituted with one or more $CH_2OH$ or OH.

In some embodiments, $R^1$ is substituted or unsubstituted non-aromatic heterocyclyl. In some embodiments, $R^1$ is substituted or unsubstituted oxetanyl, tetrahydrofuranyl, tetrahydropyranyl, tetrahydro-thiopyrandioxide, piperidyl, oxepanyl, or oxaspiroheptyl. In some embodiments, $R^1$ is substituted with one or more substituents independently selected from halogen, OR, $SO_2R^\#$, $C(=O)R^5$, $C(=O)OR^6$, $C(=O)NRR^7$, substituted or unsubstituted $C_{1-3}$ alkyl, substituted or unsubstituted aryl, substituted or unsubstituted heteroaryl, substituted or unsubstituted or alkylaryl, wherein each R is independently H or substituted or unsubstituted $C_{1-3}$ alkyl; $R^4$ is substituted or unsubstituted $C_{1-3}$ alkyl, or substituted or unsubstituted aryl; $R^5$ is substituted or unsubstituted $C_{1-3}$ alkyl; $R^6$ is substituted or unsubstituted $C_{1-6}$ alkyl; and $R^7$ is substituted or unsubstituted $C_{1-3}$ alkyl, or substituted or unsubstituted aryl. For example, $R^1$ is oxetanyl, tetrahydrofuranyl, tetrahydropyranyl, tetrahydro-thiopyrandioxide, piperidyl, oxepanyl, or oxaspiroheptyl, optionally substituted with one or more substituents independently selected from F, OH, $SO_2CH_3$, $SO_2$-tosyl, $C(=O)CH_3$, $C(=O)OCH_3$, $C(=O)O$-tert-butyl, $C(=O)O$-isopropyl, $C(=O)NHCH_3$, $C(=O)NH$-phenyl, methyl, ethyl, isopropyl, $CH_2OH$, phenyl, pyridyl, or benzyl. In one embodiment, $R^1$ is

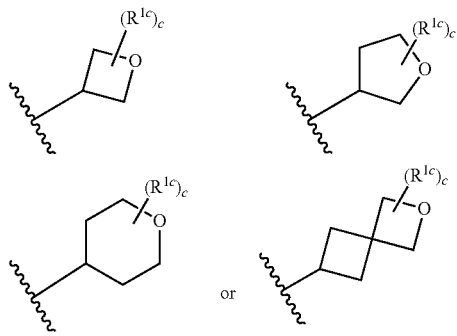

wherein each $R^{1c}$ is independently F, OH, methyl, or $CH_2OH$;
and c is 0-3.

In some such embodiments, $R^{1c}$ is F or methyl and c is 1 or 2.

In some embodiments of compounds of formula (I), $R^2$ is H. In others, $R^2$ is $CH_3$.

In some embodiments of compounds of formula (I), $R^3$ is ortho-halogen substituted phenyl. In one embodiment $R^3$ is o-fluoro or o-chloro substituted phenyl. In some embodiments, the phenyl is additionally para substituted, for example, the phenyl is additionally substituted with p-chloro, p-bromo, p-fluoro, p-CN, p-methyl, p-$CF_3$, or p-$OCH_3$. In other embodiments, $R^3$ is para-halogen substituted phenyl. In some embodiments, $R^3$ is p-fluoro or p-chloro substituted phenyl. In some embodiments, the phenyl is additionally ortho substituted, for example, the phenyl is additionally substituted with o-chloro, o-fluoro, or o-methyl. In other embodiments, $R^3$ is para-CN substituted phenyl. In some embodiments, the phenyl is additionally ortho substituted, for example, the phenyl is additionally substituted with o-chloro, or o-fluoro. In yet other embodiments, $R^3$ is ortho, ortho-dihalogen substituted phenyl. In one embodiment $R^3$ is o,o-difluoro or o,o-dichloro substituted phenyl. In some embodiments, the phenyl is additionally para substituted, for example, the phenyl is additionally substituted with p-chloro, p-bromo, p-fluoro, p-CN, p-methyl, p-$CF_3$, or p-$OCH_3$. In yet other embodiments, $R^3$ is ortho, para-dihalogen substituted phenyl. In one embodiment $R^3$ is o,p-difluoro substituted phenyl or o,p-dichloro substituted phenyl. In some embodiments, the phenyl is additionally ortho substituted, for example, the phenyl is additionally substituted with o-chloro, o-fluoro, or o-methyl. In still other embodiments, $R^3$ is 2,4,6-trihalogen substituted phenyl. In one embodiment $R^3$ is 2,4,6-trifluoro substituted phenyl, 4-chloro-2,6-difluoro substituted phenyl, or 2,4,6-trichloro substituted phenyl. In yet another embodiment, $R^3$ is ortho-halogen, para-CN substituted phenyl. In one embodiment $R^3$ is o-fluoro-p-CN substituted phenyl, or o-chloro-para-CN substituted phenyl. In some embodiments, the phenyl is additionally ortho substituted, for example, the phenyl is additionally substituted with o-chloro, or o-fluoro.

Further embodiments provided herein include combinations of one or more of the particular embodiments set forth above.

TABLE 1

Representative compounds of formula (I).

| Compound | Compound Name |
|---|---|
| 1 | (1s,4s)-4-(2-((3S,4R)-3-fluorotetrahydro-2H-pyran-4-ylamino)-8-(2,4,6-trichlorophenylamino)-9H-purin-9-yl)-1-methylcyclohexanecarboxamide |
| 2 | (1s,4s)-4-(8-(3-chlorophenylamino)-2-(isopropylamino)-9H-purin-9-yl)cyclohexanecarboxamide; |
| 3 | (1s,4s)-4-(8-(3-chlorophenylamino)-2-(cyclopentylamino)-9H-purin-9-yl)cyclohexanecarboxamide; |
| 4 | (1s,4s)-4-(2-(cyclopentylamino)-8-(2,4-difluorophenylamino)-9H-purin-9-yl)cyclohexanecarboxamide; |
| 5 | (1s,4s)-4-(8-(3-chlorophenylamino)-2-(4-methyltetrahydro-2H-pyran-4-ylamino)-9H-purin-9-yl)cyclohexanecarboxamide; |
| 6 | (1s,4s)-4-(8-(2,4-difluorophenylamino)-2-(3-methyltetrahydro-2H-pyran-4-ylamino)-9H-purin-9-yl)cyclohexanecarboxamide; |
| 7 | (1s,4s)-4-(8-(2,4-difluorophenylamino)-2-(1-methylcyclobutylamino)-9H-purin-9-yl)cyclohexanecarboxamide; |
| 8 | (1s,4s)-4-(2-(tert-butylamino)-8-(2,4,6-trifluorophenylamino)-9H-purin-9-yl)cyclohexanecarboxamide; |
| 9 | (1s,4s)-4-(8-(2,4-difluorophenylamino)-2-((3R,4R)-3-methyltetrahydro-2H-pyran-4-ylamino)-9H-purin-9-yl)cyclohexanecarboxamide; |
| 10 | (1s,4s)-4-(2-(4-methyltetrahydro-2H-pyran-4-ylamino)-8-(2,4,6-trifluorophenylamino)-9H-purin-9-yl)cyclohexanecarboxamide; |
| 11 | (1s,4s)-4-(8-(3-chloro-2-fluorophenylamino)-2-(4-methyltetrahydro-2H-pyran-4-ylamino)-9H-purin-9-yl)cyclohexanecarboxamide; |
| 12 | (1s,4s)-4-(2-(tetrahydro-2H-pyran-4-ylamino)-8-(2,4,6-trifluorophenylamino)-9H-purin-9-yl)cyclohexanecarboxamide; |
| 13 | (1s,4s)-4-(8-(2,6-difluorophenylamino)-2-(tetrahydro-2H-pyran-4-ylamino)-9H-purin-9-yl)cyclohexanecarboxamide; |
| 14 | (1s,4s)-4-(8-(2-fluorophenylamino)-2-(tetrahydro-2H-pyran-4-ylamino)-9H-purin-9-yl)cyclohexanecarboxamide; |
| 15 | (1s,4s)-4-(2-((3R,4R)-3-methyltetrahydro-2H-pyran-4-ylamino)-8-(2,4,6-trifluorophenylamino)-9H-purin-9-yl)cyclohexanecarboxamide; |
| 16 | (1s,4s)-4-(8-(2,6-difluorophenylamino)-2-((3R,4R)-3-methyltetrahydro-2H-pyran-4-ylamino)-9H-purin-9-yl)cyclohexanecarboxamide; |
| 17 | (1s,4s)-4-(8-(2-chloro-6-methylphenylamino)-2-(tetrahydro-2H-pyran-4-ylamino)-9H-purin-9-yl)cyclohexanecarboxamide; |
| 18 | (1s,4s)-4-(8-(2,6-dichlorophenylamino)-2-(tetrahydro-2H-pyran-4-ylamino)-9H-purin-9-yl)cyclohexanecarboxamide; |
| 19 | (1s,4s)-4-(8-(3-chlorophenylamino)-2-(tetrahydro-2H-pyran-4-ylamino)-9H-purin-9-yl)cyclohexanecarboxamide; |
| 20 | (1s,4s)-4-(8-(2,4-difluorophenylamino)-2-(tetrahydro-2H-pyran-4-ylamino)-9H-purin-9-yl)cyclohexanecarboxamide; |
| 21 | (1s,4s)-4-(8-(3,4-dichlorophenylamino)-2-(tetrahydro-2H-pyran-4-ylamino)-9H-purin-9-yl)cyclohexanecarboxamide; |
| 22 | (1s,4s)-4-(8-(5-chloro-2-fluorophenylamino)-2-(tetrahydro-2H-pyran-4-ylamino)-9H-purin-9-yl)cyclohexanecarboxamide; |
| 23 | (1s,4s)-4-(8-(3-chloro-2-fluorophenylamino)-2-(tetrahydro-2H-pyran-4-ylamino)-9H-purin-9-yl)cyclohexanecarboxamide; |
| 24 | (1s,4s)-4-(8-(2,5-difluorophenylamino)-2-(tetrahydro-2H-pyran-4-ylamino)-9H-purin-9-yl)cyclohexanecarboxamide; |
| 25 | (1s,4s)-4-(8-(3-chloro-2-methylphenylamino)-2-(tetrahydro-2H-pyran-4-ylamino)-9H-purin-9-yl)cyclohexanecarboxamide; |
| 26 | (1s,4s)-4-(2-(tetrahydro-2H-pyran-4-ylamino)-8-(2,4,6-trichlorophenylamino)-9H-purin-9-yl)cyclohexanecarboxamide; |
| 27 | (1s,4s)-4-(8-(2,3-difluorophenylamino)-2-(tetrahydro-2H-pyran-4-ylamino)-9H-purin-9-yl)cyclohexanecarboxamide; |
| 28 | (1s,4s)-4-(8-(2,4-dichlorophenylamino)-2-(tetrahydro-2H-pyran-4-ylamino)-9H-purin-9-yl)cyclohexanecarboxamide; |
| 29 | (1s,4s)-4-(8-(2-chloro-5-fluorophenylamino)-2-(tetrahydro-2H-pyran-4-ylamino)-9H-purin-9-yl)cyclohexanecarboxamide; |
| 30 | (1s,4s)-4-(8-(2-chloro-4-fluorophenylamino)-2-(tetrahydro-2H-pyran-4-ylamino)-9H-purin-9-yl)cyclohexanecarboxamide; |
| 31 | (1s,4s)-4-(8-(2-chloro-4-methylphenylamino)-2-(tetrahydro-2H-pyran-4-ylamino)-9H-purin-9-yl)cyclohexanecarboxamide; |
| 32 | (1s,4s)-4-(8-(3-fluoro-2-methylphenylamino)-2-(tetrahydro-2H-pyran-4-ylamino)-9H-purin-9-yl)cyclohexanecarboxamide; |
| 33 | (1s,4s)-4-(8-(4-bromo-2-fluorophenylamino)-2-(tetrahydro-2H-pyran-4-ylamino)-9H-purin-9-yl)cyclohexanecarboxamide; |
| 34 | (1s,4s)-4-(8-(2-fluoro-4-methylphenylamino)-2-(tetrahydro-2H-pyran-4-ylamino)-9H-purin-9-yl)cyclohexanecarboxamide; |
| 35 | (1s,4s)-4-(8-(2-chloro-4-(trifluoromethyl)phenylamino)-2-(tetrahydro-2H-pyran-4-ylamino)-9H-purin-9-yl)cyclohexanecarboxamide; |
| 36 | (1s,4s)-4-(8-(2,6-difluorophenylamino)-2-(tetrahydro-2H-pyran-4-ylamino)-9H-purin-9-yl)-1-methylcyclohexanecarboxamide; |
| 37 | (1s,4s)-4-(8-(2-chloro-6-fluorophenylamino)-2-(tetrahydro-2H-pyran-4-ylamino)-9H-purin-9-yl)cyclohexanecarboxamide; |
| 38 | (1s,4s)-4-(8-(4-fluoro-2-methylphenylamino)-2-(tetrahydro-2H-pyran-4-ylamino)-9H-purin-9-yl)cyclohexanecarboxamide; |

TABLE 1-continued

Representative compounds of formula (I).

| Compound | Compound Name |
|---|---|
| 39 | (1s,4s)-4-(2-(tetrahydro-2H-pyran-4-ylamino)-8-(2,3,6-trifluorophenylamino)-9H-purin-9-yl)cyclohexanecarboxamide; |
| 40 | (1s,4s)-1-methyl-4-(2-(tetrahydro-2H-pyran-4-ylamino)-8-(2,4,6-trifluorophenylamino)-9H-purin-9-yl)cyclohexanecarboxamide; |
| 41 | (1s,4s)-4-(8-(2,4-dichloro-6-fluorophenylamino)-2-(tetrahydro-2H-pyran-4-ylamino)-9H-purin-9-yl)cyclohexanecarboxamide; |
| 42 | (1s,4s)-4-(2-(cyclobutylamino)-8-(2,4,6-trifluorophenylamino)-9H-purin-9-yl)cyclohexanecarboxamide; |
| 43 | (1s,4s)-4-(2-(cyclobutylamino)-8-(2,6-difluorophenylamino)-9H-purin-9-yl)cyclohexanecarboxamide; |
| 44 | (1s,4s)-4-(8-(2-chloro-6-fluorophenylamino)-2-(cyclobutylamino)-9H-purin-9-yl)cyclohexanecarboxamide; |
| 45 | (1s,4s)-4-(2-(cyclopentylamino)-8-(2,4,6-trifluorophenylamino)-9H-purin-9-yl)cyclohexanecarboxamide; |
| 46 | (1s,4s)-4-(2-(cyclopentylamino)-8-(2,6-difluorophenylamino)-9H-purin-9-yl)cyclohexanecarboxamide; |
| 47 | (1s,4s)-4-(8-(2-chloro-6-fluorophenylamino)-2-(cyclopentylamino)-9H-purin-9-yl)cyclohexanecarboxamide; |
| 48 | (1s,4s)-4-(8-(2,6-difluorophenylamino)-2-(isopropylamino)-9H-purin-9-yl)cyclohexanecarboxamide; |
| 49 | (1s,4s)-4-(8-(2-chloro-6-fluorophenylamino)-2-(isopropylamino)-9H-purin-9-yl)cyclohexanecarboxamide; |
| 50 | (1s,4s)-4-(8-(4-chloro-2,6-difluorophenylamino)-2-(tetrahydro-2H-pyran-4-ylamino)-9H-purin-9-yl)cyclohexanecarboxamide; |
| 51 | (1s,4s)-4-(8-(2,6-dichloro-4-fluorophenylamino)-2-(tetrahydro-2H-pyran-4-ylamino)-9H-purin-9-yl)cyclohexanecarboxamide; |
| 52 | (1s,4s)-4-(2-(cyclobutylamino)-8-(2,6-dichlorophenylamino)-9H-purin-9-yl)cyclohexanecarboxamide; |
| 53 | (1s,4s)-4-(8-(2,6-dichlorophenylamino)-2-(isopropylamino)-9H-purin-9-yl)cyclohexanecarboxamide; |
| 54 | (1s,4s)-4-(8-(2-chloro-4,6-difluorophenylamino)-2-(tetrahydro-2H-pyran-4-ylamino)-9H-purin-9-yl)cyclohexanecarboxamide; |
| 55 | (1s,4s)-4-(2-(cyclopentylamino)-8-(2,6-dichlorophenylamino)-9H-purin-9-yl)cyclohexanecarboxamide; |
| 56 | (1s,4s)-4-(2-(oxetan-3-ylamino)-8-(2,4,6-trifluorophenylamino)-9H-purin-9-yl)cyclohexanecarboxamide; |
| 57 | (1s,4s)-4-(8-(2,6-dichlorophenylamino)-2-(oxetan-3-ylamino)-9H-purin-9-yl)cyclohexanecarboxamide; |
| 58 | (1s,4s)-4-(8-(2-chloro-6-fluorophenylamino)-2-(oxetan-3-ylamino)-9H-purin-9-yl)cyclohexanecarboxamide; |
| 59 | (1s,4s)-4-(2-(tetrahydro-2H-pyran-4-ylamino)-8-(2,4,5-trifluorophenylamino)-9H-purin-9-yl)cyclohexanecarboxamide; |
| 60 | (1s,4s)-4-(2-(isopropylamino)-8-(2,4,6-trichlorophenylamino)-9H-purin-9-yl)cyclohexanecarboxamide; |
| 61 | (1s,4s)-4-(8-(4-chloro-2-fluorophenylamino)-2-(tetrahydro-2H-pyran-4-ylamino)-9H-purin-9-yl)cyclohexanecarboxamide; |
| 62 | (1s,4s)-4-(8-(2-chloro-3-fluorophenylamino)-2-(tetrahydro-2H-pyran-4-ylamino)-9H-purin-9-yl)cyclohexanecarboxamide; |
| 63 | (1s,4s)-4-(8-(2,3-dichlorophenylamino)-2-(tetrahydro-2H-pyran-4-ylamino)-9H-purin-9-yl)cyclohexanecarboxamide; |
| 64 | (1s,4s)-4-(8-(2-fluoro-6-methylphenylamino)-2-(tetrahydro-2H-pyran-4-ylamino)-9H-purin-9-yl)cyclohexanecarboxamide; |
| 65 | (1s,4s)-4-(8-(5-chloro-2,4-difluorophenylamino)-2-(tetrahydro-2H-pyran-4-ylamino)-9H-purin-9-yl)cyclohexanecarboxamide; |
| 66 | (1s,4s)-4-(2-(tetrahydro-2H-pyran-4-ylamino)-8-(2,4,5-trichlorophenylamino)-9H-purin-9-yl)cyclohexanecarboxamide; |
| 67 | (1s,4s)-4-(2-(tetrahydro-2H-pyran-4-ylamino)-8-(2,3,4-trifluorophenylamino)-9H-purin-9-yl)cyclohexanecarboxamide; |
| 68 | (1s,4s)-4-(8-(3-chloro-2,6-difluorophenylamino)-2-(tetrahydro-2H-pyran-4-ylamino)-9H-purin-9-yl)cyclohexanecarboxamide; |
| 69 | (1s,4s)-4-(2-(cyclopentylamino)-8-(2,4,6-trichlorophenylamino)-9H-purin-9-yl)cyclohexanecarboxamide; |
| 70 | (1s,4s)-4-(8-(2-chloro-3-methylphenylamino)-2-(tetrahydro-2H-pyran-4-ylamino)-9H-purin-9-yl)cyclohexanecarboxamide; |
| 71 | (1s,4s)-4-(8-(4-chloro-2,5-difluorophenylamino)-2-(tetrahydro-2H-pyran-4-ylamino)-9H-purin-9-yl)cyclohexanecarboxamide; |
| 72 | (1s,4s)-4-(8-(4-chloro-2-fluoro-5-methylphenylamino)-2-(tetrahydro-2H-pyran-4-ylamino)-9H-purin-9-yl)cyclohexanecarboxamide; |
| 73 | (1s,4s)-4-(8-(4-chloro-2,3-difluorophenylamino)-2-(tetrahydro-2H-pyran-4-ylamino)-9H-purin-9-yl)cyclohexanecarboxamide; |
| 74 | (1s,4s)-4-(2-(tetrahydro-2H-pyran-4-ylamino)-8-(2,3,4-trichlorophenylamino)-9H-purin-9-yl)cyclohexanecarboxamide; |
| 75 | (1s,4s)-4-(8-(2-chloro-4-fluoro-6-methylphenylamino)-2-(tetrahydro-2H-pyran-4-ylamino)-9H-purin-9-yl)cyclohexanecarboxamide; |
| 76 | (1s,4s)-4-(8-(4-chloro-2-fluoro-6-methylphenylamino)-2-(tetrahydro-2H-pyran-4-ylamino)-9H-purin-9-yl)cyclohexanecarboxamide; |

TABLE 1-continued

Representative compounds of formula (I).

| Compound | Compound Name |
|---|---|
| 77 | (1s,4s)-4-(2-((R)-tetrahydrofuran-3-ylamino)-8-(2,4,6-trichlorophenylamino)-9H-purin-9-yl)cyclohexanecarboxamide; |
| 78 | (1s,4s)-4-(2-((1r,4r)-4-methoxycyclohexylamino)-8-(2,4,6-trichlorophenylamino)-9H-purin-9-yl)cyclohexanecarboxamide; |
| 79 | (1s,4s)-4-(2-((1r,4r)-4-hydroxycyclohexylamino)-8-(2,4,6-trichlorophenylamino)-9H-purin-9-yl)cyclohexanecarboxamide; |
| 80 | (1s,4s)-4-(8-(3-chloro-6-fluoro-2-methylphenylamino)-2-(tetrahydro-2H-pyran-4-ylamino)-9H-purin-9-yl)cyclohexanecarboxamide; |
| 81 | (1s,4s)-4-(8-(2,5-dichloro-4-methylphenylamino)-2-(tetrahydro-2H-pyran-4-ylamino)-9H-purin-9-yl)cyclohexanecarboxamide; |
| 82 | (1s,4s)-4-(8-(2,3-dichloro-4-fluorophenylamino)-2-(tetrahydro-2H-pyran-4-ylamino)-9H-purin-9-yl)cyclohexanecarboxamide; |
| 83 | (1s,4s)-4-(8-(2,4-dichloro-3-fluorophenylamino)-2-(tetrahydro-2H-pyran-4-ylamino)-9H-purin-9-yl)cyclohexanecarboxamide; |
| 84 | (1s,4s)-4-(8-(2,3-difluoro-4-methylphenylamino)-2-(tetrahydro-2H-pyran-4-ylamino)-9H-purin-9-yl)cyclohexanecarboxamide; |
| 85 | (1s,4s)-4-(8-(2-chloro-3-fluoro-4-methylphenylamino)-2-(tetrahydro-2H-pyran-4-ylamino)-9H-purin-9-yl)cyclohexanecarboxamide; |
| 86 | (1s,4s)-4-(8-(2,3-dichloro-4-methylphenylamino)-2-(tetrahydro-2H-pyran-4-ylamino)-9H-purin-9-yl)cyclohexanecarboxamide; |
| 87 | (1s,4s)-4-(8-(2,4-difluoro-6-methylphenylamino)-2-(tetrahydro-2H-pyran-4-ylamino)-9H-purin-9-yl)cyclohexanecarboxamide; |
| 88 | (1r,4s)-4-(2-((S)-tetrahydrofuran-3-ylamino)-8-(2,4,6-trichlorophenylamino)-9H-purin-9-yl)cyclohexanecarboxamide; |
| 89 | (1s,4s)-4-(2-(4,4-difluorocyclohexylamino)-8-(2,4,6-trichlorophenylamino)-9H-purin-9-yl)cyclohexanecarboxamide; |
| 90 | (1s,4s)-4-(8-(4-chloro-3-fluoro-2-methylphenylamino)-2-(tetrahydro-2H-pyran-4-ylamino)-9H-purin-9-yl)cyclohexanecarboxamide; |
| 91 | (1s,4s)-4-(8-(2-chloro-3,6-difluorophenylamino)-2-(tetrahydro-2H-pyran-4-ylamino)-9H-purin-9-yl)cyclohexanecarboxamide; |
| 92 | (1s,4s)-4-(8-(2-chloro-6-fluoro-3-methylphenylamino)-2-(tetrahydro-2H-pyran-4-ylamino)-9H-purin-9-yl)cyclohexanecarboxamide; |
| 93 | (1s,4s)-4-(2-(((1,1-dioxidotetrahydro-2H-thiopyran-4-yl)amino)-8-((2,4,6-trichlorophenyl)amino)-9H-purin-9-yl)cyclohexane-1-carboxamide; |
| 94 | (1s,4s)-4-(8-(2-chlorophenylamino)-2-(cyclopentylamino)-9H-purin-9-yl)cyclohexanecarboxamide; |
| 95 | (1s,4s)-4-(2-(cyclopentylamino)-8-(2,4-dichlorophenylamino)-9H-purin-9-yl)cyclohexanecarboxamide; |
| 96 | (1s,4s)-4-(8-(4-chloro-2-fluorophenylamino)-2-(cyclopentylamino)-9H-purin-9-yl)cyclohexanecarboxamide; |
| 97 | (1s,4s)-4-(8-(2,4-dichlorophenylamino)-2-(isopropylamino)-9H-purin-9-yl)cyclohexanecarboxamide; |
| 98 | (1s,4s)-4-(8-(2-chloro-4-fluorophenylamino)-2-(isopropylamino)-9H-purin-9-yl)cyclohexanecarboxamide; |
| 99 | (1s,4s)-4-(2-(isopropylamino)-8-(2,3,6-trifluorophenylamino)-9H-purin-9-yl)cyclohexanecarboxamide; |
| 100 | (1s,4s)-4-(8-(2,4-dichloro-6-fluorophenylamino)-2-(isopropylamino)-9H-purin-9-yl)cyclohexanecarboxamide; |
| 101 | (1s,4s)-4-(8-(2-chloro-4,5-difluorophenylamino)-2-(tetrahydro-2H-pyran-4-ylamino)-9H-purin-9-yl)cyclohexanecarboxamide; |
| 102 | (1s,4s)-4-(8-(2-chloro-4,5-dimethylphenylamino)-2-(tetrahydro-2H-pyran-4-ylamino)-9H-purin-9-yl)cyclohexanecarboxamide; |
| 103 | (1s,4s)-4-(8-(4-chloro-2-fluoro-3-methylphenylamino)-2-(tetrahydro-2H-pyran-4-ylamino)-9H-purin-9-yl)cyclohexanecarboxamide; |
| 104 | (1s,4s)-4-(8-(2,4-dichloro-6-methylphenylamino)-2-(tetrahydro-2H-pyran-4-ylamino)-9H-purin-9-yl)cyclohexanecarboxamide; |
| 105 | (1s,4s)-4-(8-(2,3-dichloro-6-fluorophenylamino)-2-(tetrahydro-2H-pyran-4-ylamino)-9H-purin-9-yl)cyclohexanecarboxamide; |
| 106 | (1s,4s)-4-(8-(2,4-dichloro-5-fluorophenylamino)-2-(tetrahydro-2H-pyran-4-ylamino)-9H-purin-9-yl)cyclohexanecarboxamide; |
| 107 | (1s,4s)-4-(8-(2,5-difluoro-4-methylphenylamino)-2-(tetrahydro-2H-pyran-4-ylamino)-9H-purin-9-yl)cyclohexanecarboxamide; |
| 108 | (1s,4s)-4-(8-(2-chloro-6-fluorophenylamino)-2-(1-(pyridin-3-yl)piperidin-4-ylamino)-9H-purin-9-yl)cyclohexanecarboxamide; |
| 109 | (1s,4s)-4-(8-(2-chloro-6-fluorophenylamino)-2-(1-phenylpiperidin-4-ylamino)-9H-purin-9-yl)cyclohexanecarboxamide; |
| 110 | (1s,4s)-4-(8-(2,4,6-trichlorophenylamino)-2-(2,2,2-trifluoroethylamino)-9H-purin-9-yl)cyclohexanecarboxamide; |
| 111 | (1s,4s)-4-(2-(cyclobutylmethylamino)-8-(2,4,6-trichlorophenylamino)-9H-purin-9-yl)cyclohexanecarboxamide; |
| 112 | (1s,4s)-4-(2-((R)-tetrahydro-2H-pyran-3-ylamino)-8-(2,4,6-trichlorophenylamino)-9H-purin-9-yl)cyclohexanecarboxamide; |
| 113 | (1s,4s)-4-(8-(3,4-dichloro-2-fluorophenylamino)-2-(tetrahydro-2H-pyran-4-ylamino)-9H-purin-9-yl)cyclohexanecarboxamide; |
| 114 | (1s,4s)-4-(8-(6-chloro-2,3-difluorophenylamino)-2-(tetrahydro-2H-pyran-4-ylamino)-9H-purin-9-yl)cyclohexanecarboxamide; |

TABLE 1-continued

Representative compounds of formula (I).

| Compound | Compound Name |
|---|---|
| 115 | (1s,4s)-4-(8-(2-chloro-6-fluorophenylamino)-2-(1-(methylsulfonyl)piperidin-4-ylamino)-9H-purin-9-yl)cyclohexanecarboxamide; |
| 116 | (1s,4s)-4-(8-(2,6-difluoro-4-methylphenylamino)-2-(tetrahydro-2H-pyran-4-ylamino)-9H-purin-9-yl)cyclohexanecarboxamide; |
| 117 | (1s,4s)-4-(8-(2,6-dichloro-4-methylphenylamino)-2-(tetrahydro-2H-pyran-4-ylamino)-9H-purin-9-yl)cyclohexanecarboxamide; |
| 118 | (1s,4s)-4-(8-(2-chloro-4,6-difluorophenylamino)-2-(cyclobutylamino)-9H-purin-9-yl)cyclohexanecarboxamide; |
| 119 | (1s,4s)-4-(2-(cyclobutylamino)-8-(2,6-dichloro-4-fluorophenylamino)-9H-purin-9-yl)cyclohexanecarboxamide; |
| 120 | (1s,4s)-4-(8-(2-chloro-4,6-difluorophenylamino)-2-(cyclopentylamino)-9H-purin-9-yl)cyclohexanecarboxamide; |
| 121 | (1s,4s)-4-(8-(4-chloro-2,6-difluorophenylamino)-2-(cyclopentylamino)-9H-purin-9-yl)cyclohexanecarboxamide; |
| 122 | (1s,4s)-4-(2-(cyclopentylamino)-8-(2,6-dichloro-4-fluorophenylamino)-9H-purin-9-yl)cyclohexanecarboxamide; |
| 123 | (1s,4s)-4-(2-(cyclopentylamino)-8-(2,4-dichloro-6-fluorophenylamino)-9H-purin-9-yl)cyclohexanecarboxamide; |
| 124 | (1s,4s)-4-(8-(2,6-dichloro-4-fluorophenylamino)-2-(isopropylamino)-9H-purin-9-yl)cyclohexanecarboxamide; |
| 125 | (1s,4s)-4-(8-(4-chloro-2,6-difluorophenylamino)-2-(isopropylamino)-9H-purin-9-yl)cyclohexanecarboxamide; |
| 126 | (1s,4s)-4-(8-(2-chloro-4,6-difluorophenylamino)-2-(isopropylamino)-9H-purin-9-yl)cyclohexanecarboxamide; |
| 127 | (1s,4s)-4-(8-(2,6-dichloro-4-fluorophenylamino)-2-((R)-1-hydroxybutan-2-ylamino)-9H-purin-9-yl)cyclohexanecarboxamide; |
| 128 | (3R,4S)-tert-butyl 4-(9-((1s,4r)-4-carbamoylcyclohexyl)-8-(2,4,6-trifluorophenylamino)-9H-purin-2-ylamino)-3-fluoropiperidine-1-carboxylate; |
| 129 | (3R,4S)-tert-butyl 4-(9-((1s,4r)-4-carbamoylcyclohexyl)-8-(2,6-difluorophenylamino)-9H-purin-2-ylamino)-3-fluoropiperidine-1-carboxylate; |
| 130 | (1s,4s)-4-(8-(4-chloro-2,6-difluorophenylamino)-2-(cyclobutylamino)-9H-purin-9-yl)cyclohexanecarboxamide; |
| 131 | (1s,4s)-4-(2-(cyclobutylamino)-8-(2,4-dichloro-6-fluorophenylamino)-9H-purin-9-yl)cyclohexanecarboxamide; |
| 132 | (1s,4s)-4-(8-(2,6-dichloro-4-fluorophenylamino)-2-((R)-1-hydroxypropan-2-ylamino)-9H-purin-9-yl)cyclohexanecarboxamide; |
| 133 | (1s,4s)-4-(8-(4-chloro-2,6-difluorophenylamino)-2-((R)-1-hydroxypropan-2-ylamino)-9H-purin-9-yl)cyclohexanecarboxamide; |
| 134 | (1s,4s)-4-(8-(2,4-dichloro-6-fluorophenylamino)-2-((R)-1-hydroxypropan-2-ylamino)-9H-purin-9-yl)cyclohexanecarboxamide; |
| 135 | (1s,4s)-4-(8-(2-chloro-4,6-difluorophenylamino)-2-((R)-1-hydroxypropan-2-ylamino)-9H-purin-9-yl)cyclohexanecarboxamide; |
| 136 | (1r,4s)-4-(8-(2,4-dichloro-6-fluorophenylamino)-2-((S)-1-hydroxypropan-2-ylamino)-9H-purin-9-yl)cyclohexanecarboxamide; |
| 137 | (1r,4s)-4-(8-(2-chloro-4,6-difluorophenylamino)-2-((S)-1-hydroxypropan-2-ylamino)-9H-purin-9-yl)cyclohexanecarboxamide; |
| 138 | (1s,4s)-4-(2-((R)-1-hydroxybutan-2-ylamino)-8-(2,4,6-trichlorophenylamino)-9H-purin-9-yl)cyclohexanecarboxamide; |
| 139 | (1r,4s)-4-(2-((3R,4S)-3-fluoropiperidin-4-ylamino)-8-(2,4,6-trichlorophenylamino)-9H-purin-9-yl)cyclohexanecarboxamide; |
| 140 | (1s,4s)-4-(2-(cyclopentylamino)-8-(2,3-difluorophenylamino)-9H-purin-9-yl)cyclohexanecarboxamide; |
| 141 | (1s,4s)-4-(8-(3-chloro-2-fluorophenylamino)-2-(cyclopentylamino)-9H-purin-9-yl)cyclohexanecarboxamide; |
| 142 | (1s,4s)-4-(2-(cyclopentylamino)-8-(2,3,6-trifluorophenylamino)-9H-purin-9-yl)cyclohexanecarboxamide; |
| 143 | (1r,4s)-4-(2-((S)-1-methoxypropan-2-ylamino)-8-(2,4,6-trichlorophenylamino)-9H-purin-9-yl)cyclohexanecarboxamide; |
| 144 | (1r,4s)-4-(2-((S)-1-hydroxybutan-2-ylamino)-8-(2,4,6-trifluorophenylamino)-9H-purin-9-yl)cyclohexanecarboxamide; |
| 145 | (1r,4s)-4-(8-(2-chloro-6-fluorophenylamino)-2-((S)-1-hydroxybutan-2-ylamino)-9H-purin-9-yl)cyclohexanecarboxamide; |
| 146 | (1r,4s)-4-(8-(2,6-dichloro-4-fluorophenylamino)-2-((S)-1-hydroxybutan-2-ylamino)-9H-purin-9-yl)cyclohexanecarboxamide; |
| 147 | (1r,4s)-4-(8-(4-chloro-2,6-difluorophenylamino)-2-((S)-1-hydroxybutan-2-ylamino)-9H-purin-9-yl)cyclohexanecarboxamide; |
| 148 | (1r,4s)-4-(8-(2-chloro-4,6-difluorophenylamino)-2-((S)-1-hydroxybutan-2-ylamino)-9H-purin-9-yl)cyclohexanecarboxamide; |
| 149 | (1r,4s)-4-(2-((S)-1-hydroxybutan-2-ylamino)-8-(2,3,6-trifluorophenylamino)-9H-purin-9-yl)cyclohexanecarboxamide; |
| 150 | (1r,4s)-4-(8-(2,4-dichlorophenylamino)-2-((S)-1-hydroxybutan-2-ylamino)-9H-purin-9-yl)cyclohexanecarboxamide; |
| 151 | (1r,4s)-4-(8-(3-chloro-2-fluorophenylamino)-2-((S)-1-hydroxybutan-2-ylamino)-9H-purin-9-yl)cyclohexanecarboxamide; |
| 152 | (1r,4s)-4-(2-((S)-1-hydroxybutan-2-ylamino)-8-(2,3,4-trifluorophenylamino)-9H-purin-9-yl)cyclohexanecarboxamide; |

TABLE 1-continued

Representative compounds of formula (I).

| Compound | Compound Name |
|---|---|
| 153 | (1s,4s)-4-(2-((R)-2-hydroxypropylamino)-8-(2,4,6-trichlorophenylamino)-9H-purin-9-yl)cyclohexanecarboxamide; |
| 154 | (1r,4s)-4-(8-(2,6-dichlorophenylamino)-2-((S)-1-hydroxybutan-2-ylamino)-9H-purin-9-yl)cyclohexanecarboxamide; |
| 155 | (1r,4s)-4-(2-((S)-1-hydroxybutan-2-ylamino)-8-(2,4,6-trichlorophenylamino)-9H-purin-9-yl)cyclohexanecarboxamide; |
| 156 | (3R,4S)-tert-butyl 4-(9-((1s,4r)-4-carbamoylcyclohexyl)-8-(4-chloro-2,6-difluorophenylamino)-9H-purin-2-ylamino)-3-fluoropiperidine-1-carboxylate; |
| 157 | (1s,4s)-4-(8-((4-chloro-2,6-difluorophenyl)amino)-2-((1,1-dioxidotetrahydro-2H-thiopyran-4-yl)amino)-9H-purin-9-yl)cyclohexane-1-carboxamide; |
| 158 | (1s,4s)-4-(8-((2,4-dichloro-6-fluorophenyl)amino)-2-((1,1-dioxidotetrahydro-2H-thiopyran-4-yl)amino)-9H-purin-9-yl)cyclohexane-1-carboxamide; |
| 159 | (R)-tert-butyl 3-(9-((1s,4s)-4-carbamoylcyclohexyl)-8-(2,4,6-trifluorophenylamino)-9H-purin-2-ylamino)piperidine-1-carboxylate; |
| 160 | (R)-tert-butyl 3-(9-((1s,4s)-4-carbamoylcyclohexyl)-8-(2,6-difluorophenylamino)-9H-purin-2-ylamino)piperidine-1-carboxylate; |
| 161 | (R)-tert-butyl 3-(9-((1s,4s)-4-carbamoylcyclohexyl)-8-(2,6-dichlorophenylamino)-9H-purin-2-ylamino)piperidine-1-carboxylate; |
| 162 | (R)-tert-butyl 3-(9-((1s,4s)-4-carbamoylcyclohexyl)-8-(2-chloro-4,6-difluorophenylamino)-9H-purin-2-ylamino)piperidine-1-carboxylate; |
| 163 | (R)-tert-butyl 3-(9-((1s,4s)-4-carbamoylcyclohexyl)-8-(4-chloro-2,6-difluorophenylamino)-9H-purin-2-ylamino)piperidine-1-carboxylate; |
| 164 | (R)-tert-butyl 3-(9-((1s,4s)-4-carbamoylcyclohexyl)-8-(2,4,6-trichlorophenylamino)-9H-purin-2-ylamino)piperidine-1-carboxylate; |
| 165 | (1r,4s)-4-(2-((S)-1-hydroxypropan-2-ylamino)-8-(2,4,6-trifluorophenylamino)-9H-purin-9-yl)cyclohexanecarboxamide; |
| 166 | (1r,4s)-4-(2-((S)-1-hydroxypropan-2-ylamino)-8-(2,4,6-trichlorophenylamino)-9H-purin-9-yl)cyclohexanecarboxamide; |
| 167 | (1r,4s)-4-(8-(2,6-dichloro-4-fluorophenylamino)-2-((S)-1-hydroxypropan-2-ylamino)-9H-purin-9-yl)cyclohexanecarboxamide; |
| 168 | (1r,4s)-4-(8-(2,6-difluorophenylamino)-2-((S)-1-hydroxypropan-2-ylamino)-9H-purin-9-yl)cyclohexanecarboxamide; |
| 169 | (1r,4s)-4-(8-(2,6-dichlorophenylamino)-2-((S)-1-hydroxypropan-2-ylamino)-9H-purin-9-yl)cyclohexanecarboxamide; |
| 170 | (1r,4s)-4-(8-(4-chloro-2,6-difluorophenylamino)-2-((S)-1-hydroxypropan-2-ylamino)-9H-purin-9-yl)cyclohexanecarboxamide; |
| 171 | (1r,4s)-4-(8-(2,4-dichlorophenylamino)-2-((S)-1-hydroxypropan-2-ylamino)-9H-purin-9-yl)cyclohexanecarboxamide; |
| 172 | (1r,4s)-4-(8-(5-chloro-2-fluorophenylamino)-2-((S)-1-hydroxypropan-2-ylamino)-9H-purin-9-yl)cyclohexanecarboxamide; |
| 173 | (1r,4s)-4-(8-(3-chloro-2-fluorophenylamino)-2-((S)-1-hydroxypropan-2-ylamino)-9H-purin-9-yl)cyclohexanecarboxamide; |
| 174 | (1s,4s)-4-(2-(2-oxaspiro[3.3]heptan-6-ylamino)-8-(2,6-difluorophenylamino)-9H-purin-9-yl)cyclohexanecarboxamide; |
| 175 | (1s,4s)-4-(2-(2-oxaspiro[3.3]heptan-6-ylamino)-8-(2,6-dichlorophenylamino)-9H-purin-9-yl)cyclohexanecarboxamide; |
| 176 | (1s,4s)-4-(2-(2-oxaspiro[3.3]heptan-6-ylamino)-8-(2-chloro-4,6-difluorophenylamino)-9H-purin-9-yl)cyclohexanecarboxamide; |
| 177 | (1s,4s)-4-(2-(2-oxaspiro[3.3]heptan-6-ylamino)-8-(4-chloro-2,6-difluorophenylamino)-9H-purin-9-yl)cyclohexanecarboxamide; |
| 178 | (1s,4s)-4-(2-(2-oxaspiro[3.3]heptan-6-ylamino)-8-(2,4,6-trichlorophenylamino)-9H-purin-9-yl)cyclohexanecarboxamide; |
| 179 | (1s,4s)-4-(2-(4-hydroxytetrahydrofuran-3-ylamino)-8-(2,4,6-trifluorophenylamino)-9H-purin-9-yl)cyclohexanecarboxamide; |
| 180 | (1s,4s)-4-(8-(2-chloro-4,6-difluorophenylamino)-2-(4-hydroxytetrahydrofuran-3-ylamino)-9H-purin-9-yl)cyclohexanecarboxamide; |
| 181 | (1s,4s)-4-(8-(2,6-dichlorophenylamino)-2-(4-hydroxytetrahydrofuran-3-ylamino)-9H-purin-9-yl)cyclohexanecarboxamide; |
| 182 | (1s,4s)-4-(2-(4-hydroxytetrahydrofuran-3-ylamino)-8-(2,4,6-trichlorophenylamino)-9H-purin-9-yl)cyclohexanecarboxamide; |
| 183 | (1s,4s)-4-(8-(2,4-dichloro-6-fluorophenylamino)-2-(4-hydroxytetrahydrofuran-3-ylamino)-9H-purin-9-yl)cyclohexanecarboxamide; |
| 184 | (1s,4s)-4-(8-(2,6-dichloro-4-fluorophenylamino)-2-(4-hydroxytetrahydrofuran-3-ylamino)-9H-purin-9-yl)cyclohexanecarboxamide; |
| 185 | (1s,4s)-4-(8-(4-chloro-2,6-difluorophenylamino)-2-(4-hydroxytetrahydrofuran-3-ylamino)-9H-purin-9-yl)cyclohexanecarboxamide; |
| 186 | (1s,4s)-4-(8-(2-chloro-4,6-difluorophenylamino)-2-(4,4-difluorocyclohexylamino)-9H-purin-9-yl)cyclohexanecarboxamide; |
| 187 | (1s,4s)-4-(8-(2,4-dichloro-6-fluorophenylamino)-2-(4,4-difluorocyclohexylamino)-9H-purin-9-yl)cyclohexanecarboxamide; |
| 188 | (1s,4s)-4-(8-(2-chloro-4,6-difluorophenylamino)-2-((R)-tetrahydro-2H-pyran-3-ylamino)-9H-purin-9-yl)cyclohexanecarboxamide; |
| 189 | (1s,4s)-4-(8-(4-chloro-2,6-difluorophenylamino)-2-((R)-tetrahydro-2H-pyran-3-ylamino)-9H-purin-9-yl)cyclohexanecarboxamide; |
| 190 | (1s,4s)-4-(8-(2,6-dichloro-4-fluorophenylamino)-2-((R)-tetrahydro-2H-pyran-3-ylamino)-9H-purin-9-yl)cyclohexanecarboxamide; |

TABLE 1-continued

Representative compounds of formula (I).

| Compound | Compound Name |
|---|---|
| 191 | (1s,4s)-4-(8-(2,4-dichloro-6-fluorophenylamino)-2-((R)-tetrahydro-2H-pyran-3-ylamino)-9H-purin-9-yl)cyclohexanecarboxamide; |
| 192 | (1s,4s)-4-(8-(2,4-dichlorophenylamino)-2-(4-hydroxytetrahydrofuran-3-ylamino)-9H-purin-9-yl)cyclohexanecarboxamide; |
| 193 | (1s,4s)-4-(8-(3-chloro-2-fluorophenylamino)-2-(4-hydroxytetrahydrofuran-3-ylamino)-9H-purin-9-yl)cyclohexanecarboxamide; |
| 194 | (1s,4s)-4-(2-(2-oxaspiro[3.3]heptan-6-ylamino)-8-(2,6-dichloro-4-fluorophenylamino)-9H-purin-9-yl)cyclohexanecarboxamide; |
| 195 | (1s,4s)-4-(2-(2-oxaspiro[3.3]heptan-6-ylamino)-8-(4-chloro-2,3-difluorophenylamino)-9H-purin-9-yl)cyclohexanecarboxamide; |
| 196 | (1s,4s)-4-(2-(2-oxaspiro[3.3]heptan-6-ylamino)-8-(2,4-dichloro-6-fluorophenylamino)-9H-purin-9-yl)cyclohexanecarboxamide; |
| 197 | (1s,4s)-4-(2-(2-oxaspiro[3.3]heptan-6-ylamino)-8-(3-chloro-2,6-difluorophenylamino)-9H-purin-9-yl)cyclohexanecarboxamide; |
| 198 | (1s,4s)-4-(2-(1-acetylpiperidin-4-ylamino)-8-(2,4,6-trichlorophenylamino)-9H-purin-9-yl)cyclohexanecarboxamide; |
| 199 | (1s,4s)-4-(2-(1-acetylpiperidin-4-ylamino)-8-(2,4-dichloro-6-fluorophenylamino)-9H-purin-9-yl)cyclohexanecarboxamide; |
| 200 | (1s,4s)-4-(8-(2-chloro-4,6-difluorophenylamino)-2-((R)-tetrahydrofuran-3-ylamino)-9H-purin-9-yl)cyclohexanecarboxamide; |
| 201 | (1s,4s)-4-(8-(4-chloro-2,6-difluorophenylamino)-2-(4,4-difluorocyclohexylamino)-9H-purin-9-yl)cyclohexanecarboxamide; |
| 202 | (1s,4s)-4-(8-(2,6-dichloro-4-fluorophenylamino)-2-(4,4-difluorocyclohexylamino)-9H-purin-9-yl)cyclohexanecarboxamide; |
| 203 | (1r,4s)-4-(8-(2,6-dichloro-4-fluorophenylamino)-2-((S)-tetrahydro-2H-pyran-3-ylamino)-9H-purin-9-yl)cyclohexanecarboxamide; |
| 204 | (1r,4s)-4-(8-(4-chloro-2,6-difluorophenylamino)-2-((S)-tetrahydro-2H-pyran-3-ylamino)-9H-purin-9-yl)cyclohexanecarboxamide; |
| 205 | (1r,4s)-4-(8-(2,4-dichloro-6-fluorophenylamino)-2-((S)-tetrahydro-2H-pyran-3-ylamino)-9H-purin-9-yl)cyclohexanecarboxamide; |
| 206 | (1s,4s)-4-(2-((1-(hydroxymethyl)cyclopropyl)methylamino)-8-(2,4,6-trichlorophenylamino)-9H-purin-9-yl)cyclohexanecarboxamide; |
| 207 | (1s,4s)-4-(8-(2,4-dichloro-6-fluorophenylamino)-2-((1-(hydroxymethyl)cyclopropyl)methylamino)-9H-purin-9-yl)cyclohexanecarboxamide; |
| 208 | (1s,4s)-4-(2-((1R,3R)-3-hydroxycyclopentylamino)-8-(2,4,6-trifluorophenylamino)-9H-purin-9-yl)cyclohexanecarboxamide; |
| 209 | (1s,4s)-4-(8-(2-chloro-6-fluorophenylamino)-2-((1R,3R)-3-hydroxycyclopentylamino)-9H-purin-9-yl)cyclohexanecarboxamide; |
| 210 | (1s,4s)-4-(8-(2,6-difluorophenylamino)-2-((1R,3R)-3-hydroxycyclopentylamino)-9H-purin-9-yl)cyclohexanecarboxamide; |
| 211 | (1s,4s)-4-(8-(2-chloro-4,6-difluorophenylamino)-2-((1R,3R)-3-hydroxycyclopentylamino)-9H-purin-9-yl)cyclohexanecarboxamide; |
| 212 | (1s,4s)-4-(8-(2,6-dichlorophenylamino)-2-((1R,3R)-3-hydroxycyclopentylamino)-9H-purin-9-yl)cyclohexanecarboxamide; |
| 213 | (1s,4s)-4-(2-((1R,3R)-3-hydroxycyclopentylamino)-8-(2,4,6-trichlorophenylamino)-9H-purin-9-yl)cyclohexanecarboxamide; |
| 214 | (1s,4s)-4-(8-(2,4-dichloro-6-fluorophenylamino)-2-((1R,3R)-3-hydroxycyclopentylamino)-9H-purin-9-yl)cyclohexanecarboxamide; |
| 215 | (1s,4s)-4-(8-(2,6-dichloro-4-fluorophenylamino)-2-((1R,3R)-3-hydroxycyclopentylamino)-9H-purin-9-yl)cyclohexanecarboxamide; |
| 216 | (1s,4s)-4-(8-(4-chloro-2,6-difluorophenylamino)-2-((1R,3R)-3-hydroxycyclopentylamino)-9H-purin-9-yl)cyclohexanecarboxamide; |
| 217 | (1s,4s)-4-(8-(4-chloro-2,3-difluorophenylamino)-2-((1R,3R)-3-hydroxycyclopentylamino)-9H-purin-9-yl)cyclohexanecarboxamide; |
| 218 | (1s,4s)-4-(8-(3-chloro-2,6-difluorophenylamino)-2-((1R,3R)-3-hydroxycyclopentylamino)-9H-purin-9-yl)cyclohexanecarboxamide; |
| 219 | (1s,4s)-4-(2-((1R,3R)-3-hydroxycyclopentylamino)-8-(2,3,6-trifluorophenylamino)-9H-purin-9-yl)cyclohexanecarboxamide; |
| 220 | (1s,4s)-4-(8-(2,4-dichlorophenylamino)-2-((1R,3R)-3-hydroxycyclopentylamino)-9H-purin-9-yl)cyclohexanecarboxamide; |
| 221 | (1s,4s)-4-(2-((1R,3R)-3-hydroxycyclopentylamino)-8-(2,3,4-trifluorophenylamino)-9H-purin-9-yl)cyclohexanecarboxamide; |
| 222 | (1s,4s)-4-(8-(4-chloro-2,6-difluorophenylamino)-2-((R)-tetrahydrofuran-3-ylamino)-9H-purin-9-yl)cyclohexanecarboxamide; |
| 223 | (1s,4s)-4-(8-(2,6-dichloro-4-fluorophenylamino)-2-((R)-tetrahydrofuran-3-ylamino)-9H-purin-9-yl)cyclohexanecarboxamide; |
| 224 | (1s,4s)-4-(8-(2,4-dichloro-6-fluorophenylamino)-2-((R)-tetrahydrofuran-3-ylamino)-9H-purin-9-yl)cyclohexanecarboxamide; |
| 225 | (1s,4s)-4-(2-(3,3-difluorocyclobutylamino)-8-(2,4,6-trichlorophenylamino)-9H-purin-9-yl)cyclohexanecarboxamide; |
| 226 | (1s,4s)-4-(8-(2-chloro-6-fluorophenylamino)-2-(3,3-difluorocyclobutylamino)-9H-purin-9-yl)cyclohexanecarboxamide; |
| 227 | (1s,4s)-4-(2-(3,3-difluorocyclobutylamino)-8-(2,4,6-trifluorophenylamino)-9H-purin-9-yl)cyclohexanecarboxamide; |

TABLE 1-continued

Representative compounds of formula (I).

| Compound | Compound Name |
|---|---|
| 228 | (1s,4s)-4-(2-(3,3-difluorocyclobutylamino)-8-(2,6-difluorophenylamino)-9H-purin-9-yl)cyclohexanecarboxamide; |
| 229 | (1s,4s)-4-(8-(2-chloro-4,6-difluorophenylamino)-2-(3,3-difluorocyclobutylamino)-9H-purin-9-yl)cyclohexanecarboxamide; |
| 230 | (1s,4s)-4-(8-(4-chloro-2,6-difluorophenylamino)-2-(3,3-difluorocyclobutylamino)-9H-purin-9-yl)cyclohexanecarboxamide; |
| 231 | (1s,4s)-4-(8-(2,4-dichloro-6-fluorophenylamino)-2-(3,3-difluorocyclobutylamino)-9H-purin-9-yl)cyclohexanecarboxamide; |
| 232 | (1s,4s)-4-(8-(2,6-dichloro-4-fluorophenylamino)-2-(3,3-difluorocyclobutylamino)-9H-purin-9-yl)cyclohexanecarboxamide; |
| 233 | (1s,4s)-4-(8-(4-chloro-2,3-difluorophenylamino)-2-(3,3-difluorocyclobutylamino)-9H-purin-9-yl)cyclohexanecarboxamide; |
| 234 | (1s,4s)-4-(2-(3,3-difluorocyclobutylamino)-8-(2,3,6-trifluorophenylamino)-9H-purin-9-yl)cyclohexanecarboxamide; |
| 235 | (1s,4s)-4-(8-(3-chloro-2,6-difluorophenylamino)-2-(3,3-difluorocyclobutylamino)-9H-purin-9-yl)cyclohexanecarboxamide; |
| 236 | (1s,4s)-4-(8-(2-chloro-6-fluorophenylamino)-2-(4,4-difluorocyclohexylamino)-9H-purin-9-yl)cyclohexanecarboxamide; |
| 237 | (1s,4s)-4-(8-(2,6-dichlorophenylamino)-2-(4,4-difluorocyclohexylamino)-9H-purin-9-yl)cyclohexanecarboxamide; |
| 238 | (1s,4s)-4-(8-(3-chloro-2-fluorophenylamino)-2-(4,4-difluorocyclohexylamino)-9H-purin-9-yl)cyclohexanecarboxamide; |
| 239 | (1s,4s)-4-(8-(4-chloro-2,5-difluorophenylamino)-2-(4,4-difluorocyclohexylamino)-9H-purin-9-yl)cyclohexanecarboxamide; |
| 240 | (1s,4s)-4-(2-(4,4-difluorocyclohexylamino)-8-(2,3,6-trifluorophenylamino)-9H-purin-9-yl)cyclohexanecarboxamide; |
| 241 | (1s,4s)-4-(8-(2,4-dichlorophenylamino)-2-(4,4-difluorocyclohexylamino)-9H-purin-9-yl)cyclohexanecarboxamide; |
| 242 | (1r,4s)-4-(8-(2-chloro-4,6-difluorophenylamino)-2-((S)-tetrahydrofuran-3-ylamino)-9H-purin-9-yl)cyclohexanecarboxamide; |
| 243 | (1r,4s)-4-(8-(4-chloro-2,6-difluorophenylamino)-2-((S)-tetrahydrofuran-3-ylamino)-9H-purin-9-yl)cyclohexanecarboxamide; |
| 244 | (1r,4s)-4-(8-(2,6-dichloro-4-fluorophenylamino)-2-((S)-tetrahydrofuran-3-ylamino)-9H-purin-9-yl)cyclohexanecarboxamide; |
| 245 | (1r,4s)-4-(8-(2,4-dichloro-6-fluorophenylamino)-2-((S)-tetrahydrofuran-3-ylamino)-9H-purin-9-yl)cyclohexanecarboxamide; |
| 246 | (1r,4s)-4-(8-(2-chloro-4,6-difluorophenylamino)-2-((S)-tetrahydro-2H-pyran-3-ylamino)-9H-purin-9-yl)cyclohexanecarboxamide; |
| 247 | (1r,4s)-4-(2-((3R,4S)-3-fluorotetrahydro-2H-pyran-4-ylamino)-8-(2,4,6-trichlorophenylamino)-9H-purin-9-yl)cyclohexanecarboxamide; |
| 248 | (1r,4s)-4-(8-(2,6-difluorophenylamino)-2-((3R,4S)-3-fluorotetrahydro-2H-pyran-4-ylamino)-9H-purin-9-yl)cyclohexanecarboxamide; |
| 249 | (1s,4s)-4-(8-(2-chloro-4-cyanophenylamino)-2-(tetrahydro-2H-pyran-4-ylamino)-9H-purin-9-yl)cyclohexanecarboxamide; |
| 250 | (1s,4s)-4-(2-((1R,2R)-2-hydroxycyclopentylamino)-8-(2,4,6-trifluorophenylamino)-9H-purin-9-yl)cyclohexanecarboxamide; |
| 251 | (1s,4s)-4-(8-(2-chloro-6-fluorophenylamino)-2-((1R,2R)-2-hydroxycyclopentylamino)-9H-purin-9-yl)cyclohexanecarboxamide; |
| 252 | (1s,4s)-4-(8-(2,6-difluorophenylamino)-2-((1R,2R)-2-hydroxycyclopentylamino)-9H-purin-9-yl)cyclohexanecarboxamide; |
| 253 | (1s,4s)-4-(8-(2-chloro-4,6-difluorophenylamino)-2-((1R,2R)-2-hydroxycyclopentylamino)-9H-purin-9-yl)cyclohexanecarboxamide; |
| 254 | (1s,4s)-4-(8-(2,6-dichlorophenylamino)-2-((1R,2R)-2-hydroxycyclopentylamino)-9H-purin-9-yl)cyclohexanecarboxamide; |
| 255 | (1s,4s)-4-(2-((1R,2R)-2-hydroxycyclopentylamino)-8-(2,4,6-trichlorophenylamino)-9H-purin-9-yl)cyclohexanecarboxamide; |
| 256 | (1s,4s)-4-(8-(2,4-dichloro-6-fluorophenylamino)-2-((1R,2R)-2-hydroxycyclopentylamino)-9H-purin-9-yl)cyclohexanecarboxamide; |
| 257 | (1s,4s)-4-(8-(2,6-dichloro-4-fluorophenylamino)-2-((1R,2R)-2-hydroxycyclopentylamino)-9H-purin-9-yl)cyclohexanecarboxamide; |
| 258 | (1s,4s)-4-(8-(4-chloro-2,6-difluorophenylamino)-2-((1R,2R)-2-hydroxycyclopentylamino)-9H-purin-9-yl)cyclohexanecarboxamide; |
| 259 | (1s,4s)-4-(8-(4-chloro-2,3-difluorophenylamino)-2-((1R,2R)-2-hydroxycyclopentylamino)-9H-purin-9-yl)cyclohexanecarboxamide; |
| 260 | (1s,4s)-4-(8-(3-chloro-2,6-difluorophenylamino)-2-((1R,2R)-2-hydroxycyclopentylamino)-9H-purin-9-yl)cyclohexanecarboxamide; |
| 261 | (1s,4s)-4-(2-((1R,2R)-2-hydroxycyclopentylamino)-8-(2,3,6-trifluorophenylamino)-9H-purin-9-yl)cyclohexanecarboxamide; |
| 262 | (1s,4s)-4-(8-(2,4-dichlorophenylamino)-2-((1R,2R)-2-hydroxycyclopentylamino)-9H-purin-9-yl)cyclohexanecarboxamide; |
| 263 | (1s,4s)-4-(8-(5-chloro-2-fluorophenylamino)-2-((1R,2R)-2-hydroxycyclopentylamino)-9H-purin-9-yl)cyclohexanecarboxamide; |
| 264 | (1s,4s)-4-(8-(3-chloro-2-fluorophenylamino)-2-((1R,2R)-2-hydroxycyclopentylamino)-9H-purin-9-yl)cyclohexanecarboxamide; |
| 265 | (1s,4s)-4-(2-((1R,2R)-2-hydroxycyclopentylamino)-8-(2,3,4-trifluorophenylamino)-9H-purin-9-yl)cyclohexanecarboxamide; |

TABLE 1-continued

Representative compounds of formula (I).

| Compound | Compound Name |
|---|---|
| 266 | (1s,4s)-4-(8-(4-chloro-2,5-difluorophenylamino)-2-((1R,2R)-2-hydroxycyclopentylamino)-9H-purin-9-yl)cyclohexanecarboxamide; |
| 267 | (1r,4s)-4-(2-((1S,2S)-2-hydroxycyclopentylamino)-8-(2,4,6-trifluorophenylamino)-9H-purin-9-yl)cyclohexanecarboxamide; |
| 268 | (1r,4s)-4-(8-(2,6-difluorophenylamino)-2-((1S,2S)-2-hydroxycyclopentylamino)-9H-purin-9-yl)cyclohexanecarboxamide; |
| 269 | (1r,4s)-4-(8-(2,6-dichlorophenylamino)-2-((1S,2S)-2-hydroxycyclopentylamino)-9H-purin-9-yl)cyclohexanecarboxamide; |
| 270 | (1r,4s)-4-(8-(4-chloro-2,6-difluorophenylamino)-2-((1S,2S)-2-hydroxycyclopentylamino)-9H-purin-9-yl)cyclohexanecarboxamide; |
| 271 | (1r,4s)-4-(2-((1S,2S)-2-hydroxycyclopentylamino)-8-(2,4,6-trichlorophenylamino)-9H-purin-9-yl)cyclohexanecarboxamide; |
| 272 | (1r,4s)-4-(8-(2,4-dichloro-6-fluorophenylamino)-2-((1S,2S)-2-hydroxycyclopentylamino)-9H-purin-9-yl)cyclohexanecarboxamide; |
| 273 | (1r,4s)-4-(8-(2,6-dichloro-4-fluorophenylamino)-2-((1S,2S)-2-hydroxycyclopentylamino)-9H-purin-9-yl)cyclohexanecarboxamide; |
| 274 | (1r,4s)-4-(8-(3-chloro-2,6-difluorophenylamino)-2-((1S,2S)-2-hydroxycyclopentylamino)-9H-purin-9-yl)cyclohexanecarboxamide; |
| 275 | (1s,4s)-4-(2-((3S,4R)-3-fluorotetrahydro-2H-pyran-4-ylamino)-8-(2,4,6-trichlorophenylamino)-9H-purin-9-yl)cyclohexanecarboxamide; |
| 276 | (1s,4s)-4-(8-(2,6-difluorophenylamino)-2-((3S,4R)-3-fluorotetrahydro-2H-pyran-4-ylamino)-9H-purin-9-yl)cyclohexanecarboxamide; |
| 277 | (1s,4s)-4-(2-((3S,4R)-3-fluorotetrahydro-2H-pyran-4-ylamino)-8-(2,4,6-trifluorophenylamino)-9H-purin-9-yl)cyclohexanecarboxamide; |
| 278 | (1r,4s)-4-(2-((3R,4S)-3-fluorotetrahydro-2H-pyran-4-ylamino)-8-(2,4,6-trifluorophenylamino)-9H-purin-9-yl)cyclohexanecarboxamide; |
| 279 | (1s,4s)-4-(8-(2,6-dichloro-4-cyanophenylamino)-2-(tetrahydro-2H-pyran-4-ylamino)-9H-purin-9-yl)cyclohexanecarboxamide; |
| 280 | (1s,4s)-4-(2-((1r,3r)-3-hydroxycyclobutylamino)-8-(2,4,6-trifluorophenylamino)-9H-purin-9-yl)cyclohexanecarboxamide; |
| 281 | (1s,4s)-4-(8-(2,6-dichlorophenylamino)-2-((1r,3r)-3-hydroxycyclobutylamino)-9H-purin-9-yl)cyclohexanecarboxamide; |
| 282 | (1s,4s)-4-(8-(2-chloro-6-fluorophenylamino)-2-((1r,3r)-3-hydroxycyclobutylamino)-9H-purin-9-yl)cyclohexanecarboxamide; |
| 283 | (1s,4s)-4-(8-(2-chloro-4,6-difluorophenylamino)-2-((1r,3r)-3-hydroxycyclobutylamino)-9H-purin-9-yl)cyclohexanecarboxamide; |
| 284 | (1s,4s)-4-(8-(4-chloro-2,6-difluorophenylamino)-2-((1r,3r)-3-hydroxycyclobutylamino)-9H-purin-9-yl)cyclohexanecarboxamide; |
| 285 | (1s,4s)-4-(8-(2,6-dichloro-4-fluorophenylamino)-2-((1r,3r)-3-hydroxycyclobutylamino)-9H-purin-9-yl)cyclohexanecarboxamide; |
| 286 | (1s,4s)-4-(8-(4-chloro-2,3-difluorophenylamino)-2-((1r,3r)-3-hydroxycyclobutylamino)-9H-purin-9-yl)cyclohexanecarboxamide; |
| 287 | (1s,4s)-4-(8-(3-chloro-2,6-difluorophenylamino)-2-((1r,3r)-3-hydroxycyclobutylamino)-9H-purin-9-yl)cyclohexanecarboxamide; |
| 288 | (1s,4s)-4-(8-(3-chloro-2,5-difluorophenylamino)-2-((1r,3r)-3-hydroxycyclobutylamino)-9H-purin-9-yl)cyclohexanecarboxamide; |
| 289 | (1s,4s)-4-(2-(4,4-difluorocyclohexylamino)-8-(2,4,6-trifluorophenylamino)-9H-purin-9-yl)cyclohexanecarboxamide; |
| 290 | (1s,4s)-4-(2-(4,4-difluorocyclohexylamino)-8-(2,6-difluorophenylamino)-9H-purin-9-yl)cyclohexanecarboxamide; |
| 291 | (1s,4s)-4-(8-(4-chloro-2,3-difluorophenylamino)-2-(4,4-difluorocyclohexylamino)-9H-purin-9-yl)cyclohexanecarboxamide; |
| 292 | (1s,4s)-4-(8-(3-chloro-2,6-difluorophenylamino)-2-(4,4-difluorocyclohexylamino)-9H-purin-9-yl)cyclohexanecarboxamide; |
| 293 | (1s,4s)-4-(2-(1-(methylsulfonyl)piperidin-4-ylamino)-8-(2,4,6-trichlorophenylamino)-9H-purin-9-yl)cyclohexanecarboxamide; |
| 294 | (1s,4s)-4-(8-(2,6-dichlorophenylamino)-2-(1-(methylsulfonyl)piperidin-4-ylamino)-9H-purin-9-yl)cyclohexanecarboxamide; |
| 295 | (1s,4s)-4-(8-(2-chloro-4,6-difluorophenylamino)-2-(1-(methylsulfonyl)piperidin-4-ylamino)-9H-purin-9-yl)cyclohexanecarboxamide; |
| 296 | (1s,4s)-4-(8-(4-chloro-2,6-difluorophenylamino)-2-(1-(methylsulfonyl)piperidin-4-ylamino)-9H-purin-9-yl)cyclohexanecarboxamide; |
| 297 | (1s,4s)-4-(8-(2,4-dichloro-6-fluorophenylamino)-2-(1-(methylsulfonyl)piperidin-4-ylamino)-9H-purin-9-yl)cyclohexanecarboxamide; |
| 298 | (1s,4s)-4-(8-(2,6-dichloro-4-fluorophenylamino)-2-(1-(methylsulfonyl)piperidin-4-ylamino)-9H-purin-9-yl)cyclohexanecarboxamide; |
| 299 | (1s,4s)-4-(8-(4-chloro-2,3-difluorophenylamino)-2-(1-(methylsulfonyl)piperidin-4-ylamino)-9H-purin-9-yl)cyclohexanecarboxamide; |
| 300 | (1s,4s)-4-(8-(2,4-dichlorophenylamino)-2-(1-(methylsulfonyl)piperidin-4-ylamino)-9H-purin-9-yl)cyclohexanecarboxamide; |
| 301 | (1s,4s)-4-(2-((1r,3r)-3-hydroxycyclobutylamino)-8-(2,4,6-trichlorophenylamino)-9H-purin-9-yl)cyclohexanecarboxamide; |
| 302 | (1s,4s)-4-(8-(2,4-dichloro-6-fluorophenylamino)-2-((1r,3r)-3-hydroxycyclobutylamino)-9H-purin-9-yl)cyclohexanecarboxamide; |
| 303 | (1s,4s)-4-(2-((3R,4R)-3-fluorotetrahydro-2H-pyran-4-ylamino)-8-(2,4,6-trichlorophenylamino)-9H-purin-9-yl)cyclohexanecarboxamide; |

TABLE 1-continued

Representative compounds of formula (I).

| Compound | Compound Name |
|---|---|
| 304 | (1r,4s)-4-(2-((3S,4S)-3-fluorotetrahydro-2H-pyran-4-ylamino)-8-(2,4,6-trichlorophenylamino)-9H-purin-9-yl)cyclohexanecarboxamide; |
| 305 | (1s,4s)-4-(8-(2,6-difluorophenylamino)-2-((3R,4R)-3-fluorotetrahydro-2H-pyran-4-ylamino)-9H-purin-9-yl)cyclohexanecarboxamide; |
| 306 | (1r,4s)-4-(8-(2,6-difluorophenylamino)-2-((3S,4S)-3-fluorotetrahydro-2H-pyran-4-ylamino)-9H-purin-9-yl)cyclohexanecarboxamide; |
| 307 | (1r,4s)-4-(2-((3S,4S)-3-fluorotetrahydro-2H-pyran-4-ylamino)-8-(2,4,6-trifluorophenylamino)-9H-purin-9-yl)cyclohexanecarboxamide; |
| 308 | (1s,4s)-4-(2-((3R,4R)-3-fluorotetrahydro-2H-pyran-4-ylamino)-8-(2,4,6-trifluorophenylamino)-9H-purin-9-yl)cyclohexanecarboxamide; |
| 309 | (1s,4s)-4-(8-(2-chloro-4-cyano-6-fluorophenylamino)-2-(tetrahydro-2H-pyran-4-ylamino)-9H-purin-9-yl)cyclohexanecarboxamide; |
| 310 | (1s,4s)-4-(8-(4-cyano-2,6-difluorophenylamino)-2-(tetrahydro-2H-pyran-4-ylamino)-9H-purin-9-yl)cyclohexanecarboxamide; |
| 311 | (1s,4s)-4-(8-(4-chloro-2,3-difluorophenylamino)-2-((1s,3s)-3-hydroxycyclobutylamino)-9H-purin-9-yl)cyclohexanecarboxamide; |
| 312 | (1r,4s)-4-(2-((3S,4R)-4-hydroxytetrahydrofuran-3-ylamino)-8-(2,4,6-trifluorophenylamino)-9H-purin-9-yl)cyclohexanecarboxamide; |
| 313 | (1r,4s)-4-(8-(2-chloro-4,6-difluorophenylamino)-2-((3S,4R)-4-hydroxytetrahydrofuran-3-ylamino)-9H-purin-9-yl)cyclohexanecarboxamide; |
| 314 | (1r,4s)-4-(2-((3S,4R)-4-hydroxytetrahydrofuran-3-ylamino)-8-(2,4,6-trichlorophenylamino)-9H-purin-9-yl)cyclohexanecarboxamide; |
| 315 | (1s,4s)-4-(8-(2,4-dichloro-6-fluorophenylamino)-2-((3R,4S)-4-hydroxytetrahydrofuran-3-ylamino)-9H-purin-9-yl)cyclohexanecarboxamide; |
| 316 | (1s,4s)-4-(8-(2,6-dichloro-4-fluorophenylamino)-2-((3R,4S)-4-hydroxytetrahydrofuran-3-ylamino)-9H-purin-9-yl)cyclohexanecarboxamide; |
| 317 | (1s,4s)-4-(8-(4-chloro-2,6-difluorophenylamino)-2-((3R,4S)-4-hydroxytetrahydrofuran-3-ylamino)-9H-purin-9-yl)cyclohexanecarboxamide; |
| 318 | (1r,4s)-4-(8-(4-chloro-2,3-difluorophenylamino)-2-((3S,4R)-4-hydroxytetrahydrofuran-3-ylamino)-9H-purin-9-yl)cyclohexanecarboxamide; |
| 319 | (1r,4s)-4-(8-(3-chloro-2,6-difluorophenylamino)-2-((3S,4R)-4-hydroxytetrahydrofuran-3-ylamino)-9H-purin-9-yl)cyclohexanecarboxamide; |
| 320 | (1r,4s)-4-(8-(2,4-dichlorophenylamino)-2-((3S,4R)-4-hydroxytetrahydrofuran-3-ylamino)-9H-purin-9-yl)cyclohexanecarboxamide; |
| 321 | (1r,4s)-4-(8-(5-chloro-2-fluorophenylamino)-2-((3S,4R)-4-hydroxytetrahydrofuran-3-ylamino)-9H-purin-9-yl)cyclohexanecarboxamide; |
| 322 | (1s,4s)-4-(8-(4-chloro-2,5-difluorophenylamino)-2-((3R,4S)-4-hydroxytetrahydrofuran-3-ylamino)-9H-purin-9-yl)cyclohexanecarboxamide; |
| 323 | (1s,4s)-4-(8-(4-chloro-2,6-difluorophenylamino)-2-((1s,3s)-3-hydroxycyclobutylamino)-9H-purin-9-yl)cyclohexanecarboxamide; |
| 324 | (1s,4s)-4-(2-((1s,3s)-3-hydroxycyclobutylamino)-8-(2,4,6-trichlorophenylamino)-9H-purin-9-yl)cyclohexanecarboxamide; |
| 325 | (1s,4s)-4-(8-(2,4-dichloro-6-fluorophenylamino)-2-((1s,3s)-3-hydroxycyclobutylamino)-9H-purin-9-yl)cyclohexanecarboxamide; |
| 326 | (1r,4s)-4-(8-(2-chloro-6-fluorophenylamino)-2-((1S,3S)-3-hydroxycyclopentylamino)-9H-purin-9-yl)cyclohexanecarboxamide; |
| 327 | (1r,4s)-4-(8-(2,6-difluorophenylamino)-2-((1S,3S)-3-hydroxycyclopentylamino)-9H-purin-9-yl)cyclohexanecarboxamide; |
| 328 | (1r,4s)-4-(8-(2,6-dichlorophenylamino)-2-((1S,3S)-3-hydroxycyclopentylamino)-9H-purin-9-yl)cyclohexanecarboxamide; |
| 329 | (1s,4s)-4-(8-(4-chloro-2,6-difluorophenylamino)-2-((1R,3S)-3-hydroxycyclopentylamino)-9H-purin-9-yl)cyclohexanecarboxamide; |
| 330 | (1r,4s)-4-(8-(4-chloro-2,6-difluorophenylamino)-2-((1S,3S)-3-hydroxycyclopentylamino)-9H-purin-9-yl)cyclohexanecarboxamide; |
| 331 | (1r,4s)-4-(2-((1S,3S)-3-hydroxycyclopentylamino)-8-(2,4,6-trichlorophenylamino)-9H-purin-9-yl)cyclohexanecarboxamide; |
| 332 | (1r,4s)-4-(2-((1S,3S)-3-hydroxycyclopentylamino)-8-(2,4,6-trifluorophenylamino)-9H-purin-9-yl)cyclohexanecarboxamide; |
| 333 | (1s,4s)-4-(2-((1R,3S)-3-hydroxycyclopentylamino)-8-(2,4,6-trifluorophenylamino)-9H-purin-9-yl)cyclohexanecarboxamide; |
| 334 | (1s,4s)-4-(2-((1R,3S)-3-hydroxycyclopentylamino)-8-(2,4,6-trichlorophenylamino)-9H-purin-9-yl)cyclohexanecarboxamide; |
| 335 | (1r,4s)-4-(2-(sec-butylamino)-8-(2,4,6-trifluorophenylamino)-9H-purin-9-yl)cyclohexanecarboxamide; |
| 336 | (1r,4s)-4-(2-(sec-butylamino)-8-(2,6-difluorophenylamino)-9H-purin-9-yl)cyclohexanecarboxamide; |
| 337 | (1r,4s)-4-(2-(sec-butylamino)-8-(2,6-dichlorophenylamino)-9H-purin-9-yl)cyclohexanecarboxamide; |
| 338 | (1r,4s)-4-(2-(sec-butylamino)-8-(2-chloro-6-fluorophenylamino)-9H-purin-9-yl)cyclohexanecarboxamide; |
| 339 | (1r,4s)-4-(2-(sec-butylamino)-8-(2-chloro-4,6-difluorophenylamino)-9H-purin-9-yl)cyclohexanecarboxamide; |
| 340 | (1r,4s)-4-(2-(sec-butylamino)-8-(2,4-dichloro-6-fluorophenylamino)-9H-purin-9-yl)cyclohexanecarboxamide; |
| 341 | (1r,4s)-4-(2-(sec-butylamino)-8-(3-chloro-2,6-difluorophenylamino)-9H-purin-9-yl)cyclohexanecarboxamide; |

TABLE 1-continued

Representative compounds of formula (I).

| Compound | Compound Name |
|---|---|
| 342 | (1s,4s)-4-(2-((1R,3R,4R)-3-hydroxy-4-methylcyclohexylamino)-8-(2,4,6-trifluorophenylamino)-9H-purin-9-yl)cyclohexanecarboxamide; |
| 343 | (1s,4s)-4-(8-(2-chloro-6-fluorophenylamino)-2-((1R,3R,4R)-3-hydroxy-4-methylcyclohexylamino)-9H-purin-9-yl)cyclohexanecarboxamide; |
| 344 | (1s,4s)-4-(8-(2,6-difluorophenylamino)-2-((1R,3R,4R)-3-hydroxy-4-methylcyclohexylamino)-9H-purin-9-yl)cyclohexanecarboxamide; |
| 345 | (1s,4s)-4-(8-(2-chloro-4,6-difluorophenylamino)-2-((1R,3R,4R)-3-hydroxy-4-methylcyclohexylamino)-9H-purin-9-yl)cyclohexanecarboxamide; |
| 346 | (1s,4s)-4-(8-(2,6-dichlorophenylamino)-2-((1R,3R,4R)-3-hydroxy-4-methylcyclohexylamino)-9H-purin-9-yl)cyclohexanecarboxamide; |
| 347 | (1s,4s)-4-(8-(2,4-dichloro-6-fluorophenylamino)-2-((1R,3R,4R)-3-hydroxy-4-methylcyclohexylamino)-9H-purin-9-yl)cyclohexanecarboxamide; |
| 348 | (1s,4s)-4-(2-((1R,3S)-3-hydroxycyclohexylamino)-8-(2,4,6-trifluorophenylamino)-9H-purin-9-yl)cyclohexanecarboxamide; |
| 349 | (1s,4s)-4-(8-(2,6-difluorophenylamino)-2-((1R,3S)-3-hydroxycyclohexylamino)-9H-purin-9-yl)cyclohexanecarboxamide; |
| 350 | (1s,4s)-4-(8-(2,6-dichlorophenylamino)-2-((1R,3S)-3-hydroxycyclohexylamino)-9H-purin-9-yl)cyclohexanecarboxamide; |
| 351 | (1s,4s)-4-(8-(2-chloro-6-fluorophenylamino)-2-((1R,3S)-3-hydroxycyclohexylamino)-9H-purin-9-yl)cyclohexanecarboxamide; |
| 352 | (1s,4s)-4-(8-(2-chloro-4,6-difluorophenylamino)-2-((1R,3S)-3-hydroxycyclohexylamino)-9H-purin-9-yl)cyclohexanecarboxamide; |
| 353 | (1s,4s)-4-(8-(4-chloro-2,6-difluorophenylamino)-2-((1R,3S)-3-hydroxycyclohexylamino)-9H-purin-9-yl)cyclohexanecarboxamide; |
| 354 | (1s,4s)-4-(2-((1R,3S)-3-hydroxycyclohexylamino)-8-(2,4,6-trichlorophenylamino)-9H-purin-9-yl)cyclohexanecarboxamide; |
| 355 | (1s,4s)-4-(8-(2,6-dichloro-4-fluorophenylamino)-2-((1R,3S)-3-hydroxycyclohexylamino)-9H-purin-9-yl)cyclohexanecarboxamide; |
| 356 | (1s,4s)-4-(8-(2,6-dichloro-4-fluorophenylamino)-2-((1R,3R,4R)-3-hydroxy-4-methylcyclohexylamino)-9H-purin-9-yl)cyclohexanecarboxamide; |
| 357 | (1s,4s)-4-(8-(4-chloro-2,6-difluorophenylamino)-2-((1R,3R,4R)-3-hydroxy-4-methylcyclohexylamino)-9H-purin-9-yl)cyclohexanecarboxamide; |
| 358 | (1s,4s)-4-(8-(4-chloro-2,3-difluorophenylamino)-2-((1R,3R,4R)-3-hydroxy-4-methylcyclohexylamino)-9H-purin-9-yl)cyclohexanecarboxamide; |
| 359 | (1s,4s)-4-(8-(3-chloro-2,6-difluorophenylamino)-2-((1R,3R,4R)-3-hydroxy-4-methylcyclohexylamino)-9H-purin-9-yl)cyclohexanecarboxamide; |
| 360 | (1s,4s)-4-(2-((1R,3R,4R)-3-hydroxy-4-methylcyclohexylamino)-8-(2,3,6-trifluorophenylamino)-9H-purin-9-yl)cyclohexanecarboxamide; |
| 361 | (1s,4s)-4-(8-(4-chloro-2,3-difluorophenylamino)-2-((1R,3S)-3-hydroxycyclohexylamino)-9H-purin-9-yl)cyclohexanecarboxamide; |
| 362 | (1s,4s)-4-(8-(2,4-dichloro-6-fluorophenylamino)-2-((1R,3S)-3-hydroxycyclohexylamino)-9H-purin-9-yl)cyclohexanecarboxamide; |
| 363 | (1s,4s)-4-(8-(3-chloro-2,6-difluorophenylamino)-2-((1R,3S)-3-hydroxycyclohexylamino)-9H-purin-9-yl)cyclohexanecarboxamide; |
| 364 | (1s,4s)-4-(8-(4-chloro-2,5-difluorophenylamino)-2-((1R,3S)-3-hydroxycyclohexylamino)-9H-purin-9-yl)cyclohexanecarboxamide; |
| 365 | (1s,4s)-4-(2-((1R,3S)-3-hydroxycyclohexylamino)-8-(2,3,4-trifluorophenylamino)-9H-purin-9-yl)cyclohexanecarboxamide; |
| 366 | (1s,4s)-4-(8-(2,6-dichloro-4-(trifluoromethoxy)phenylamino)-2-(tetrahydro-2H-pyran-4-ylamino)-9H-purin-9-yl)cyclohexanecarboxamide; |
| 367 | (1r,4s)-4-(8-(2,6-dichloro-4-cyanophenylamino)-2-((S)-1-hydroxypropan-2-ylamino)-9H-purin-9-yl)cyclohexanecarboxamide; |
| 368 | (1s,4s)-4-(2-(cyclopentylamino)-8-(2,6-dichloro-4-cyanophenylamino)-9H-purin-9-yl)cyclohexanecarboxamide; |
| 369 | (1s,4s)-4-(8-(4-cyano-2,6-difluorophenylamino)-2-(cyclobutylamino)-9H-purin-9-yl)cyclohexanecarboxamide; |
| 370 | (1s,4s)-4-(8-(2-chloro-4-cyano-6-fluorophenylamino)-2-(cyclopentylamino)-9H-purin-9-yl)cyclohexanecarboxamide; |
| 371 | (1r,4s)-4-(8-(2,6-dichlorophenylamino)-2-((1S,3R)-3-hydroxycyclohexylamino)-9H-purin-9-yl)cyclohexanecarboxamide; |
| 372 | (1r,4s)-4-(8-(2-chloro-4,6-difluorophenylamino)-2-((1S,3R)-3-hydroxycyclohexylamino)-9H-purin-9-yl)cyclohexanecarboxamide; |
| 373 | (1r,4s)-4-(8-(4-chloro-2,6-difluorophenylamino)-2-((1S,3R)-3-hydroxycyclohexylamino)-9H-purin-9-yl)cyclohexanecarboxamide; |
| 374 | (1r,4s)-4-(2-((1S,3R)-3-hydroxycyclohexylamino)-8-(2,4,6-trichlorophenylamino)-9H-purin-9-yl)cyclohexanecarboxamide; |
| 375 | (1r,4s)-4-(8-(2,6-dichloro-4-fluorophenylamino)-2-((1S,3R)-3-hydroxycyclohexylamino)-9H-purin-9-yl)cyclohexanecarboxamide; |
| 376 | (1r,4s)-4-(8-(4-chloro-2,3-difluorophenylamino)-2-((1S,3R)-3-hydroxycyclohexylamino)-9H-purin-9-yl)cyclohexanecarboxamide; |
| 377 | (1r,4s)-4-(8-(2,4-dichloro-6-fluorophenylamino)-2-((1S,3R)-3-hydroxycyclohexylamino)-9H-purin-9-yl)cyclohexanecarboxamide; |
| 378 | (1r,4s)-4-(8-(3-chloro-2,6-difluorophenylamino)-2-((1S,3R)-3-hydroxycyclohexylamino)-9H-purin-9-yl)cyclohexanecarboxamide; |
| 379 | (1s,4s)-4-(8-(2-chloro-4-cyano-6-fluorophenylamino)-2-(4,4-difluorocyclohexylamino)-9H-purin-9-yl)cyclohexanecarboxamide; |

TABLE 1-continued

Representative compounds of formula (I).

| Compound | Compound Name |
|---|---|
| 380 | (1s,4s)-4-(8-(4-cyano-2,3-difluorophenylamino)-2-(tetrahydro-2H-pyran-4-ylamino)-9H-purin-9-yl)cyclohexanecarboxamide; |
| 381 | (1s,4s)-4-(8-(2,3-difluoro-4-methoxyphenylamino)-2-(tetrahydro-2H-pyran-4-ylamino)-9H-purin-9-yl)cyclohexanecarboxamide; |
| 382 | (1s,4s)-4-(2-((1R,3R)-3-hydroxy-4,4-dimethylcyclohexylamino)-8-(2,4,6-trifluorophenylamino)-9H-purin-9-yl)cyclohexanecarboxamide; |
| 383 | (1s,4s)-4-(8-(2,6-difluorophenylamino)-2-((1R,3R)-3-hydroxy-4,4-dimethylcyclohexylamino)-9H-purin-9-yl)cyclohexanecarboxamide; |
| 384 | (1s,4s)-4-(8-(2,6-dichlorophenylamino)-2-((1R,3R)-3-hydroxy-4,4-dimethylcyclohexylamino)-9H-purin-9-yl)cyclohexanecarboxamide; |
| 385 | (1s,4s)-4-(8-(2-chloro-6-fluorophenylamino)-2-((1R,3R)-3-hydroxy-4,4-dimethylcyclohexylamino)-9H-purin-9-yl)cyclohexanecarboxamide; |
| 386 | (1s,4s)-4-(8-(2-chloro-4,6-difluorophenylamino)-2-((1R,3R)-3-hydroxy-4,4-dimethylcyclohexylamino)-9H-purin-9-yl)cyclohexanecarboxamide; |
| 387 | (1s,4s)-4-(8-(4-chloro-2,6-difluorophenylamino)-2-((1R,3R)-3-hydroxy-4,4-dimethylcyclohexylamino)-9H-purin-9-yl)cyclohexanecarboxamide; |
| 388 | (1s,4s)-4-(2-((1R,3R)-3-hydroxy-4,4-dimethylcyclohexylamino)-8-(2,4,6-trichlorophenylamino)-9H-purin-9-yl)cyclohexanecarboxamide; |
| 389 | (1s,4s)-4-(8-(2,6-dichloro-4-fluorophenylamino)-2-((1R,3R)-3-hydroxy-4,4-dimethylcyclohexylamino)-9H-purin-9-yl)cyclohexanecarboxamide; |
| 390 | (1s,4s)-4-(8-(2,4-dichloro-6-fluorophenylamino)-2-((1R,3R)-3-hydroxy-4,4-dimethylcyclohexylamino)-9H-purin-9-yl)cyclohexanecarboxamide; |
| 391 | (1s,4s)-4-(8-(3-chloro-2,6-difluorophenylamino)-2-((1R,3R)-3-hydroxy-4,4-dimethylcyclohexylamino)-9H-purin-9-yl)cyclohexanecarboxamide; |
| 392 | (1s,4s)-4-(8-(2,4-dichlorophenylamino)-2-((1R,3R,4R)-3-hydroxy-4-methylcyclohexylamino)-9H-purin-9-yl)cyclohexanecarboxamide; |
| 393 | (1s,4s)-4-(2-(cyclobutylamino)-8-(2,6-dichloro-4-cyanophenylamino)-9H-purin-9-yl)cyclohexanecarboxamide; |
| 394 | (1s,4s)-4-(8-(2-chloro-4-cyano-6-fluorophenylamino)-2-(cyclobutylamino)-9H-purin-9-yl)cyclohexanecarboxamide; |
| 395 | (1r,4s)-4-(8-(4-cyano-2,6-difluorophenylamino)-2-((S)-1-hydroxypropan-2-ylamino)-9H-purin-9-yl)cyclohexanecarboxamide; |
| 396 | (1r,4s)-4-(8-(2-chloro-4-cyano-6-fluorophenylamino)-2-((S)-1-hydroxypropan-2-ylamino)-9H-purin-9-yl)cyclohexanecarboxamide; |
| 397 | (1s,4s)-4-(8-(4-cyano-2,6-difluorophenylamino)-2-(4,4-difluorocyclohexylamino)-9H-purin-9-yl)cyclohexanecarboxamide; |
| 398 | (1s,4s)-4-(8-(2,6-dichloro-4-cyanophenylamino)-2-(4,4-difluorocyclohexylamino)-9H-purin-9-yl)cyclohexanecarboxamide; |
| 399 | (1s,4s)-4-(8-(2-chloro-6-fluoro-4-(trifluoromethyl)phenylamino)-2-(tetrahydro-2H-pyran-4-ylamino)-9H-purin-9-yl)cyclohexanecarboxamide; |
| 400 | (1s,4s)-4-(8-(2,6-dichloro-4-cyanophenylamino)-2-(3,3-difluorocyclobutylamino)-9H-purin-9-yl)cyclohexanecarboxamide; |
| 401 | (1s,4s)-4-(8-(2-chloro-4-cyano-6-fluorophenylamino)-2-(3,3-difluorocyclobutylamino)-9H-purin-9-yl)cyclohexanecarboxamide; |
| 402 | (1s,4s)-4-(8-(4-cyano-2,6-difluorophenylamino)-2-(3,3-difluorocyclobutylamino)-9H-purin-9-yl)cyclohexanecarboxamide; |
| 403 | (1r,4s)-4-(8-(4-cyano-2,6-difluorophenylamino)-2-((S)-1-hydroxybutan-2-ylamino)-9H-purin-9-yl)cyclohexanecarboxamide; |
| 404 | (R)-methyl 3-(9-((1s,4s)-4-carbamoylcyclohexyl)-8-(2,4,6-trifluorophenylamino)-9H-purin-2-ylamino)piperidine-1-carboxylate; |
| 405 | (R)-methyl 3-(9-((1s,4s)-4-carbamoylcyclohexyl)-8-(2,6-difluorophenylamino)-9H-purin-2-ylamino)piperidine-1-carboxylate; |
| 406 | (R)-methyl 3-(9-((1s,4s)-4-carbamoylcyclohexyl)-8-(2,6-dichlorophenylamino)-9H-purin-2-ylamino)piperidine-1-carboxylate; |
| 407 | (R)-methyl 3-(9-((1s,4s)-4-carbamoylcyclohexyl)-8-(2-chloro-6-fluorophenylamino)-9H-purin-2-ylamino)piperidine-1-carboxylate; |
| 408 | (R)-methyl 3-(9-((1s,4s)-4-carbamoylcyclohexyl)-8-(2-chloro-4,6-difluorophenylamino)-9H-purin-2-ylamino)piperidine-1-carboxylate; |
| 409 | (R)-methyl 3-(9-((1s,4s)-4-carbamoylcyclohexyl)-8-(4-chloro-2,6-difluorophenylamino)-9H-purin-2-ylamino)piperidine-1-carboxylate; |
| 410 | (R)-methyl 3-(9-((1s,4s)-4-carbamoylcyclohexyl)-8-(2,4,6-trichlorophenylamino)-9H-purin-2-ylamino)piperidine-1-carboxylate; |
| 411 | (R)-methyl 3-(9-((1s,4s)-4-carbamoylcyclohexyl)-8-(2,6-dichloro-4-fluorophenylamino)-9H-purin-2-ylamino)piperidine-1-carboxylate; |
| 412 | (R)-methyl 3-(9-((1s,4s)-4-carbamoylcyclohexyl)-8-(4-chloro-2,3-difluorophenylamino)-9H-purin-2-ylamino)piperidine-1-carboxylate; |
| 413 | (R)-methyl 3-(9-((1s,4s)-4-carbamoylcyclohexyl)-8-(2,4-dichloro-6-fluorophenylamino)-9H-purin-2-ylamino)piperidine-1-carboxylate; |
| 414 | (R)-methyl 3-(9-((1s,4s)-4-carbamoylcyclohexyl)-8-(3-chloro-2,6-difluorophenylamino)-9H-purin-2-ylamino)piperidine-1-carboxylate; |
| 415 | (R)-methyl 3-(9-((1s,4s)-4-carbamoylcyclohexyl)-8-(2,3,4-trifluorophenylamino)-9H-purin-2-ylamino)piperidine-1-carboxylate; |
| 416 | (1s,4s)-4-(2-((1R,3R)-3-hydroxycyclohexylamino)-8-(2,4,6-trichlorophenylamino)-9H-purin-9-yl)cyclohexanecarboxamide; |
| 417 | (1s,4s)-4-(8-(2-chloro-6-fluorophenylamino)-2-((1R,3R)-3-hydroxycyclohexylamino)-9H-purin-9-yl)cyclohexanecarboxamide; |

TABLE 1-continued

Representative compounds of formula (I).

| Compound | Compound Name |
|---|---|
| 418 | (1s,4s)-4-(8-(2,6-dichlorophenylamino)-2-((1R,3R)-3-hydroxycyclohexylamino)-9H-purin-9-yl)cyclohexanecarboxamide; |
| 419 | (1s,4s)-4-(2-((1R,3R)-3-hydroxycyclohexylamino)-8-(2,4,6-trifluorophenylamino)-9H-purin-9-yl)cyclohexanecarboxamide; |
| 420 | (1s,4s)-4-(8-(2,6-difluorophenylamino)-2-((1R,3R)-3-hydroxycyclohexylamino)-9H-purin-9-yl)cyclohexanecarboxamide; |
| 421 | (1s,4s)-4-(8-(2-chloro-4,6-difluorophenylamino)-2-((1R,3R)-3-hydroxycyclohexylamino)-9H-purin-9-yl)cyclohexanecarboxamide; |
| 422 | (1s,4s)-4-(8-(4-chloro-2,6-difluorophenylamino)-2-((1R,3R)-3-hydroxycyclohexylamino)-9H-purin-9-yl)cyclohexanecarboxamide; |
| 423 | (1s,4s)-4-(8-(2,4-dichloro-6-fluorophenylamino)-2-((1R,3R)-3-hydroxycyclohexylamino)-9H-purin-9-yl)cyclohexanecarboxamide; |
| 424 | (1s,4s)-4-(8-(2,6-dichloro-4-fluorophenylamino)-2-((1R,3R)-3-hydroxycyclohexylamino)-9H-purin-9-yl)cyclohexanecarboxamide; |
| 425 | (1s,4s)-4-(8-(2,6-dichlorophenylamino)-2-((1R,3S)-3-hydroxy-3-methylcyclohexylamino)-9H-purin-9-yl)cyclohexanecarboxamide; |
| 426 | (1s,4s)-4-(8-(2-chloro-4,6-difluorophenylamino)-2-((1R,3S)-3-hydroxy-3-methylcyclohexylamino)-9H-purin-9-yl)cyclohexanecarboxamide; |
| 427 | (1s,4s)-4-(8-(4-chloro-2,6-difluorophenylamino)-2-((1R,3S)-3-hydroxy-3-methylcyclohexylamino)-9H-purin-9-yl)cyclohexanecarboxamide; |
| 428 | (1s,4s)-4-(8-(2,4-dichloro-6-fluorophenylamino)-2-((1R,3S)-3-hydroxy-3-methylcyclohexylamino)-9H-purin-9-yl)cyclohexanecarboxamide; |
| 429 | (1s,4s)-4-(8-(2,6-dichloro-4-fluorophenylamino)-2-((1R,3S)-3-hydroxy-3-methylcyclohexylamino)-9H-purin-9-yl)cyclohexanecarboxamide; |
| 430 | (1s,4s)-4-(8-(2-chloro-4-fluorophenylamino)-2-((1R,3S)-3-hydroxy-3-methylcyclohexylamino)-9H-purin-9-yl)cyclohexanecarboxamide; |
| 431 | (1s,4s)-4-(8-(2-chloro-4-cyano-6-fluorophenylamino)-2-(isopropylamino)-9H-purin-9-yl)cyclohexanecarboxamide; |
| 432 | (1s,4s)-4-(8-(2,6-dichloro-4-cyanophenylamino)-2-(isopropylamino)-9H-purin-9-yl)cyclohexanecarboxamide; |
| 433 | (1r,4s)-4-(8-(2,6-dichloro-4-cyanophenylamino)-2-((S)-1-hydroxybutan-2-ylamino)-9H-purin-9-yl)cyclohexanecarboxamide; |
| 434 | (1r,4s)-4-(8-(2-chloro-4-cyano-6-fluorophenylamino)-2-((S)-1-hydroxybutan-2-ylamino)-9H-purin-9-yl)cyclohexanecarboxamide; |
| 435 | (1s,4s)-4-(2-((1R,3S)-3-hydroxycycloheptylamino)-8-(2,4,6-trifluorophenylamino)-9H-purin-9-yl)cyclohexanecarboxamide; |
| 436 | (1s,4s)-4-(8-(2,6-dichlorophenylamino)-2-((1R,3S)-3-hydroxycycloheptylamino)-9H-purin-9-yl)cyclohexanecarboxamide; |
| 437 | (1s,4s)-4-(8-(2-chloro-6-fluorophenylamino)-2-((1R,3S)-3-hydroxycycloheptylamino)-9H-purin-9-yl)cyclohexanecarboxamide; |
| 438 | (1s,4s)-4-(8-(2-chloro-4,6-difluorophenylamino)-2-((1R,3S)-3-hydroxycycloheptylamino)-9H-purin-9-yl)cyclohexanecarboxamide; |
| 439 | (1s,4s)-4-(8-(4-chloro-2,6-difluorophenylamino)-2-((1R,3S)-3-hydroxycycloheptylamino)-9H-purin-9-yl)cyclohexanecarboxamide; |
| 440 | (1s,4s)-4-(2-((1R,3S)-3-hydroxycycloheptylamino)-8-(2,4,6-trichlorophenylamino)-9H-purin-9-yl)cyclohexanecarboxamide; |
| 441 | (1s,4s)-4-(8-(4-chloro-2,3-difluorophenylamino)-2-((1R,3S)-3-hydroxycycloheptylamino)-9H-purin-9-yl)cyclohexanecarboxamide; |
| 442 | (1s,4s)-4-(8-(4-cyano-2,6-difluorophenylamino)-2-(isopropylamino)-9H-purin-9-yl)cyclohexanecarboxamide; |
| 443 | (1s,4s)-4-(8-(2,6-dichloro-4-(trifluoromethyl)phenylamino)-2-(tetrahydro-2H-pyran-4-ylamino)-9H-purin-9-yl)cyclohexanecarboxamide; |
| 444 | (1s,4s)-4-(8-(2,6-dichloro-3-cyanophenylamino)-2-(tetrahydro-2H-pyran-4-ylamino)-9H-purin-9-yl)cyclohexanecarboxamide; |
| 445 | (1r,4s)-4-(2-((1S,3R)-3-hydroxycycloheptylamino)-8-(2,4,6-trichlorophenylamino)-9H-purin-9-yl)cyclohexanecarboxamide; |
| 446 | (1s,4s)-4-(8-(4-chloro-2,6-difluorophenylamino)-2-((2S,4R)-2-(hydroxymethyl)tetrahydro-2H-pyran-4-ylamino)-9H-purin-9-yl)cyclohexanecarboxamide; |
| 447 | (1s,4s)-4-(2-((2S,4R)-2-(hydroxymethyl)tetrahydro-2H-pyran-4-ylamino)-8-(2,4,6-trifluorophenylamino)-9H-purin-9-yl)cyclohexanecarboxamide; |
| 448 | (1s,4s)-4-(8-(3-cyano-2,6-difluorophenylamino)-2-(tetrahydro-2H-pyran-4-ylamino)-9H-purin-9-yl)cyclohexanecarboxamide; |
| 449 | (1r,4s)-4-(8-(2-chloro-4-cyano-6-fluorophenylamino)-2-((1S,3S)-3-hydroxycycloheptylamino)-9H-purin-9-yl)cyclohexanecarboxamide; |
| 450 | (1r,4s)-4-(8-(2,6-dichloro-4-cyanophenylamino)-2-((1S,3S)-3-hydroxycycloheptylamino)-9H-purin-9-yl)cyclohexanecarboxamide; |
| 451 | (1s,4s)-4-(2-(2,2-difluoro-3-hydroxypropylamino)-8-(2,4,6-trichlorophenylamino)-9H-purin-9-yl)cyclohexanecarboxamide; |
| 452 | (1s,4s)-4-(8-(2,4-dichloro-6-fluorophenylamino)-2-(2,2-difluoro-3-hydroxypropylamino)-9H-purin-9-yl)cyclohexanecarboxamide; |
| 453 | (1s,4s)-4-(8-(2,6-dichloro-4-fluorophenylamino)-2-(2,2-difluoro-3-hydroxypropylamino)-9H-purin-9-yl)cyclohexanecarboxamide; |
| 454 | (1s,4s)-4-(8-(4-chloro-2,6-difluorophenylamino)-2-(2,2-difluoro-3-hydroxypropylamino)-9H-purin-9-yl)cyclohexanecarboxamide; |

TABLE 1-continued

Representative compounds of formula (I).

| Compound | Compound Name |
|---|---|
| 455 | (1s,4s)-4-(8-(2,6-dichloro-4-(trifluoromethyl)phenylamino)-2-((1R,3S)-3-hydroxycyclohexylamino)-9H-purin-9-yl)cyclohexanecarboxamide; |
| 456 | (1s,4s)-4-(8-(2,6-dichloro-4-cyanophenylamino)-2-((1R,3S)-3-hydroxycyclohexylamino)-9H-purin-9-yl)cyclohexanecarboxamide; |
| 457 | (1s,4s)-4-(8-(2-chloro-4-cyano-6-fluorophenylamino)-2-((1R,3S)-3-hydroxycyclohexylamino)-9H-purin-9-yl)cyclohexanecarboxamide; |
| 458 | (1s,4s)-4-(8-(4-cyano-2,6-difluorophenylamino)-2-((1R,3S)-3-hydroxycyclohexylamino)-9H-purin-9-yl)cyclohexanecarboxamide; |
| 459 | (1r,4s)-4-(2-((1S,3S)-3-hydroxycyclohexylamino)-8-(2,4,6-trifluorophenylamino)-9H-purin-9-yl)cyclohexanecarboxamide; |
| 460 | (1r,4s)-4-(8-(2-chloro-4,6-difluorophenylamino)-2-((1S,3S)-3-hydroxycyclohexylamino)-9H-purin-9-yl)cyclohexanecarboxamide; |
| 461 | (1r,4s)-4-(8-(4-chloro-2,6-difluorophenylamino)-2-((1S,3S)-3-hydroxycyclohexylamino)-9H-purin-9-yl)cyclohexanecarboxamide; |
| 462 | (1r,4s)-4-(2-((1S,3S)-3-hydroxycyclohexylamino)-8-(2,4,6-trichlorophenylamino)-9H-purin-9-yl)cyclohexanecarboxamide; |
| 463 | (1r,4s)-4-(8-(2,6-dichloro-4-fluorophenylamino)-2-((1S,3S)-3-hydroxycyclohexylamino)-9H-purin-9-yl)cyclohexanecarboxamide; |
| 464 | (1r,4s)-4-(8-(4-chloro-2,3-difluorophenylamino)-2-((1S,3S)-3-hydroxycyclohexylamino)-9H-purin-9-yl)cyclohexanecarboxamide; |
| 465 | (1r,4s)-4-(8-(2,4-dichloro-6-fluorophenylamino)-2-((1S,3S)-3-hydroxycyclohexylamino)-9H-purin-9-yl)cyclohexanecarboxamide; |
| 466 | (1r,4s)-4-(8-(4-chloro-2,5-difluorophenylamino)-2-((1S,3S)-3-hydroxycyclohexylamino)-9H-purin-9-yl)cyclohexanecarboxamide; |
| 467 | (1s,4s)-4-(8-(2-chloro-4,6-difluorophenylamino)-2-((1R,2R)-2-hydroxycyclohexylamino)-9H-purin-9-yl)cyclohexanecarboxamide; |
| 468 | (1s,4s)-4-(8-(4-chloro-2,6-difluorophenylamino)-2-((1R,2R)-2-hydroxycyclohexylamino)-9H-purin-9-yl)cyclohexanecarboxamide; |
| 469 | (1s,4s)-4-(2-((1R,2R)-2-hydroxycyclohexylamino)-8-(2,4,6-trichlorophenylamino)-9H-purin-9-yl)cyclohexanecarboxamide; |
| 470 | (1s,4s)-4-(8-(2,6-dichloro-4-fluorophenylamino)-2-((1R,2R)-2-hydroxycyclohexylamino)-9H-purin-9-yl)cyclohexanecarboxamide; |
| 471 | (1s,4s)-4-(8-(2,4-dichloro-6-fluorophenylamino)-2-((1R,2R)-2-hydroxycyclohexylamino)-9H-purin-9-yl)cyclohexanecarboxamide; |
| 472 | (1s,4s)-4-(8-(2,4-dichloro-6-fluorophenylamino)-2-((R)-1,1,1-trifluoro-3-hydroxypropan-2-ylamino)-9H-purin-9-yl)cyclohexanecarboxamide; |
| 473 | (1s,4s)-4-(8-(2,6-dichloro-4-cyanophenylamino)-2-((R)-1,1,1-trifluoro-3-hydroxypropan-2-ylamino)-9H-purin-9-yl)cyclohexanecarboxamide; |
| 474 | (1r,4r)-4-(8-(4-chloro-2,6-difluorophenylamino)-2-(tetrahydro-2H-pyran-4-ylamino)-9H-purin-9-yl)-1-methylcyclohexanecarboxamide; |
| 475 | (1r,4r)-1-methyl-4-(2-(tetrahydro-2H-pyran-4-ylamino)-8-(2,4,6-trichlorophenylamino)-9H-purin-9-yl)cyclohexanecarboxamide; |
| 476 | (1r,4r)-4-(8-(2,6-dichloro-4-cyanophenylamino)-2-(tetrahydro-2H-pyran-4-ylamino)-9H-purin-9-yl)-1-methylcyclohexanecarboxamide; |
| 477 | (1r,4r)-4-(8-(2,6-dichloro-4-fluorophenylamino)-2-(4,4-difluorocyclohexylamino)-9H-purin-9-yl)-1-methylcyclohexanecarboxamide; |
| 478 | (1r,4r)-4-(8-(2-chloro-4,6-difluorophenylamino)-2-(4,4-difluorocyclohexylamino)-9H-purin-9-yl)-1-methylcyclohexanecarboxamide; |
| 479 | (1r,4r)-4-(8-(2,4-dichloro-6-fluorophenylamino)-2-(4,4-difluorocyclohexylamino)-9H-purin-9-yl)-1-methylcyclohexanecarboxamide; |
| 480 | (1r,4r)-4-(8-(2,6-dichloro-4-cyanophenylamino)-2-(4,4-difluorocyclohexylamino)-9H-purin-9-yl)-1-methylcyclohexanecarboxamide; |
| 481 | (1S,4r)-4-(8-(2,6-dichloro-4-(trifluoromethyl)phenylamino)-2-((S)-1-hydroxypropan-2-ylamino)-9H-purin-9-yl)-1-methylcyclohexanecarboxamide; |
| 482 | (1S,4r)-4-(2-((S)-1-hydroxypropan-2-ylamino)-8-(2,4,6-trichlorophenylamino)-9H-purin-9-yl)-1-methylcyclohexanecarboxamide; |
| 483 | (1s,4s)-4-(8-(2,6-dichloro-4-cyanophenylamino)-2-(3-hydroxy-2,2-dimethylpropylamino)-9H-purin-9-yl)cyclohexanecarboxamide; |
| 484 | (1s,4s)-4-(2-((1R,2S)-2-hydroxycyclohexylamino)-8-(2,4,6-trichlorophenylamino)-9H-purin-9-yl)cyclohexanecarboxamide; |
| 485 | (1R,4r)-4-(8-(2,4-dichloro-6-fluorophenylamino)-2-((1R,3S)-3-hydroxycyclohexylamino)-9H-purin-9-yl)-1-methylcyclohexanecarboxamide; |
| 486 | (1r,4r)-4-(2-(cyclopentylamino)-8-(2,6-dichloro-4-cyanophenylamino)-9H-purin-9-yl)-1-methylcyclohexanecarboxamide; |
| 487 | (1r,4r)-4-(8-(2-chloro-4-cyano-6-fluorophenylamino)-2-(cyclopentylamino)-9H-purin-9-yl)-1-methylcyclohexanecarboxamide; |
| 488 | (1r,4r)-4-(8-(4-cyano-2,6-difluorophenylamino)-2-(cyclopentylamino)-9H-purin-9-yl)-1-methylcyclohexanecarboxamide; |
| 489 | (1r,4r)-4-(2-(cyclopentylamino)-8-(2,6-dichloro-4-(trifluoromethyl)phenylamino)-9H-purin-9-yl)-1-methylcyclohexanecarboxamide; |
| 490 | (1r,4r)-4-(8-(4-chloro-2,6-difluorophenylamino)-2-(cyclopentylamino)-9H-purin-9-yl)-1-methylcyclohexanecarboxamide; |
| 491 | (1r,4r)-4-(2-(cyclopentylamino)-8-(2,4,6-trichlorophenylamino)-9H-purin-9-yl)-1-methylcyclohexanecarboxamide; |
| 492 | (1r,4r)-4-(8-(2-chloro-4,6-difluorophenylamino)-2-(cyclopentylamino)-9H-purin-9-yl)-1-methylcyclohexanecarboxamide; |

TABLE 1-continued

Representative compounds of formula (I).

| Compound | Compound Name |
|---|---|
| 493 | (1r,4r)-4-(2-(cyclopentylamino)-8-(2,4-dichloro-6-fluorophenylamino)-9H-purin-9-yl)-1-methylcyclohexanecarboxamide; |
| 494 | (1r,4r)-4-(2-(cyclopentylamino)-8-(2,6-dichloro-4-fluorophenylamino)-9H-purin-9-yl)-1-methylcyclohexanecarboxamide; |
| 495 | (1r,4r)-4-(2-(cyclopentylamino)-8-(2,4,6-trifluorophenylamino)-9H-purin-9-yl)-1-methylcyclohexanecarboxamide; |
| 496 | (1s,4s)-4-(8-(2,6-dichloro-4-cyanophenylamino)-2-((3S,4R)-3-methyltetrahydro-2H-pyran-4-ylamino)-9H-purin-9-yl)cyclohexanecarboxamide; |
| 497 | (1r,4s)-4-(8-(2,6-dichloro-4-cyanophenylamino)-2-((3R,4S)-3-methyltetrahydro-2H-pyran-4-ylamino)-9H-purin-9-yl)cyclohexanecarboxamide; |
| 498 | (1s,4s)-4-(8-(2,6-dichloro-4-cyanophenylamino)-2-((3R,4R)-3-methyltetrahydro-2H-pyran-4-ylamino)-9H-purin-9-yl)cyclohexanecarboxamide; |
| 499 | (1r,4s)-4-(8-(2,6-dichloro-4-cyanophenylamino)-2-((3S,4S)-3-methyltetrahydro-2H-pyran-4-ylamino)-9H-purin-9-yl)cyclohexanecarboxamide; |
| 500 | (1s,4s)-4-(2-((3S,4R)-3-methyltetrahydro-2H-pyran-4-ylamino)-8-(2,4,6-trichlorophenylamino)-9H-purin-9-yl)cyclohexanecarboxamide; |
| 501 | (1r,4s)-4-(2-((3R,4S)-3-methyltetrahydro-2H-pyran-4-ylamino)-8-(2,4,6-trichlorophenylamino)-9H-purin-9-yl)cyclohexanecarboxamide; |
| 502 | (1s,4s)-4-(2-((3R,4R)-3-methyltetrahydro-2H-pyran-4-ylamino)-8-(2,4,6-trichlorophenylamino)-9H-purin-9-yl)cyclohexanecarboxamide; |
| 503 | (1r,4s)-4-(2-((3S,4S)-3-methyltetrahydro-2H-pyran-4-ylamino)-8-(2,4,6-trichlorophenylamino)-9H-purin-9-yl)cyclohexanecarboxamide; |
| 504 | (1s,4s)-4-(8-(2,4-dichloro-6-fluorophenylamino)-2-((3S,4R)-3-methyltetrahydro-2H-pyran-4-ylamino)-9H-purin-9-yl)cyclohexanecarboxamide; |
| 505 | (1r,4s)-4-(8-(2,4-dichloro-6-fluorophenylamino)-2-((3R,4S)-3-methyltetrahydro-2H-pyran-4-ylamino)-9H-purin-9-yl)cyclohexanecarboxamide; |
| 506 | (1s,4s)-4-(8-(2,4-dichloro-6-fluorophenylamino)-2-((3R,4R)-3-methyltetrahydro-2H-pyran-4-ylamino)-9H-purin-9-yl)cyclohexanecarboxamide; |
| 507 | (1r,4s)-4-(8-(2,4-dichloro-6-fluorophenylamino)-2-((3S,4S)-3-methyltetrahydro-2H-pyran-4-ylamino)-9H-purin-9-yl)cyclohexanecarboxamide; |
| 508 | (1r,4s)-4-(8-(4-chloro-2,6-difluorophenylamino)-2-((3R,4S)-3-methyltetrahydro-2H-pyran-4-ylamino)-9H-purin-9-yl)cyclohexanecarboxamide; |
| 509 | (1s,4s)-4-(8-(4-chloro-2,6-difluorophenylamino)-2-((3R,4R)-3-methyltetrahydro-2H-pyran-4-ylamino)-9H-purin-9-yl)cyclohexanecarboxamide; |
| 510 | (1r,4s)-4-(8-(4-chloro-2,6-difluorophenylamino)-2-((3S,4S)-3-methyltetrahydro-2H-pyran-4-ylamino)-9H-purin-9-yl)cyclohexanecarboxamide; |
| 511 | (1r,4s)-4-(2-((3R,4S)-3-methyltetrahydro-2H-pyran-4-ylamino)-8-(2,4,6-trifluorophenylamino)-9H-purin-9-yl)cyclohexanecarboxamide; |
| 512 | (1r,4s)-4-(2-((3S,4S)-3-methyltetrahydro-2H-pyran-4-ylamino)-8-(2,4,6-trifluorophenylamino)-9H-purin-9-yl)cyclohexanecarboxamide; |
| 513 | (1r,4s)-4-(2-((1S,2R)-2-hydroxycyclohexylamino)-8-(2,4,6-trifluorophenylamino)-9H-purin-9-yl)cyclohexanecarboxamide; |
| 514 | (1r,4s)-4-(8-(2,4-dichloro-6-fluorophenylamino)-2-((1S,2R)-2-hydroxycyclohexylamino)-9H-purin-9-yl)cyclohexanecarboxamide; |
| 515 | (1r,4s)-4-(2-((1S,2R)-2-hydroxycyclohexylamino)-8-(2,4,6-trichlorophenylamino)-9H-purin-9-yl)cyclohexanecarboxamide; |
| 516 | (1r,4s)-4-(8-(4-chloro-2,6-difluorophenylamino)-2-((1S,2R)-2-hydroxycyclohexylamino)-9H-purin-9-yl)cyclohexanecarboxamide; |
| 517 | (1r,4s)-4-(8-(2,6-dichloro-4-fluorophenylamino)-2-((1S,2R)-2-hydroxycyclohexylamino)-9H-purin-9-yl)cyclohexanecarboxamide; |
| 518 | (1r,4s)-4-(8-(2-chloro-4-cyano-6-fluorophenylamino)-2-((1S,2R)-2-hydroxycyclohexylamino)-9H-purin-9-yl)cyclohexanecarboxamide; |
| 519 | (1s,4s)-4-(8-(2,6-dichloro-4-cyanophenylamino)-2-((R)-tetrahydrofuran-3-ylamino)-9H-purin-9-yl)cyclohexanecarboxamide; |
| 520 | (1r,4s)-4-(8-(2,6-dichloro-4-cyanophenylamino)-2-((1S,2R)-2-hydroxycyclohexylamino)-9H-purin-9-yl)cyclohexanecarboxamide; |
| 521 | (1s,4s)-4-(8-(2-chloro-4-cyano-6-fluorophenylamino)-2-((R)-tetrahydrofuran-3-ylamino)-9H-purin-9-yl)cyclohexanecarboxamide; |
| 522 | (1s,4s)-4-(8-(4-chloro-2,6-difluorophenylamino)-2-(tetrahydro-2H-pyran-4-ylamino)-9H-purin-9-yl)-1-methylcyclohexanecarboxamide; |
| 523 | (1s,4s)-1-methyl-4-(2-(tetrahydro-2H-pyran-4-ylamino)-8-(2,4,6-trichlorophenylamino)-9H-purin-9-yl)cyclohexanecarboxamide; |
| 524 | (1s,4s)-4-(8-(2,6-dichloro-4-(trifluoromethyl)phenylamino)-2-((R)-tetrahydrofuran-3-ylamino)-9H-purin-9-yl)cyclohexanecarboxamide; |
| 525 | (1s,4s)-4-(8-(4-cyano-2,6-difluorophenylamino)-2-(tetrahydro-2H-pyran-4-ylamino)-9H-purin-9-yl)-1-methylcyclohexanecarboxamide; |
| 526 | (1s,4s)-4-(8-(2-chloro-4-cyano-6-fluorophenylamino)-2-(tetrahydro-2H-pyran-4-ylamino)-9H-purin-9-yl)-1-methylcyclohexanecarboxamide; |
| 527 | (1s,4s)-4-(8-(2,6-dichloro-4-fluorophenylamino)-2-(4,4-difluorocyclohexylamino)-9H-purin-9-yl)-1-methylcyclohexanecarboxamide; |
| 528 | (1s,4s)-4-(8-(2-chloro-4,6-difluorophenylamino)-2-(4,4-difluorocyclohexylamino)-9H-purin-9-yl)-1-methylcyclohexanecarboxamide; |
| 529 | (1s,4s)-4-(8-(2,4-dichloro-6-fluorophenylamino)-2-(4,4-difluorocyclohexylamino)-9H-purin-9-yl)-1-methylcyclohexanecarboxamide; |
| 530 | (1s,4s)-4-(8-(4-cyano-2,6-difluorophenylamino)-2-((R)-tetrahydrofuran-3-ylamino)-9H-purin-9-yl)cyclohexanecarboxamide; |

TABLE 1-continued

Representative compounds of formula (I).

| Compound | Compound Name |
|---|---|
| 531 | (1s,4s)-4-(2-((R)-tetrahydrofuran-3-ylamino)-8-(2,4,6-trifluorophenylamino)-9H-purin-9-yl)cyclohexanecarboxamide; |
| 532 | (1s,4s)-4-(2-(1-morpholinopropan-2-ylamino)-8-(2,4,6-trichlorophenylamino)-9H-purin-9-yl)cyclohexanecarboxamide; |
| 533 | (1s,4s)-4-(8-(4-chloro-2,6-difluorophenylamino)-2-((3S,4R)-3-methyltetrahydro-2H-pyran-4-ylamino)-9H-purin-9-yl)cyclohexanecarboxamide; |
| 534 | (1s,4s)-4-(2-((3S,4R)-3-methyltetrahydro-2H-pyran-4-ylamino)-8-(2,4,6-trifluorophenylamino)-9H-purin-9-yl)cyclohexanecarboxamide; |
| 535 | (1s,4s)-4-(8-(2,6-dichloro-4-cyanophenylamino)-2-(4,4-difluorocyclohexylamino)-9H-purin-9-yl)-1-methylcyclohexanecarboxamide; |
| 536 | (1s,4s)-4-(8-(2,6-dichloro-4-cyanophenylamino)-2-(tetrahydro-2H-pyran-4-ylamino)-9H-purin-9-yl)-1-methylcyclohexanecarboxamide; |
| 537 | (1s,4s)-4-(2-(oxepan-4-ylamino)-8-(2,4,6-trifluorophenylamino)-9H-purin-9-yl)cyclohexanecarboxamide; |
| 538 | (1s,4s)-4-(8-(2,4-dichloro-6-fluorophenylamino)-2-(oxepan-4-ylamino)-9H-purin-9-yl)cyclohexanecarboxamide; |
| 539 | (1s,4s)-4-(8-(2-chloro-4,6-difluorophenylamino)-2-(oxepan-4-ylamino)-9H-purin-9-yl)cyclohexanecarboxamide; |
| 540 | (1s,4s)-4-(2-(oxepan-4-ylamino)-8-(2,4,6-trichlorophenylamino)-9H-purin-9-yl)cyclohexanecarboxamide; |
| 541 | (1s,4s)-4-(8-(4-chloro-2,6-difluorophenylamino)-2-(oxepan-4-ylamino)-9H-purin-9-yl)cyclohexanecarboxamide; |
| 542 | (1s,4s)-4-(8-(2,6-dichloro-4-fluorophenylamino)-2-(oxepan-4-ylamino)-9H-purin-9-yl)cyclohexanecarboxamide; |
| 543 | (1s,4s)-4-(8-(4-cyano-2,6-difluorophenylamino)-2-(oxepan-4-ylamino)-9H-purin-9-yl)cyclohexanecarboxamide; |
| 544 | (1s,4s)-4-(8-(2-chloro-4-cyano-6-fluorophenylamino)-2-(oxepan-4-ylamino)-9H-purin-9-yl)cyclohexanecarboxamide; |
| 545 | (1s,4s)-4-(8-(2,6-dichloro-4-(trifluoromethyl)phenylamino)-2-(oxepan-4-ylamino)-9H-purin-9-yl)cyclohexanecarboxamide; |
| 546 | (1s,4s)-4-(2-((R)-3,3-difluorocyclopentylamino)-8-(2,4,6-trifluorophenylamino)-9H-purin-9-yl)cyclohexanecarboxamide; |
| 547 | (1r,4s)-4-(2-((S)-1-hydroxypropan-2-ylamino)-8-(2,4,6-trifluorophenylamino)-9H-purin-9-yl)-1-methylcyclohexanecarboxamide; |
| 548 | (1r,4s)-4-(8-(2,4-dichloro-6-fluorophenylamino)-2-((S)-1-hydroxypropan-2-ylamino)-9H-purin-9-yl)-1-methylcyclohexanecarboxamide; |
| 549 | (1r,4s)-4-(8-(2-chloro-4,6-difluorophenylamino)-2-((S)-1-hydroxypropan-2-ylamino)-9H-purin-9-yl)-1-methylcyclohexanecarboxamide; |
| 550 | (1r,4s)-4-(2-((S)-1-hydroxypropan-2-ylamino)-8-(2,4,6-trichlorophenylamino)-9H-purin-9-yl)-1-methylcyclohexanecarboxamide; |
| 551 | (1r,4s)-4-(8-(4-chloro-2,6-difluorophenylamino)-2-((S)-1-hydroxypropan-2-ylamino)-9H-purin-9-yl)-1-methylcyclohexanecarboxamide; |
| 552 | (1r,4s)-4-(8-(2,6-dichloro-4-fluorophenylamino)-2-((S)-1-hydroxypropan-2-ylamino)-9H-purin-9-yl)-1-methylcyclohexanecarboxamide; |
| 553 | (1r,4s)-4-(8-(2-chloro-4-cyano-6-fluorophenylamino)-2-((S)-1-hydroxypropan-2-ylamino)-9H-purin-9-yl)-1-methylcyclohexanecarboxamide; |
| 554 | (1r,4s)-4-(8-(2,6-dichloro-4-cyanophenylamino)-2-((S)-1-hydroxypropan-2-ylamino)-9H-purin-9-yl)-1-methylcyclohexanecarboxamide; |
| 555 | (1r,4s)-4-(8-(2,6-dichloro-4-(trifluoromethyl)phenylamino)-2-((S)-1-hydroxypropan-2-ylamino)-9H-purin-9-yl)-1-methylcyclohexanecarboxamide; |
| 556 | (1s,4s)-4-(8-(2,6-dichloro-4-cyanophenylamino)-2-(oxepan-4-ylamino)-9H-purin-9-yl)cyclohexanecarboxamide; |
| 557 | (1s,4s)-4-(2-(cyclopentylamino)-8-(2,4,6-trifluorophenylamino)-9H-purin-9-yl)-1-methylcyclohexanecarboxamide; |
| 558 | (1s,4s)-4-(2-(cyclopentylamino)-8-(2,4-dichloro-6-fluorophenylamino)-9H-purin-9-yl)-1-methylcyclohexanecarboxamide; |
| 559 | (1s,4s)-4-(8-(2-chloro-4,6-difluorophenylamino)-2-(cyclopentylamino)-9H-purin-9-yl)-1-methylcyclohexanecarboxamide; |
| 560 | (1s,4s)-4-(8-(4-chloro-2,6-difluorophenylamino)-2-(cyclopentylamino)-9H-purin-9-yl)-1-methylcyclohexanecarboxamide; |
| 561 | (1s,4s)-4-(2-(cyclopentylamino)-8-(2,6-dichloro-4-fluorophenylamino)-9H-purin-9-yl)-1-methylcyclohexanecarboxamide; |
| 562 | (1s,4s)-4-(2-(cyclopentylamino)-8-(2,6-dichloro-4-cyanophenylamino)-9H-purin-9-yl)-1-methylcyclohexanecarboxamide; |
| 563 | (1s,4s)-4-(2-(cyclopentylamino)-8-(2,6-dichloro-4-(trifluoromethyl)phenylamino)-9H-purin-9-yl)-1-methylcyclohexanecarboxamide; |
| 564 | (1s,4s)-4-(2-((1R,3S)-3-hydroxycyclohexylamino)-8-(2,4,6-trifluorophenylamino)-9H-purin-9-yl)-1-methylcyclohexanecarboxamide; |
| 565 | (1s,4s)-4-(8-(2,4-dichloro-6-fluorophenylamino)-2-((1R,3S)-3-hydroxycyclohexylamino)-9H-purin-9-yl)-1-methylcyclohexanecarboxamide; |
| 566 | (1s,4s)-4-(2-((1R,3S)-3-hydroxycyclohexylamino)-8-(2,4,6-trichlorophenylamino)-9H-purin-9-yl)-1-methylcyclohexanecarboxamide; |
| 567 | (1s,4s)-4-(8-(4-chloro-2,6-difluorophenylamino)-2-((1R,3S)-3-hydroxycyclohexylamino)-9H-purin-9-yl)-1-methylcyclohexanecarboxamide; |
| 568 | (1s,4s)-4-(8-(2,6-dichloro-4-fluorophenylamino)-2-((1R,3S)-3-hydroxycyclohexylamino)-9H-purin-9-yl)-1-methylcyclohexanecarboxamide; |

TABLE 1-continued

Representative compounds of formula (I).

| Compound | Compound Name |
|---|---|
| 569 | (1s,4s)-4-(8-(2-chloro-4-cyano-6-fluorophenylamino)-2-((1R,3S)-3-hydroxycyclohexylamino)-9H-purin-9-yl)-1-methylcyclohexanecarboxamide; |
| 570 | (1s,4s)-4-(8-(2,6-dichloro-4-cyanophenylamino)-2-((1R,3S)-3-hydroxycyclohexylamino)-9H-purin-9-yl)-1-methylcyclohexanecarboxamide; |
| 571 | (1s,4s)-4-(2-(2-oxaspiro[3.3]heptan-6-ylamino)-8-(2,6-dichloro-4-(trifluoromethyl)phenylamino)-9H-purin-9-yl)cyclohexanecarboxamide; |
| 572 | (1s,4s)-4-(2-(2-oxaspiro[3.3]heptan-6-ylamino)-8-(2,6-dichloro-4-cyanophenylamino)-9H-purin-9-yl)cyclohexanecarboxamide; |
| 573 | (1s,4s)-4-(2-(2-oxaspiro[3.3]heptan-6-ylamino)-8-(2-chloro-4-cyano-6-fluorophenylamino)-9H-purin-9-yl)cyclohexanecarboxamide; |
| 574 | (1s,4s)-4-(2-(2-oxaspiro[3.3]heptan-6-ylamino)-8-(4-cyano-2,6-difluorophenylamino)-9H-purin-9-yl)cyclohexanecarboxamide; |
| 575 | (1s,4s)-4-(2-(cyclopentylamino)-8-(2,4,6-trichlorophenylamino)-9H-purin-9-yl)-1-methylcyclohexanecarboxamide; |
| 576 | (1s,4s)-4-(8-(2-chloro-4-cyano-6-fluorophenylamino)-2-(cyclopentylamino)-9H-purin-9-yl)-1-methylcyclohexanecarboxamide; |
| 577 | (1s,4s)-4-(8-(2-chloro-4,6-difluorophenylamino)-2-((1R,3S)-3-hydroxycyclohexylamino)-9H-purin-9-yl)-1-methylcyclohexanecarboxamide; |
| 578 | (1s,4s)-4-(8-(2,6-dichloro-4-(trifluoromethyl)phenylamino)-2-((1R,3S)-3-hydroxycyclohexylamino)-9H-purin-9-yl)-1-methylcyclohexanecarboxamide; |
| 579 | (1s,4s)-4-(2-(3,3-difluorocyclobutylamino)-8-(2,4,6-trifluorophenylamino)-9H-purin-9-yl)-1-methylcyclohexanecarboxamide; |
| 580 | (1s,4s)-4-(8-(2-chloro-4,6-difluorophenylamino)-2-(3,3-difluorocyclobutylamino)-9H-purin-9-yl)-1-methylcyclohexanecarboxamide; |
| 581 | (1s,4s)-4-(2-(3,3-difluorocyclobutylamino)-8-(2,4,6-trichlorophenylamino)-9H-purin-9-yl)-1-methylcyclohexanecarboxamide; |
| 582 | (1s,4s)-4-(8-(4-chloro-2,6-difluorophenylamino)-2-(3,3-difluorocyclobutylamino)-9H-purin-9-yl)-1-methylcyclohexanecarboxamide; |
| 583 | (1s,4s)-4-(8-(2,6-dichloro-4-fluorophenylamino)-2-(3,3-difluorocyclobutylamino)-9H-purin-9-yl)-1-methylcyclohexanecarboxamide; |
| 584 | (1s,4s)-4-(8-(2-chloro-4-cyano-6-fluorophenylamino)-2-(3,3-difluorocyclobutylamino)-9H-purin-9-yl)-1-methylcyclohexanecarboxamide; |
| 585 | (1s,4s)-4-(8-(2,6-dichloro-4-(trifluoromethyl)phenylamino)-2-(3,3-difluorocyclobutylamino)-9H-purin-9-yl)-1-methylcyclohexanecarboxamide; |
| 586 | (1r,4s)-4-(8-(2,6-dichloro-4-fluorophenylamino)-2-((S)-3,3-difluorocyclopentylamino)-9H-purin-9-yl)cyclohexanecarboxamide; |
| 587 | (1s,4s)-4-(8-(2,6-dichloro-4-fluorophenylamino)-2-((R)-3,3-difluorocyclopentylamino)-9H-purin-9-yl)cyclohexanecarboxamide; |
| 588 | (1r,4s)-4-(8-(4-chloro-2,6-difluorophenylamino)-2-((S)-3,3-difluorocyclopentylamino)-9H-purin-9-yl)cyclohexanecarboxamide; |
| 589 | (1s,4s)-4-(8-(4-chloro-2,6-difluorophenylamino)-2-((R)-3,3-difluorocyclopentylamino)-9H-purin-9-yl)cyclohexanecarboxamide; |
| 590 | (1r,4s)-4-(8-(2-chloro-4,6-difluorophenylamino)-2-((S)-3,3-difluorocyclopentylamino)-9H-purin-9-yl)cyclohexanecarboxamide; |
| 591 | (1s,4s)-4-(8-(2-chloro-4,6-difluorophenylamino)-2-((R)-3,3-difluorocyclopentylamino)-9H-purin-9-yl)cyclohexanecarboxamide; |
| 592 | (1r,4s)-4-(8-(2,4-dichloro-6-fluorophenylamino)-2-((S)-3,3-difluorocyclopentylamino)-9H-purin-9-yl)cyclohexanecarboxamide; |
| 593 | (1s,4s)-4-(8-(2,4-dichloro-6-fluorophenylamino)-2-((R)-3,3-difluorocyclopentylamino)-9H-purin-9-yl)cyclohexanecarboxamide; |
| 594 | (1r,4s)-4-(2-((S)-3,3-difluorocyclopentylamino)-8-(2,4,6-trifluorophenylamino)-9H-purin-9-yl)cyclohexanecarboxamide; |
| 595 | (1r,4s)-4-(2-((S)-3,3-difluorocyclopentylamino)-8-(2,4,6-trichlorophenylamino)-9H-purin-9-yl)cyclohexanecarboxamide; |
| 596 | (1s,4s)-4-(8-(2,6-dichloro-4-(trifluoromethoxy)phenylamino)-2-((1R,3S)-3-hydroxycyclohexylamino)-9H-purin-9-yl)cyclohexanecarboxamide; |
| 597 | (1s,4s)-4-(8-(2,6-dichloro-4-(trifluoromethoxy)phenylamino)-2-(4,4-difluorocyclohexylamino)-9H-purin-9-yl)cyclohexanecarboxamide; |
| 598 | (1s,4s)-4-(2-(cyclopentylamino)-8-(2,6-dichloro-4-(trifluoromethoxy)phenylamino)-9H-purin-9-yl)cyclohexanecarboxamide; |
| 599 | (1s,4s)-4-(2-(cyclobutylamino)-8-(2,6-dichloro-4-(trifluoromethoxy)phenylamino)-9H-purin-9-yl)-1-methylcyclohexanecarboxamide; |
| 600 | (1s,4s)-4-(2-(cyclobutylamino)-8-(2,6-dichloro-4-cyanophenylamino)-9H-purin-9-yl)-1-methylcyclohexanecarboxamide; |
| 601 | (1s,4s)-4-(8-(2-chloro-4-cyano-6-fluorophenylamino)-2-(cyclobutylamino)-9H-purin-9-yl)-1-methylcyclohexanecarboxamide; |
| 602 | (1s,4s)-4-(8-(4-cyano-2,6-difluorophenylamino)-2-(cyclobutylamino)-9H-purin-9-yl)-1-methylcyclohexanecarboxamide; |
| 603 | (1s,4s)-4-(2-(cyclobutylamino)-8-(2,6-dichloro-4-(trifluoromethyl)phenylamino)-9H-purin-9-yl)-1-methylcyclohexanecarboxamide; |
| 604 | (1s,4s)-4-(2-(cyclobutylamino)-8-(2,4,6-trichlorophenylamino)-9H-purin-9-yl)-1-methylcyclohexanecarboxamide; |
| 605 | (1s,4s)-4-(8-(2-chloro-4,6-difluorophenylamino)-2-(cyclobutylamino)-9H-purin-9-yl)-1-methylcyclohexanecarboxamide; |
| 606 | (1s,4s)-4-(2-(cyclobutylamino)-8-(2,4-dichloro-6-fluorophenylamino)-9H-purin-9-yl)-1-methylcyclohexanecarboxamide; |

TABLE 1-continued

Representative compounds of formula (I).

| Compound | Compound Name |
|---|---|
| 607 | (1s,4s)-4-(2-(cyclobutylamino)-8-(2,6-dichloro-4-fluorophenylamino)-9H-purin-9-yl)-1-methylcyclohexanecarboxamide; |
| 608 | (1s,4s)-4-(2-(cyclobutylamino)-8-(2,4,6-trifluorophenylamino)-9H-purin-9-yl)-1-methylcyclohexanecarboxamide; |
| 609 | (1s,4s)-4-(8-(4-chloro-2,6-difluorophenylamino)-2-(cyclobutylamino)-9H-purin-9-yl)-1-methylcyclohexanecarboxamide; |
| 610 | (1r,4s)-4-(2-((1S,3S)-3-hydroxycyclohexylamino)-8-(2,4,6-trifluorophenylamino)-9H-purin-9-yl)-1-methylcyclohexanecarboxamide; |
| 611 | (1r,4s)-4-(8-(2-chloro-4,6-difluorophenylamino)-2-((1S,3S)-3-hydroxycyclohexylamino)-9H-purin-9-yl)-1-methylcyclohexanecarboxamide; |
| 612 | (1r,4s)-4-(2-((1S,3S)-3-hydroxycyclohexylamino)-8-(2,4,6-trichlorophenylamino)-9H-purin-9-yl)-1-methylcyclohexanecarboxamide; |
| 613 | (1r,4s)-4-(8-(2,4-dichloro-6-fluorophenylamino)-2-((1S,3S)-3-hydroxycyclohexylamino)-9H-purin-9-yl)-1-methylcyclohexanecarboxamide; |
| 614 | (1r,4s)-4-(8-(2,6-dichloro-4-fluorophenylamino)-2-((1S,3S)-3-hydroxycyclohexylamino)-9H-purin-9-yl)-1-methylcyclohexanecarboxamide; |
| 615 | (1r,4s)-4-(8-(4-chloro-2,6-difluorophenylamino)-2-((1S,3S)-3-hydroxycyclohexylamino)-9H-purin-9-yl)-1-methylcyclohexanecarboxamide; |
| 616 | (1r,4s)-4-(8-(2-chloro-4-cyano-6-fluorophenylamino)-2-((1S,3S)-3-hydroxycyclohexylamino)-9H-purin-9-yl)-1-methylcyclohexanecarboxamide; |
| 617 | (1r,4s)-4-(8-(2,6-dichloro-4-cyanophenylamino)-2-((1S,3S)-3-hydroxycyclohexylamino)-9H-purin-9-yl)-1-methylcyclohexanecarboxamide; |
| 618 | (1s,4s)-4-(2-((1R,3R)-3-hydroxycyclohexylamino)-8-(2,4,6-trifluorophenylamino)-9H-purin-9-yl)-1-methylcyclohexanecarboxamide; |
| 619 | (1s,4s)-4-(8-(2-chloro-4,6-difluorophenylamino)-2-((1R,3R)-3-hydroxycyclohexylamino)-9H-purin-9-yl)-1-methylcyclohexanecarboxamide; |
| 620 | (1s,4s)-4-(2-((1R,3R)-3-hydroxycyclohexylamino)-8-(2,4,6-trichlorophenylamino)-9H-purin-9-yl)-1-methylcyclohexanecarboxamide; |
| 621 | (1s,4s)-4-(8-(2,4-dichloro-6-fluorophenylamino)-2-((1R,3R)-3-hydroxycyclohexylamino)-9H-purin-9-yl)-1-methylcyclohexanecarboxamide; |
| 622 | (1s,4s)-4-(8-(2,6-dichloro-4-fluorophenylamino)-2-((1R,3R)-3-hydroxycyclohexylamino)-9H-purin-9-yl)-1-methylcyclohexanecarboxamide; |
| 623 | (1s,4s)-4-(8-(4-chloro-2,6-difluorophenylamino)-2-((1R,3R)-3-hydroxycyclohexylamino)-9H-purin-9-yl)-1-methylcyclohexanecarboxamide; |
| 624 | (1s,4s)-4-(8-(2-chloro-4-cyano-6-fluorophenylamino)-2-((1R,3R)-3-hydroxycyclohexylamino)-9H-purin-9-yl)-1-methylcyclohexanecarboxamide; |
| 625 | (1s,4s)-4-(8-(2,6-dichloro-4-cyanophenylamino)-2-((1R,3R)-3-hydroxycyclohexylamino)-9H-purin-9-yl)-1-methylcyclohexanecarboxamide; |
| 626 | (1r,4s)-4-(2-((1S,3R)-3-hydroxycyclohexylamino)-8-(2,4,6-trifluorophenylamino)-9H-purin-9-yl)-1-methylcyclohexanecarboxamide; |
| 627 | (1r,4s)-4-(8-(2-chloro-4,6-difluorophenylamino)-2-((1S,3R)-3-hydroxycyclohexylamino)-9H-purin-9-yl)-1-methylcyclohexanecarboxamide; |
| 628 | (1r,4s)-4-(2-((1S,3R)-3-hydroxycyclohexylamino)-8-(2,4,6-trichlorophenylamino)-9H-purin-9-yl)-1-methylcyclohexanecarboxamide; |
| 629 | (1r,4s)-4-(8-(2,4-dichloro-6-fluorophenylamino)-2-((1S,3R)-3-hydroxycyclohexylamino)-9H-purin-9-yl)-1-methylcyclohexanecarboxamide; |
| 630 | (1s,4s)-4-(8-(2-chloro-4-cyano-6-fluorophenylamino)-2-((3S,4R)-3-fluorotetrahydro-2H-pyran-4-ylamino)-9H-purin-9-yl)cyclohexanecarboxamide; |
| 631 | (1s,4s)-4-(8-(2-chloro-4,6-difluorophenylamino)-2-((3S,4R)-3-fluorotetrahydro-2H-pyran-4-ylamino)-9H-purin-9-yl)cyclohexanecarboxamide; |
| 632 | (1r,4s)-4-(8-(2,6-dichloro-4-fluorophenylamino)-2-((1S,3R)-3-hydroxycyclohexylamino)-9H-purin-9-yl)-1-methylcyclohexanecarboxamide; |
| 633 | (1r,4s)-4-(8-(4-chloro-2,6-difluorophenylamino)-2-((1S,3R)-3-hydroxycyclohexylamino)-9H-purin-9-yl)-1-methylcyclohexanecarboxamide; |
| 634 | (1r,4s)-4-(8-(2-chloro-4-cyano-6-fluorophenylamino)-2-((1S,3R)-3-hydroxycyclohexylamino)-9H-purin-9-yl)-1-methylcyclohexanecarboxamide; |
| 635 | (1s,4s)-4-(2-((1R,3R)-3-hydroxycyclopentylamino)-8-(2,4,6-trifluorophenylamino)-9H-purin-9-yl)-1-methylcyclohexanecarboxamide; |
| 636 | (1s,4s)-4-(8-(2-chloro-4,6-difluorophenylamino)-2-((1R,3R)-3-hydroxycyclopentylamino)-9H-purin-9-yl)-1-methylcyclohexanecarboxamide; |
| 637 | (1s,4s)-4-(2-((1R,3R)-3-hydroxycyclopentylamino)-8-(2,4,6-trichlorophenylamino)-9H-purin-9-yl)-1-methylcyclohexanecarboxamide; |
| 638 | (1s,4s)-4-(8-(2,4-dichloro-6-fluorophenylamino)-2-((1R,3R)-3-hydroxycyclopentylamino)-9H-purin-9-yl)-1-methylcyclohexanecarboxamide; |
| 639 | (1s,4s)-4-(8-(2,6-dichloro-4-fluorophenylamino)-2-((1R,3R)-3-hydroxycyclopentylamino)-9H-purin-9-yl)-1-methylcyclohexanecarboxamide; |
| 640 | (1s,4s)-4-(8-(4-chloro-2,6-difluorophenylamino)-2-((1R,3R)-3-hydroxycyclopentylamino)-9H-purin-9-yl)-1-methylcyclohexanecarboxamide; |
| 641 | (1s,4s)-4-(8-(2-chloro-4-cyano-6-fluorophenylamino)-2-((1R,3R)-3-hydroxycyclopentylamino)-9H-purin-9-yl)-1-methylcyclohexanecarboxamide; |
| 642 | (1s,4s)-4-(8-(2,6-dichloro-4-cyanophenylamino)-2-((1R,3R)-3-hydroxycyclopentylamino)-9H-purin-9-yl)-1-methylcyclohexanecarboxamide; |
| 643 | (1s,4s)-4-(8-(4-cyano-2,6-difluorophenylamino)-2-((1R,3R)-3-hydroxycyclohexylamino)-9H-purin-9-yl)-1-methylcyclohexanecarboxamide; |
| 644 | (1r,4s)-4-(2-((1S,3S)-3-hydroxycyclopentylamino)-8-(2,4,6-trifluorophenylamino)-9H-purin-9-yl)-1-methylcyclohexanecarboxamide; |

TABLE 1-continued

Representative compounds of formula (I).

| Compound | Compound Name |
|---|---|
| 645 | (1r,4s)-4-(8-(2-chloro-4,6-difluorophenylamino)-2-((1S,3S)-3-hydroxycyclopentylamino)-9H-purin-9-yl)-1-methylcyclohexanecarboxamide; |
| 646 | (1r,4s)-4-(2-((1S,3S)-3-hydroxycyclopentylamino)-8-(2,4,6-trichlorophenylamino)-9H-purin-9-yl)-1-methylcyclohexanecarboxamide; |
| 647 | (1r,4s)-4-(8-(2,4-dichloro-6-fluorophenylamino)-2-((1S,3S)-3-hydroxycyclopentylamino)-9H-purin-9-yl)-1-methylcyclohexanecarboxamide; |
| 648 | (1r,4s)-4-(8-(2,6-dichloro-4-fluorophenylamino)-2-((1S,3S)-3-hydroxycyclopentylamino)-9H-purin-9-yl)-1-methylcyclohexanecarboxamide; |
| 649 | (1r,4s)-4-(8-(4-chloro-2,6-difluorophenylamino)-2-((1S,3S)-3-hydroxycyclopentylamino)-9H-purin-9-yl)-1-methylcyclohexanecarboxamide; |
| 650 | (1r,4s)-4-(8-(2-chloro-4-cyano-6-fluorophenylamino)-2-((1S,3S)-3-hydroxycyclopentylamino)-9H-purin-9-yl)-1-methylcyclohexanecarboxamide; |
| 651 | (1r,4s)-4-(8-(2,6-dichloro-4-cyanophenylamino)-2-((1S,3S)-3-hydroxycyclopentylamino)-9H-purin-9-yl)-1-methylcyclohexanecarboxamide; |
| 652 | (1s,4s)-4-(8-(2,4-dichloro-6-fluorophenylamino)-2-(3,3-difluorocyclobutylamino)-9H-purin-9-yl)-1-methylcyclohexanecarboxamide; |
| 653 | (1r,4s)-4-(2-(((1S,2S)-2-hydroxycyclohexyl)methylamino)-8-(2,4,6-trifluorophenylamino)-9H-purin-9-yl)cyclohexanecarboxamide; |
| 654 | (1r,4s)-4-(8-(2-chloro-4,6-difluorophenylamino)-2-(((1S,2S)-2-hydroxycyclohexyl)methylamino)-9H-purin-9-yl)cyclohexanecarboxamide; |
| 655 | (1r,4s)-4-(2-(((1S,2S)-2-hydroxycyclohexyl)methylamino)-8-(2,4,6-trichlorophenylamino)-9H-purin-9-yl)cyclohexanecarboxamide; |
| 656 | (1r,4s)-4-(8-(2,4-dichloro-6-fluorophenylamino)-2-(((1S,2S)-2-hydroxycyclohexyl)methylamino)-9H-purin-9-yl)cyclohexanecarboxamide; |
| 657 | (1r,4s)-4-(8-(2,6-dichloro-4-fluorophenylamino)-2-(((1S,2S)-2-hydroxycyclohexyl)methylamino)-9H-purin-9-yl)cyclohexanecarboxamide; |
| 658 | (1r,4s)-4-(8-(4-chloro-2,6-difluorophenylamino)-2-(((1S,2S)-2-hydroxycyclohexyl)methylamino)-9H-purin-9-yl)cyclohexanecarboxamide; |
| 659 | (1r,4s)-4-(8-(2-chloro-4-cyano-6-fluorophenylamino)-2-(((1S,2S)-2-hydroxycyclohexyl)methylamino)-9H-purin-9-yl)cyclohexanecarboxamide; |
| 660 | (1r,4s)-4-(8-(2,6-dichloro-4-cyanophenylamino)-2-(((1S,2S)-2-hydroxycyclohexyl)methylamino)-9H-purin-9-yl)cyclohexanecarboxamide; |
| 661 | (1r,4s)-4-(8-(2-chloro-4,6-difluorophenylamino)-2-(((1S,2R)-2-hydroxycyclohexyl)methylamino)-9H-purin-9-yl)cyclohexanecarboxamide; |
| 662 | (1r,4s)-4-(2-(((1S,2R)-2-hydroxycyclohexyl)methylamino)-8-(2,4,6-trichlorophenylamino)-9H-purin-9-yl)cyclohexanecarboxamide; |
| 663 | (1r,4s)-4-(8-(2,4-dichloro-6-fluorophenylamino)-2-(((1S,2R)-2-hydroxycyclohexyl)methylamino)-9H-purin-9-yl)cyclohexanecarboxamide; |
| 664 | (1r,4s)-4-(8-(4-chloro-2,6-difluorophenylamino)-2-(((1S,2R)-2-hydroxycyclohexyl)methylamino)-9H-purin-9-yl)cyclohexanecarboxamide; |
| 665 | (1r,4s)-4-(8-(2-chloro-4-cyano-6-fluorophenylamino)-2-(((1S,2R)-2-hydroxycyclohexyl)methylamino)-9H-purin-9-yl)cyclohexanecarboxamide; |
| 666 | (1r,4s)-4-(8-(2,6-dichloro-4-cyanophenylamino)-2-(((1S,2R)-2-hydroxycyclohexyl)methylamino)-9H-purin-9-yl)cyclohexanecarboxamide; |
| 667 | (1s,4s)-4-(8-(2,6-dichloro-4-cyanophenylamino)-2-(3,3-difluorocyclobutylamino)-9H-purin-9-yl)-1-methylcyclohexanecarboxamide; |
| 668 | (1s,4s)-4-(8-(2,4-dichloro-6-fluorophenylamino)-2-(4-(2,5-dioxopyrrolidin-1-yl)cyclohexylamino)-9H-purin-9-yl)cyclohexanecarboxamide; |
| 669 | (1s,4s)-4-(8-(2,6-dichloro-4-cyanophenylamino)-2-(4-(2,5-dioxopyrrolidin-1-yl)cyclohexylamino)-9H-purin-9-yl)cyclohexanecarboxamide; |
| 670 | (1r,4s)-4-(8-(4-cyano-2,6-difluorophenylamino)-2-((3S,4S)-3-fluorotetrahydro-2H-pyran-4-ylamino)-9H-purin-9-yl)cyclohexanecarboxamide; |
| 671 | (1r,4s)-4-(8-(2-chloro-4-cyano-6-fluorophenylamino)-2-((3S,4S)-3-fluorotetrahydro-2H-pyran-4-ylamino)-9H-purin-9-yl)cyclohexanecarboxamide; |
| 672 | (1s,4s)-4-(8-(4-chloro-2,6-difluorophenylamino)-2-((3S,4R)-3-fluorotetrahydro-2H-pyran-4-ylamino)-9H-purin-9-yl)cyclohexanecarboxamide; |
| 673 | (1r,4s)-4-(8-(4-chloro-2,6-difluorophenylamino)-2-((3S,4S)-3-fluorotetrahydro-2H-pyran-4-ylamino)-9H-purin-9-yl)cyclohexanecarboxamide; |
| 674 | (1s,4s)-4-(8-(2-chloro-4,6-difluorophenylamino)-2-(tetrahydro-2H-pyran-4-ylamino)-9H-purin-9-yl)-1-methylcyclohexanecarboxamide; |
| 675 | (1s,4s)-4-(8-(2,4-dichloro-6-fluorophenylamino)-2-(tetrahydro-2H-pyran-4-ylamino)-9H-purin-9-yl)-1-methylcyclohexanecarboxamide; |
| 676 | (1s,4s)-4-(8-(2,6-dichloro-4-fluorophenylamino)-2-(tetrahydro-2H-pyran-4-ylamino)-9H-purin-9-yl)-1-methylcyclohexanecarboxamide; |
| 677 | (1s,4s)-4-(2-(4-(1,2,4-oxadiazol-5-yl)cyclohexylamino)-8-(2,4-dichloro-6-fluorophenylamino)-9H-purin-9-yl)cyclohexanecarboxamide; |
| 678 | (1s,4s)-4-(2-(4-(1,2,4-oxadiazol-5-yl)cyclohexylamino)-8-(2-chloro-4,6-difluorophenylamino)-9H-purin-9-yl)cyclohexanecarboxamide; |
| 679 | (1s,4s)-4-(2-(4-(1,2,4-oxadiazol-5-yl)cyclohexylamino)-8-(2,4,6-trichlorophenylamino)-9H-purin-9-yl)cyclohexanecarboxamide; |
| 680 | (1s,4s)-4-(2-(4-(1,2,4-oxadiazol-5-yl)cyclohexylamino)-8-(2,6-dichloro-4-fluorophenylamino)-9H-purin-9-yl)cyclohexanecarboxamide; |
| 681 | (1s,4s)-4-(2-(4-(1,2,4-oxadiazol-5-yl)cyclohexylamino)-8-(2-chloro-4-cyano-6-fluorophenylamino)-9H-purin-9-yl)cyclohexanecarboxamide; |
| 682 | (1s,4s)-4-(2-(4-(1,2,4-oxadiazol-5-yl)cyclohexylamino)-8-(2,6-dichloro-4-cyanophenylamino)-9H-purin-9-yl)cyclohexanecarboxamide; |

TABLE 1-continued

Representative compounds of formula (I).

| Compound | Compound Name |
|---|---|
| 683 | (1s,4s)-4-(8-(2-chloro-4-cyano-6-fluorophenylamino)-2-((1R,3R)-3-hydroxycyclopentylamino)-9H-purin-9-yl)cyclohexanecarboxamide; |
| 684 | (1s,4s)-4-(8-(2,6-dichloro-4-cyanophenylamino)-2-((1R,3R)-3-hydroxycyclopentylamino)-9H-purin-9-yl)cyclohexanecarboxamide; |
| 685 | (1s,4s)-4-(8-(2,6-dichloro-4-cyanophenylamino)-2-((1R,3R)-3-hydroxycyclohexylamino)-9H-purin-9-yl)cyclohexanecarboxamide; |
| 686 | (1s,4s)-4-(8-(2-chloro-4-cyano-6-fluorophenylamino)-2-((1R,3R)-3-hydroxycyclohexylamino)-9H-purin-9-yl)cyclohexanecarboxamide; |
| 687 | (1r,4s)-4-(8-(2,6-dichloro-4-cyanophenylamino)-2-((1S,3R)-3-hydroxycyclohexylamino)-9H-purin-9-yl)cyclohexanecarboxamide; |
| 688 | (1r,4s)-4-(8-(2-chloro-4-cyano-6-fluorophenylamino)-2-((1S,3R)-3-hydroxycyclohexylamino)-9H-purin-9-yl)cyclohexanecarboxamide; |
| 689 | (1r,4s)-4-(8-(2,6-dichloro-4-cyanophenylamino)-2-((1S,3S)-3-hydroxycyclohexylamino)-9H-purin-9-yl)cyclohexanecarboxamide; |
| 690 | (1r,4s)-4-(8-(2-chloro-4-cyano-6-fluorophenylamino)-2-((1S,3S)-3-hydroxycyclohexylamino)-9H-purin-9-yl)cyclohexanecarboxamide; |
| 691 | (1s,4s)-4-(8-(4-bromo-2,6-dichlorophenylamino)-2-(tetrahydro-2H-pyran-4-ylamino)-9H-purin-9-yl)cyclohexanecarboxamide; |
| 692 | (1s,4s)-4-(8-(4-bromo-2,6-dichlorophenylamino)-2-(4,4-difluorocyclohexylamino)-9H-purin-9-yl)cyclohexanecarboxamide; |
| 693 | (1r,4s)-4-(8-(2-chloro-4,6-difluorophenylamino)-2-((3S,4S)-3-fluorotetrahydro-2H-pyran-4-ylamino)-9H-purin-9-yl)cyclohexanecarboxamide; |
| 694 | (1s,4s)-4-(2-(cyclopentylamino)-8-(2,3-dichloro-4-cyanophenylamino)-9H-purin-9-yl)cyclohexanecarboxamide; |
| 695 | (1r,4s)-4-(8-(2,3-dichloro-4-cyanophenylamino)-2-((S)-1-hydroxypropan-2-ylamino)-9H-purin-9-yl)cyclohexanecarboxamide; |
| 696 | (1s,4s)-4-(8-(2,3-dichloro-4-cyanophenylamino)-2-(4,4-difluorocyclohexylamino)-9H-purin-9-yl)cyclohexanecarboxamide; |
| 697 | (1s,4s)-4-(8-(2,3-dichloro-4-cyanophenylamino)-2-(tetrahydro-2H-pyran-4-ylamino)-9H-purin-9-yl)cyclohexanecarboxamide; |
| 698 | (1s,4s)-4-(8-(4-cyano-2,6-difluorophenylamino)-2-((R)-3,3-difluorocyclopentylamino)-9H-purin-9-yl)cyclohexanecarboxamide; |
| 699 | (1s,4s)-4-(8-(2-chloro-4-cyano-6-fluorophenylamino)-2-((R)-3,3-difluorocyclopentylamino)-9H-purin-9-yl)cyclohexanecarboxamide; |
| 700 | (1s,4s)-4-(8-(2,6-dichloro-4-cyanophenylamino)-2-((R)-3,3-difluorocyclopentylamino)-9H-purin-9-yl)cyclohexanecarboxamide; |
| 701 | (1s,4s)-4-(2-((R)-1-(methylsulfonyl)piperidin-3-ylamino)-8-(2,4,6-trichlorophenylamino)-9H-purin-9-yl)cyclohexanecarboxamide; |
| 702 | (1s,4s)-4-(8-(2,4-dichloro-6-fluorophenylamino)-2-((R)-1-(methylsulfonyl)piperidin-3-ylamino)-9H-purin-9-yl)cyclohexanecarboxamide; |
| 703 | (1s,4s)-4-(8-(2,6-dichloro-4-cyanophenylamino)-2-((R)-1-(methylsulfonyl)piperidin-3-ylamino)-9H-purin-9-yl)cyclohexanecarboxamide; |
| 704 | (1s,4s)-4-(8-(4-chloro-2,6-difluorophenylamino)-2-((R)-1-(methylsulfonyl)piperidin-3-ylamino)-9H-purin-9-yl)cyclohexanecarboxamide; |
| 705 | (1s,4s)-4-(8-(2-chloro-4-cyano-6-fluorophenylamino)-2-((R)-1-(methylsulfonyl)piperidin-3-ylamino)-9H-purin-9-yl)cyclohexanecarboxamide; |
| 706 | (R)-3-(9-((1s,4s)-4-carbamoylcyclohexyl)-8-(2,4,6-trichlorophenylamino)-9H-purin-2-ylamino)-N-methylpiperidine-1-carboxamide; |
| 707 | (R)-3-(9-((1s,4s)-4-carbamoylcyclohexyl)-8-(2,4-dichloro-6-fluorophenylamino)-9H-purin-2-ylamino)-N-methylpiperidine-1-carboxamide; |
| 708 | (R)-3-(9-((1s,4s)-4-carbamoylcyclohexyl)-8-(2,6-dichloro-4-cyanophenylamino)-9H-purin-2-ylamino)-N-methylpiperidine-1-carboxamide; |
| 709 | (R)-methyl 3-(9-((1s,4s)-4-carbamoylcyclohexyl)-8-(2,6-dichloro-4-cyanophenylamino)-9H-purin-2-ylamino)piperidine-1-carboxylate; |
| 710 | (R)-methyl 3-(9-((1s,4s)-4-carbamoylcyclohexyl)-8-(2-chloro-4-cyano-6-fluorophenylamino)-9H-purin-2-ylamino)piperidine-1-carboxylate; |
| 711 | (1s,4s)-4-(2-((R)-1-acetylpiperidin-3-ylamino)-8-(2,4,6-trichlorophenylamino)-9H-purin-9-yl)cyclohexanecarboxamide; |
| 712 | (1s,4s)-4-(2-((R)-1-acetylpiperidin-3-ylamino)-8-(2,4-dichloro-6-fluorophenylamino)-9H-purin-9-yl)cyclohexanecarboxamide; |
| 713 | (1s,4s)-4-(2-((R)-1-acetylpiperidin-3-ylamino)-8-(2,6-dichloro-4-cyanophenylamino)-9H-purin-9-yl)cyclohexanecarboxamide; |
| 714 | (1s,4s)-4-(2-((R)-1-acetylpiperidin-3-ylamino)-8-(4-chloro-2,6-difluorophenylamino)-9H-purin-9-yl)cyclohexanecarboxamide; |
| 715 | (1r,4s)-4-(8-(2,4-dichloro-6-fluorophenylamino)-2-((3S,4S)-3-fluorotetrahydro-2H-pyran-4-ylamino)-9H-purin-9-yl)cyclohexanecarboxamide; |
| 716 | (1s,4s)-4-(8-(2-chloro-4,6-difluorophenylamino)-2-((3S,4R)-3-fluorotetrahydro-2H-pyran-4-ylamino)-9H-purin-9-yl)-1-methylcyclohexanecarboxamide; |
| 717 | (1r,4s)-4-(8-(2,4-dichloro-6-fluorophenylamino)-2-((3S,4S)-3-fluorotetrahydro-2H-pyran-4-ylamino)-9H-purin-9-yl)-1-methylcyclohexanecarboxamide; |
| 718 | (1s,4s)-4-(8-(2,4-dichloro-6-fluorophenylamino)-2-((3S,4R)-3-methyltetrahydro-2H-pyran-4-ylamino)-9H-purin-9-yl)-1-methylcyclohexanecarboxamide; |
| 720 | (1r,4s)-4-(2-((3S,4S)-3-fluorotetrahydro-2H-pyran-4-ylamino)-8-(2,4,6-trichlorophenylamino)-9H-purin-9-yl)-1-methylcyclohexanecarboxamide; |
| 721 | (1s,4s)-4-(8-(4-chloro-2,6-difluorophenylamino)-2-((3S,4R)-3-fluorotetrahydro-2H-pyran-4-ylamino)-9H-purin-9-yl)-1-methylcyclohexanecarboxamide; |

TABLE 1-continued

Representative compounds of formula (I).

| Compound | Compound Name |
|---|---|
| 722 | (1r,4s)-4-(8-(4-chloro-2,6-difluorophenylamino)-2-((3S,4S)-3-fluorotetrahydro-2H-pyran-4-ylamino)-9H-purin-9-yl)-1-methylcyclohexanecarboxamide; |
| 723 | (1s,4s)-4-(8-(4-chloro-2,6-difluorophenylamino)-2-((3S,4R)-3-methyltetrahydro-2H-pyran-4-ylamino)-9H-purin-9-yl)-1-methylcyclohexanecarboxamide; |
| 724 | (1s,4s)-4-(8-(2-chloro-4,6-difluorophenylamino)-2-((3S,4R)-3-methyltetrahydro-2H-pyran-4-ylamino)-9H-purin-9-yl)cyclohexanecarboxamide; |
| 725 | (1r,4s)-4-(8-(2-chloro-4,6-difluorophenylamino)-2-((3S,4S)-3-fluorotetrahydro-2H-pyran-4-ylamino)-9H-purin-9-yl)-1-methylcyclohexanecarboxamide; |
| 726 | (1s,4s)-4-(8-(2-chloro-4,6-difluorophenylamino)-2-((3S,4R)-3-methyltetrahydro-2H-pyran-4-ylamino)-9H-purin-9-yl)-1-methylcyclohexanecarboxamide; |
| 727 | (1s,4s)-4-(8-(2,4-dichloro-6-fluorophenylamino)-2-((3S,4R)-3-fluorotetrahydro-2H-pyran-4-ylamino)-9H-purin-9-yl)-1-methylcyclohexanecarboxamide; |
| 728 | (1s,4s)-1-methyl-4-(2-((3S,4R)-3-methyltetrahydro-2H-pyran-4-ylamino)-8-(2,4,6-trichlorophenylamino)-9H-purin-9-yl)cyclohexanecarboxamide; |
| 729 | (1s,4s)-4-(8-(2,4-dichloro-6-fluorophenylamino)-2-((3S,4R)-3-fluorotetrahydro-2H-pyran-4-ylamino)-9H-purin-9-yl)cyclohexanecarboxamide; |
| 730 | (1s,4s)-4-(2-(3-(methylsulfonyl)cyclobutylamino)-8-(2,4,6-trichlorophenylamino)-9H-purin-9-yl)cyclohexanecarboxamide; |
| 731 | (1s,4s)-4-(8-(2,6-dichloro-4-cyanophenylamino)-2-(3-(methylsulfonyl)cyclobutylamino)-9H-purin-9-yl)cyclohexanecarboxamide; |
| 732 | (1s,4s)-4-(8-(2,4-dichloro-6-fluorophenylamino)-2-(3-(methylsulfonyl)cyclobutylamino)-9H-purin-9-yl)cyclohexanecarboxamide; |
| 733 | (1s,4s)-4-(2-((R)-1-ethylpiperidin-3-ylamino)-8-(2,4,6-trichlorophenylamino)-9H-purin-9-yl)cyclohexanecarboxamide; |
| 734 | (1s,4s)-4-(8-(2,6-dichloro-4-cyanophenylamino)-2-((R)-1-ethylpiperidin-3-ylamino)-9H-purin-9-yl)cyclohexanecarboxamide; |
| 735 | (1s,4s)-4-(8-(2,4-dichloro-6-fluorophenylamino)-2-((R)-1-ethylpiperidin-3-ylamino)-9H-purin-9-yl)cyclohexanecarboxamide; |
| 736 | (1s,4s)-4-(8-(2,6-dichloro-4-(trifluoromethyl)phenylamino)-2-(3-(methylsulfonyl)cyclobutylamino)-9H-purin-9-yl)cyclohexanecarboxamide; |
| 737 | (1s,4s)-4-(8-(4-chloro-2,6-difluorophenylamino)-2-(3-(methylsulfonyl)cyclobutylamino)-9H-purin-9-yl)cyclohexanecarboxamide; |
| 738 | (1s,4s)-4-(8-(2,6-dichloro-4-(trifluoromethyl)phenylamino)-2-((R)-1-ethylpiperidin-3-ylamino)-9H-purin-9-yl)cyclohexanecarboxamide; |
| 739 | (1s,4s)-4-(2-((R)-1-isopropylpiperidin-3-ylamino)-8-(2,4,6-trichlorophenylamino)-9H-purin-9-yl)cyclohexanecarboxamide; |
| 740 | (1s,4s)-4-(8-(2,6-dichloro-4-cyanophenylamino)-2-((R)-1-isopropylpiperidin-3-ylamino)-9H-purin-9-yl)cyclohexanecarboxamide; |
| 741 | (1s,4s)-4-(8-(4-chloro-2,6-difluorophenylamino)-2-((R)-1-isopropylpiperidin-3-ylamino)-9H-purin-9-yl)cyclohexanecarboxamide; |
| 742 | (1s,4s)-4-(8-(2,4-dichloro-6-fluorophenylamino)-2-((R)-1-isopropylpiperidin-3-ylamino)-9H-purin-9-yl)cyclohexanecarboxamide; |
| 743 | (1s,4s)-4-(8-(2-chloro-4,6-difluorophenylamino)-2-((R)-1-phenylpiperidin-3-ylamino)-9H-purin-9-yl)cyclohexanecarboxamide; |
| 744 | (1s,4s)-4-(2-((R)-1-phenylpiperidin-3-ylamino)-8-(2,4,6-trichlorophenylamino)-9H-purin-9-yl)cyclohexanecarboxamide; |
| 745 | (1s,4s)-4-(8-(2,6-dichloro-4-cyanophenylamino)-2-((R)-1-phenylpiperidin-3-ylamino)-9H-purin-9-yl)cyclohexanecarboxamide; |
| 746 | (1s,4s)-4-(8-(4-cyano-2,6-difluorophenylamino)-2-((R)-1-phenylpiperidin-3-ylamino)-9H-purin-9-yl)cyclohexanecarboxamide; |
| 747 | (1s,4s)-4-(2-((R)-1-phenylpiperidin-3-ylamino)-8-(2,4,6-trifluorophenylamino)-9H-purin-9-yl)cyclohexanecarboxamide; |
| 748 | (1s,4s)-4-(8-(4-chloro-2,6-difluorophenylamino)-2-((R)-1-phenylpiperidin-3-ylamino)-9H-purin-9-yl)cyclohexanecarboxamide; |
| 749 | (1s,4s)-4-(8-(2,4-dichloro-6-fluorophenylamino)-2-((R)-1-phenylpiperidin-3-ylamino)-9H-purin-9-yl)cyclohexanecarboxamide; |
| 750 | (1s,4s)-4-(8-(2,6-dichloro-4-fluorophenylamino)-2-((R)-1-phenylpiperidin-3-ylamino)-9H-purin-9-yl)cyclohexanecarboxamide; |
| 751 | (1s,4s)-4-(8-(2-chloro-4-cyano-6-fluorophenylamino)-2-((R)-1-phenylpiperidin-3-ylamino)-9H-purin-9-yl)cyclohexanecarboxamide; |
| 752 | (1s,4s)-4-(2-((R)-1-benzylpiperidin-3-ylamino)-8-(2-chloro-4,6-difluorophenylamino)-9H-purin-9-yl)cyclohexanecarboxamide; |
| 753 | (1s,4s)-4-(2-((R)-1-benzylpiperidin-3-ylamino)-8-(2,4,6-trichlorophenylamino)-9H-purin-9-yl)cyclohexanecarboxamide; |
| 754 | (1s,4s)-4-(2-((R)-1-benzylpiperidin-3-ylamino)-8-(2,6-dichloro-4-cyanophenylamino)-9H-purin-9-yl)cyclohexanecarboxamide; |
| 755 | (1s,4s)-4-(2-((R)-1-benzylpiperidin-3-ylamino)-8-(2,6-dichloro-4-(trifluoromethyl)phenylamino)-9H-purin-9-yl)cyclohexanecarboxamide; |
| 756 | (1s,4s)-4-(2-((R)-1-benzylpiperidin-3-ylamino)-8-(4-cyano-2,6-difluorophenylamino)-9H-purin-9-yl)cyclohexanecarboxamide; |
| 757 | (1s,4s)-4-(2-((R)-1-benzylpiperidin-3-ylamino)-8-(2,4,6-trifluorophenylamino)-9H-purin-9-yl)cyclohexanecarboxamide; |
| 758 | (1s,4s)-4-(2-((R)-1-benzylpiperidin-3-ylamino)-8-(4-chloro-2,6-difluorophenylamino)-9H-purin-9-yl)cyclohexanecarboxamide; |
| 759 | (1s,4s)-4-(2-((R)-1-benzylpiperidin-3-ylamino)-8-(2,4-dichloro-6-fluorophenylamino)-9H-purin-9-yl)cyclohexanecarboxamide; |

TABLE 1-continued

Representative compounds of formula (I).

| Compound | Compound Name |
|---|---|
| 760 | (1s,4s)-4-(2-((R)-1-benzylpiperidin-3-ylamino)-8-(2,6-dichloro-4-fluorophenylamino)-9H-purin-9-yl)cyclohexanecarboxamide; |
| 761 | (1s,4s)-4-(8-(2,6-dichloro-4-cyanophenylamino)-2-((3S,4R)-3-fluorotetrahydro-2H-pyran-4-ylamino)-9H-purin-9-yl)-1-methylcyclohexanecarboxamide; |
| 762 | (1r,4s)-4-(8-(2,6-dichloro-4-cyanophenylamino)-2-((3S,4S)-3-fluorotetrahydro-2H-pyran-4-ylamino)-9H-purin-9-yl)-1-methylcyclohexanecarboxamide; |
| 763 | (1s,4s)-4-(8-(2,6-dichloro-4-cyanophenylamino)-2-((3S,4R)-3-fluorotetrahydro-2H-pyran-4-ylamino)-9H-purin-9-yl)cyclohexanecarboxamide; |
| 764 | (1s,4s)-4-(8-(2,6-dichloro-4-cyanophenylamino)-2-((3S,4R)-3-methyltetrahydro-2H-pyran-4-ylamino)-9H-purin-9-yl)-1-methylcyclohexanecarboxamide; |
| 765 | (1s,4s)-4-(8-(2,4-dichloro-6-fluorophenylamino)-2-((R)-3,3-dimethyltetrahydro-2H-pyran-4-ylamino)-9H-purin-9-yl)cyclohexanecarboxamide; |
| 766 | (1r,4s)-4-(8-(2,6-dichloro-4-cyanophenylamino)-2-((3S,4S)-3-fluorotetrahydro-2H-pyran-4-ylamino)-9H-purin-9-yl)cyclohexanecarboxamide; |
| 767 | (1s,4s)-4-(2-((R)-3,3-dimethyltetrahydro-2H-pyran-4-ylamino)-8-(2,4,6-trichlorophenylamino)-9H-purin-9-yl)cyclohexanecarboxamide; |
| 768 | (R)-isopropyl 3-(9-((1s,4s)-4-carbamoylcyclohexyl)-8-(2-chloro-4,6-difluorophenylamino)-9H-purin-2-ylamino)piperidine-1-carboxylate; |
| 769 | (R)-isopropyl 3-(9-((1s,4s)-4-carbamoylcyclohexyl)-8-(2,4,6-trichlorophenylamino)-9H-purin-2-ylamino)piperidine-1-carboxylate; |
| 770 | (R)-isopropyl 3-(9-((1s,4s)-4-carbamoylcyclohexyl)-8-(2,6-dichloro-4-cyanophenylamino)-9H-purin-2-ylamino)piperidine-1-carboxylate; |
| 771 | (R)-isopropyl 3-(9-((1s,4s)-4-carbamoylcyclohexyl)-8-(2,6-dichloro-4-(trifluoromethyl)phenylamino)-9H-purin-2-ylamino)piperidine-1-carboxylate; |
| 772 | (R)-isopropyl 3-(9-((1s,4s)-4-carbamoylcyclohexyl)-8-(4-cyano-2,6-difluorophenylamino)-9H-purin-2-ylamino)piperidine-1-carboxylate; |
| 773 | (R)-isopropyl 3-(9-((1s,4s)-4-carbamoylcyclohexyl)-8-(2,4,6-trifluorophenylamino)-9H-purin-2-ylamino)piperidine-1-carboxylate; |
| 774 | (R)-isopropyl 3-(9-((1s,4s)-4-carbamoylcyclohexyl)-8-(4-chloro-2,6-difluorophenylamino)-9H-purin-2-ylamino)piperidine-1-carboxylate; |
| 775 | (R)-isopropyl 3-(9-((1s,4s)-4-carbamoylcyclohexyl)-8-(2,4-dichloro-6-fluorophenylamino)-9H-purin-2-ylamino)piperidine-1-carboxylate; |
| 776 | (R)-isopropyl 3-(9-((1s,4s)-4-carbamoylcyclohexyl)-8-(2,6-dichloro-4-fluorophenylamino)-9H-purin-2-ylamino)piperidine-1-carboxylate; |
| 777 | (R)-isopropyl 3-(9-((1s,4s)-4-carbamoylcyclohexyl)-8-(2-chloro-4-cyano-6-fluorophenylamino)-9H-purin-2-ylamino)piperidine-1-carboxylate; |
| 778 | (1s,4s)-4-(2-((R)-1-benzylpiperidin-3-ylamino)-8-(2-chloro-4-cyano-6-fluorophenylamino)-9H-purin-9-yl)cyclohexanecarboxamide; |
| 779 | (R)-3-(9-((1s,4s)-4-carbamoylcyclohexyl)-8-(2-chloro-4,6-difluorophenylamino)-9H-purin-2-ylamino)-N-phenylpiperidine-1-carboxamide; |
| 780 | (R)-3-(9-((1s,4s)-4-carbamoylcyclohexyl)-8-(2,4,6-trichlorophenylamino)-9H-purin-2-ylamino)-N-phenylpiperidine-1-carboxamide; |
| 781 | (R)-3-(9-((1s,4s)-4-carbamoylcyclohexyl)-8-(2,6-dichloro-4-cyanophenylamino)-9H-purin-2-ylamino)-N-phenylpiperidine-1-carboxamide; |
| 782 | (R)-3-(9-((1s,4s)-4-carbamoylcyclohexyl)-8-(2,4,6-trifluorophenylamino)-9H-purin-2-ylamino)-N-phenylpiperidine-1-carboxamide; |
| 783 | (R)-3-(9-((1s,4s)-4-carbamoylcyclohexyl)-8-(4-chloro-2,6-difluorophenylamino)-9H-purin-2-ylamino)-N-phenylpiperidine-1-carboxamide; |
| 784 | (R)-3-(9-((1s,4s)-4-carbamoylcyclohexyl)-8-(2,4-dichloro-6-fluorophenylamino)-9H-purin-2-ylamino)-N-phenylpiperidine-1-carboxamide; |
| 785 | (R)-3-(9-((1s,4s)-4-carbamoylcyclohexyl)-8-(2,6-dichloro-4-fluorophenylamino)-9H-purin-2-ylamino)-N-phenylpiperidine-1-carboxamide; |
| 786 | (R)-3-(9-((1s,4s)-4-carbamoylcyclohexyl)-8-(2-chloro-4-cyano-6-fluorophenylamino)-9H-purin-2-ylamino)-N-phenylpiperidine-1-carboxamide; |
| 787 | (1s,4s)-4-(8-(4-chloro-2,6-difluorophenylamino)-2-((R)-3,3-dimethyltetrahydro-2H-pyran-4-ylamino)-9H-purin-9-yl)cyclohexanecarboxamide; |
| 788 | (1s,4s)-4-(8-(2-chloro-4,6-difluorophenylamino)-2-((R)-1-tosylpiperidin-3-ylamino)-9H-purin-9-yl)cyclohexanecarboxamide; |
| 789 | (1s,4s)-4-(2-((R)-1-tosylpiperidin-3-ylamino)-8-(2,4,6-trichlorophenylamino)-9H-purin-9-yl)cyclohexanecarboxamide; |
| 790 | (1s,4s)-4-(8-(2,6-dichloro-4-cyanophenylamino)-2-((R)-1-tosylpiperidin-3-ylamino)-9H-purin-9-yl)cyclohexanecarboxamide; |
| 791 | (1s,4s)-4-(8-(4-cyano-2,6-difluorophenylamino)-2-((R)-1-tosylpiperidin-3-ylamino)-9H-purin-9-yl)cyclohexanecarboxamide; |
| 792 | (1s,4s)-4-(2-((R)-1-tosylpiperidin-3-ylamino)-8-(2,4,6-trifluorophenylamino)-9H-purin-9-yl)cyclohexanecarboxamide; |
| 793 | (1s,4s)-4-(8-(4-chloro-2,6-difluorophenylamino)-2-((R)-1-tosylpiperidin-3-ylamino)-9H-purin-9-yl)cyclohexanecarboxamide; |
| 794 | (1s,4s)-4-(8-(2,4-dichloro-6-fluorophenylamino)-2-((R)-1-tosylpiperidin-3-ylamino)-9H-purin-9-yl)cyclohexanecarboxamide; |
| 795 | (1s,4s)-4-(8-(2,6-dichloro-4-fluorophenylamino)-2-((R)-1-tosylpiperidin-3-ylamino)-9H-purin-9-yl)cyclohexanecarboxamide; |
| 796 | (1s,4s)-4-(8-(2-chloro-4-cyano-6-fluorophenylamino)-2-((R)-1-tosylpiperidin-3-ylamino)-9H-purin-9-yl)cyclohexanecarboxamide; |

TABLE 1-continued

Representative compounds of formula (I).

| Compound | Compound Name |
|---|---|
| 797 | (R)-3-(9-((1s,4s)-4-carbamoylcyclohexyl)-8-(2,6-dichloro-4-(trifluoromethyl)phenylamino)-9H-purin-2-ylamino)-N-methylpiperidine-1-carboxamide; |
| 798 | (1s,4s)-4-(2-((R)-1-acetylpiperidin-3-ylamino)-8-(2-chloro-4,6-difluorophenylamino)-9H-purin-9-yl)cyclohexanecarboxamide; |
| 799 | (1s,4s)-4-(2-((R)-1-acetylpiperidin-3-ylamino)-8-(2,6-dichloro-4-(trifluoromethyl)phenylamino)-9H-purin-9-yl)cyclohexanecarboxamide; |
| 800 | (1s,4s)-4-(2-((R)-1-acetylpiperidin-3-ylamino)-8-(2,6-dichloro-4-fluorophenylamino)-9H-purin-9-yl)cyclohexanecarboxamide; |
| 801 | (1s,4s)-4-(2-((R)-1-acetylpiperidin-3-ylamino)-8-(2,6-dichlorophenylamino)-9H-purin-9-yl)cyclohexanecarboxamide; |
| 802 | (1s,4s)-4-(8-(4-cyano-2,6-difluorophenylamino)-2-((3S,4R)-3-fluorotetrahydro-2H-pyran-4-ylamino)-9H-purin-9-yl)cyclohexanecarboxamide; or |
| 803 | (1r,4s)-4-(2-(((3R,4S)-3-fluorotetrahydro-2H-pyran-4-yl)amino)-8-((2,4,6-trichlorophenyl)amino)-9H-purin-9-yl)-1-methylcyclohexane-1-carboxamide. |

Methods for Making Aminopurine Compounds

The Aminopurine Compounds can be made using conventional organic syntheses and commercially available starting materials. By way of example and not limitation, Aminopurine Compounds of formula (I) can be prepared as described in U.S. Pat. Nos. 7,723,340, 8,158,635, and U.S. patent application Ser. No. 14/874,513, or as outlined in Scheme 1, shown below, as well as in the examples set forth herein. It should be noted that one skilled in the art would know how to modify the procedures set forth in the illustrative schemes and examples to arrive at the desired products.

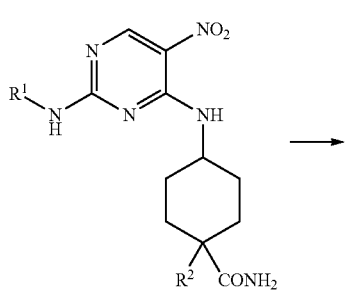

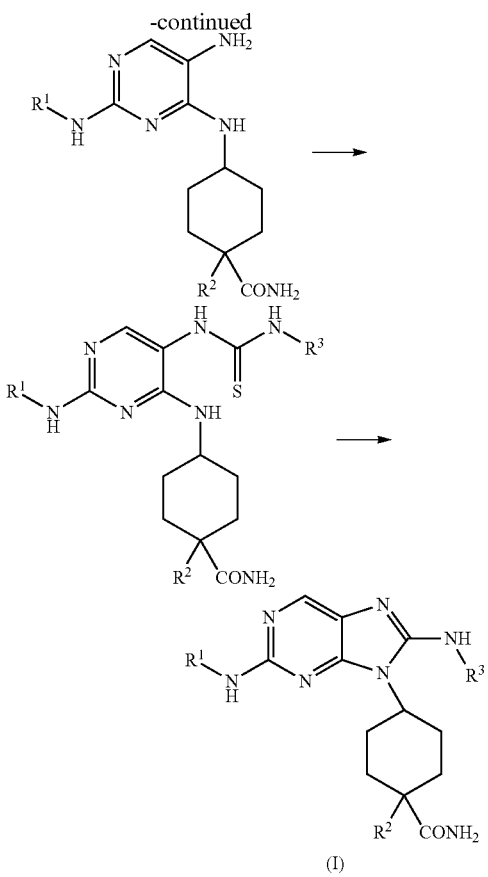

As shown in Scheme 1, compounds of formula (I), wherein $R^1$, $R^2$ and $R^3$ are as defined herein, can be prepared starting from an appropriately derivatized nitropyrimidine, wherein $Hal^1$ is Cl, and $Hal^2$ is Cl. Treatment of the dihalogenated nitropyrimidine with the appropriate 4-aminocyclohexane-1-carboxamide derivative, in the presence of a base, such as, for example, DIEA, TEA, or pyridine, in a solvent, such as for example, DCM or THF, at reduced temperature (for example, −78° C.), provided incorporation of the cyclohexylamide sidechain. Treatment of this product with $R^1NH_2$, in the presence of a base, such as DIEA, TEA, or pyridine, in a solvent such as DCM, THF, dioxane or DMF, at elevated temperature (for example 25-80° C.), resulted in incorporation of the $R^1$ sidechain. Reduction of the nitro moiety, using, for example hydrogen in the presence of a catalyst such as Pd/C, in a solvent, such as MeOH or ethyl acetate, provided the aminopyrimidine derivative. The aminopyrimidine derivative was treated with $R^3$NCS, in a solvent, such as THF, DMF, NMP, dioxane, or EtOH, to obtain the (optionally isolated) thiourea derivative, which was cyclized, using for example, EDC or DIC, in a solvent, for example, THF, dioxane, NMP or DMF, optionally at elevated temperature (for example, 40-80° C.), to provide compounds of formula (I).

Scheme 2

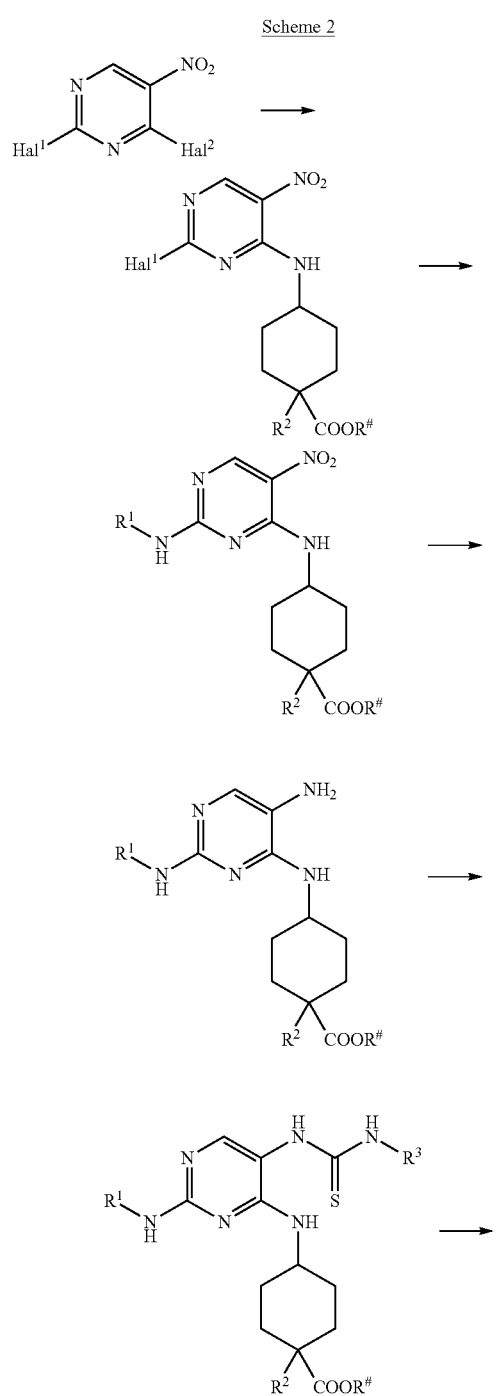

-continued

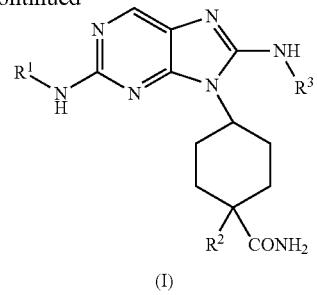

(I)

Alternatively, as shown in Scheme 2, compounds of formula (I), wherein $R^1$, $R^2$ and $R^3$ are as defined herein, and $R^\#$ is $C_{1-2}$ alkyl, can be prepared starting from, as before, an appropriately derivatized nitropyrimidine, wherein $Hal^1$ is Cl, and $Hal^2$ is Cl. Treatment of the dihalogenated nitropyrimidine with the appropriate 4-aminocyclohexane-1-carboxylate alkyl ester derivative, in the presence of a base, such as DIEA, TEA or pyridine, in a solvent, such as DCM or THF, at reduced temperature (for example, −78° C.), provided incorporation of the cyclohexylalkyl ester sidechain. Treatment of this product with $R^1NH_2$, in the presence of a base, such as DIEA, TEA, or pyridine, in a solvent such as DCM, THF, dioxane or DMF, at elevated temperature (for example 25-80° C.), resulted in incorporation of the $R^1$ sidechain. Reduction of the nitro moiety, using, for example hydrogen in the presence of a catalyst such as Pd/C, in a solvent, such as MeOH or ethyl acetate, provided the aminopyrimidine derivative. The aminopyrimidine derivative was treated with $R^3$NCS, in a solvent, such as THF, DMF, NMP, dioxane, or EtOH, to obtain the (optionally isolated) thiourea derivative, which was cyclized, using for example, EDC or DIC, in a solvent, for example, THF, NMP, dioxane, or DMF, optionally at elevated temperature (for example, 40° C. to 80° C.), to provide the derivatized diaminopurine derivative. Saponification of the alkyl ester, using a base (such as lithium hydroxide, sodium hydroxide, or potassium hydroxide), in a solvent (such as aqueous THF, MeOH, or EtOH), optionally at elevated temperature (for example, 40-80° C.), followed by amide formation, via treatment with $NH_4Cl$, in the presence of a coupling agent (such as, for example, HATU, CDI, HBTU, EDC, optionally in combination with HOBt, or ethyl chloroformate) and a base (such as DIEA, TEA, pyridine, DBU, or NMM), in a solvent, for example, DMF, provided the compounds of formula (I).

Scheme 3

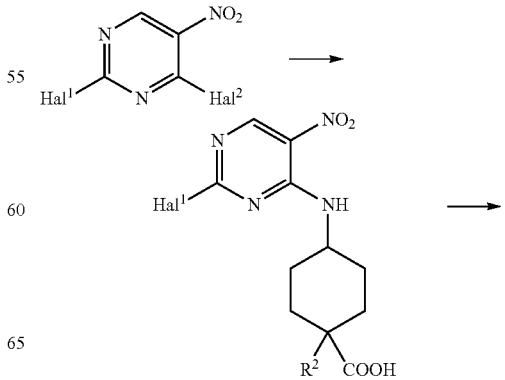

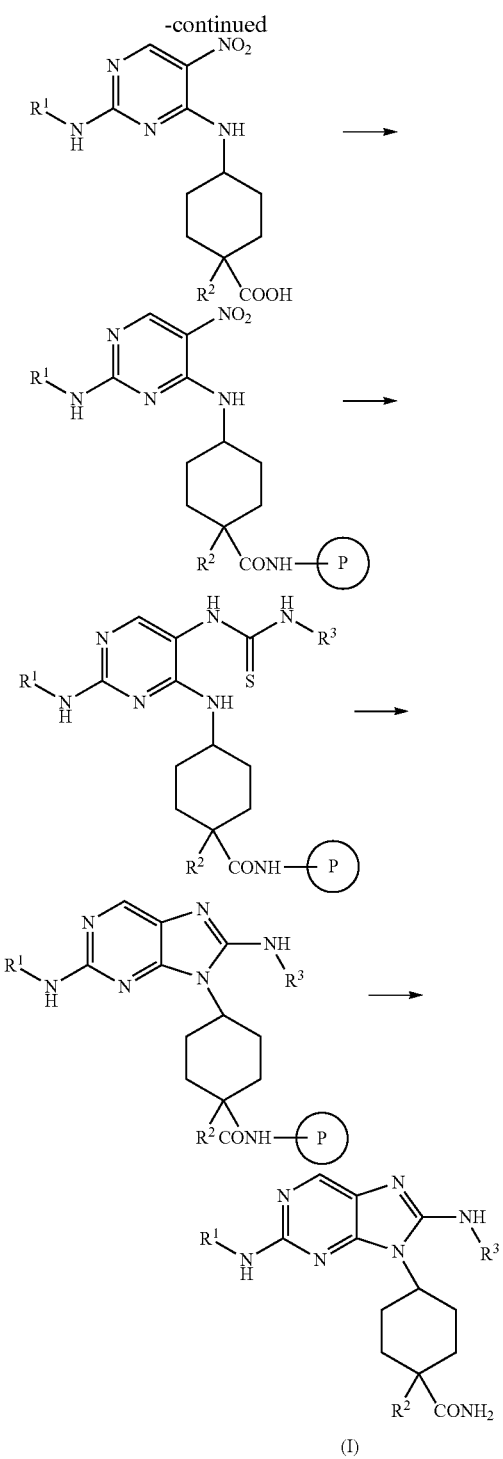

base, such as DIEA, TEA, or pyridine, in a solvent such as DCM, THF, dioxane or DMF, at elevated temperature (for example 25-80° C.), resulted in incorporation of the $R^1$ sidechain. This intermediate was coupled to a solid support, such as a polymeric resin (for example, Rink-H resin) using a coupling agent (for example, HATU, CDI, HBTU, EDC, optionally in combination with HOBt, or ethyl chloroformate), in a solvent, for example DMF, at elevated temperature, for example 50° C. Treatment of the resin-bound intermediate with a reducing agent (such as chromium(II) chloride), in a solvent (such as DMF/MeOH mixture), resulted in reduction of the nitro group. The resulting amine moiety was reacted with $R^3NCS$, in a solvent, for example, EtOH, at elevated temperature, for example, 40° C. to 60° C., providing the thiourea derivative intermediate. This intermediate was cyclized using, for example, EDC or DIC, in a solvent, for example, THF, NMP, dioxane, or DMF, optionally at elevated temperature (for example, 40° C. to 80° C.), to provide the resin-bound diaminopurine derivative. Finally, acid treatment (for example, treatment with TFA in a solvent such as DCM), resulted in cleavage of compounds of formula (I) from the resin.

Methods of Use

The Aminopurine Compounds have utility as pharmaceuticals to treat, prevent or improve conditions in animals or humans. Accordingly, provided herein are Aminopurine Compounds and pharmaceutical compositions thereof that can be used in all the methods as provided herein. Particularly, the Aminopurine Compounds as provided herein are for uses in the treatment or prevention of a cancer. The methods provided herein comprise the administration of an effective amount of one or more Aminopurine Compound(s) to a subject in need thereof. It is to be understood that the methods described herein also include treatment with a pharmaceutical composition, such as those provided below, where the pharmaceutical composition includes an Aminopurine Compound described herein and optionally at least one pharmaceutically acceptable excipient.

In another aspect, provided herein are methods for treating or preventing a cancer, comprising administering to a subject in need thereof an effective amount of an Aminopurine Compound or a pharmaceutical composition thereof, as described herein. In some embodiments, the cancer is a solid tumor or a hematological tumor. In some embodiments, the cancer is not melanoma.

In some embodiments, the solid tumor is melanoma, colorectal cancer, stomach cancer, head and neck cancer, thyroid cancer, bladder cancer, CNS cancer, lung cancer, pancreatic cancer, and soft tissue cancer. In one embodiment, the solid tumor is endocrine cancer, bladder cancer, breast cancer, cervix cancer, colon cancer, duodenum cancer, glioma, head and d neck cancer, kidney cancer, liver cancer, lung cancer (e.g. non-small cell lung cancer NSCLC), esophageal cancer, thyroid cancer, or pancreatic cancer.

In other embodiment, the cancer is bladder cancer, breast cancer (for example Her positive, Her negative, or EGFR positive), CNS cancer (including neuroblastoma, and glioma), colon cancer, gastrointestinal cancer (for example, stomach cancer, and colon cancer), endocrine cancer (for example, thyroid cancer, or adrenal gland cancer), female genitoureal cancer (for example, cervix cancer, ovary clear cell cancer, vulva cancer, uterus cancer, or ovary cancer), head and neck cancer, hematopoietic cancer (for example, leukemia or myeloma), kidney cancer, liver cancer, lung cancer (for example, NSCLC, or SCLC), melanoma, pan- In a third approach, compounds of formula (I), wherein $R^1$, $R^2$ and $R^3$ are as defined herein, and P is a solid support, such as a resin, can be prepared starting from, as before, an appropriately derivatized nitropyrimidine, wherein $Hal^1$ is Cl, and $Hal^2$ is Cl. Treatment of the dihalogenated nitropyrimidine with the appropriate 4-aminocyclohexane-1-carboxylate derivative, in the presence of a base, such as DIEA, TEA or pyridine, in a solvent, such as DCM or THF, at reduced temperature (for example, −78° C.), provided incorporation of the cyclohexylalkyl carboxylate sidechain. Treatment of this product with $R^1NH_2$, in the presence of a creas cancer, prostate cancer, or soft tissue cancer (for example, sarcoma, or osteosarcoma).

In another embodiment, the cancer is bladder cancer, breast cancer (for example Her positive, Her negative, or EGFR positive), CNS cancer (for example, glioma, or neuroblastoma), colon cancer, gastrointestinal cancer (for example, stomach cancer), endocrine cancer (for example, thyroid cancer or adrenal gland cancer), female genitoureal cancer (for example, cancer of the uterus, cervix, ovary clear cell, or vulva), head and neck cancer, hematopoietic cancer (for example, leukemia or myeloma), kidney cancer, liver cancer, lung cancer (for example, NSCLC, or SCLC), melanoma, pancreas cancer, prostate cancer, or soft tissue cancer (for example, sarcoma or osteosarcoma).

In still another embodiment, the cancer is a cancer set forth in Table 3.

Also provided herein are methods for treating or preventing hepatocellular carcinoma (HCC), comprising administering to a subject in need thereof an effective amount of an Aminopurine Compound or a pharmaceutical composition thereof, as described herein.

Also provided herein are methods for treating or preventing colorectal cancer (CRC), melanoma, gastric cancer, HCC, lung cancer, pancreatic cancer, leukemia, or multiple myeloma, comprising administering to a subject in need thereof an effective amount of an Aminopurine Compound or a pharmaceutical composition thereof, as described herein. In one embodiment, the CRC, gastric, or HCC is a cancer characterized by a β-catenin mutation. Also provided herein are methods for treating or preventing colorectal cancer (CRC), gastric cancer, HCC, lung cancer, pancreatic cancer, leukemia, and multiple myeloma, comprising administering to a subject in need thereof an effective amount of an Aminopurine Compound, as described herein.

In another embodiment provided herein are methods of treating leukemia comprising administering an Aminopurine Compound or a pharmaceutical composition thereof. The leukemia can be chronic myelogenous leukemia (CIVIL). In another embodiment, the leukemia is acute myelogenous leukemia (AML). In one embodiment, the leukemia is FLT-3 mutated AML.

In another embodiment provided herein are methods of treating lymphoma comprising administering an Aminopurine Compound or a pharmaceutical composition thereof. The lymphoma can be Burkitt's lymphoma. In one embodiment, the leukemia is Hodgkin's lymphoma. In another embodiment, the leukemia is a B-cell lymphoma. In another embodiment, the leukemia is a T-cell lymphoma. In still another embodiment, the lymphoma is primary effusion lymphoma (PEL).

Aminopurine Compounds (exemplified by Compound 1) show anti-proliferative activity in a variety of cancer cell lines. (Table 3) Anti-proliferative activity in these cancer cell lines indicates that the Aminopurine Compounds are useful in the treatment of cancers, including hematopoietic and solid tumors. In one embodiment, the hematopoietic and solid tumors are selected from bladder cancer, breast cancer, CNS cancer (for example, neuroblastoma, medulloblastoma and glioma), colon cancer, duodenum cancer, endocrine cancer (for example, thyroid cancer and adrenal gland cancer), female genitourinary cancer (for example, uterus cancer, cervix cancer, ovary cancer and vulva cancer), head and neck cancer (for example, esophageal cancer), hematopoietic and lymphoid cancer (for example, lymphoma, leukemia, and myeloma), kidney cancer, liver cancer, lung cancer (for example, NSCLC and SCLC), pancreas cancer, prostate cancer, skin cancer (for example, melanoma and carcinoma), soft tissue cancer (for example, sarcoma and osteosarcoma), stomach cancer, and testis cancer. In one embodiment, the hematopoietic and solid tumors are selected from bladder cancer, breast cancer, CNS cancer (for example, neuroblastoma, medulloblastoma and glioma), colon cancer, duodenum cancer, endocrine cancer (for example, thyroid cancer and adrenal gland cancer), female genitourinary cancer (for example, uterus cancer, cervix cancer, and vulva cancer), head and neck cancer, hematopoietic and lymphoid cancer (for example, lymphoma, leukemia, and myeloma), kidney cancer, liver cancer, lung cancer (for example, NSCLC and SCLC), pancreas cancer, prostate cancer, skin cancer (for example, melanoma and carcinoma), soft tissue cancer (for example, sarcoma and osteosarcoma), stomach cancer, and testis cancer. In one embodiment, the cancer is HCC. In one embodiment, the cancer is gastric cancer. In one embodiment, the cancer is CRC. Such cancers can be characterized by a β-catenin mutation. In still another embodiment, such cancers can be characterized by a BRAF mutation. In still another embodiment, such cancers are characterized by having both a β-catenin mutation and a BRAF mutation.

In another embodiment, Aminopurine Compounds (exemplified by Compound 1) induce apoptosis in a variety of cancer cell lines. Induction of apoptosis indicates that the Aminopurine compounds are useful in the treatment of cancers, including hematopoietic and solid tumors. In one embodiment, the hematopoietic and solid tumors are selected from bladder cancer, breast cancer, CNS cancer (for example, neuroblastoma, and glioma), colon cancer, duodenum cancer, endocrine cancer (for example, thyroid cancer and adrenal gland cancer), female genitourinary cancer (for example, uterus cancer, cervix cancer, ovary cancer and vulva cancer), head and neck cancer (for example, esophageal cancer), hematopoietic and lymphoid cancer (for example, lymphoma, leukemia, and myeloma), kidney cancer, liver cancer, lung cancer (for example, NSCLC and SCLC), pancreas cancer, prostate cancer, skin cancer (for example, melanoma and carcinoma), soft tissue cancer (for example, sarcoma and osteosarcoma), stomach cancer, and testis cancer. In one embodiment, the hematopoietic and solid tumors are selected from bladder cancer, breast cancer, CNS cancer (for example, neuroblastoma, and glioma), colon cancer, duodenum cancer, endocrine cancer (for example, thyroid cancer and adrenal gland cancer), female genitourinary cancer (for example, vulva cancer), head and neck cancer (for example, esophageal cancer), hematopoietic and lymphoid cancer (for example, lymphoma, and leukemia), kidney cancer, liver cancer, lung cancer (for example, NSCLC and SCLC), pancreas cancer, prostate cancer, skin cancer (for example, melanoma), soft tissue cancer (for example, sarcoma and osteosarcoma), stomach cancer, and testis cancer. In one embodiment, the hematopoietic and solid tumors are selected from bladder cancer, breast cancer, CNS cancer (for example, medulloblastoma, neuroblastoma, and glioma), colon cancer, duodenum cancer, endocrine cancer (for example, thyroid cancer and adrenal gland cancer), female genitourinary cancer (for example, placenta cancer, uterus cancer, cervix cancer, ovary cancer and vulva cancer), head and neck cancer (for example, esophageal cancer), hematopoietic and lymphoid cancer (for example, lymphoma, leukemia, and myeloma), kidney cancer, liver cancer, lung cancer (for example, NSCLC and SCLC), pancreas cancer, prostate cancer, skin cancer (for example, melanoma and carcinoma), soft tissue cancer (for example, sarcoma and osteosarcoma), stomach cancer, and testis cancer.

Also provided herein are methods for treating or preventing a cancer characterized by a BRAF mutation and/or a beta-catenin mutation (alternatively referred to as CTNNB1 mutation), comprising administering to a subject in need thereof an effective amount of an Aminopurine Compound or a pharmaceutical composition thereof, as described herein. In some such embodiments, the cancer is characterized by a BRAF mutation. In another embodiment, the cancer is characterized by a beta-catenin mutation. In yet another embodiment, the cancer is characterized by an activated beta-catenin pathway. In some such embodiments, the cancer is CRC or melanoma characterized by a BRAF mutation. In other embodiments, the cancer is CRC characterized by a beta-catenin mutation, additionally comprising an EGFR mutation or increased EGFR activity (for example, CRC characterized by an activated beta-catenin pathway and an EGFR mutation, or CRC characterized by an activated beta-catenin pathway and increased EGFR activity). In still other embodiments, the cancer is gastric cancer characterized by a beta-catenin mutation, additionally comprising a KRAS mutation (i.e. gastric cancer characterized by an activated beta-catenin pathway and a KRAS mutation). In another embodiment the cancer is HCC, characterized by an activated beta-catenin pathway. In some such embodiments, the BRAF mutation is BRAF V660E. In some such embodiments, the BRAF mutation is BRAF V600E. In other embodiments, the BRAF mutation is one or more of BRAF V600E, BRAF T119S, or BRAF G596R. In some such embodiments, the beta-catenin mutation is one or more of beta-catenin S33Y, G34E, S45del, or S33C. In some such embodiments, the EGFR mutation is one or more of EGFR E282K, G719S, P753S, or V1011M. In some such embodiments, the KRAS mutation is A146T, G12C, G12D, G12V, G13D, or Q61L.

Provided herein are methods of treating CRC characterized by a beta-catenin mutation where the beta-catenin mutation is one or more of beta-catenin S33Y, G34E, S45del, or S33C comprising administering to a subject in need thereof an effective amount of an Aminopurine Compound or a pharmaceutical composition thereof, as described herein. In one embodiment, the Aminopurine Compound is Compound 1. Further provided herein are methods of treating CRC characterized by a beta-catenin mutation, additionally comprising an EGFR mutation or increased EGFR activity where the beta-catenin mutation is one or more of beta-catenin S33Y, G34E, S45del, or S33C and the EGFR mutation is one or more of EGFR E282K, G719S, P753S, or V1011M comprising administering to a subject in need thereof an effective amount of an Aminopurine Compound or a pharmaceutical composition thereof, as described herein. In one embodiment, the Aminopurine Compound is Compound 1.

Also provided herein are methods for treating or preventing a cancer expressing PD-L1, comprising administering to a subject in need thereof an effective amount of an Aminopurine Compound or a pharmaceutical composition thereof, as described herein. In some such embodiments, the PD-L1 expressing cancer is melanoma, lung cancer, renal cell carcinoma (RCC), or HCC.

Also provided herein are methods for treating or preventing a cancer characterized by a BRAF mutation, comprising administering to a subject in need thereof an effective amount of an Aminopurine Compound or a pharmaceutical composition thereof, as described herein. In some such embodiments, the cancer characterized by a BRAF mutation is CRC, thyroid cancer, melanoma or lung cancer. In some such embodiments, the cancer characterized by a BRAF mutation is CRC, thyroid cancer, or lung cancer. In some such embodiments, the BRAF mutation is BRAF V660E. In some such embodiments, the BRAF mutation is BRAF V600E. In other embodiments, the BRAF mutation is one or more of BRAF V600E, BRAF T119S, or BRAF G596R.

Also provided herein are methods for treating or preventing a cancer characterized by an NRAS mutation, comprising administering to a subject in need thereof an effective amount of an Aminopurine Compound or a pharmaceutical composition thereof, as described herein. In some such embodiments, the cancer characterized by an NRAS mutation is melanoma.

Also provided herein are methods for treating or preventing a cancer characterized by a KRAS mutation, comprising administering to a subject in need thereof an effective amount of an Aminopurine Compound or a pharmaceutical composition thereof, as described herein. In some such embodiments, the cancer characterized by a KRAS mutation is CRC, pancreas cancer or lung cancer. The KRAS mutation can be a KRAS mutation as described above.

Also provided herein are methods for treating or preventing a cancer characterized by a beta-catenin mutation, comprising administering to a subject in need thereof an effective amount of an Aminopurine Compound or a pharmaceutical composition thereof, as described herein. Also provided herein are methods for treating or preventing a cancer characterized by an activated beta-catenin pathway, comprising administering to a subject in need thereof an effective amount of an Aminopurine Compound, as described herein. In some such embodiments, the cancer characterized by a beta-catenin mutation is CRC, stomach cancer, HCC or sarcoma. In some such embodiments, the cancer characterized by an activated beta-catenin pathway is CRC, stomach cancer, HCC or sarcoma. The beta-catenin mutation can be a mutation as described herein.

Also provided herein are methods for treating or preventing hepatocellular carcinoma (HCC), comprising administering to a subject in need thereof an effective amount of an Aminopurine Compound or a pharmaceutical composition thereof, as described herein. In some such embodiments, the HCC is characterized by a beta-catenin mutation and/or increased YAP expression. In some such embodiments, the HCC is characterized by an activated beta-catenin pathway and/or increased YAP amplification expression. In some embodiments, the increased YAP expression is due to amplification or a mutation.

Also provided herein are methods for treating or preventing colorectal cancer (CRC), comprising administering to a subject in need thereof an effective amount of an Aminopurine Compound or a pharmaceutical composition thereof, as described herein. In some such embodiments, the CRC is characterized by a BRAF mutation and/or beta-catenin mutation. In some such embodiments, the CRC is characterized by a BRAF mutation and/or an activated beta-catenin pathway.

Also provided herein are methods for treating or preventing gastric cancer, comprising administering to a subject in need thereof an effective amount of an Aminopurine Compound or a pharmaceutical composition thereof, as described herein. In some such embodiments, the gastric cancer is characterized by a beta-catenin mutation. In some such embodiments, the gastric cancer is characterized by activated beta-catenin activation. The beta-catenin mutation can be a mutation as described herein.

Also provided herein are methods for treating or preventing melanoma, comprising administering to a subject in need thereof an effective amount of an Aminopurine Compound or a pharmaceutical composition thereof, as described herein. In some such embodiments, the melanoma is characterized by a BRAF mutation and/or NRAS mutation.

Also proved herein are methods of treating or preventing C-Met amplified hepatocellular carcinoma (HCC). In one embodiment, the method comprises treating C-Met amplified HCC by administering an effective amount of an Aminopurine Compound described herein to a subject having C-Met amplified HCC. In another embodiment, the method comprises preventing C-Met amplified HCC by administering a prophylactic amount of an Aminopurine Compound described herein to a subject having C-Met amplified HCC Further provided herein are methods for predicting response to treatment with an Aminopurine Compound in a patient having a cancer characterized by a gene mutation, the method comprising: a) obtaining a biological test sample from the patient's cancer; b) obtaining the gene sequence of one or more genes selected from BRAF, NRAS, KRAS, and/or CTNNB1 in said biological test sample; c) comparing said gene sequence(s) to the gene sequence(s) of a biological wild-type sample; wherein the presence of a mutation indicates an increased likelihood of response to Aminopurine Compound treatment of said patient's cancer. In some such embodiments, the method additionally comprises administering an effective amount of an Aminopurine Compound or a pharmaceutical composition thereof, as described herein.

Further provided herein are methods for predicting therapeutic efficacy of Aminopurine Compound treatment of a patient having a cancer characterized by a gene mutation, the method comprising: a) obtaining a biological test sample from the patient's cancer; b) obtaining the gene sequence(s) of one or more genes selected from BRAF, NAS, KRAS, and/or CTNNB1 in said biological test sample; c) comparing said gene sequence(s) to the gene sequence(s) of a biological wild-type sample; wherein the presence of a mutation indicates an increased likelihood of therapeutic efficacy of said Aminopurine Compound treatment for said patient. In some such embodiments, the method additionally comprises administering an effective amount of an Aminopurine Compound or a pharmaceutical composition thereof, as described herein.

In some embodiments, provided herein are methods for treating and preventing cancer metastasis, comprising administering to a subject in need thereof an effective amount of an Aminopurine Compound or a pharmaceutical composition thereof, as described herein. In some embodiments, the cancer is a metastatic cancer, in particular, a metastatic solid tumor or metastatic hematologic cancer, wherein the solid tumor and hematologic cancer is as described herein. In other embodiments, provided herein are methods of treating and preventing cancer metastasis, comprising administering to a subject in need thereof an effective amount of an Aminopurine Compound or a pharmaceutical composition thereof, as described herein.

In yet another aspect, provided herein is methods of eradicating cancer stem cells in a subject, comprising administering to a subject in need thereof an effective amount of an Aminopurine Compound or a pharmaceutical composition thereof, as described herein.

In still another aspect, provided herein are methods of inducing differentiation in cancer stem cells in a subject, comprising administering to a subject in need thereof an effective amount of an Aminopurine Compound or a pharmaceutical composition thereof, as described herein. In other embodiments, provided herein are methods of inducing cancer stem cell death in a subject, comprising administering to a subject in need thereof an effective amount of an Aminopurine Compound or a pharmaceutical composition thereof, as described herein. In some such embodiments, the cancer is a solid tumor or a hematological cancer, as described herein.

In one embodiment, provided herein are methods for achieving a Response Evaluation Criteria in Solid Tumors (RECIST 1.1) of complete response, partial response or stable disease in a patient comprising administering an effective amount of an Aminopurine Compound or a pharmaceutical composition thereof to a patient having a cancer, in particular a solid tumor as described herein. In another embodiment, provided herein are methods to increase Progression Free Survival rates, as determined by Kaplan-Meier estimates. Such methods are applicable and can be in addition to the methods of treating cancers as described herein.

In one embodiment, provided herein are methods for preventing or delaying a Response Evaluation Criteria in Solid Tumors (RECIST 1.1) of progressive disease in a patient, comprising administering an effective amount of an Aminopurine Compound or a pharmaceutical composition thereof to a patient having a solid tumor as described herein. In one embodiment the prevention or delaying of progressive disease is characterized or achieved by a change in overall size of the target lesions, of for example, between −30% and +20% compared to pre-treatment. In another embodiment, the change in size of the target lesions is a reduction in overall size of more than 30%, for example, more than 50% reduction in target lesion size compared to pre-treatment. In another, the prevention is characterized or achieved by a reduction in size or a delay in progression of non-target lesions compared to pre-treatment. In one embodiment, the prevention is achieved or characterized by a reduction in the number of target lesions compared to pre-treatment. In another, the prevention is achieved or characterized by a reduction in the number or quality of non-target lesions compared to pre-treatment. In one embodiment, the prevention is achieved or characterized by the absence or the disappearance of target lesions compared to pre-treatment. In another, the prevention is achieved or characterized by the absence or the disappearance of non-target lesions compared to pre-treatment. In another embodiment, the prevention is achieved or characterized by the prevention of new lesions compared to pre-treatment. In yet another embodiment, the prevention is achieved or characterized by the prevention of clinical signs or symptoms of disease progression compared to pre-treatment, such as cancer-related cachexia or increased pain. In one embodiment, the cancer is cancer set forth in Table 3. Such methods are applicable and can be in addition to the methods of treating cancers as described herein.

In certain embodiments, provided herein are methods for decreasing the size of target lesions in a patient compared to pre-treatment, comprising administering an effective amount of an Aminopurine Compound or a pharmaceutical composition thereof to a patient having a cancer, in particular a solid tumor as described herein. Such methods are applicable and can be in addition to the methods of treating cancers as described herein.

In certain embodiments, provided herein are methods for decreasing the size of a non-target lesion in a patient compared to pre-treatment, comprising administering an effective amount of an Aminopurine Compound or a pharmaceutical composition thereof to a patient having a cancer, in particular a solid tumor as described herein. Such methods are applicable and can be in addition to the methods of treating cancers as described herein.

In certain embodiments, provided herein are methods for achieving a reduction in the number of target lesions in a patient compared to pre-treatment, comprising administering an effective amount of an Aminopurine Compound to a patient having a cancer, in particular a solid tumor as described herein. Such methods are applicable and can be in addition to the methods of treating cancers as described herein.

In certain embodiments, provided herein are methods for achieving a reduction in the number of non-target lesions in a patient compared to pre-treatment, comprising administering an effective amount an Aminopurine Compound or a pharmaceutical composition thereof to a patient having a cancer, in particular a solid tumor as described herein. Such methods are applicable and can be in addition to the methods of treating cancers as described herein.

In certain embodiments, provided herein are methods for achieving a disappearance of all target lesions in a patient, comprising administering an effective amount of an Aminopurine Compound or a pharmaceutical composition thereof to a patient having a cancer, in particular a solid tumor as described herein. Such methods are applicable and can be in addition to the methods of treating cancers as described herein.

In certain embodiments, provided herein are methods for achieving a disappearance of all non-target lesions in a patient, comprising administering an effective amount of an Aminopurine Compound or a pharmaceutical composition thereof to a patient having a cancer, in particular a solid tumor as described herein. Such methods are applicable and can be in addition to the methods of treating cancers as described herein.

In certain embodiments, provided herein are methods for treating a cancer, in particular a solid tumor as described herein, the methods comprising administering an effective amount of an Aminopurine Compound or a pharmaceutical composition thereof to a patient having a cancer, in particular a solid tumor, wherein the treatment results in a complete response, partial response or stable disease, as determined by Response Evaluation Criteria in Solid Tumors (RECIST 1.1). Such methods are applicable and can be in addition to the methods of treating cancers as described herein.

In certain embodiments, provided herein are methods for treating a cancer, in particular a solid tumor as described herein, the methods comprising administering an effective amount of an Aminopurine Compound or a pharmaceutical composition thereof to a patient having a cancer, in particular a solid tumor as described herein, wherein the treatment results in a reduction in target lesion size, a reduction in non-target lesion size and/or the absence of new target and/or non-target lesions, compared to pre-treatment. In one embodiment, the cancer is a cancer set forth in Table 3. Such methods are applicable and can be in addition to the methods of treating cancers as described herein.

In certain embodiments, provided herein are methods for treating a cancer, in particular a solid tumor as described herein, the methods comprising administering an effective amount an Aminopurine Compound or a pharmaceutical composition thereof to a patient having a cancer, in particular a solid tumor as described herein, wherein the treatment results in prevention or retarding of clinical progression, such as cancer-related cachexia or increased pain.

In another embodiment, provided herein are methods for inducing a therapeutic response characterized with the International Workshop Criteria (IWC) for NHL (see Cheson B D, Pfistner B, Juweid, M E, et. al. Revised Response Criteria for Malignant Lymphoma. J. Clin. Oncol: 2007: (25) 579-586) of a patient, comprising administering an effective amount an Aminopurine Compound or a pharmaceutical composition thereof to a patient having a cancer, in particular hematological cancers such as lymphoma, as described herein. In another embodiment, provided herein are methods for achieving complete remission, partial remission or stable disease, as determined by the International Workshop Criteria (IWC) for NHL in a patient, comprising administering an effective amount of an Aminopurine Compound to a patient having a cancer, in particular hematological cancers such as lymphoma, as described herein. In another embodiment, provided herein are methods for achieving an increase in overall survival, progression-free survival, event-free survival, time to progression, disease-free survival or lymphoma-free survival as determined by the International Workshop Criteria (IWC) for NHL in a patient, comprising administering an effective amount of an Aminopurine Compound to a patient having a cancer, in particular hematological cancers such as lymphoma, as described herein. Such methods are applicable and can be in addition to the methods of treating cancers as described herein.

In another embodiment, provided herein are methods for inducing a therapeutic response assessed with the International Uniform Response Criteria for Multiple Myeloma (IURC) (see Durie B G M, Harousseau J-L, Miguel J S, et al. International uniform response criteria for multiple myeloma. Leukemia, 2006; (10) 10: 1-7) of a patient, comprising administering an effective amount of an Aminopurine Compound or a pharmaceutical composition thereof to a patient having a cancer, in particular multiple myeloma. In another embodiment, provided herein are methods for achieving a stringent complete response, complete response, very good partial response, or partial response, as determined by the International Uniform Response Criteria for Multiple Myeloma (IURC) in a patient, comprising administering an effective amount of an Aminopurine Compound or a pharmaceutical composition thereof to a patient having a cancer, in particular multiple myeloma. In another embodiment, provided herein are methods for achieving an increase in overall survival, progression-free survival, event-free survival, time to progression, or disease-free survival in a patient, comprising administering an effective amount of an Aminopurine Compound or a pharmaceutical composition thereof to a patient having a cancer, in particular multiple myeloma. Such methods are applicable and can be in addition to the methods of treating cancers as described herein.

In another embodiment, provided herein are methods for inducing a therapeutic response assessed with the Response Assessment for Neuro-Oncology (RANO) Working Group for GBM (see Wen P., Macdonald, D R., Reardon, D A., et al. Updated response assessment criteria for high-grade gliomas: Response assessment in neuro-oncology working group. J. Clin. Oncol. 2010; 28: 1963-1972) of a patient, comprising administering an effective amount of an Aminopurine Compound or a pharmaceutical composition thereof to a patient having a cancer, in particular glioblastoma multiforme (GBM). In one embodiment, RANO will be used to establish the proportion of subjects progression-free at 6 months from Day 1 of treatment relative to efficacy evaluable subjects in the GBM type. Such methods are applicable and can be in addition to the methods of treating cancers as described herein.

In another embodiment, provided herein are methods for improving the Eastern Cooperative Oncology Group Performance Status (ECOG) of a patient, comprising administering an effective amount an Aminopurine Compound or a pharmaceutical composition thereof to a patient having a cancer, in particular a solid tumor or hematological cancer as described herein. Such methods are applicable and can be in addition to the methods of treating cancers as described herein.

In another embodiment, provided herein are methods for inducing a therapeutic response assessed by Positron Emission Tomography (PET) outcome of a patient, comprising administering an effective amount of an Aminopurine Compound or a pharmaceutical composition thereof to a patient having a cancer, in particular a solid tumor or hematological cancer as described herein. In certain embodiments, provided herein are methods for treating a cancer, in particular a solid tumor or hematological cancer as described herein, the methods comprising administering an effective amount of an Aminopurine Compound or a pharmaceutical composition thereof to a patient having a cancer, in particular a solid tumor or hematological cancer as described herein, wherein the treatment results in a reduction in tumor metabolic activity, for example, as measured by PET imaging. Such methods are applicable and can be in addition to the methods of treating cancers as described herein.

In some embodiments of the methods described herein, the Aminopurine Compound is a compound as described herein. In one embodiment, the Aminopurine Compound is a compound of formula (I). In another embodiment, the Aminopurine Compound is a compound from Table 1. In one embodiment, the Aminopurine Compound is an Aminopurine Compound set forth herein having molecular formula $C_{24}H_{27}N_7O_2FCl_3$. In one embodiment, the Aminopurine Compound is (1s,4s)-4-(2-(((3S,4R)-3-fluorotetrahydro-2H-pyran-4-yl)amino)-8-((2,4,6-trichlorophenyl)amino)-9H-purin-9-yl)-1-methylcyclohexane-1-carboxamide, alternatively named cis-4-[2-{[(3S,4R)-3-fluorooxan-4-yl]amino}-8-(2,4,6-trichloroanilino)-9H-purin-9-yl]-1-methylcyclohexane-1-carboxamide (Compound 1).

Further provided herein are methods for treating patients who have been previously treated for a cancer, in particular a solid tumor or a hematological cancer as described herein, as well as those who have not previously been treated. In one embodiment, the cancer is a cancer provided in Table 3. Such cancers can be treated using the Aminopurine Compounds described herein, including compounds set forth in Table 1 and/or Compound 1. Because patients with a cancer have heterogeneous clinical manifestations and varying clinical outcomes, the treatment given to a patient may vary, depending on his/her prognosis. The skilled clinician will be able to readily determine without undue experimentation specific secondary agents, types of surgery, and types of non-drug based standard therapy that can be effectively used to treat an individual patient with a cancer.

Biomarkers

In one embodiment, provided herein are methods for modulating the levels of a biomarker in a subject having a cancer as described herein, comprising administering an effective amount of a Aminopurine Compound or a pharmaceutical composition thereof, to said subject. In some such embodiments, the modulation of the biomarker is assessed in a biological sample of the subject, such as in circulating blood, skin biopsies, tumor biopsies, circulating tumor cells, hair, and/or urine. In one embodiment, the biological sample is peripheral blood mononuclear cells (PBMC). In such embodiments, the amount of biomarker modulation is assessed by comparison of the amount of biomarker before and after administration of the Aminopurine Compound or pharmaceutical composition thereof. In some embodiments, the modulation in biomarker is a reduction of about 10%, 20%, 25%, 30%, 40%, 50%, 60%, 70%, 75%, 80%, 90%, 95%, 99%, or about 100% compared to baseline levels. In some other embodiments, the modulation in biomarker is an increase of about 10%, 20%, 25%, 30%, 40%, 50%, 60%, 70%, 75%, 80%, 90%, 95%, 99%, or about 100% compared to baseline levels.

In some embodiments, the biomarker is ERK, RSK1, DUSP4, DUSP5, DUSP6, BMF, EFNA1, EGR1, ETV5, FOS, FOSL1, GJA1, IL-8, cMyc, Cyclin D1, YAP, SPRY2, SPRY4, Axin2, CTGF, AREG, CYR61, CXCL1, HAS2, HES1, MAFF, CITED2, ELF3, or PD-L1. In some such embodiments, the modulation is measured by measurement of the reduction of phosphorylation levels of one or more of ERK and RSK1. In some embodiments, the modulation in biomarker is a reduction of about 10%, 20%, 25%, 30%, 40%, 50%, 60%, 70%, 75%, 80%, 90%, 95%, 99%, or about 100% compared to baseline levels. In some other embodiments, the modulation in biomarker is an increase of about 10%, 20%, 25%, 30%, 40%, 50%, 60%, 70%, 75%, 80%, 90%, 95%, 99%, or about 100% compared to baseline levels.

In some embodiments, the biomarker is one or more of DUSP4, DUSP6, cyclin D1, c-Myc, SPRY2, and YAP. In some such embodiments, the modulation is measured by measurement of the reduction in mRNA and/or protein expression levels of one or more of DUSP4, DUSP6, cyclin D1, c-Myc, and YAP. In some such embodiments, the modulation is measured by measurement of the reduction in mRNA and/or protein expression levels of one or more of DUSP4, DUSP6, SPRY2, c-Myc and cyclin D1. In some embodiments, the modulation in biomarker is a reduction of about 10%, 20%, 25%, 30%, 40%, 50%, 60%, 70%, 75%, 80%, 90%, 95%, 99%, or about 100% compared to baseline levels.

In some embodiments, the biomarker is one or more of DUSP4, DUSP6, cyclin D1, c-Myc, SPRY2, and YAP. In some such embodiments, the modulation is measured by measurement of the reduction in mRNA and/or protein expression levels of one or more of DUSP4, DUSP6, cyclin D1, c-Myc, and YAP. In some such embodiments, the modulation is measured by measurement of the reduction in mRNA and/or protein expression levels of one or more of DUSP4, DUSP6, SPRY2, c-Myc and cyclin D1. In some embodiments, the modulation in biomarker is a reduction of about 10%, 20%, 25%, 30%, 40%, 50%, 60%, 70%, 75%, 80%, 90%, 95%, 99%, or about 100% compared to baseline levels.

In some embodiments, the biomarker is one or more of DUSP5, DUSP6, EGR1, ETV5, FOS, FOSL1, IL-8, SPRY2, and SPRY4. In some such embodiments, the modulation is measured by measurement of the reduction in mRNA and/or protein expression levels of one or more of DUSP5, DUSP6, EGR1, ETV5, FOS, FOSL1, IL-8, SPRY2, and SPRY4. In some embodiments, the modulation in biomarker is a reduction of about 10%, 20%, 25%, 30%, 40%, 50%, 60%, 70%, 75%, 80%, 90%, 95%, 99%, or about 100% compared to baseline levels.

In some embodiments, the biomarker is one or more of BMF and EFNA. In some such embodiments, the modulation is measured by measurement of the increase in mRNA and/or protein expression levels of one or more of BMF and EFNA1. In some embodiments, the modulation in biomarker is an increase of about 10%, 20%, 25%, 30%, 40%, 50%, 60%, 70%, 75%, 80%, 90%, 95%, 99%, or about 100% compared to baseline levels.

In some embodiments, the biomarker is GJA1. In some such embodiments, the modulation is measured by measurement of the modulation in mRNA and/or protein expression levels of one or more of GJA1. In some such embodiments, the modulation in biomarker is a reduction of about 10%, 20%, 25%, 30%, 40%, 50%, 60%, 70%, 75%, 80%, 90%, 95%, 99%, or about 100% compared to baseline levels. In some embodiments, the modulation in biomarker is an increase of about 10%, 20%, 25%, 30%, 40%, 50%, 60%, 70%, 75%, 80%, 90%, 95%, 99%, or about 100% compared to baseline levels.

In some embodiments, the biomarker is one or more of Axin2, CTGF, Cur61 and AREG. In some such embodiments, the modulation is measured by measurement of the reduction in mRNA and/or protein expression levels of one or more of Axin2, CTGF, and AREG. In some embodiments, the modulation in biomarker is a reduction of about 10%, 20%, 25%, 30%, 40%, 50%, 60%, 70%, 75%, 80%, 90%, 95%, 99%, or about 100% compared to baseline levels.

In some embodiments, the biomarker is one or more of CYR61, CXCL1, HAS2, HES1 and MAFF. In some such embodiments, the modulation is measured by measurement of the reduction in mRNA and/or protein expression levels of one or more of CYR61, CXCL1, HAS2, HES1 and MAFF. In some embodiments, the modulation in biomarker is a reduction of about 10%, 20%, 25%, 30%, 40%, 50%, 60%, 70%, 75%, 80%, 90%, 95%, 99%, or about 100% compared to baseline levels.

In some embodiments, the biomarker is one or more of CITED2 and ELF3. In some such embodiments, the modulation is measured by measurement of the increase in mRNA and/or protein expression levels of one or more of CITED2 and ELF3. In some embodiments, the modulation in biomarker is an increase of about 10%, 20%, 25%, 30%, 40%, 50%, 60%, 70%, 75%, 80%, 90%, 95%, 99%, or about 100% compared to baseline levels.

In some embodiments, the biomarker is PD-L1. In some embodiments, the modulation in the levels of biomarker is a reduction in cell surface expression levels of PD-L1. In some embodiments, the modulation in biomarker is a reduction of about 10%, 20%, 25%, 30%, 40%, 50%, 60%, 70%, 75%, 80%, 90%, 95%, 99%, or about 100% compared to baseline levels.

In another embodiment, the biomarker is IFNγ or IL-2. In some such embodiments, the modulation in the levels of biomarker is an increase in mRNA and/or protein expression levels of IFNγ or IL-2. In some such embodiments, the modulation in mRNA and/or protein expression levels of IFNγ or IL-2 is an increase of about 10%, 20%, 25%, 30%, 40%, 50%, 60%, 70%, 75%, 80%, 90%, 95%, 99%, or about 100% compared to baseline levels.

In another embodiment, the biomarker is IL-8. In some such embodiments, the modulation in the levels of biomarker is a decrease in mRNA and/or protein expression levels of IL-8. In some such embodiments, the modulation in mRNA and/or protein expression levels of IL-8 is an decrease of about 10%, 20%, 25%, 30%, 40%, 50%, 60%, 70%, 75%, 80%, 90%, 95%, 99%, or about 100% compared to baseline levels.

In one embodiment, provided herein are methods for inhibiting phosphorylation of ERK and/or RSK1 in a subject having a cancer as described herein, comprising administering an effective amount of an Aminopurine compound or a pharmaceutical composition thereof as described herein to said subject. In some such embodiments, the inhibition of phosphorylation is assessed in a biological sample of the subject, such as in circulating blood and/or tumor cells, skin biopsies and/or tumor biopsies or aspirate. In such embodiments, the amount of inhibition of phosphorylation is assessed by comparison of the amount of phospho-ERK and/or RSK1 before and after administration of the Aminopurine Compound or a pharmaceutical composition thereof provided herein. In certain embodiments, provided herein are methods for measuring inhibition of phosphorylation of ERK and/or RSK1, in a subject having a cancer as described herein, comprising administering an effective amount of Aminopurine Compound or a pharmaceutical composition thereof provided herein to said subject, measuring the amount of phosphorylated ERK and/or RSK1 in said subject, and comparing said amount of phosphorylated ERK and/or RSK to that of said subject prior to administration of an effective amount of the Aminopurine Compound or a pharmaceutical composition thereof provided herein. In some embodiments, the biological sample is a tumor biopsy. In another embodiment, the biological sample is PBMC. In still another embodiment, the biological sample is circulating tumor cells.

In certain embodiments, provided herein are methods for inhibiting phosphorylation of ERK and/or RSK1 in a biological sample of a subject having a cancer as described herein, comprising administering an effective amount of an Aminopurine Compound or a pharmaceutical composition thereof provided herein to said subject and comparing the amount of phosphorylated ERK and/or RSK1 in a biological sample of a subject obtained prior to and after administration of said Aminopurine Compound or a pharmaceutical composition thereof provided herein, wherein less phosphorylated ERK and/or RSK1 in said biological sample obtained after administration of said Aminopurine Compound provided herein relative to the amount of phosphorylated ERK and/or RSK1 in said biological sample obtained prior to administration of said Aminopurine Compound or a pharmaceutical composition thereof provided herein indicates inhibition. In some embodiments, the biological sample is a tumor biopsy. In another embodiment, the biological sample is PBMC. In still another embodiment, the biological sample is circulating tumor cells.

Further provided herein are methods for determining whether a patient is sensitive to an Aminopurine Compound or a pharmaceutical composition thereof, comprising administering said patient said Aminopurine Compound or a pharmaceutical composition thereof and determining whether or not ERK and/or RSK1 phosphorylation is inhibited in said patient by measuring the amount of phosphorylated ERK and/or RSK1 in a biological sample from said patient prior to and after the administration of Aminopurine Compound or a pharmaceutical composition thereof to said patient, wherein inhibition of ERK and/or RSK1 phosphorylation indicates that said patient is sensitive to said Aminopurine Compound. In some such embodiments, the method additionally comprises administering an effective amount of an Aminopurine Compound or a pharmaceutical composition thereof, as described herein. In some embodiments, the biological sample is a tumor biopsy. In another embodiment, the biological sample is PBMC. In still another embodiment, the biological sample is circulating tumor cells.

Further provided herein are methods for determining the effective amount of an Aminopurine Compound or a pharmaceutical composition thereof for the treatment of a cancer treatable by inhibition of phosphorylation of ERK and/or RSK1 in a patient, comprising administering said patient varying doses of said Aminopurine Compound or a pharmaceutical composition thereof and determining the amount of ERK and/or RSK1 phosphorylation inhibition in said patient resulting from each dose of said Aminopurine Compound or a pharmaceutical composition thereof by measuring the amount of phosphorylated ERK and/or RSK1 in a biological sample from said patient prior to and after the administration of each dose of Aminopurine Compound to said patient, wherein inhibition of ERK and/or RSK1 phosphorylation by at least about 10%, about 20%, about 30%, about 40%, about 50% or greater than about 50%, corresponds to an effective amount of an Aminopurine compound. In some such embodiments, the method additionally comprises administering an effective amount of an Aminopurine Compound or a pharmaceutical composition thereof, as described herein. In some embodiments, the biological sample is a tumor biopsy. In another embodiment, the biological sample is PBMC. In still another embodiment, the biological sample is circulating tumor cells.

Further provided herein are methods for predicting response to treatment with an Aminopurine Compound in a patient having a cancer, the method comprising: a) obtaining a biological test sample from the patient's cancer; b) obtaining the mRNA and/or protein expression levels of one or more of DUSP4, DUSP5, DUSP6, EGR1, ETV5, FOS, FOSL1, IL-8, cMyc, Cyclin D1, YAP, SPRY2, SPRY4, Axin2, CTGF, AREG, CYR61, CXCL1, HAS2, HES1, and MAFF in said biological test sample; c) comparing said mRNA and/or protein expression levels to the mRNA and/or protein expression levels of a biological wild-type sample; wherein a reduction in mRNA and/or protein expression levels in said patient's biological test sample relative to said biological wild-type sample, indicates an increased likelihood of response to Aminopurine Compound treatment of said patient's cancer. In some such embodiments, the method additionally comprises administering an effective amount of an Aminopurine Compound, as described herein. In some embodiments, the biological sample is a tumor biopsy. In another embodiment, the biological sample is PBMC. In still another embodiment, the biological sample is circulating tumor cells.

Further provided herein are methods for predicting therapeutic efficacy of Aminopurine Compound treatment of a patient having a cancer, the method comprising: a) obtaining a biological test sample from the patient's cancer; b) obtaining the mRNA and/or protein expression levels of one or more of DUSP4, DUSP5, DUSP6, EGR1, ETV5, FOS, FOSL1, IL-8, cMyc, Cyclin D1, YAP, SPRY2, SPRY4, Axin2, CTGF, AREG, CYR61, CXCL1, HAS2, HES1, and MAFF in said biological test sample; c) comparing said mRNA and/or protein expression levels to the mRNA and/or protein expression levels of a biological wild-type sample; wherein a reduction in mRNA and/or protein expression levels indicates an increased likelihood of therapeutic efficacy of said Aminopurine Compound treatment for said patient. In some such embodiments, the method additionally comprises administering an effective amount of an Aminopurine Compound, as described herein. In some embodiments, the biological sample is a tumor biopsy. In another embodiment, the biological sample is PBMC. In still another embodiment, the biological sample is circulating tumor cells.

Further provided herein are methods for determining whether a patient is sensitive to an Aminopurine Compound, comprising administering said patient said Aminopurine Compound and determining whether or not mRNA and/or protein expression levels of one or more of DUSP4, DUSP5, DUSP6, EGR1, ETV5, FOS, FOSL1, IL-8, cMyc, Cyclin D1, YAP, SPRY2, SPRY4, Axin2, CTGF, AREG, CYR61, CXCL1, HAS2, HES1, and MAFF, are inhibited in said patient, by measuring the amount of mRNA and/or protein expression levels of one or more of DUSP4, DUSP5, DUSP6, EGR1, ETV5, FOS, FOSL1, IL-8, cMyc, Cyclin D1, YAP, SPRY2, SPRY4, Axin2, CTGF, AREG, CYR61, CXCL1, HAS2, HES1, and MAFF in a biological sample from said patient, prior to and after the administration of Aminopurine Compound to said patient. In some such embodiments, the method additionally comprises administering an effective amount of an Aminopurine Compound, as described herein. In some embodiments, the biological sample is a tumor biopsy. In another embodiment, the biological sample is PBMC. In still another embodiment, the biological sample is circulating tumor cells.

Further provided herein are methods for determining the effective amount of an Aminopurine Compound for the treatment of a cancer treatable by inhibition of mRNA and/or protein expression levels of one or more of DUSP4, DUSP5, DUSP6, EGR1, ETV5, FOS, FOSL1, IL-8, cMyc, Cyclin D1, YAP, SPRY2, SPRY4, Axin2, CTGF, AREG, CYR61, CXCL1, HAS2, HES1, and MAFF in a patient, comprising administering said patient varying doses of said Aminopurine Compound and determining the amount of mRNA and/or protein expression levels of one or more of DUSP4, DUSP5, DUSP6, EGR1, ETV5, FOS, FOSL1, IL-8, cMyc, Cyclin D1, YAP, SPRY2, SPRY4, Axin2, CTGF, AREG, CYR61, CXCL1, HAS2, HES1, and MAFF inhibition in said patient, resulting from each dose of said Aminopurine Compound by measuring the amount of mRNA and/or protein expression levels of one or more of DUSP4, DUSP5, DUSP6, EGR1, ETV5, FOS, FOSL1, IL-8, cMyc, Cyclin D1, YAP, SPRY2, SPRY4, Axin2, CTGF, AREG, CYR61, CXCL1, HAS2, HES1, and MAFF in a biological sample from said patient, prior to and after the administration of each dose of Aminopurine Compound to said patient. In some such embodiments, the method additionally comprises administering an effective amount of an Aminopurine Compound, as described herein. In some embodiments, the biological sample is a tumor biopsy. In another embodiment, the biological sample is PBMC. In still another embodiment, the biological sample is circulating tumor cells.

Further provided herein are methods for predicting response to treatment with an Aminopurine Compound in a patient having a cancer, the method comprising: a) obtaining a biological test sample from the patient's cancer; b) obtaining the mRNA and/or protein expression levels of one or more of BMF, EFNA1, CITED2, and ELF3 in said biological test sample; c) comparing said mRNA and/or protein expression levels to the mRNA and/or protein expression levels of a biological wild-type sample; wherein an increase in mRNA and/or protein expression levels in said patient's biological test sample relative to said biological wild-type sample, indicates an increased likelihood of response to Aminopurine Compound treatment of said patient's cancer. In some such embodiments, the method additionally comprises administering an effective amount of an Aminopurine Compound, as described herein. In some embodiments, the biological sample is a tumor biopsy. In another embodiment, the biological sample is PBMC. In still another embodiment, the biological sample is circulating tumor cells.

Further provided herein are methods for predicting therapeutic efficacy of Aminopurine Compound treatment of a patient having a cancer, the method comprising: a) obtaining a biological test sample from the patient's cancer; b) obtaining the mRNA and/or protein expression levels of one or more of BMF, EFNA1, CITED2, and ELF3 in said biological test sample; c) comparing said mRNA and/or protein expression levels to the mRNA and/or protein expression levels of a biological wild-type sample; wherein an increase in mRNA and/or protein expression levels indicates an increased likelihood of therapeutic efficacy of said Aminopurine Compound treatment for said patient. In some such embodiments, the method additionally comprises administering an effective amount of an Aminopurine Compound, as described herein. In some embodiments, the biological sample is a tumor biopsy. In another embodiment, the biological sample is PBMC. In still another embodiment, the biological sample is circulating tumor cells.

Further provided herein are methods for determining whether a patient is sensitive to an Aminopurine Compound, comprising administering said patient said Aminopurine Compound and determining whether or not mRNA and/or protein expression levels of one or more of BMF, EFNA1, CITED2, and ELF3 are increased in said patient, by measuring the amount of mRNA and/or protein expression levels of one or more of BMF, EFNA1, CITED2, and ELF3 in a biological sample from said patient, prior to and after the administration of Aminopurine Compound to said patient. In some such embodiments, the method additionally comprises administering an effective amount of an Aminopurine Compound, as described herein. In some embodiments, the biological sample is a tumor biopsy. In another embodiment, the biological sample is PBMC. In still another embodiment, the biological sample is circulating tumor cells.

Further provided herein are methods for determining the effective amount of an Aminopurine Compound for the treatment of a cancer treatable by an increase of mRNA and/or protein expression levels of one or more of BMF, EFNA1, CITED2, and ELF3 in a patient, comprising administering said patient varying doses of said Aminopurine Compound, and determining the amount of mRNA and/or protein expression levels of one or more of BMF, EFNA1, CITED2, and ELF3 increase in said patient resulting from each dose of said Aminopurine Compound by measuring the amount of mRNA and/or protein expression levels of one or more of BMF, EFNA1, CITED2, and ELF3 in a biological sample from said patient, prior to and after the administration of each dose of Aminopurine Compound to said patient. In some such embodiments, the method additionally comprises administering an effective amount of an Aminopurine Compound, as described herein. In some embodiments, the biological sample is a tumor biopsy. In another embodiment, the biological sample is PBMC. In still another embodiment, the biological sample is circulating tumor cells.

Further provided herein are methods for predicting response to treatment with an Aminopurine Compound or a pharmaceutical composition thereof in a patient having a cancer, the method comprising: a) obtaining a biological test sample from the patient's cancer; b) obtaining the mRNA and/or protein expression levels of GJA1 in said biological test sample; c) comparing said mRNA and/or protein expression levels to the mRNA and/or protein expression levels of a biological wild-type sample; wherein a reduction in mRNA and/or protein expression levels in said patient's biological test sample relative to said biological wild-type sample, indicates an increased likelihood of response to Aminopurine Compound treatment of said patient's cancer. In some such embodiments, the method additionally comprises administering an effective amount of an Aminopurine Compound, as described herein. In some embodiments, the biological sample is a tumor biopsy. In another embodiment, the biological sample is PBMC. In still another embodiment, the biological sample is circulating tumor cells.

Further provided herein are methods for predicting therapeutic efficacy of Aminopurine Compound treatment of a patient having a cancer, the method comprising: a) obtaining a biological test sample from the patient's cancer; b) obtaining the mRNA and/or protein expression levels of GJA1 in said biological test sample; c) comparing said mRNA and/or protein expression levels to the mRNA and/or protein expression levels of a biological wild-type sample; wherein a reduction in mRNA and/or protein expression levels indicates an increased likelihood of therapeutic efficacy of said Aminopurine Compound treatment for said patient. In some such embodiments, the method additionally comprises administering an effective amount of an Aminopurine Compound, as described herein. In some embodiments, the biological sample is a tumor biopsy. In another embodiment, the biological sample is PBMC. In still another embodiment, the biological sample is circulating tumor cells.

Further provided herein are methods for determining whether a patient is sensitive to an Aminopurine Compound, comprising administering said patient said Aminopurine Compound and determining whether or not mRNA and/or protein expression levels of GJA1 are inhibited in said patient, by measuring the amount of mRNA and/or protein expression levels of GJA1 in a biological sample from said patient, prior to and after the administration of Aminopurine Compound to said patient. In some such embodiments, the method additionally comprises administering an effective amount of an Aminopurine Compound, as described herein. In some embodiments, the biological sample is a tumor biopsy. In another embodiment, the biological sample is PBMC. In still another embodiment, the biological sample is circulating tumor cells.

Further provided herein are methods for determining the effective amount of an Aminopurine Compound for the treatment of a cancer treatable by inhibition of mRNA and/or protein expression levels of GJA1 in a patient, comprising administering said patient varying doses of said Aminopurine Compound and determining the amount of mRNA and/or protein expression levels of GJA1 inhibition in said patient, resulting from each dose of said Aminopurine Compound by measuring the amount of mRNA and/or protein expression levels of GJA1 in a biological sample from said patient, prior to and after the administration of each dose of Aminopurine Compound to said patient. In some such embodiments, the method additionally comprises administering an effective amount of an Aminopurine Compound, as described herein. In some embodiments, the biological sample is a tumor biopsy. In another embodiment, the biological sample is PBMC. In still another embodiment, the biological sample is circulating tumor cells.

Further provided herein are methods for predicting response to treatment with an Aminopurine Compound in a patient having a cancer, the method comprising: a) obtaining a biological test sample from the patient's cancer; b) obtaining the mRNA and/or protein expression levels of GJA1 in said biological test sample; c) comparing said mRNA and/or protein expression levels to the mRNA and/or protein expression levels of a biological wild-type sample; wherein an increase in mRNA and/or protein expression levels in said patient's biological test sample relative to said biological wild-type sample, indicates an increased likelihood of response to Aminopurine Compound treatment of said patient's cancer. In some such embodiments, the method additionally comprises administering an effective amount of an Aminopurine Compound, as described herein. In some embodiments, the biological sample is a tumor biopsy. In another embodiment, the biological sample is PBMC. In still another embodiment, the biological sample is circulating tumor cells.

Further provided herein are methods for predicting therapeutic efficacy of Aminopurine Compound treatment of a patient having a cancer, the method comprising: a) obtaining a biological test sample from the patient's cancer; b) obtaining the mRNA and/or protein expression levels of GJA1 in said biological test sample; c) comparing said mRNA and/or protein expression levels to the mRNA and/or protein expression levels of a biological wild-type sample; wherein an increase in mRNA and/or protein expression levels indicates an increased likelihood of therapeutic efficacy of said Aminopurine Compound treatment for said patient. In some such embodiments, the method additionally comprises administering an effective amount of an Aminopurine Compound, as described herein. In some embodiments, the biological sample is a tumor biopsy. In another embodiment, the biological sample is PBMC. In still another embodiment, the biological sample is circulating tumor cells.

Further provided herein are methods for determining whether a patient is sensitive to an Aminopurine Compound, comprising administering said patient said Aminopurine Compound and determining whether or not mRNA and/or protein expression levels of GJA1 are increased in said patient, by measuring the amount of mRNA and/or protein expression levels of GJA1 in a biological sample from said patient, prior to and after the administration of Aminopurine Compound to said patient. In some such embodiments, the method additionally comprises administering an effective amount of an Aminopurine Compound, as described herein. In some embodiments, the biological sample is a tumor biopsy. In another embodiment, the biological sample is PBMC. In still another embodiment, the biological sample is circulating tumor cells.

Further provided herein are methods for determining the effective amount of an Aminopurine Compound for the treatment of a cancer treatable by an increase of mRNA and/or protein expression levels of GJA1 in a patient, comprising administering said patient varying doses of said Aminopurine Compound, and determining the amount of mRNA and/or protein expression levels of GJA1 increase in said patient resulting from each dose of said Aminopurine Compound by measuring the amount of mRNA and/or protein expression levels of GJA1 in a biological sample from said patient, prior to and after the administration of each dose of Aminopurine Compound to said patient. In some such embodiments, the method additionally comprises administering an effective amount of an Aminopurine Compound, as described herein. In some embodiments, the biological sample is a tumor biopsy. In another embodiment, the biological sample is PBMC. In still another embodiment, the biological sample is circulating tumor cells.

Further provided herein are methods for predicting response to treatment with an Aminopurine Compound in a patient having a cancer, the method comprising: a) obtaining a biological test sample from the patient's cancer; b) obtaining the cell surface expression levels of PD-L1 in said biological test sample; c) comparing said cell surface expression levels of PD-L1 to the cell surface expression levels of PD-L1 of a biological wild-type sample; wherein a reduction in cell surface expression levels of PD-L1 indicates an increased likelihood of response to Aminopurine Compound treatment of said patient's cancer. In some such embodiments, the method additionally comprises administering an effective amount of an Aminopurine Compound, as described herein. In some embodiments, the biological sample is a tumor biopsy. In another embodiment, the biological sample is PBMC. In still another embodiment, the biological sample is circulating tumor cells.

Further provided herein are methods for predicting therapeutic efficacy of Aminopurine Compound treatment of a patient having a cancer, the method comprising: a) obtaining a biological test sample from the patient's cancer; b) obtaining the cell surface expression levels of PD-L1 in said biological test sample; c) comparing said cell surface expression levels of PD-L1 to the cell surface expression levels of PD-L1 of a biological wild-type sample; wherein a reduction in cell surface expression levels of PD-L1 indicates an increased likelihood of therapeutic efficacy of said Aminopurine Compound treatment for said patient. In some such embodiments, the method additionally comprises administering an effective amount of an Aminopurine Compound, as described herein. In some embodiments, the biological sample is a tumor biopsy. In another embodiment, the biological sample is PBMC. In still another embodiment, the biological sample is circulating tumor cells.

Further provided herein are methods for determining whether a patient is sensitive to an Aminopurine Compound, comprising administering said patient said Aminopurine Compound and determining whether or not cell surface expression levels of PD-L1 are inhibited in said patient by measuring the amount of cell surface expression levels of PD-L1 in a biological sample from said patient prior to and after the administration of Aminopurine Compound to said patient. In some such embodiments, the method additionally comprises administering an effective amount of an Aminopurine Compound, as described herein. In some embodiments, the biological sample is a tumor biopsy. In another embodiment, the biological sample is PBMC. In still another embodiment, the biological sample is circulating tumor cells.

Further provided herein are methods for determining the effective amount of an Aminopurine Compound for the treatment of a cancer treatable by cell surface expression levels of PD-L1 in a patient, comprising administering said patient varying doses of said Aminopurine Compound and determining the amount of cell surface expression levels of PD-L1 inhibition in said patient resulting from each dose of said Aminopurine Compound by measuring the amount of cell surface expression levels of PD-L1 in a biological sample from said patient prior to and after the administration of each dose of Aminopurine Compound to said patient. In some such embodiments, the method additionally comprises administering an effective amount of an Aminopurine Compound, as described herein. In some embodiments, the biological sample is a tumor biopsy. In another embodiment, the biological sample is PBMC. In still another embodiment, the biological sample is circulating tumor cells.

Combination Therapy

Aminopurine Compounds provided herein can also be combined or used in combination with other therapeutic agents useful in the treatment and/or prevention of cancer described herein.

In one embodiment, provided herein is a method of treating, preventing, or managing cancer, comprising administering to a patient an Aminopurine Compound provided herein in combination with one or more second active agents, and optionally in combination with radiation therapy, blood transfusions, or surgery. Examples of second active agents are disclosed herein.

As used herein, the term "in combination" includes the use of more than one therapy (e.g., one or more prophylactic and/or therapeutic agents). However, the use of the term "in combination" does not restrict the order in which therapies (e.g., prophylactic and/or therapeutic agents) are administered to a patient with a disease or disorder. A first therapy (e.g., a prophylactic or therapeutic agent such as an Aminopurine Compound provided herein, can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to the subject. Triple therapy is also contemplated herein.

Administration of an Aminopurine Compound provided herein and one or more second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the cancer being treated.

The route of administration of an Aminopurine Compound is independent of the route of administration of a second therapy. Thus, in accordance with these embodiments, an Aminopurine Compound is administered intravenously, and the second therapy can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form. In one embodiment, an Aminopurine Compound and a second therapy are administered by the same mode of administration, for example, orally. In another embodiment, an Aminopurine Compound is administered by one mode of administration, e.g., orally, whereas the second agent (an anticancer agent) is administered by another mode of administration, e.g., IV.

In one embodiment, the second active agent is administered, for example, orally, intravenously or subcutaneously, and once or twice daily in an amount of from about 1 to about 1000 mg, from about 5 to about 500 mg, from about 10 to about 350 mg, from about 50 to about 200 mg, from about 1 to about 100 mg, from about 1 to about 200 mg, from about 1 to about 300 mg, from about 1 to about 400 mg, or from about 1 to about 500 mg. The specific amount of the second active agent will depend on the specific agent used, the type of disease being treated or managed, the severity and stage of disease, and the amount of Aminopurine Compound described herein and any optional additional active agents concurrently administered to the patient. In one embodiment, dosing amounts described herein are for human patients.

One or more second active ingredients or agents can be used together with an Aminopurine Compound in the methods and compositions provided herein. Second active agents can be large molecules (e.g., proteins) or small molecules (e.g., synthetic inorganic, organometallic, or organic molecules).

Examples of large molecule active agents include, but are not limited to, hematopoietic growth factors, cytokines, and monoclonal and polyclonal antibodies, particularly, therapeutic antibodies to cancer antigens. Typical large molecule active agents are biological molecules, such as naturally occurring or synthetic or recombinant proteins. Proteins that are particularly useful in the methods and compositions provided herein include proteins that stimulate the survival and/or proliferation of hematopoietic precursor cells lymphopoietic cells in vitro or in vivo. Other useful proteins stimulate the division and differentiation of committed hematopoietic progenitors in cells in vitro or in vivo. Particular proteins include, but are not limited to: interleukins, such as IL-2 (including recombinant IL-2 ("rIL2") and canarypox IL-2), IL-10, IL-12, and IL-18; interferons, such as interferon alfa-2a, interferon alfa-2b, interferon alfa-n1, interferon alfa-n3, interferon beta-Ia, and interferon gamma-I b; GM-CF and GM-CSF; and EPO.

In certain embodiments, GM-CSF, G-CSF, SCF or EPO is administered subcutaneously during about five days in a four or six week cycle in an amount ranging from about 1 to about 750 mg/m$^2$/day, from about 25 to about 500 mg/m$^2$/day, from about 50 to about 250 mg/m$^2$/day, or from about 50 to about 200 mg/m$^2$/day. In certain embodiments, GM-CSF may be administered in an amount of from about 60 to about 500 mcg/m$^2$ intravenously over 2 hours or from about 5 to about 12 mcg/m$^2$/day subcutaneously. In certain embodiments, G-CSF may be administered subcutaneously in an amount of about 1 mcg/kg/day initially and can be adjusted depending on rise of total granulocyte counts. The maintenance dose of G-CSF may be administered in an amount of about 300 (in smaller patients) or 480 mcg subcutaneously. In certain embodiments, EPO may be administered subcutaneously in an amount of 10,000 Unit 3 times per week.

Particular proteins that can be used in the methods and compositions include, but are not limited to: filgrastim, sargramostim, and recombinant EPO.

Recombinant and mutated forms of GM-CSF can be prepared as described in U.S. Pat. Nos. 5,391,485; 5,393,870; and 5,229,496; all of which are incorporated herein by reference. Recombinant and mutated forms of G-CSF can be prepared as described in U.S. Pat. Nos. 4,810,643; 4,999,291; 5,528,823; and 5,580,755; the entireties of which are incorporated herein by reference.

Also provided for use in combination with an Aminopurine Compound provided herein are native, naturally occurring, and recombinant proteins. Further encompassed are mutants and derivatives (e.g., modified forms) of naturally occurring proteins that exhibit, in vivo, at least some of the pharmacological activity of the proteins upon which they are based. Examples of mutants include, but are not limited to, proteins that have one or more amino acid residues that differ from the corresponding residues in the naturally occurring forms of the proteins. Also encompassed by the term "mutants" are proteins that lack carbohydrate moieties normally present in their naturally occurring forms (e.g., nonglycosylated forms). Examples of derivatives include, but are not limited to, pegylated derivatives and fusion proteins, such as proteins formed by fusing IgG1 or IgG3 to the protein or active portion of the protein of interest. See, e.g., Penichet, M. L. and Morrison, S. L., *J. Immunol. Methods* 248:91-101 (2001).

Antibodies that can be used in combination with an Aminopurine Compound provided herein include monoclonal and polyclonal antibodies. Examples of antibodies include, but are not limited to, trastuzumab, rituximab, bevacizumab, pertuzumab, tositumomab, edrecolomab, and G250. Aminopurine Compounds can also be combined with, or used in combination with, anti-TNF-α antibodies, and/or anti-EGFR antibodies, such as, for example, cetuximab or panitumumab.

Antibodies that can be used in combination with an Aminopurine Compound provided herein include immune checkpoint inhibitors, such as, anti-CTLA4, anti-PD1, anti-PD-L1, anti-Tim-3, anti-Lag-3 antibodies. In some such embodiments, the PD-1 or PD-L1 antibodies are, for example, avelumab, durvalumab, MEDI0680, atezolizumab, BMS-936559, nivolumab, pembrolizumab, pidilizumab, or PDR-001. In one such embodiment, the anti-Lag-3 antibody is BMS-986016.

Additional antibodies that can be used in combination with an Aminopurine compound provided herein include anti-RSPO antibodies.

Large molecule active agents may be administered in the form of anti-cancer vaccines. For example, vaccines that secrete, or cause the secretion of, cytokines such as IL-2, G-CSF, and GM-CSF can be used in the methods and pharmaceutical compositions provided. See, e.g., Emens, L. A., et al., Curr. Opinion Mol. Ther. 3(1):77-84 (2001).

Second active agents that are small molecules can also be used to alleviate adverse effects associated with the administration of an Aminopurine Compound provided herein. However, like some large molecules, many are believed to be capable of providing an additive or synergistic effect when administered with (e.g., before, after or simultaneously) an Aminopurine Compound provided herein. Examples of small molecule second active agents include, but are not limited to, anti-cancer agents, antibiotics, immunosuppressive agents, and steroids.

In certain embodiments, the second agent is a BRAF inhibitor, an HSP inhibitor, a proteasome inhibitor, a FLT3 inhibitor, a MEK inhibitor, a PI3K inhibitor, an EGFR inhibitor, an immunomodulatory compound, or a TOR kinase inhibitor. In some such embodiments, the BRAF inhibitor is sorafenib, dabrafenib, encorafenib, or vemurafenib. In some such embodiment, the HSP inhibitor is geldanamycin, gamitrinib, luminespib, or radicicol. In some embodiments, the proteasome inhibitor is bortezomib, carfilzomib, ixazomib, disulfiram, oprozomib, delanzomib, or ixazomib. In other embodiments, the FLT3 inhibitor is quizartinib, midostaurin, sorafenib, sunitinib, or lestaurtinib. In some such embodiments, the MEK inhibitor is trametinib, cobimetinib, binimetinib, selumetinib, PD-325901, CI-1040 (PD184352) or TAK-733. In some other embodiments, the PI3K inhibitor is AT7867, AZD 8055, BX-912, silmitasertib, pictilisib, MK-2206, or pilaralisib. In another embodiment, the EGFR inhibitor is gefitinib, erlotinib, afatinib, osimertinib (TAGRISSO), rociletinib, or lapatinib. In some other embodiments, the TOR kinase inhibitor is CC-115, CC-223, OSI-027, AZD8055, sapanisertib, dactolisib, BGT226, voxtalisib (SAR-245409), apitolisib, omipalisib (GSK-2126458), PF-04691502, gedatolisib or PP242. In some embodiments, the immunomodulatory compound is thalidomide, lenalidomide, pomalidomide, CC-220, or CC-122.

Examples of additional anti-cancer agents to be used within the methods or compositions described herein include, but are not limited to: acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib (COX-2 inhibitor); chlorambucil; cirolemycin; cisplatin; cladribine; clofarabine; crisnatol mesylate; cyclophosphamide; arabinoxylcytosine; dacarbazine; dabrafenib; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; omacetaxine; ormaplatin; oxisuran; paclitaxel; paclitaxel protein-bound particles for injectable suspension, albumin bound (ABRAXANE®); pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sorafenib; sparfosate sodium; sparsomycin; spirogermanium hydrochloride; spiromustine; spiroplatin; streptonigrin; streptozocin; sulofenur; talisomycin; tecogalan sodium; docetaxel; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; vemurafenib; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer drugs to be included within the methods or compositions include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogens, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; beta-clamycin B; betulinic acid; bFGF inhibitor; bicalutamide;

bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; cetuximab, human chorionic gonadotrophin; monophosphoryl lipid A+mycobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen; $O^6$-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; paclitaxel protein-bound particles for injectable suspension, albumin bound (ABRAXANE®); palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; sarmustine; sarcophytol A; sargramostim; Sdi 1 mimetics; semustine; senescence derived inhibitor 1; sense oligonucleotides; signal transduction inhibitors; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

Specific second active agents particularly useful in the methods or compositions include, but are not limited to, rituximab, oblimersen, infliximab, docetaxel, celecoxib, melphalan, dexamethasone, steroids, gemcitabine, cisplatinum, temozolomide, etoposide, cyclophosphamide, temodar, carboplatin, procarbazine, carmustine, tamoxifen, topotecan, methotrexate, gefitinib, paclitaxel, fluorouracil, leucovorin, irinotecan, capecitabine, interferon alpha, pegylated interferon alpha, cisplatin, thiotepa, fludarabine, carboplatin, liposomal daunorubicin, cytarabine, vinblastine, IL-2, GM-CSF, dacarbazine, vinorelbine, zoledronic acid, palmitronate, clarithormycin, busulphan, prednisone, bisphosphonate, arsenic trioxide, vincristine, doxorubicin, ganciclovir, estramustine sodium phosphate, clinoril, and etoposide.

Other specific second active agents particularly useful in the methods or compositions include, but are not limited to, sorafenib, dabrafenib, vemurafenib, trametinib, cobimetinib, binimetinib, selumetinib, PD-325901, CI-1040 (PD184352), TAK-733, AT7867, AZD 8055, BX-912, silmitasertib, pictilisib, MK-2206, pilaralisib, gefitinib, erlotinib, lapatinib, osimertinib, CC-115, CC-223, OSI-027, AZD8055, sapanisertib, dactolisib, BGT226, voxtalisib, apitolisib, omipalisib, PF-04691502, gedatolisib, PP242, lenalidomide, pomalidomide, or CC-122.

Other specific second active agents particularly useful in the methods or compositions include, but are not limited to, avelumab, durvalumab, MEDI0680, atezolizumab, BMS-936559, nivolumab, pembrolizumab, pidilizumab, PDR-001, sorafenib, cetuximab, panatumumab, erlotinib, trametinib, trastuzumab, CC-223, CC-122 or lapatinib.

In certain embodiments of the methods provided herein, use of a second active agent in combination with an Aminopurine Compound provided herein may be modified or delayed during or shortly following administration of an Aminopurine Compound provided herein as deemed appropriate by the practitioner of skill in the art. In certain embodiments, subjects being administered an Aminopurine Compound provided herein alone or in combination with other therapies may receive supportive care including antiemetics, myeloid growth factors, and transfusions of blood products, when appropriate. In some embodiments, subjects being administered an Aminopurine Compound provided herein may be administered a growth factor as a second active agent according to the judgment of the practitioner of skill in the art.

In certain embodiments, an Aminopurine Compound provided herein is administered with gemcitabine, cisplatinum, 5-fluorouracil, mitomycin, methotrexate, vinblastine, doxorubicin, carboplatin, thiotepa, paclitaxel, paclitaxel protein-bound particles for injectable suspension-albumin bound (ABRAXANE®), or docetaxel to patients with locally advanced or metastatic urothelial carcinoma.

In certain embodiments, an Aminopurine Compound provided herein is administered in combination with a second active ingredient as follows: temozolomide to pediatric patients with relapsed or progressive brain tumors or recurrent neuroblastoma; celecoxib, etoposide and cyclophosphamide for relapsed or progressive CNS cancer; temozolomide to patients with recurrent or progressive meningioma, malignant meningioma, hemangiopericytoma, multiple brain metastases, relapsed brain tumors, or newly diagnosed glioblastoma multiforme; irinotecan to patients with recurrent glioblastoma; carboplatin to pediatric patients with brain stem gliomas; procarbazine to pediatric patients with progressive malignant gliomas; cyclophosphamide to patients with poor prognosis malignant brain tumors, newly diagnosed or recurrent glioblastoma multiforms; carmustine for high grade recurrent malignant gliomas; temozolomide and tamoxifen for anaplastic astrocytoma; or topotecan for gliomas, glioblastoma, anaplastic astrocytoma or anaplastic oligodendroglioma.

In certain embodiments, an Aminopurine Compound provided herein is administered with methotrexate, cyclophosphamide, 5-fluorouracil, everolimus, paclitaxel, paclitaxel protein-bound particles for injectable suspension-albumin bound (ABRAXANE®), lapatinib, trastuzumab, pamidronate disodium, eribulin mesylate, everolimus, gemcitabine, palbociclib, ixabepilone, ado-trastuzumab emtansine, pertuzumab, thiotepa, aromatase inhibitors, exemestane, selective estrogen modulators, estrogen receptor antagonists, anthracyclines, emtansine, and/or pexidartinib to patients with metastatic breast cancer.

In certain embodiments, an Aminopurine Compound provided herein is administered with temozolomide, doxorubicin, everolimus, fluorouracil, 5-fluorouracil, or streptozocin to patients with neuroendocrine tumors.

In certain embodiments, an Aminopurine Compound provided herein is administered with methotrexate, gemcitabine, cisplatin, cetuximab, 5-fluorouracil, bleomycin, docetaxel or carboplatin to patients with recurrent or metastatic head or neck cancer. In one embodiment, an Aminopurine Compound provided herein is administered with cetuximab, to patients with head or neck cancer.

In certain embodiments, an Aminopurine Compound provided herein is administered with gemcitabine, paclitaxel, paclitaxel protein-bound particles for injectable suspension-albumin bound (ABRAXANE®), 5-fluorouracil, everolimus, irinotecan, mitomycin C, sunitinib or erlotinib to patients with pancreatic cancer.

In certain embodiments, an Aminopurine Compound provided herein is administered to patients with colon cancer in combination with getfitinib, erlotinib, oxaliplatin, 5-fluorouracil, irinotecan, capecitabine, cetuximab, ramucirumab, panitumumab, bevacizumab, leucovorin calcium, LONSURF, regorafenib, ziv-aflibercept, trametinib, paclitaxel, paclitaxel protein-bound particles for injectable suspension-albumin bound (ABRAXANE®), and/or docetaxel. In certain embodiments, an Aminopurine Compound provided herein is administered to patients with colon cancer in combination with bevacizumab, irinotecan hydrochloride, capecitabine, cetuximab, ramucirumab, oxaliplatin, cetuximab, fluorouracil, leucovorin calcium, trifluridine and tipiracil hydrochloride, panitumumab, regorafenib, or ziv-aflibercept. In some embodiments, an Aminopurine Compound provided herein is administered to patients with colon cancer in combination with an EGFR inhibitor (for example cetuximab or erlotinib) and/or a BRAF inhibitor (for example, sorafenib, dabrafenib, or vemurafenib).

In certain embodiments, an Aminopurine Compound provided herein is administered with capecitabine, cetuximab, erlotinib, trametinib, and/or vemurafenib to patients with refractory colorectal cancer or patients who fail first line therapy or have poor performance in colon or rectal adenocarcinoma. In some embodiments, an Aminopurine Compound provided herein is administered to patients with refractory colorectal cancer or patients who fail first line therapy or have poor performance in colon or rectal adenocarcinoma in combination with an EGFR inhibitor (for example cetuximab or erlotinib) and a BRAF inhibitor (for example, sorafenib, dabrafenib, or vemurafenib). In some embodiments, an Aminopurine Compound provided herein is administered to patients with refractory colorectal cancer or patients who fail first line therapy or have poor performance in colon or rectal adenocarcinoma in combination with an anti-RSPO antibody.

In certain embodiments, an Aminopurine Compound provided herein is administered in combination with fluorouracil, leucovorin, trametinib and/or irinotecan to patients with Stage Ma to IV colorectal cancer or to patients who have been previously treated for metastatic colorectal cancer. In some embodiments, an Aminopurine Compound provided herein is administered to patients with Stage Ma to IV colorectal cancer or to patients who have been previously treated for metastatic colorectal cancer, in combination with an EGFR inhibitor (for example cetuximab or erlotinib) and a BRAF inhibitor (for example, sorafenib, dabrafenib, or vemurafenib). In certain embodiments, an Aminopurine Compound provided herein is administered to patients with refractory colorectal cancer in combination with capecitabine, xeloda, trametinib, oxaliplatin and/or irinotecan. In some embodiments, an Aminopurine Compound provided herein is administered to patients with refractory colorectal cancer, in combination with an EGFR inhibitor (for example cetuximab or erlotinib) and a BRAF inhibitor (for example, sorafenib, dabrafenib, or vemurafenib). In certain embodiments, an Aminopurine Compound provided herein is administered with capecitabine, trametinib, and/or irinotecan to patients with refractory colorectal cancer or to patients with unresectable or metastatic colorectal carcinoma. In some embodiments, an Aminopurine Compound provided herein is administered to patients with refractory colorectal cancer or to patients with unresectable or metastatic colorectal carcinoma, in combination with an EGFR inhibitor (for example cetuximab or erlotinib) and a BRAF inhibitor (for example, sorafenib, dabrafenib, or vemurafenib).

In certain embodiments, an Aminopurine Compound provided herein is administered alone or in combination with interferon alpha, 5-fluorouracil/leucovorin or capecitabine to patients with unresectable or metastatic hepatocellular carcinoma; or with cisplatin and thiotepa, or with sorafenib to patients with primary or metastatic liver cancer. In certain embodiments, an Aminopurine Compound provided herein is administered alone or in combination with sorafenib, sunitinib, erlotinib, and/or sirolimus, to patients with unresectable or metastatic hepatocellular carcinoma; or with sorafenib, sunitinib, erlotinib, and/or rapamycin to patients with primary or metastatic liver cancer. In some embodiments, an Aminopurine Compound provided herein is administered to patients with primary, unresectable, or metastatic liver cancer, in combination with an immune checkpoint inhibitor (for example, an anti-CTLA4, anti-PD1, anti-PD-L1, anti-Tim-3, or anti-Lag-3 antibody) or a BRAF inhibitor (for example, sorafenib, dabrafenib, or vemurafenib). In some such embodiments, the anti-PD-1 or anti-PD-L1 antibody is avelumab, durvalumab, MEDI0680, atezolizumab, BMS-936559, nivolumab, pembrolizumab, pidilizumab, or PDR-001. In certain embodiments, an Aminopurine Compound provided herein is administered alone or in combination with lenalidomide, pomalidomide or CC-122 to patients with primary, unresectable or metastatic hepatocellular carcinoma. In certain embodiments, an Aminopurine Compound provided herein is administered alone or in combination CC-223 to patients with primary, unresectable or metastatic hepatocellular carcinoma.

In certain embodiments, an Aminopurine Compound provided herein is administered in combination with cisplatin/5-fluorouracil, ramucirumab, docetaxel, doxorubicin hydrochloride, fluorouracil injection, trastuzumab, and/or mitomycin C to patients with gastric (stomach) cancer.

In certain embodiments, an Aminopurine Compound provided herein is administered in combination with an immune checkpoint inhibitor (for example, an anti-CTLA4, anti-PD1, anti-PD-L1, anti-Tim-3, or anti-Lag-3 antibody) and/or a BRAF inhibitor (for example, sorafenib, dabrafenib, or vemurafenib) to patients with various types or stages of melanoma. In some embodiments, an Aminopurine Compound provided herein is administered in combination with aldesleukin, cobimetinib, dabrafenib, dacarbazine, IL-2, talimogene laherparepvec, recombinant interferon alfa-2b, ipilimumab, pembrolizumab, lapatinib, trametinib, nivolumab, peginterferon alfa-2b, aldesleukin, dabrafenib, and/or vemurafenib to patients with various types or stages of melanoma.

In certain embodiments, an Aminopurine Compound provided herein is administered in combination with doxorubicin, paclitaxel, paclitaxel protein-bound particles for injectable suspension-albumin bound (ABRAXANE®), vinblastine or pegylated interferon alpha to patients with Kaposi's sarcoma.

In certain embodiments, an Aminopurine Compound provided herein is administered in combination with methotrexate, mechlorethamine hydrochloride, afatinib dimaleate, pemetrexed, bevacizumab, carboplatin, cisplatin, ceritinib, crizotinib, ramucirumab, pembrolizumab, docetaxel, vinorelbine tartrate, gemcitabine, paclitaxel, paclitaxel protein-bound particles for injectable suspension-albumin bound (ABRAXANE®), erlotinib, geftinib, and/or irinotecan to patients with non-small cell lung cancer.

In certain embodiments, an Aminopurine Compound provided herein is administered in combination with carboplatin and irinotecan to patients with non-small cell lung cancer.

In certain embodiments, an Aminopurine Compound provided herein is administered with docetaxel to patients with non-small cell lung cancer who have been previously treated with carboplatin/etoposide and radiotherapy.

In certain embodiments, an Aminopurine Compound provided herein is administered in combination with carboplatin and/or docetaxel, or in combination with carboplatin, pacilitaxel, paclitaxel protein-bound particles for injectable suspension-albumin bound (ABRAXANE®), and/or thoracic radiotherapy to patients with non-small cell lung cancer.

In certain embodiments, an Aminopurine Compound provided herein is administered in combination with docetaxel to patients with stage IIIB or IV non-small cell lung cancer.

In certain embodiments, an Aminopurine Compound provided herein is administered in combination with oblimersen, methotrexate, mechlorethamine hydrochloride, etoposide, topotecan or doxorubicin to patients with small cell lung cancer.

In certain embodiments, an Aminopurine Compound provided herein and doxetaxol are administered to patients with small cell lung cancer who were previously treated with carbo/VP 16 and radiotherapy.

In certain embodiments, an Aminopurine Compound provided herein is administered to patients with various types or stages of ovarian cancer such as peritoneal carcinoma, papillary serous carcinoma, refractory ovarian cancer or recurrent ovarian cancer, in combination with carboplatin, doxorubicin, gemcitabine, cisplatin, capecitabine, paclitaxel, paclitaxel protein-bound particles for injectable suspension-albumin bound (ABRAXANE®), dexamethasone, avastin, cyclophosphamide, topotecan, olaparib, thiotepa, or a combination thereof.

In certain embodiments, an Aminopurine Compound provided herein is administered to patients with various types or stages of prostate cancer, in combination with capecitabine, 5-fluorouracil plus leucovorin, gemcitabine, irinotecan plus gemcitabine, cyclophosphamide, vincristine, dexamethasone, GM-CSF, celecoxib, ganciclovir, paclitaxel, paclitaxel protein-bound particles for injectable suspension-albumin bound (ABRAXANE®), docetaxel, estramustine, denderon, abiraterone, bicalutamide, cabazitaxel, degarelix, enzalutamide, goserelin, leuprolide acetate, mitoxantrone hydrochloride, prednisone, sipuleucel-T, radium 223 dichloride, or a combination thereof.

In certain embodiments, an Aminopurine Compound provided herein is administered to patients with various types or stages of renal cell cancer, in combination with capecitabine, IFN, tamoxifen, IL-2, GM-CSF, celecoxib, or a combination thereof.

In certain embodiments, an Aminopurine Compound provided herein is administered to patients with various types or stages of gynecologic, uterus or soft tissue sarcoma cancers in combination with IFN, dactinomycin, doxorubicin, imatinib mesylate, pazopanib, hydrochloride, trabectedin, a COX-2 inhibitor such as celecoxib, and/or sulindac.

In certain embodiments, an Aminopurine Compound provided herein is administered to patients with various types or stages of solid tumors in combination with celecoxib, etoposide, cyclophosphamide, docetaxel, apecitabine, IFN, tamoxifen, IL-2, GM-CSF, or a combination thereof.

In certain embodiments, an Aminopurine Compound provided herein is administered alone or in combination with vinorelbine to patients with malignant mesothelioma, or stage IIIB non-small cell lung cancer with pleural implants or malignant mesothelioma syndrome.

In certain embodiments, an Aminopurine Compound provided herein is administered in combination with navitoclax, venetoclax and/or obatoclax to patients with lymphoma and other blood cancers.

In certain embodiments, an Aminopurine Compound provided herein is administered in combination with arsenic trioxide, fludarabine, carboplatin, daunorubicin, cyclophosphamide, cytarabine, doxorubicin, idarubicin, mitoxantrone hydrochloride, thioguanine, vincristine, and/or topotecan to patients with acute myeloid leukemia, including refractory or relapsed or high-risk acute myeloid leukemia.

In certain embodiments, an Aminopurine Compound provided herein is administered in combination with liposomal daunorubicin, topotecan and/or cytarabine to patients with unfavorable karotype acute myeloblastic leukemia.

In certain embodiments, an Aminopurine Compound provided herein is administered alone or in combination with a second active ingredient such as vinblastine or fludarabine, chlorambucil, bleomycin, brentuximab vedotin, carmustine, chlorambucil, cyclophosphamide, dacarbazine, doxorubicin, lomustine, mechlorethamine hydrochloride, prednisone, procarbazine hydrochloride or vincristine to patients with various types of lymphoma, including, but not limited to, Hodgkin's lymphoma, non-Hodgkin's lymphoma, cutaneous T-Cell lymphoma, cutaneous B-Cell lymphoma, diffuse large B-Cell lymphoma or relapsed or refractory low grade follicular lymphoma.

In certain embodiments, an Aminopurine Compound provided herein is administered to patients with various types or stages of multiple myeloma in combination with dexamethasone, zoledronic acid, pamitronate, GM-CSF, clarithromycin, vinblastine, melphalan, busulphan, cyclophosphamide, IFN, prednisone, bisphosphonate, celecoxib, arsenic trioxide, peginterferon alfa-2b, vincristine, carmustine, bortezomib, carfilzomib, doxorubicin, panobinostat, lenalidomide, pomalidomide, thalidomide, plerixafor or a combination thereof.

In certain embodiments, an Aminopurine Compound provided herein is administered to patients with various types or stages of multiple myeloma in combination with chimeric antigen receptor (CAR) T-cells.

In certain embodiments, an Aminopurine Compound provided herein is administered to patients with relapsed or refractory multiple myeloma in combination with doxorubicin, vincristine and/or dexamethasone.

In certain embodiments, an Aminopurine Compound provided herein is administered to patients with scleroderma or cutaneous vasculitis in combination with celecoxib, etoposide, cyclophosphamide, docetaxel, capecitabine, IFN, tamoxifen, IL-2, GM-CSF, or a combination thereof.

Also encompassed herein is a method of increasing the dosage of an anti-cancer drug or agent that can be safely and effectively administered to a patient, which comprises administering to the patient (e.g., a human) an Aminopurine Compound provided herein. Patients that can benefit by this method are those likely to suffer from an adverse effect associated with anti-cancer drugs for treating a specific cancer of the skin, subcutaneous tissue, lymph nodes, brain, lung, liver, bone, intestine, colon, heart, pancreas, adrenal, kidney, prostate, breast, colorectal, or combinations thereof. The administration of an Aminopurine Compound provided herein alleviates or reduces adverse effects which are of such severity that it would otherwise limit the amount of anti-cancer drug.

In one embodiment, an Aminopurine Compound provided herein is administered daily in an amount ranging from about 0.1 to about 150 mg, from about 1 to about 100 mg, from about 2 to about 50 mg, or from about 1 to about 10 mg prior to, during, or after the occurrence of the adverse effect associated with the administration of an anti-cancer drug to a patient. In certain embodiments, an Aminopurine Compound provided herein is administered in combination with specific agents such as heparin, aspirin, coumadin, anti-Factor Xa, or G-CSF to avoid adverse effects that are associated with anti-cancer drugs such as but not limited to thromboembolism, neutropenia or thrombocytopenia.

In one embodiment, an Aminopurine Compound provided herein is administered to patients with diseases and disorders associated with or characterized by, undesired angiogenesis in combination with additional active ingredients, including, but not limited to, anti-cancer drugs, anti-inflammatories, antihistamines, antibiotics, and steroids.

In another embodiment, encompassed herein is a method of treating, preventing and/or managing cancer, which comprises administering an Aminopurine Compound provided herein in conjunction with (e.g. before, during, or after) conventional therapy including, but not limited to, surgery, immunotherapy, biological therapy, radiation therapy, or other non-drug based therapy presently used to treat, prevent or manage cancer. The combined use of the compound provided herein and conventional therapy may provide a unique treatment regimen that is unexpectedly effective in certain patients. Without being limited by theory, it is believed that an Aminopurine Compound provided herein may provide additive or synergistic effects when given concurrently with conventional therapy.

As discussed elsewhere herein, encompassed herein is a method of reducing, treating and/or preventing adverse or undesired effects associated with conventional therapy including, but not limited to, surgery, chemotherapy, radiation therapy, hormonal therapy, biological therapy and immunotherapy. An Aminopurine Compound provided herein and other active ingredient can be administered to a patient prior to, during, or after the occurrence of the adverse effect associated with conventional therapy.

Cycling Therapy

In certain embodiments, the prophylactic or therapeutic agents provided herein are cyclically administered to a patient. Cycling therapy involves the administration of an active agent for a period of time, followed by a rest for a period of time, and repeating this sequential administration. Cycling therapy can reduce the development of resistance to one or more of the therapies, avoid, or reduce the side effects of one of the therapies, and/or improves the efficacy of the treatment.

Consequently, in certain embodiments, an Aminopurine Compound provided herein is administered daily in a single or divided dose in a four to six week cycle with a rest period of about a week or two weeks. In certain embodiments, an Aminopurine Compound provided herein is administered daily in a single or divided doses for one to ten consecutive days of a 28 day cycle, then a rest period with no administration for rest of the 28 day cycle. The cycling method further allows the frequency, number, and length of dosing cycles to be increased. Thus, encompassed herein in certain embodiments is the administration of an Aminopurine Compound provided herein for more cycles than are typical when it is administered alone. In certain embodiments, an Aminopurine Compound provided herein is administered for a greater number of cycles that would typically cause dose-limiting toxicity in a patient to whom a second active ingredient is not also being administered.

In one embodiment, an Aminopurine Compound provided herein is administered daily and continuously for three or four weeks at a dose of from about 0.1 to about 150 mg/day followed by a break of one or two weeks.

In another embodiment, an Aminopurine Compound provided herein is administered intravenously and a second active ingredient is administered orally, with administration of Aminopurine Compounds occurring 30 to 60 minutes prior to a second active ingredient, during a cycle of four to six weeks. In certain embodiments, the combination of an Aminopurine Compound provided herein and a second active ingredient is administered by intravenous infusion over about 90 minutes every cycle. In certain embodiments, one cycle comprises the administration from about 0.1 to about 150 mg/day of an Aminopurine Compound provided herein and from about 50 to about 200 mg/m$^2$/day of a second active ingredient daily for three to four weeks and then one or two weeks of rest. In certain embodiments, the number of cycles during which the combinatorial treatment is administered to a patient is ranging from about one to about 24 cycles, from about two to about 16 cycles, or from about four to about three cycles.

Pharmaceutical Compositions and Routes of Administration

The Aminopurine Compounds can be administered to a subject orally, topically or parenterally in the conventional form of preparations, such as capsules, microcapsules, tablets, granules, powder, troches, pills, suppositories, injections, suspensions, syrups, patches, creams, lotions, ointments, gels, sprays, solutions and emulsions. Suitable formulations can be prepared by methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g., sodium benzoate, sodium bisulfate, methylparaben or propylparaben), a stabilizer (e.g., citric acid, sodium citrate or acetic acid), a suspending agent (e.g., methylcellulose, polyvinyl pyrrolidone or aluminum stearate), a dispersing agent (e.g., hydroxypropylmethylcellulose), a diluent (e.g., water), and base wax (e.g., cocoa butter, white petrolatum or polyethylene glycol). The effective amount of the Aminopurine Compounds in the pharmaceutical composition may be at a level that will exercise the desired effect; for example, about 0.005 mg/kg of a subject's body weight to about 10 mg/kg of a subject's body weight in unit dosage for both oral and parenteral administration.

The dose of an Aminopurine Compound to be administered to a subject is rather widely variable and can be subject to the judgment of a health-care practitioner. In general, the Aminopurine Compounds can be administered one to four times a day in a dose of about 0.005 mg/kg of a subject's body weight to about 10 mg/kg of a subject's body weight in a subject, but the above dosage may be properly varied depending on the age, body weight and medical condition of the subject and the type of administration. In one embodiment, the dose is about 0.01 mg/kg of a subject's body weight to about 10 mg/kg of a subject's body weight, about 0.1 mg/kg of a subject's body weight to about 10 mg/kg of a subject's body weight, about 1 mg/kg of a subject's body weight to about 10 mg/kg of a subject's body weight or about 1 mg/kg of a subject's body weight to about 5 mg/kg of a subject's body weight. In one embodiment, one dose is given per day. In any given case, the amount of the Aminopurine Compound administered will depend on such factors as the solubility of the active component, the formulation used and the route of administration. In one embodiment, application of a topical concentration provides intracellular exposures or concentrations of about 0.01-10 µM.

In another embodiment, provided herein are methods for the treatment or prevention of a disease or disorder comprising the administration of about 1 mg/day to about 1000 mg/day, about 1 mg/day to about 750 mg/day, about 1 mg/day to about 500 mg/day, about 1 mg/day to about 250 mg/day or about 100 mg/day to about 1000 mg/day of an Aminopurine Compound to a subject in need thereof.

In another embodiment, provided herein are unit dosage formulations that comprise between about 1 mg and 1000 mg, about 5 mg and about 1000 mg, about 10 mg and about 1000 mg, about 25 mg and about 1000 mg, about 50 mg and about 1000 mg, about 100 mg and about 1000 mg, or about 250 mg and about 1000 mg of an Aminopurine Compound.

An Aminopurine Compound can be administered once, twice, three, four or more times daily. In a particular embodiment, doses of 600 mg or less are administered as a once daily dose and doses of more than 600 mg are administered twice daily in an amount equal to one half of the total daily dose.

An Aminopurine Compound can be administered orally for reasons of convenience. In one embodiment, when administered orally, an Aminopurine Compound is administered with a meal and water. In another embodiment, the Aminopurine Compound is dispersed in water or juice (e.g., apple juice or orange juice) and administered orally as a suspension.

The Aminopurine Compound can also be administered intradermally, intramuscularly, intraperitoneally, percutaneously, intravenously, subcutaneously, intranasally, epidurally, sublingually, intracerebrally, intravaginally, transdermally, rectally, mucosally, by inhalation, or topically to the ears, nose, eyes, or skin. The mode of administration is left to the discretion of the health-care practitioner, and can depend in part upon the site of the medical condition.

In one embodiment, provided herein are capsules containing an Aminopurine Compound without an additional carrier, excipient or vehicle.

In another embodiment, provided herein are compositions comprising an effective amount of an Aminopurine Compound and a pharmaceutically acceptable carrier or vehicle, wherein a pharmaceutically acceptable carrier or vehicle can comprise an excipient, diluent, or a mixture thereof. In one embodiment, the composition is a pharmaceutical composition.

The compositions can be in the form of tablets, chewable tablets, capsules, solutions, parenteral solutions, troches, suppositories and suspensions and the like. Compositions can be formulated to contain a daily dose, or a convenient fraction of a daily dose, in a dosage unit, which may be a single tablet or capsule or convenient volume of a liquid. In one embodiment, the solutions are prepared from water-soluble salts, such as the hydrochloride salt. In general, all of the compositions are prepared according to known methods in pharmaceutical chemistry. Capsules can be prepared by mixing an Aminopurine Compound with a suitable carrier or diluent and filling the proper amount of the mixture in capsules. The usual carriers and diluents include, but are not limited to, inert powdered substances such as starch of many different kinds, powdered cellulose, especially crystalline and microcrystalline cellulose, sugars such as fructose, mannitol and sucrose, grain flours and similar edible powders.

Tablets can be prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant might be necessary in a tablet formulation to prevent the tablet and punches from sticking in the dye. The lubricant can be chosen from such slippery solids as talc, magnesium and calcium stearate, stearic acid and hydrogenated vegetable oils. Tablet disintegrators are substances that swell when wetted to break up the tablet and release the compound. They include starches, clays, celluloses, aligns and gums. More particularly, corn and potato starches, methylcellulose, agar, bentonite, wood cellulose, powdered natural sponge, cation-exchange resins, alginic acid, guar gum, citrus pulp and carboxymethyl cellulose, for example, can be used as well as sodium lauryl sulfate. Tablets can be coated with sugar as a flavor and sealant, or with film-forming protecting agents to modify the dissolution properties of the tablet. The compositions can also be formulated as chewable tablets, for example, by using substances such as mannitol in the formulation.

When it is desired to administer an Aminopurine Compound as a suppository, typical bases can be used. Cocoa butter is a traditional suppository base, which can be modified by addition of waxes to raise its melting point slightly. Water-miscible suppository bases comprising, particularly, polyethylene glycols of various molecular weights are in wide use.

The effect of the Aminopurine Compound can be delayed or prolonged by proper formulation. For example, a slowly soluble pellet of the Aminopurine Compound can be prepared and incorporated in a tablet or capsule, or as a slow-release implantable device. The technique also includes making pellets of several different dissolution rates and filling capsules with a mixture of the pellets. Tablets or capsules can be coated with a film that resists dissolution for a predictable period of time. Even the parenteral preparations can be made long-acting, by dissolving or suspending the Aminopurine Compound in oily or emulsified vehicles that allow it to disperse slowly in the serum.

EXAMPLES

The following Examples are presented by way of illustration, not limitation. Compounds are named using the automatic name generating tool provided in Chemdraw Ultra 9.0 (Cambridgesoft), which generates systematic names for chemical structures, with support for the Cahn-Ingold-Prelog rules for stereochemistry.

Cell Assays

Multiplexed Cytotoxicity Assay.

Cells are grown in RPMI1640, 10% FBS, 2 mM L-alanyl-L-Glutamine, 1 mM Na pyruvate or a special medium in a humidified atmosphere of 5% $CO_2$ at 37° C. Cells are seeded into 384-well plates and incubated in a humidified atmosphere of 5% $CO_2$ at 37° C. Compounds are added 24 h post cell seeding. At the same time, a time zero untreated cell plate is generated. After a 72 hour incubation period, cells are fixed and stained with fluorescently labeled antibodies and nuclear dye to allow visualization of nuclei, apoptotic cells and mitotic cells. Apoptotic cells are detected using an anti-active caspase-3 antibody. Mitotic cells are detected using an anti phospho-histone-3 antibody. Compounds are serially diluted 3.16-fold and assayed over 10 concentrations in a final assay concentration of 0.1% DMSO from the highest test concentration of 10 µM. Automated fluorescence microscopy was carried out using a Molecular Devices ImageXpress Micro XL high-content imager, and images are collected with a 4× objective.

Data Analysis.

Sixteen-bit TIFF images are acquired and analyzed with MetaXpress 5.1.0.41 software. Cell proliferation is measured by the signal intensity of the incorporated nuclear dye. The cell proliferation assay output is referred to as the relative cell count. To determine the cell proliferation end point, the cell proliferation data output is transformed to percentage of control (POC) using the following formula:

POC=relative cell count(compound wells)/relative cell count(vehicle wells)×100

Relative cell count $IC_{50}$ is the test compound concentration at 50% of maximal possible response relative to the DMSO control. $GI_{50}$ is the concentration needed to reduce the observed growth by half. This is the concentration that inhibits the growth to the level midway between growth in untreated cells and the number of cells seeded in the well (Time zero value). The $IC_{50}$ values are calculated using nonlinear regression to fit data to a sigmoidal 4 point, 4 parameter One-Site dose response model, where:

$y(\text{fit})=A+[(B-A)/(1+((C/x)\hat{\ }D))]$.

The activated caspase-3 marker labels cells from early to late stage apoptosis. Concentrations of test compound that cause a 5-fold induction in the caspase-3 signal (Cal_X5) indicate significant apoptosis induction. The maximal induction of caspase 3 by compound in comparison with DMSO control is reported as Max_Fold_Change.

TABLE 2

| Cell lines used in multiplexed cytotoxicity assays | | |
|---|---|---|
| Cell Line | Type | Subtype |
| SW-13 | Endocrine | Adrenal gland |
| NCI-H295R | Endocrine | Adrenal gland |
| 639-V | Bladder | Bladder |
| BFTC-905 | Bladder | Bladder |
| HT1376 | Bladder | Bladder |
| SCaBER | Bladder | Bladder |
| T24 | Bladder | Bladder |
| 5637 | Bladder | Bladder |

TABLE 2-continued

Cell lines used in multiplexed cytotoxicity assays

| Cell Line | Type | Subtype |
|---|---|---|
| 647-V | Bladder | Bladder |
| HT-1197 | Bladder | Bladder |
| TCCSUP | Bladder | Bladder |
| J82 | Bladder | Bladder |
| UM-UC-3 | Bladder | Bladder |
| MDA-MB-436 | Breast | Breast |
| Hs 578T | Breast | Breast |
| AU565 | Breast | Breast |
| BT20 | Breast | Breast |
| SK-BR-3 | Breast | Breast |
| BT474 | Breast | Breast |
| CAMA-1 | Breast | Breast |
| EFM-19 | Breast | Breast |
| KPL-1 | Breast | Breast |
| MDA MB 231 | Breast | Breast |
| MDA MB 453 | Breast | Breast |
| MCF7 | Breast | Breast |
| T47D | Breast | Breast |
| MDA-MB-415 | Breast | Breast |
| ZR-75-1 | Breast | Breast |
| BT-549 | Breast | Breast |
| MDA MB 468 | Breast | Breast |
| C-33A | Female GU | Cervix |
| C-4 I | Female GU | Cervix |
| C-4 II | Female GU | Cervix |
| HeLa | Female GU | Cervix |
| SiHa | Female GU | Cervix |
| DoTc2 4510 | Female GU | Cervix |
| HT-3 | Female GU | Cervix |
| LS513 | Colon | Colon |
| LS411N | Colon | Colon |
| SNU-C2B | Colon | Colon |
| LS123 | Colon | Colon |
| MT-3 | Colon | Colon |
| SW403 | Colon | Colon |
| RKO-AS45-1 | Colon | Colon |
| SW480 | Colon | Colon |
| SW948 | Colon | Colon |
| Colo 320 HSR | Colon | Colon |
| HCT-15 | Colon | Colon |
| HCT-116 | Colon | Colon |
| RKOE6 | Colon | Colon |
| SW48 | Colon | Colon |
| SW837 | Colon | Colon |
| SW1463 | Colon | Colon |
| Colo 320DM | Colon | Colon |
| HT-29 | Colon | Colon |
| LS1034 | Colon | Colon |
| Colo 201 | Colon | Colon |
| Colo 205 | Colon | Colon |
| NCI-H747 | Colon | Colon |
| RKO | Colon | Colon |
| SW1417 | Colon | Colon |
| DLD-1 | Colon | Colon |
| NCI-H508 | Colon | Colon |
| SW620 | Colon | Colon |
| WiDr | Colon | Colon |
| HRT-18 | Colon | Colon |
| LS-174T | Colon | Colon |
| HuTu 80 | Duodenum | Duodenum |
| Y79 | Eye | Eye |
| Hs 683 | Central Nervous System | Glioma |
| U-118 MG | Central Nervous System | Glioma |
| M059J | Central Nervous System | Glioma |
| PFSK-1 | Central Nervous System | Glioma |
| SW1783 | Central Nervous System | Glioma |
| SW1088 | Central Nervous System | Glioma |
| T98G | Central Nervous System | Glioma |
| CCF-STTG1 | Central Nervous System | Glioma |
| A172 | Central Nervous System | Glioma |
| DBTRG-05MG | Central Nervous System | Glioma |
| H4 | Central Nervous System | Glioma |
| SNB-19 | Central Nervous System | Glioma |
| U-138MG | Central Nervous System | Glioma |
| U-87 MG | Central Nervous System | Glioma |
| DK-MG | Central Nervous System | Glioma |
| A-253 | Head and Neck | Head and Neck |
| A388 | Head and Neck | Head and Neck |
| Detroit 562 | Head and Neck | Head and Neck |
| A431 | Head and Neck | Head and Neck |
| Cal 27 | Head and Neck | Head and Neck |
| OE19 | Head and Neck | Head and Neck |
| OE33 | Head and Neck | Head and Neck |
| SCC-4 | Head and Neck | Head and Neck |
| FaDu | Head and Neck | Head and Neck |
| OE21 | Head and Neck | Head and Neck |
| SCC-25 | Head and Neck | Head and Neck |
| SCC-9 | Head and Neck | Head and Neck |
| A-704 | Kidney | Kidney |
| 769-P | Kidney | Kidney |
| 786-O | Kidney | Kidney |
| G-402 | Kidney | Kidney |
| ACHN | Kidney | Kidney |
| Caki-1 | Kidney | Kidney |
| Caki-2 | Kidney | Kidney |
| SK-NEP-1 | Kidney | Kidney |
| G-401 | Kidney | Kidney |
| A498 | Kidney | Kidney |
| KG-1 | Hematopoietic | Leukemia |
| RS4; 11 | Hematopoietic | Leukemia |
| KU812 | Hematopoietic | Leukemia |
| TF-1 | Hematopoietic | Leukemia |
| MX1 | Hematopoietic | Leukemia |
| NALM-6 | Hematopoietic | Leukemia |
| MOLT-3 | Hematopoietic | Leukemia |
| MOLT-16 | Hematopoietic | Leukemia |
| MEG01 | Hematopoietic | Leukemia |
| MHH-PREB-1 | Hematopoietic | Leukemia |
| MV-4-11 | Hematopoietic | Leukemia |
| Thp1 | Hematopoietic | Leukemia |
| BV-173 | Hematopoietic | Leukemia |
| CCRFCEM | Hematopoietic | Leukemia |
| CML-T1 | Hematopoietic | Leukemia |
| HEL-92-1-7 | Hematopoietic | Leukemia |
| J-RT3-T3-5 | Hematopoietic | Leukemia |
| Jurkat | Hematopoietic | Leukemia |
| CEM-C1 | Hematopoietic | Leukemia |
| EM-2 | Hematopoietic | Leukemia |
| K562 | Hematopoietic | Leukemia |
| HuCCT1 | Liver | Liver |
| HLE | Liver | Liver |
| HUH-6 Clone 5 | Liver | Liver |
| HepG2 | Liver | Liver |
| HLF | Liver | Liver |
| OCUG-1 | Liver | Liver |
| SNU-423 | Liver | Liver |
| Hs 611.T | Hematopoietic | Lymphoma |
| EB2 | Hematopoietic | Lymphoma |
| GA-10 | Hematopoietic | Lymphoma |
| H9 | Hematopoietic | Lymphoma |
| JeKo-1 | Hematopoietic | Lymphoma |
| SU-DHL-8 | Hematopoietic | Lymphoma |
| SUP-T1 | Hematopoietic | Lymphoma |
| TUR | Hematopoietic | Lymphoma |
| Hs 445 | Hematopoietic | Lymphoma |
| BCP-1 | Hematopoietic | Lymphoma |
| CA46 | Hematopoietic | Lymphoma |
| Jiyoye | Hematopoietic | Lymphoma |
| MC116 | Hematopoietic | Lymphoma |
| NAMALWA | Hematopoietic | Lymphoma |
| REC-1 | Hematopoietic | Lymphoma |
| SU-DHL-4 | Hematopoietic | Lymphoma |
| SU-DHL-5 | Hematopoietic | Lymphoma |
| SU-DHL-10 | Hematopoietic | Lymphoma |
| DB | Hematopoietic | Lymphoma |
| DOHH-2 | Hematopoietic | Lymphoma |
| HT | Hematopoietic | Lymphoma |
| RPMI 6666 | Hematopoietic | Lymphoma |
| Raji | Hematopoietic | Lymphoma |
| SR | Hematopoietic | Lymphoma |
| ST486 | Hematopoietic | Lymphoma |
| BC-1 | Hematopoietic | Lymphoma |

TABLE 2-continued

Cell lines used in multiplexed cytotoxicity assays

| Cell Line | Type | Subtype |
|---|---|---|
| Daudi | Hematopoietic | Lymphoma |
| L-428 | Hematopoietic | Lymphoma |
| EB-3 | Hematopoietic | Lymphoma |
| Ramos (RA 1) | Hematopoietic | Lymphoma |
| CRO-AP2 | Hematopoietic | Lymphoma |
| D341 Med | Central Nervous System | Medulloblastoma |
| D283 Med | Central Nervous System | Medulloblastoma |
| Daoy | Central Nervous System | Medulloblastoma |
| Hs 852.T | Skin (Melanoma) | Melanoma |
| WM-266-4 | Skin (Melanoma) | Melanoma |
| Hs 934.T | Skin (Melanoma) | Melanoma |
| A2058 | Skin (Melanoma) | Melanoma |
| G-361 | Skin (Melanoma) | Melanoma |
| Hs 688(A).T | Skin (Melanoma) | Melanoma |
| Hs 936.T(C1) | Skin (Melanoma) | Melanoma |
| Hs 895.T | Skin (Melanoma) | Melanoma |
| A7 | Skin (Melanoma) | Melanoma |
| C32 | Skin (Melanoma) | Melanoma |
| CHL-1 | Skin (Melanoma) | Melanoma |
| SK-MEL-28 | Skin (Melanoma) | Melanoma |
| SH-4 | Skin (Melanoma) | Melanoma |
| RPMI-7951 | Skin (Melanoma) | Melanoma |
| MALME3M | Skin (Melanoma) | Melanoma |
| MeWo | Skin (Melanoma) | Melanoma |
| SK-MEL-1 | Skin (Melanoma) | Melanoma |
| SK-MEL-3 | Skin (Melanoma) | Melanoma |
| C32TG | Skin (Melanoma) | Melanoma |
| Hs 294T | Skin (Melanoma) | Melanoma |
| Hs 695T | Skin (Melanoma) | Melanoma |
| A101D | Skin (Melanoma) | Melanoma |
| A375 | Skin (Melanoma) | Melanoma |
| COLO 829 | Skin (Melanoma) | Melanoma |
| HMCB | Skin (Melanoma) | Melanoma |
| IM-9 | Hematopoietic | Myeloma |
| SKO-007 | Hematopoietic | Myeloma |
| U266B1 | Hematopoietic | Myeloma |
| RPMI 8226 | Hematopoietic | Myeloma |
| ARH-77 | Hematopoietic | Myeloma |
| BE(2)C | Central Nervous System | Neuroblastoma |
| SK-N-FI | Central Nervous System | Neuroblastoma |
| CHP-212 | Central Nervous System | Neuroblastoma |
| SK-N-AS | Central Nervous System | Neuroblastoma |
| MC-IXC | Central Nervous System | Neuroblastoma |
| SK-N-DZ | Central Nervous System | Neuroblastoma |
| Hs 229.T | Lung | NSCLC |
| NCI-H661 | Lung | NSCLC |
| A427 | Lung | NSCLC |
| Calu6 | Lung | NSCLC |
| NCI-H460 | Lung | NSCLC |
| NCI-H520 | Lung | NSCLC |
| NCI-H596 | Lung | NSCLC |
| NCIH441 | Lung | NSCLC |
| A549 | Lung | NSCLC |
| ChaGoK1 | Lung | NSCLC |
| Calu1 | Lung | NSCLC |
| COR-L23 | Lung | NSCLC |
| SKMES1 | Lung | NSCLC |
| NCI-H292 | Lung | NSCLC |
| COR-L105 | Lung | NSCLC |
| G-292, clone A141B1 | Soft Tissue | Osteosarcoma |
| Hs 888.Sk | Soft Tissue | Osteosarcoma |
| HOS | Soft Tissue | Osteosarcoma |
| MG-63 | Soft Tissue | Osteosarcoma |
| SJSA1 | Soft Tissue | Osteosarcoma |
| SW1353 | Soft Tissue | Osteosarcoma |
| SaOS2 | Soft Tissue | Osteosarcoma |
| U2OS | Soft Tissue | Osteosarcoma |
| KHOS-240S | Soft Tissue | Osteosarcoma |
| ME-180 | Female GU | Ovary |
| PA-1 | Female GU | Ovary |
| Ca Ski | Female GU | Ovary |
| MS751 | Female GU | Ovary |
| CaOV3 | Female GU | Ovary |
| OVCAR3 | Female GU | Ovary |
| SKOV3 | Female GU | Ovary |
| PSN-1 | Pancreas | Pancreas |
| AsPC-1 | Pancreas | Pancreas |
| PANC-1 | Pancreas | Pancreas |
| Hs 766T | Pancreas | Pancreas |
| Mia PaCa-2 | Pancreas | Pancreas |
| SU.86.86 | Pancreas | Pancreas |
| YAPC | Pancreas | Pancreas |
| BxPC-3 | Pancreas | Pancreas |
| CFPAC-1 | Pancreas | Pancreas |
| Capan-1 | Pancreas | Pancreas |
| Capan-2 | Pancreas | Pancreas |
| HPAF-II | Pancreas | Pancreas |
| HuP-T4 | Pancreas | Pancreas |
| BeWo | Placenta | Placenta |
| JAR | Placenta | Placenta |
| JEG-3 | Placenta | Placenta |
| 22Rv1 | Prostate | Prostate |
| DU145 | Prostate | Prostate |
| PC-3 | Prostate | Prostate |
| LNCaP | Prostate | Prostate |
| BM-1604 | Prostate | Prostate |
| BPH1 | Prostate | Prostate |
| Hs 729 | Soft Tissue | Sarcoma |
| VA-ES-BJ | Soft Tissue | Sarcoma |
| Hs 821.T | Soft Tissue | Sarcoma |
| TE 125.T | Soft Tissue | Sarcoma |
| RD | Soft Tissue | Sarcoma |
| SK-UT-1 | Soft Tissue | Sarcoma |
| A-673 | Soft Tissue | Sarcoma |
| SW684 | Soft Tissue | Sarcoma |
| A204 | Soft Tissue | Sarcoma |
| SW872 | Soft Tissue | Sarcoma |
| SW982 | Soft Tissue | Sarcoma |
| HT-1080 | Soft Tissue | Sarcoma |
| MES-SA | Soft Tissue | Sarcoma |
| SJRH30 | Soft Tissue | Sarcoma |
| SK-LMS-1 | Soft Tissue | Sarcoma |
| TE 381.T | Soft Tissue | Sarcoma |
| NCI-H510A | Lung | SCLC |
| NCIH446 | Lung | SCLC |
| SHP-77 | Lung | SCLC |
| DMS114 | Lung | SCLC |
| SW900 | Lung | SCLC |
| DMS53 | Lung | SCLC |
| NCI-H69 | Lung | SCLC |
| DMS273 | Lung | SCLC |
| SK-PN-DW | Stomach | Stomach |
| AGS | Stomach | Stomach |
| HS 746T | Stomach | Stomach |
| SNU-1 | Stomach | Stomach |
| KATO III | Stomach | Stomach |
| SNU-16 | Stomach | Stomach |
| SNU-5 | Stomach | Stomach |
| NTERA-2 cl.D1 | Testis | Testis |
| TT | Endocrine | Thyroid |
| BHT-101 | Endocrine | Thyroid |
| CAL-62 | Endocrine | Thyroid |
| CGTH-W-1 | Endocrine | Thyroid |
| SW579 | Endocrine | Thyroid |
| HEC-1-A | Female GU | Uterus |
| RL95-2 | Female GU | Uterus |
| KLE | Female GU | Uterus |
| AN3 CA | Female GU | Uterus |
| SW962 | Female GU | Vulva |
| SW954 | Female GU | Vulva |

Aminopurine Compounds (exemplified by Compound 1) show or will be shown to have anti-proliferative activity in a variety of cancer cell lines. Anti-proliferative activity in these cancer cell lines indicates that the Aminopurine compounds may be useful in the treatment of cancers, including solid tumors, as exemplified by melanoma, colorectal cancer, stomach cancer, head and neck cancer, thyroid cancer, bladder cancer, CNS cancer, lung cancer, pancreatic cancer, and soft tissue cancer.

In another embodiment, Aminopurine Compounds (exemplified by Compound 1) show or will be shown to induce apoptosis in a variety of cancer cell lines. Induction of apoptosis indicates that the Aminopurine compounds may be useful in the treatment of cancers, including solid tumors, as exemplified by bladder cancer, breast cancer, CNS cancer (including neuroblastoma and glioma), colon cancer, gastrointestinal cancer (for example, stomach cancer or colon cancer), endocrine cancer (for example, thyroid cancer or adrenal gland cancer), female genitoureal cancer (for example, cervix cancer or ovary clear cell cancer, vulva cancer, uterus cancer, or ovary cancer), head and neck cancer, hematopoietic cancer (for example, leukemia or myeloma), kidney cancer, liver cancer, lung (for example, NSCLC or SCLC), melanoma, pancreas cancer, prostate cancer, or soft tissue cancer (for example, sarcoma or osteosarcoma).

In another embodiment, Aminopurine Compounds (exemplified by Compound 1) show or will be shown to cause G1/S arrest in a variety of cancer cell lines. Causing G1/S arrest in these cancer cell lines indicates that the Aminopurine compounds may be useful in the treatment of cancers, including solid tumors, as exemplified by bladder cancer, breast cancer, CNS cancer (for example, glioma or neuroblastoma), colon cancer, gastrointestinal cancer (for example, stomach cancer), endocrine cancer (for example, thyroid cancer or adrenal gland cancer), female genitoureal cancer (for example, uterus cancer, cervix cancer, ovary clear cell cancer, or vulva cancer), head and neck cancer, hematopoietic cancer (for example, leukemia or myeloma), kidney cancer, liver cancer, lung cancer (for example, NSCLC or SCLC), melanoma, pancreas cancer, prostate cancer, or soft tissue cancer (sarcoma or osteosarcoma).

Multiplexed Cytotoxicity Assay.

In Another Experiment, Cells were Grown in RPMI1640, 10% FBS, 2 mM L-alanyl-L-Glutamine, 1 mM Na pyruvate or a special medium in a humidified atmosphere of 5% $CO_2$ at 37° C. Cells were seeded into 384-well plates and incubated in a humidified atmosphere of 5% $CO_2$ at 37° C. Compounds were added 24 h post cell seeding. At the same time, a time zero untreated cell plate was generated. After a 72 hour incubation period, cells were fixed and stained with fluorescently labeled antibodies and nuclear dye to allow visualization of nuclei, apoptotic cells and mitotic cells. Apoptotic cells were detected using an anti-active caspase-3 antibody. Mitotic cells were detected using an anti phospho-histone-3 antibody. Compounds were serially diluted 3.16-fold and assayed over 10 concentrations in a final assay concentration of 0.1% DMSO from the highest test concentration of 10 µM. Automated fluorescence microscopy was carried out using a Molecular Devices ImageXpress Micro XL high-content imager, and images were collected with a 4× objective.

Data Analysis.

Sixteen-bit TIFF images were acquired and analyzed with MetaXpress 5.1.0.41 software. Cell proliferation was measured by the signal intensity of the incorporated nuclear dye. The cell proliferation assay output was referred to as the relative cell count. To determine the cell proliferation end point, the cell proliferation data output was transformed to percentage of control (POC) using the following formula:

POC=relative cell count(compound wells)/relative cell count(vehicle wells)×100

Relative cell count $IC_{50}$ was the test compound concentration at 50% of maximal possible response relative to the DMSO control. $GI_{50}$ refers to the concentration needed to reduce the observed growth by half. This corresponds to the concentration that inhibits the growth to the level midway between growth in untreated cells and the number of cells seeded in the well (Time zero value). The $IC_{50}$ values were calculated using nonlinear regression to fit data to a sigmoidal 4 point, 4 parameter One-Site dose response model, where:

$$y(\text{fit})=A+[(B-A)/(1+((C/x)^D))].$$

The activated caspase-3 marker labels cells from early to late stage apoptosis. Concentrations of test compound that cause a 2-fold (Cal-X2) or 5-fold induction in the caspase-3 signal (Cal_X5) indicated significant apoptosis induction. The maximal induction of caspase 3 by compound in comparison with DMSO control was reported as Max_Fold_Change.

TABLE 3

Results of Cytotoxicity Assays

| Cell line | Tumor Type | Subtype | GI50 (µM) | IC50 (µM) | CalX2 (µM) | CalX5 (µM) | Max fold change |
|---|---|---|---|---|---|---|---|
| NCIH295R | Endocrine | Adrenal gland | 10 | 10 | 10 | 10 | 1.74 |
| SW13 | Endocrine | Adrenal gland | 0.0711 | 0.135 | 0.04 | 0.535 | 8.74 |
| 5637 | Bladder | Bladder | 6.85 | 9.77 | 10 | 10 | 2.12 |
| 639V | Bladder | Bladder | 0.184 | 0.206 | 0.0841 | 0.465 | 6.33 |
| 647V | Bladder | Bladder | 6.93 | 7.82 | 2.7413 | 4.45 | 19.29 |
| BFTC905 | Bladder | Bladder | 0.0515 | 0.0546 | 0.0179 | 0.0414 | 45.3 |
| HT1197 | Bladder | Bladder | 0.444 | 10 | 0.1601 | 10 | 4.16 |
| HT1376 | Bladder | Bladder | 0.792 | 3.48 | 0.0524 | 0.167 | 10.87 |
| J82 | Bladder | Bladder | 10 | 10 | 2.4365 | 10 | 3.17 |
| SCABER | Bladder | Bladder | 0.0665 | 0.0772 | 0.0086 | 0.0506 | 29.47 |
| T24 | Bladder | Bladder | 0.233 | 0.274 | 4.5443 | 10 | 2.61 |
| TCCSUP | Bladder | Bladder | 2.21 | 6.59 | 5.6435 | 10 | 3.67 |
| UMUC3 | Bladder | Bladder | 0.149 | 0.201 | 2.7934 | 5.76 | 6.56 |
| AU565 | Breast | Breast | 8.15 | 8.77 | 3.8749 | 7.14 | 14.18 |
| BT20 | Breast | Breast | 8.36 | 10 | 10 | 10 | 1.81 |
| BT474 | Breast | Breast | 10 | 10 | 10 | 10 | 0.94 |
| BT549 | Breast | Breast | 10 | 10 | 5.4537 | 10 | 3.14 |
| CAMA1 | Breast | Breast | 0.298 | 2.24 | 6.4981 | 10 | 2.85 |
| EFM19 | Breast | Breast | 4.2 | 10 | 10 | 10 | 2.1 |
| HS578T | Breast | Breast | 0.153 | 0.837 | 2.6723 | 6.58 | 5.94 |
| KPL1 | Breast | Breast | 10 | 10 | 0.0481 | 10 | 2.63 |
| MCF7 | Breast | Breast | 0.636 | 3.47 | 6.5592 | 9.74 | 5.78 |

TABLE 3-continued

Results of Cytotoxicity Assays

| Cell line | Tumor Type | Subtype | GI50 (µM) | IC50 (µM) | CalX2 (µM) | CalX5 (µM) | Max fold change |
|---|---|---|---|---|---|---|---|
| MDAMB231 | Breast | Breast | 0.0339 | 0.0624 | 0.0242 | 0.257 | 5.94 |
| MDAMB415 | Breast | Breast | 0.729 | 10 | 10 | 10 | 1.85 |
| MDAMB436 | Breast | Breast | 0.262 | 10 | 5.118 | 10 | 4.25 |
| MDAMB453 | Breast | Breast | 0.656 | 2.82 | 10 | 10 | 1.07 |
| MDAMB468 | Breast | Breast | 0.0363 | 0.0721 | 0.0969 | 10 | 3.81 |
| MT3 | Breast | Breast | 0.674 | 1.08 | 7.6544 | 10 | 2.81 |
| SKBR3 | Breast | Breast | 6.81 | 8.45 | 3.2211 | 6.2 | 12.79 |
| T47D | Breast | Breast | 10 | 10 | 10 | 10 | 2 |
| ZR751 | Breast | Breast | 0.0943 | 7.7 | 5.9055 | 6.44 | 7.36 |
| A431 | Skin | Carcinoma | 0.228 | 0.311 | 0.0801 | 1.76 | 5.11 |
| C33A | Female GU | Cervix | 0.191 | 0.407 | 3.6798 | 5.39 | 9.45 |
| C4I | Female GU | Cervix | 10 | 10 | 5.7177 | 7.94 | 7.38 |
| C4II | Female GU | Cervix | 10 | 10 | 0.044 | 10 | 3.7 |
| DOTC24510 | Female GU | Cervix | 0.04 | 0.132 | 0.0268 | 10 | 5.03 |
| HELA | Female GU | Cervix | 6.75 | 8.71 | 7.0794 | 10 | 3.65 |
| HT3 | Female GU | Cervix | 0.856 | 3.21 | 0.2906 | 3.74 | 7.49 |
| SIHA | Female GU | Cervix | 10 | 10 | 7.6882 | 8.82 | 5.49 |
| COLO201 | Colon | Colon | 0.0128 | 0.0172 | 0.0225 | 0.267 | 6.09 |
| COLO205 | Colon | Colon | 0.0095 | 0.0117 | 0.0102 | 0.0248 | 9.86 |
| COLO320DM | Colon | Colon | 9.11 | 10 | 6.1862 | 9.53 | 5.28 |
| COLO320HSR | Colon | Colon | 4.19 | 4.44 | 2.0186 | 3.53 | 49.73 |
| DLD1 | Colon | Colon | 0.162 | 0.197 | 0.0474 | 0.104 | 21.95 |
| HCT116 | Colon | Colon | 0.0194 | 0.0204 | 0.0196 | 0.0448 | 45.43 |
| HCT15 | Colon | Colon | 1.97 | 2.23 | 5.1211 | 7.03 | 7.97 |
| HRT18 | Colon | Colon | 0.0775 | 0.0819 | 0.0657 | 0.147 | 11.1 |
| HT29 | Colon | Colon | 0.0129 | 0.0167 | 0.0092 | 0.0318 | 61.59 |
| LS1034 | Colon | Colon | 0.224 | 0.676 | 1.4781 | 10 | 2.52 |
| LS123 | Colon | Colon | 0.061 | 0.188 | 0.0766 | 10 | 4.74 |
| LS174T | Colon | Colon | 0.194 | 0.259 | 0.2846 | 0.412 | 5.63 |
| LS411N | Colon | Colon | 0.0358 | 0.053 | 0.0575 | 10 | 5.58 |
| LS513 | Colon | Colon | 0.0353 | 0.0386 | 0.0233 | 0.0356 | 64.31 |
| NCIH508 | Colon | Colon | 0.0288 | 0.0481 | 0.0778 | 1.25 | 5.37 |
| NCIH747 | Colon | Colon | 0.012 | 0.0445 | 0.0226 | 0.0756 | 8.21 |
| RKO | Colon | Colon | 0.0353 | 0.0405 | 0.0407 | 0.378 | 11.14 |
| RKOAS451 | Colon | Colon | 0.0405 | 0.0449 | 0.1873 | 1.16 | 10.06 |
| RKOE6 | Colon | Colon | 0.0753 | 0.107 | 1.6988 | 3.6 | 29.26 |
| SNUC2B | Colon | Colon | 0.0544 | 0.722 | 10 | 10 | 1.67 |
| SW1417 | Colon | Colon | 0.0088 | 0.0351 | 0.0221 | 0.0693 | 6.76 |
| SW1463 | Colon | Colon | 0.135 | 0.181 | 2.4138 | 10 | 2.82 |
| SW403 | Colon | Colon | 0.0476 | 0.173 | 0.1084 | 10 | 4.02 |
| SW48 | Colon | Colon | 0.0018 | 0.0031 | 0.0047 | 0.0266 | 13.66 |
| SW480 | Colon | Colon | 0.0184 | 0.0311 | 0.0638 | 0.248 | 6.26 |
| SW620 | Colon | Colon | 0.0492 | 0.0798 | 1.4774 | 3.88 | 14.66 |
| SW837 | Colon | Colon | 0.172 | 0.348 | 0.325 | 10 | 4.34 |
| SW948 | Colon | Colon | 0.195 | 0.327 | 10 | 10 | 1.57 |
| WIDR | Colon | Colon | 0.0104 | 0.0133 | 0.0085 | 0.021 | 79.03 |
| HUTU80 | Duodenum | Duodenum | 0.057 | 0.0695 | 0.0161 | 0.354 | 9.27 |
| Y79 | Eye-retinoblastoma | Eye | 10 | 10 | 7.8739 | 10 | 2.58 |
| A172 | CNS | Glioma | 0.0649 | 0.139 | 0.1174 | 2.36 | 5.95 |
| CCFSTTG1 | CNS | Glioma | 10 | 10 | 10 | 10 | 1.03 |
| DBTRG05MG | CNS | Glioma | 0.0432 | 0.0984 | 0.1963 | 10 | 3.94 |
| DKMG | CNS | Glioma | 0.0207 | 0.126 | 0.0463 | 0.16 | 10.86 |
| H4 | CNS | Glioma | 0.758 | 0.943 | 1.7285 | 3.78 | 14.47 |
| HS683 | CNS | Glioma | 0.148 | 0.305 | 10 | 10 | 2.54 |
| M059J | CNS | Glioma | 0.612 | 3.31 | 4.9633 | 10 | 2.8 |
| PFSK1 | CNS | Glioma | 0.0234 | 10 | 10 | 10 | 1.06 |
| SNB19 | CNS | Glioma | 0.163 | 0.244 | 0.4478 | 10 | 3.29 |
| SW1088 | CNS | Glioma | 3.35 | 5.98 | 5.2615 | 7.5 | 9.59 |
| SW1783 | CNS | Glioma | 5.92 | 9.85 | 9.0994 | 10 | 2.49 |
| T98G | CNS | Glioma | 10 | 10 | 5.4225 | 10 | 3.16 |
| U118MG | CNS | Glioma | 0.175 | 10 | 10 | 10 | 1.92 |
| U138MG | CNS | Glioma | 0.053 | 10 | 0.1598 | 0.417 | 8.01 |
| U87MG | CNS | Glioma | 0.0692 | 0.101 | 9.3615 | 10 | 2.14 |
| A253 | Head and Neck | Head and Neck | 0.171 | 10 | 8.7811 | 10 | 2.85 |
| A388 | Head and Neck | Head and Neck | 0.422 | 1.12 | 0.0902 | 3.52 | 6.48 |
| CAL27 | Head and Neck | Head and Neck | 0.0592 | 0.0661 | 0.0877 | 0.46 | 7.98 |
| DETROIT562 | Head and Neck | Head and Neck | 0.347 | 10 | 4.9484 | 7.16 | 6.02 |
| FADU | Head and Neck | Head and Neck | 0.435 | 0.787 | 4.0608 | 5.64 | 8.64 |
| SCC25 | Head and Neck | Head and Neck | 0.0439 | 0.051 | 0.1187 | 0.304 | 6.72 |
| SCC4 | Head and Neck | Head and Neck | 0.0512 | 0.108 | 0.0317 | 0.065 | 7.38 |
| SCC9 | Head and Neck | Head and Neck | 0.117 | 0.28 | 0.6679 | 3.86 | 9.58 |
| 769P | Kidney | Kidney | 0.194 | 0.255 | 0.2023 | 5.11 | 5.67 |
| 786O | Kidney | Kidney | 2.04 | 6.92 | 10 | 10 | 0.83 |

TABLE 3-continued

Results of Cytotoxicity Assays

| Cell line | Tumor Type | Subtype | GI50 (μM) | IC50 (μM) | CalX2 (μM) | CalX5 (μM) | Max fold change |
|---|---|---|---|---|---|---|---|
| A498 | Kidney | Kidney | 0.522 | 0.808 | 0.5562 | 10 | 4.72 |
| A704 | Kidney | Kidney | 10 | 10 | 10 | 10 | 0.96 |
| ACHN | Kidney | Kidney | 0.306 | 0.55 | 0.78 | 10 | 2.97 |
| CAKI1 | Kidney | Kidney | 0.0914 | 0.151 | 0.2015 | 10 | 4.12 |
| CAKI2 | Kidney | Kidney | 0.139 | 0.193 | 0.1631 | 0.449 | 6.26 |
| G401 | Kidney | Kidney | 0.0774 | 0.086 | 0.0717 | 0.179 | 30.87 |
| G402 | Kidney | Kidney | 0.0504 | 0.0925 | 0.0162 | 0.637 | 7.34 |
| SKNEP1 | Kidney | Kidney | 10 | 10 | 10 | 10 | 1.15 |
| BV173 | Hematopoietic and lymphoid | Leukemia | 1.1 | 10 | 0.4959 | 10 | 2.91 |
| CCRFCEM | Hematopoietic and lymphoid | Leukemia | 5.03 | 6.05 | 3.4279 | 6.95 | 12.74 |
| CEMC1 | Hematopoietic and lymphoid | Leukemia | 10 | 10 | 4.1828 | 5.22 | 11.27 |
| CMLT1 | Hematopoietic and lymphoid | Leukemia | 0.149 | 10 | 0.0948 | 10 | 4.85 |
| EM2 | Hematopoietic and lymphoid | Leukemia | 0.0481 | 0.0936 | 10 | 10 | 1.55 |
| HEL9217 | Hematopoietic and lymphoid | Leukemia | 4.62 | 8.23 | 3.2991 | 6.57 | 6.23 |
| JRT3T35 | Hematopoietic and lymphoid | Leukemia | 3.58 | 4.78 | 2.6364 | 3.8 | 14.26 |
| JURKAT | Hematopoietic and lymphoid | Leukemia | 3.34 | 3.73 | 1.6173 | 3.28 | 14.48 |
| K562 | Hematopoietic and lymphoid | Leukemia | 10 | 10 | 2.9298 | 4.86 | 51.89 |
| KG1 | Hematopoietic and lymphoid | Leukemia | 0.0017 | 0.0325 | 2.5811 | 10 | 2.5 |
| KU812 | Hematopoietic and lymphoid | Leukemia | 0.003 | 0.0159 | 0.03 | 8.02 | 5.63 |
| MEG01 | Hematopoietic and lymphoid | Leukemia | 0.0818 | 0.221 | 0.5718 | 10 | 2.77 |
| MHHPREB1 | Hematopoietic and lymphoid | Leukemia | 6.69 | 6.97 | 5.1142 | 7.66 | 11.43 |
| MOLT16 | Hematopoietic and lymphoid | Leukemia | 2.88 | 3.35 | 2.4102 | 4.97 | 8.06 |
| MOLT3 | Hematopoietic and lymphoid | Leukemia | 0.946 | 3.03 | 5.88 | 10 | 3.63 |
| MV411 | Hematopoietic and lymphoid | Leukemia | 0.107 | 0.184 | 0.0933 | 1.15 | 8.12 |
| MX1 | Hematopoietic and lymphoid | Leukemia | 0.0401 | 0.0619 | 1.1016 | 10 | 3.78 |
| NALM6 | Hematopoietic and lymphoid | Leukemia | 10 | 10 | 0.1241 | 10 | 5 |
| RS411 | Hematopoietic and lymphoid | Leukemia | 0.359 | 2.96 | 3.8025 | 8.4 | 5.83 |
| TF1 | Hematopoietic and lymphoid | Leukemia | 0.0015 | 0.0095 | 0.006 | 0.0296 | 16.1 |
| THP1 | Hematopoietic and lymphoid | Leukemia | 0.0251 | 0.0495 | 0.132 | 3.9 | 6.3 |
| HEPG2 | Liver | Liver | 0.0224 | 0.0643 | 0.0041 | 0.0108 | 62.47 |
| HLE | Liver | Liver | 0.683 | 1.04 | 0.8174 | 10 | 2.5 |
| HLF | Liver | Liver | 4.76 | 6.47 | 10 | 10 | 1.95 |
| HUCCT1 | Liver | Liver | 0.0537 | 0.0633 | 0.0222 | 0.0406 | 11.54 |
| HUH6CLONE5 | Liver | Liver | 0.145 | 0.354 | 0.0631 | 0.302 | 8.25 |
| OCUG1 | Liver | Liver | 0.464 | 1.29 | 0.0848 | 0.49 | 5.49 |
| SNU423 | Liver | Liver | 0.192 | 0.276 | 0.0909 | 1.65 | 7.32 |
| BC1 | Hematopoietic and lymphoid | Lymphoma | 10 | 10 | 5.1005 | 6.54 | 8.72 |
| BCP1 | Hematopoietic and lymphoid | Lymphoma | 0.0205 | 0.0797 | 4.8663 | 7.36 | 6.56 |
| CA46 | Hematopoietic and lymphoid | Lymphoma | 0.0146 | 0.0213 | 3.2395 | 8.08 | 9.46 |
| CROAP2 | Hematopoietic and lymphoid | Lymphoma | 0.996 | 2.58 | 2.9603 | 4.2 | 50.79 |
| DAUDI | Hematopoietic and lymphoid | Lymphoma | 0.0177 | 10 | 3.9392 | 5.33 | 10.08 |
| DB | Hematopoietic and lymphoid | Lymphoma | 0.0131 | 10 | 6.1153 | 6.5 | 7.11 |
| DOHH2 | Hematopoietic and lymphoid | Lymphoma | 5.54 | 5.79 | 2.4833 | 3.99 | 20.41 |
| EB2 | Hematopoietic and lymphoid | Lymphoma | 0.389 | 0.55 | 5.7381 | 10 | 4.16 |

TABLE 3-continued

Results of Cytotoxicity Assays

| Cell line | Tumor Type | Subtype | GI50 (μM) | IC50 (μM) | CalX2 (μM) | CalX5 (μM) | Max fold change |
|---|---|---|---|---|---|---|---|
| EB3 | Hematopoietic and lymphoid | Lymphoma | 1.63 | 2.15 | 6.1469 | 7.66 | 5.5 |
| GA10 | Hematopoietic and lymphoid | Lymphoma | 0.0468 | 0.0567 | 0.6477 | 1.94 | 6.49 |
| H9 | Hematopoietic and lymphoid | Lymphoma | 0.0232 | 0.039 | 0.0222 | 0.4 | 7.33 |
| HS445 | Hematopoietic and lymphoid | Lymphoma | 0.0143 | 0.0377 | 4.9128 | 7.7 | 5.65 |
| HS611T | Hematopoietic and lymphoid | Lymphoma | 0.0106 | 0.0123 | 2.8507 | 10 | 3.84 |
| HT | Hematopoietic and lymphoid | Lymphoma | 8.3 | 10 | 8.6354 | 10 | 2.44 |
| JEKO1 | Hematopoietic and lymphoid | Lymphoma | 0.461 | 0.83 | 4.3369 | 10 | 3.11 |
| JIYOYE | Hematopoietic and lymphoid | Lymphoma | 0.0814 | 0.21 | 4.4004 | 5.35 | 11.1 |
| L428 | Hematopoietic and lymphoid | Lymphoma | 1.63 | 3.46 | 4.2384 | 5.88 | 7.51 |
| MC116 | Hematopoietic and lymphoid | Lymphoma | 6.02 | 6.49 | 2.8763 | 5.18 | 9.46 |
| NAMALWA | Hematopoietic and lymphoid | Lymphoma | 0.0181 | 0.0239 | 5.9431 | 10 | 2.68 |
| RAJI | Hematopoietic and lymphoid | Lymphoma | 0.179 | 10 | 2.5564 | 4.07 | 24.81 |
| RAMOSRA1 | Hematopoietic and lymphoid | Lymphoma | 3.66 | 3.84 | 4.5496 | 7.39 | 25.1 |
| REC1 | Hematopoietic and lymphoid | Lymphoma | 0.0053 | 0.193 | 10 | 10 | 1.86 |
| RPMI6666 | Hematopoietic and lymphoid | Lymphoma | 0.0801 | 0.37 | 3.0419 | 4.37 | 26.35 |
| SR | Hematopoietic and lymphoid | Lymphoma | 1.42 | 1.84 | 1.2842 | 3.07 | 33.52 |
| ST486 | Hematopoietic and lymphoid | Lymphoma | 5.02 | 6.14 | 4.2422 | 6.11 | 10.85 |
| SUDHL10 | Hematopoietic and lymphoid | Lymphoma | 1.23 | 1.4 | 3.611 | 4.87 | 11.63 |
| SUDHL4 | Hematopoietic and lymphoid | Lymphoma | 0.168 | 0.332 | 2.5668 | 4.83 | 10.75 |
| SUDHL5 | Hematopoietic and lymphoid | Lymphoma | 0.0011 | 0.0013 | 1.6359 | 4.54 | 10.37 |
| SUDHL8 | Hematopoietic and lymphoid | Lymphoma | 0.0193 | 0.0406 | 1.2344 | 4.19 | 10.79 |
| SUPT1 | Hematopoietic and lymphoid | Lymphoma | 0.0196 | 0.0466 | 4.5476 | 9.21 | 5.76 |
| TUR | Hematopoietic and lymphoid | Lymphoma | 0.0415 | 0.0539 | 0.6984 | 3.45 | 17.35 |
| D283MED | CNS | Medulloblastoma | 2.56 | 7.55 | 8.3456 | 10 | 2.23 |
| D341MED | CNS | Medulloblastoma | 10 | 0.0219 | 7.7855 | 10 | 2.14 |
| DAOY | CNS | Medulloblastoma | 0.749 | 1.09 | 3.2773 | 5.22 | 16.68 |
| A101D | Skin | Melanoma | 0.0424 | 0.0815 | 0.4207 | 3.71 | 7.93 |
| A2058 | Skin | Melanoma | 0.212 | 0.288 | 0.065 | 0.204 | 11.68 |
| A375 | Skin | Melanoma | 0.0065 | 0.0072 | 0.0673 | 0.0827 | 103.79 |
| A7 | Skin | Melanoma | 1.72 | 7.27 | 5.0814 | 9.4 | 5.51 |
| C32 | Skin | Melanoma | 0.0289 | 0.111 | 0.0451 | 0.0778 | 110.9 |
| C32TG | Skin | Melanoma | 0.0408 | 0.109 | 0.0608 | 0.117 | 42.82 |
| CHL1 | Skin | Melanoma | 0.103 | 0.117 | 1.2376 | 10 | 3.46 |
| COLO829 | Skin | Melanoma | 0.0121 | 0.0343 | 0.0421 | 0.125 | 24.28 |
| G361 | Skin | Melanoma | 0.102 | 0.15 | 0.0428 | 0.12 | 24.48 |
| HMCB | Skin | Melanoma | 0.0724 | 0.113 | 10 | 10 | 1.8 |
| HS294T | Skin | Melanoma | 0.0507 | 0.0706 | 0.154 | 2.15 | 5.74 |
| HS688AT | Skin | Melanoma | 0.0822 | 10 | 10 | 10 | 1.61 |
| HS695T | Skin | Melanoma | 0.0363 | 0.16 | 0.0253 | 0.0727 | 22.05 |
| HS852T | Skin | Melanoma | 0.0564 | 0.715 | 0.05 | 0.234 | 6.51 |
| HS895T | Skin | Melanoma | 10 | 10 | 10 | 10 | 1.52 |
| HS934T | Skin | Melanoma | 0.0052 | 10 | 0.3638 | 1.4 | 5.1 |
| HS936TC1 | Skin | Melanoma | 0.0184 | 0.0258 | 0.0084 | 0.0224 | 134.98 |
| MALME3M | Skin | Melanoma | 0.0034 | 0.012 | 0.0025 | 0.0045 | 102.73 |
| MEWO | Skin | Melanoma | 0.102 | 0.159 | 0.167 | 0.373 | 14.34 |
| RPMI7951 | Skin | Melanoma | 0.0716 | 0.0945 | 0.1237 | 1.29 | 28.15 |
| SH4 | Skin | Melanoma | 0.0208 | 0.029 | 0.0157 | 0.0382 | 66.44 |
| SKMEL1 | Skin | Melanoma | 0.001 | 0.0291 | 0.1019 | 0.194 | 7.63 |
| SKMEL28 | Skin | Melanoma | 0.0279 | 0.0571 | 0.2907 | 0.344 | 16.64 |
| SKMEL3 | Skin | Melanoma | 0.0284 | 0.0625 | 10 | 10 | 1.74 |
| WM2664 | Skin | Melanoma | 0.012 | 0.0354 | 0.0023 | 0.0151 | 83.29 |

TABLE 3-continued

Results of Cytotoxicity Assays

| Cell line | Tumor Type | Subtype | GI50 (μM) | IC50 (μM) | CalX2 (μM) | CalX5 (μM) | Max fold change |
|---|---|---|---|---|---|---|---|
| ARH77 | Hematopoietic and lymphoid | Myeloma | 10 | 10 | 10 | 10 | 1.86 |
| IM9 | Hematopoietic and lymphoid | Myeloma | 0.0911 | 0.143 | 0.043 | 10 | 4.85 |
| RPMI8226 | Hematopoietic and lymphoid | Myeloma | 1.09 | 2.48 | 3.3103 | 5.34 | 8.35 |
| SKO007 | Hematopoietic and lymphoid | Myeloma | 0.0274 | 0.482 | 0.1758 | 2.79 | 7.24 |
| U266B1 | Hematopoietic and lymphoid | Myeloma | 0.0133 | 0.109 | 0.0493 | 10 | 4.36 |
| BE2C | CNS | Neuroblastoma | 0.146 | 0.21 | 0.1223 | 10 | 5.47 |
| CHP212 | CNS | Neuroblastoma | 0.0066 | 0.0165 | 0.019 | 0.341 | 5.97 |
| MCIXC | CNS | Neuroblastoma | 2.04 | 2.33 | 1.9309 | 4.62 | 5.15 |
| SKNAS | CNS | Neuroblastoma | 0.0489 | 0.132 | 0.0675 | 0.227 | 8.86 |
| SKNDZ | CNS | Neuroblastoma | 7.4 | 10 | 10 | 10 | 1.23 |
| SKNFI | CNS | Neuroblastoma | 0.0151 | 0.135 | 0.0897 | 10 | 3.51 |
| A427 | Lung | NSCLC | 0.0475 | 0.0763 | 0.0018 | 10 | 3.34 |
| A549 | Lung | NSCLC | 0.102 | 0.128 | 0.0297 | 0.0946 | 13.03 |
| CALU1 | Lung | NSCLC | 0.0967 | 0.149 | 0.2575 | 10 | 3.73 |
| CALU6 | Lung | NSCLC | 0.0463 | 0.083 | 0.11 | 10 | 4.86 |
| CHAGOK1 | Lung | NSCLC | 10 | 10 | 10 | 10 | 1.23 |
| CORL105 | Lung | NSCLC | 0.0165 | 0.0414 | 0.0583 | 0.571 | 6.55 |
| CORL23 | Lung | NSCLC | 0.0238 | 0.0283 | 0.0176 | 0.0569 | 12.96 |
| HS229T | Lung | NSCLC | 0.415 | 10 | 0.8448 | 7.22 | 5.29 |
| NCIH292 | Lung | NSCLC | 0.278 | 0.686 | 2.4602 | 4.85 | 10.26 |
| NCIH441 | Lung | NSCLC | 0.271 | 1.25 | 7.7406 | 10 | 4.32 |
| NCIH460 | Lung | NSCLC | 10 | 10 | 10 | 10 | 0.98 |
| NCIH520 | Lung | NSCLC | 0.991 | 2.13 | 3.637 | 5.03 | 13.95 |
| NCIH596 | Lung | NSCLC | 2.75 | 10 | 10 | 10 | 1.11 |
| NCIH661 | Lung | NSCLC | 1.44 | 2.64 | 0.0833 | 10 | 4.58 |
| SKMES1 | Lung | NSCLC | 0.103 | 0.122 | 0.0384 | 0.212 | 27.03 |
| OE19 | Head and Neck | Esophageal | 0.34 | 10 | 10 | 10 | 1.79 |
| OE21 | Head and Neck | Esophageal | 0.0939 | 0.124 | 0.0221 | 0.948 | 5.91 |
| OE33 | Head and Neck | Esophageal | 0.063 | 0.0969 | 0.0317 | 0.495 | 5.9 |
| G292CLONEA141B1 | Soft Tissue | Osteosarcoma | 0.0272 | 0.0493 | 0.0401 | 0.211 | 7.61 |
| HOS | Soft Tissue | Osteosarcoma | 2.57 | 3.69 | 6.2324 | 8.81 | 7.12 |
| HS888SK | Soft Tissue | Osteosarcoma | 0.111 | 10 | 0.1023 | 0.175 | 15.7 |
| KHOS240S | Soft Tissue | Osteosarcoma | 10 | 10 | 4.3797 | 4.93 | 18.16 |
| MG63 | Soft Tissue | Osteosarcoma | 0.108 | 0.115 | 4.1626 | 5.71 | 17.21 |
| SAOS2 | Soft Tissue | Osteosarcoma | 3.57 | 6.88 | 3.2386 | 5.98 | 6.35 |
| SJSA1 | Soft Tissue | Osteosarcoma | 1.16 | 2.46 | 2.9744 | 6.21 | 62.65 |
| SW1353 | Soft Tissue | Osteosarcoma | 0.184 | 0.292 | 0.404 | 10 | 4.79 |
| U2OS | Soft Tissue | Osteosarcoma | 0.23 | 0.373 | 0.0332 | 0.0801 | 20.57 |
| CAOV3 | Female GU | Ovary | 0.429 | 10 | 2.0076 | 10 | 2.95 |
| CASKI | Female GU | Ovary | 6.76 | 10 | 0.9719 | 10 | 2.61 |
| ME180 | Female GU | Ovary | 10 | 10 | 5.1674 | 6.32 | 12.19 |
| MS751 | Female GU | Ovary | 6.91 | 9.51 | 5.4363 | 10 | 3.62 |
| OVCAR3 | Female GU | Ovary | 10 | 10 | 10 | 10 | 1.19 |
| PA1 | Female GU | Ovary | 0.471 | 2.62 | 3.6547 | 5.1 | 11.55 |
| SKOV3 | Female GU | Ovary | 0.547 | 10 | 0.2939 | 10 | 2.65 |
| ASPC1 | Pancreas | Pancreas | 0.0308 | 10 | 0.0471 | 10 | 4.08 |
| BXPC3 | Pancreas | Pancreas | 0.0369 | 0.0455 | 0.025 | 10 | 4.98 |
| CAPAN1 | Pancreas | Pancreas | 0.105 | 10 | 10 | 10 | 1.97 |
| CAPAN2 | Pancreas | Pancreas | 0.136 | 0.291 | 10 | 0.209 | 6.62 |
| CFPAC1 | Pancreas | Pancreas | 10 | 10 | 10 | 10 | 1.46 |
| HPAFII | Pancreas | Pancreas | 0.013 | 0.0175 | 0.0034 | 0.0093 | 52.77 |
| HS766T | Pancreas | Pancreas | 0.0343 | 0.0793 | 0.0646 | 0.632 | 6.36 |
| HUPT4 | Pancreas | Pancreas | 0.0434 | 0.0505 | 0.0998 | 10 | 5.3 |
| MIAPACA2 | Pancreas | Pancreas | 0.0357 | 0.0396 | 0.0387 | 0.578 | 15.16 |
| PANC1 | Pancreas | Pancreas | 0.0416 | 0.08 | 0.0227 | 0.173 | 10.76 |
| PSN1 | Pancreas | Pancreas | 0.0083 | 0.0092 | 0.036 | 0.0701 | 8.75 |
| SU8686 | Pancreas | Pancreas | 0.0635 | 0.132 | 10 | 10 | 2.09 |
| YAPC | Pancreas | Pancreas | 0.183 | 0.67 | 10 | 10 | 1.59 |
| BEWO | Female GU | Placenta | 5.16 | 5.69 | 3.9778 | 6.42 | 10.1 |
| JAR | Female GU | Placenta | 3.17 | 3.21 | 1.0062 | 2.99 | 102.66 |
| JEG3 | Female GU | Placenta | 6.34 | 7.75 | 5.8823 | 7.95 | 6.39 |
| 22RV1 | Prostate | Prostate | 2.66 | 5.58 | 3.0283 | 4.45 | 18.69 |
| BM1604 | Prostate | Prostate | 0.141 | 0.401 | 10 | 10 | 1.8 |
| BPH1 | Prostate | Prostate | 0.0578 | 0.0675 | 0.0577 | 0.116 | 35.09 |
| DU145 | Prostate | Prostate | 0.0738 | 0.0965 | 5.1233 | 8.37 | 6.15 |
| LNCAP | Prostate | Prostate | 2.43 | 5.07 | 4.1807 | 10 | 3.85 |
| PC3 | Prostate | Prostate | 7.82 | 8.54 | 10 | 10 | 3.64 |
| A204 | Soft Tissue | Sarcoma | 10 | 10 | 0.2906 | 10 | 3.48 |
| A673 | Soft Tissue | Sarcoma | 3.75 | 3.87 | 3.411 | 4.59 | 27.78 |

TABLE 3-continued

Results of Cytotoxicity Assays

| Cell line | Tumor Type | Subtype | GI50 (µM) | IC50 (µM) | CalX2 (µM) | CalX5 (µM) | Max fold change |
|---|---|---|---|---|---|---|---|
| HS729 | Soft Tissue | Sarcoma | 0.54 | 10 | 10 | 10 | 1.87 |
| HS821T | Soft Tissue | Sarcoma | 0.169 | 10 | 10 | 10 | 1.53 |
| HT1080 | Soft Tissue | Sarcoma | 0.0648 | 0.0727 | 0.0509 | 0.107 | 63.63 |
| MESSA | Soft Tissue | Sarcoma | 0.81 | 1.1 | 4.196 | 5.47 | 8.03 |
| RD | Soft Tissue | Sarcoma | 0.0367 | 0.0443 | 0.0297 | 0.0581 | 14.86 |
| SJRH30 | Soft Tissue | Sarcoma | 0.219 | 1.47 | 0.039 | 10 | 5.61 |
| SKLMS1 | Soft Tissue | Sarcoma | 0.146 | 0.166 | 0.1405 | 0.876 | 12.5 |
| SKUT1 | Soft Tissue | Sarcoma | 10 | 10 | 6.5345 | 10 | 4.63 |
| SW684 | Soft Tissue | Sarcoma | 0.0869 | 0.37 | 0.256 | 0.308 | 16.88 |
| SW872 | Soft Tissue | Sarcoma | 0.105 | 0.136 | 0.0538 | 0.434 | 9.48 |
| SW982 | Soft Tissue | Sarcoma | 0.0156 | 0.0614 | 10 | 10 | 1.94 |
| TE125T | Soft Tissue | Sarcoma | 1.09 | 10 | 3.9673 | 10 | 2.5 |
| TE381T | Soft Tissue | Sarcoma | 0.0076 | 0.0128 | 0.0048 | 0.0143 | 15.88 |
| VAESBJ | Soft Tissue | Sarcoma | 0.336 | 0.58 | 3.1752 | 10 | 3.26 |
| DMS114 | Lung | SCLC | 0.0688 | 0.6 | 0.9142 | 10 | 3.38 |
| DMS273 | Lung | SCLC | 5.96 | 6.79 | 6.5676 | 8.53 | 6.76 |
| DMS53 | Lung | SCLC | 0.998 | 10 | 0.0661 | 1.4 | 7.01 |
| NCIH446 | Lung | SCLC | 0.327 | 10 | 10 | 10 | 1.63 |
| NCIH510A | Lung | SCLC | 3.7 | 6.61 | 3.8517 | 8.62 | 6.44 |
| NCIH69 | Lung | SCLC | 5 | 10 | 10 | 10 | 1.7 |
| SHP77 | Lung | SCLC | 4.79 | 5.82 | 6.8591 | 10 | 3.64 |
| SW900 | Lung | SCLC | 0.0216 | 0.0399 | 0.0162 | 0.0849 | 10.26 |
| AGS | Stomach | Stomach | 0.0086 | 0.0098 | 0.0075 | 0.0131 | 31.12 |
| HS746T | Stomach | Stomach | 0.0396 | 0.122 | 0.0471 | 10 | 4.41 |
| KATOIII | Stomach | Stomach | 0.0612 | 0.0787 | 0.0137 | 0.123 | 29.59 |
| SKPNDW | Stomach | Stomach | 3.6 | 10 | 7.8388 | 10 | 2.58 |
| SNU1 | Stomach | Stomach | 0.0355 | 0.0631 | 0.041 | 2.57 | 5.5 |
| SNU16 | Stomach | Stomach | 10 | 10 | 3.2968 | 5.11 | 10.66 |
| SNU5 | Stomach | Stomach | 0.0368 | 0.0943 | 0.1664 | 10 | 3.21 |
| NTERA2CLD1 | Testis | Testis | 0.044 | 0.0507 | 0.0707 | 0.0957 | 9.95 |
| BHT101 | Endocrine | Thyroid | 0.0376 | 0.0412 | 0.0438 | 0.0864 | 22.52 |
| CAL62 | Endocrine | Thyroid | 0.0836 | 0.0936 | 0.0795 | 0.129 | 6.49 |
| CGTHW1 | Endocrine | Thyroid | 0.0547 | 0.0605 | 0.065 | 0.103 | 91.55 |
| SW579 | Endocrine | Thyroid | 0.0477 | 0.0708 | 0.1374 | 0.256 | 51.22 |
| TT | Endocrine | Thyroid | 0.0863 | 10 | 0.5946 | 10 | 2.79 |
| AN3CA | Female GU | Uterus | 0.713 | 7.03 | 8.777 | 10 | 2.75 |
| HEC1A | Female GU | Uterus | 1.8 | 2.81 | 1.6552 | 3.7 | 30.12 |
| KLE | Female GU | Uterus | 10 | 10 | 10 | 10 | 1.37 |
| RL952 | Female GU | Uterus | 0.009 | 0.0599 | 0.1762 | 10 | 4.12 |
| SW954 | Female GU | Vulva | 0.114 | 0.142 | 0.1749 | 0.521 | 9.14 |
| SW962 | Female GU | Vulva | 0.0828 | 0.232 | 0.0686 | 10 | 3.39 |

Effect on HCC Proliferation.

HCC cell lines were treated with DMSO or increasing concentrations of Compound 1 for 72 h. Specifically, Compound 1 at various concentrations in dimethyl sulfoxide (DMSO) was spotted via an acoustic dispenser (EDC ATS-100) into an empty 384-well plate. Compound 1 was spotted in a 10-point serial dilution fashion (3-fold dilution) in duplicate within the plate. Replicates of plates spotted with Compound 1 were made for use with different cell lines. After compound plate replication, all plates were sealed (Agilent ThermoLoc) and stored at −20° C. for up to 1 month. When ready for testing, plates were removed from the freezer, thawed, and unsealed just prior to the addition of the test cells.

Prior to testing, cells were grown and expanded in culture flasks to provide sufficient amounts of starting material. Cells were then diluted to the appropriate densities and added directly to the compound-spotted 384-well plates. Cells were allowed to grow for 72 h at 37° C./5% $CO_2$. At the time when compound was added ($t_0$), initial cell number was assessed via a viability assay (Cell Titer-Glo) by quantifying the level of luminescence generated by ATP present in viable cells. After 72 h, cell viability of compound-treated cells was assessed via Cell Titer-Glo and luminescence measurement. The apoptotic response to Compound 1 was assessed by quantifying the activities of caspase 3 and caspase 7 (Caspase 3/7-Glo) in treated cells and DMSO control cells.

Determination of $GI_{50}$ and $IC_{50}$ Values.

A Four Parameter Logistic Model (Sigmoidal Dose-Response Model) was used to determine the compound's $GI_{50}$ value.

$$y=(A+((B-A)/(1+((C/x)^D))))$$

$A=Y_{Min}$
$B=Y_{Max}$
$C=EC_{50}$
$D=$Hill Slope $GI_{50}$ is the concentration of the compound when $Y=(Y_{Max}+Y_{t_0})/2$ $IC_{50}$ is the concentration of the compound when $Y=50\%$ of DMSO control Y=Cell viability measured as luminescence unit
$t_0$=time when compound was added Proliferation and apoptosis were measured using CellTiter-Glo and Caspase 3/7-Glo. CalX2 values are the lowest concentration at which Compound 1 induces a 2-fold increase of cleaved caspase 3/7 compared to DMSO control. Proliferation and apoptosis data is the average of 3 experiments.

TABLE 4

Effect of Compound 1 on HCC cell line proliferation

| Cell Line | GI$_{50}$ | IC$_{50}$ | Cal_X2 |
|---|---|---|---|
| JHH-1 | 0.0016 | 0.0946 | 0.0427 |
| JHH-5 | 0.0045 | 0.0072 | 0.0139 |
| Hep3B | 0.0053 | 0.0147 | 0.0028 |
| HuH-7 | 0.0212 | 0.4894 | 0.0118 |
| HuCCT1 | 0.0253 | 1.3033 | 0.0213 |
| HuH-6-Clone5 | 0.0291 | 1.2236 | 1.5813 |
| SNU-387 | 0.0332 | 0.1041 | 0.0046 |
| HepG2 | 0.0346 | 1.2420 | 0.0129 |
| SNU-182 | 0.0764 | 4.9775 | 5.2385 |
| JHH-7 | 0.0834 | 0.5476 | 4.7601 |
| JHH-2 | 0.1289 | 4.4850 | 0.2806 |
| HuH-1 | 0.2351 | 7.2643 | 6.5641 |
| SNU-398 | 0.2652 | 1.9653 | 0.0378 |
| JHH-4 | 0.3627 | 2.3178 | 0.0588 |
| PLC-PRF-5 | 0.8884 | 4.0089 | 3.8310 |
| FOCUS | 1.4994 | 4.2962 | 3.8562 |
| HepG2/C3A | 4.6211 | 10.0000 | 0.8273 |
| HLE | 4.8451 | 9.6157 | 10.0000 |
| SNU-423 | 6.2355 | 10.0000 | 10.0000 |
| HLF | 6.6814 | 7.3878 | 7.2156 |
| SK-HEP-1 | 7.0390 | 10.0000 | 10.0000 |
| SNU-475 | 9.9879 | 10.0000 | 10.0000 |
| JHH-6 | 10.0000 | 10.0000 | 10.0000 |
| SNU-449 | 10.0000 | 10.0000 | 10.0000 |

Compound 1 inhibits proliferation and induces apoptosis in multiple HCC lines.

Anti-Proliferative Activity Across a Panel of 64 Cancer Cell Lines.

Cells were treated with DMSO or increasing concentrations of Compound 1 for 72 h. Proliferation was measured using CellTiter-Glo as described. Results are shown in Table 5.

TABLE 5

Anti-proliferative activity of Compound 1 across a panel of 64 cancer cell lines

| Cell line | Tumor Type | GI$_{50}$ (µM) | IC$_{50}$ (µM) |
|---|---|---|---|
| SW48 | Colon | 0.0057 | 0.088 |
| MALME-3M | Melanoma | 0.0011 | 0.0038 |
| HT29/219 | Colon | 0.0017 | 0.0045 |
| HCT-116 | Colon | 0.017 | 0.022 |
| LOX-IMVI | Melanoma | 0.022 | 0.025 |
| HT29 | Colon | 0.016 | 0.025 |
| A375 | Melanoma | 0.021 | 0.024 |
| Colo 205 | Colon | 0.025 | 0.040 |
| AGS | Stomach | 0.023 | 0.028 |
| JHH-5 | Liver | 0.0045 | 0.007 |
| SW620 | Colon | 0.047 | 0.092 |
| MiaPaCa-2 | Pancreas | 0.047 | 0.80 |
| JHH-5 | Liver | 0.0045 | 0.0072 |
| SW620 | Colon | 0.0474 | 0.0918 |
| MiaPaCa-2 | Pancreas | 0.0471 | 0.0798 |
| JHH-1 | Liver | 0.0016 | 0.0946 |
| NCI-H2122 | Lung | 0.0318 | 0.0427 |
| Hep3B | Liver | 0.0053 | 0.0147 |
| NCI-H1755 | Lung | 0.0404 | 0.0584 |
| 92-1 | Melanoma | 0.0102 | 0.0316 |
| BxPC-3 | Pancreas | 0.0368 | 0.0708 |
| SW1417 | Colon | 0.0005 | 0.0169 |
| HOP92 | Lung | 0.1077 | 0.1173 |
| NCI-H23 | Lung | 0.0364 | 0.1821 |
| PC-9 | Lung | 0.2167 | 0.3791 |
| HuH-7 | Liver | 0.0212 | 0.4894 |
| MEL-202 | Melanoma | 0.0385 | 0.0968 |
| SW900 | Lung | 0.0048 | 0.0217 |
| NCI-H1299 | Lung | 0.2336 | 0.4982 |
| A549 | Lung | 0.0402 | 0.0822 |
| LOVO | Colon | 0.0630 | 0.1256 |
| NCI-H460 | Lung | 0.2441 | 0.6445 |
| SNU-387 | Liver | 0.0332 | 0.1041 |
| HuCCT1 | Liver | 0.0253 | 1.3033 |
| HOP62 | Lung | 0.3390 | 3.4861 |
| HuH-6-Clone5 | Liver | 0.0291 | 1.2236 |
| JHH-7 | Liver | 0.0834 | 0.5476 |
| NCI-H838 | Lung | 0.5670 | 9.1808 |
| NCI-H226 | Lung | 1.6266 | 6.1499 |
| NCI-H28 | Lung | 1.2797 | 2.3574 |
| MDA-MB-231 | Breast | 0.0353 | 3.3333 |
| JHH-2 | Liver | 0.1289 | 4.4850 |
| HepG2 | Liver | 0.0346 | 1.2420 |
| RPMI-8226 | Multiple myeloma | 3.2365 | 9.7392 |
| K-562 | Leukemia | 5.4223 | 6.0279 |
| SNU-182 | Liver | 0.0764 | 4.9775 |
| HuH-1 | Liver | 0.2351 | 7.2643 |
| SNU-398 | Liver | 0.2652 | 1.9653 |
| JHH-4 | Liver | 0.3627 | 2.3178 |
| PLC-PRF-5 | Liver | 0.8884 | 4.0089 |
| FOCUS | Liver | 1.4994 | 4.2962 |
| HepG2/C3A | Liver | 4.6211 | 10.0000 |
| HLE | Liver | 4.8451 | 9.6157 |
| SNU-423 | Liver | 6.2355 | 10.0000 |
| HLF | Liver | 6.6814 | 7.3878 |
| SK-HEP-1 | Liver | 7.0390 | 10.0000 |
| SNU-475 | Liver | 9.9879 | 10.0000 |
| JHH-6 | Liver | 10.0000 | 10.0000 |
| SNU-449 | Liver | 10.0000 | 10.0000 |
| NCI-H441 | Lung | 0.1838 | 6.3503 |
| NCI-H1703 | Lung | 1.3513 | 1.6795 |
| NCI-H1975 | Lung | 2.0476 | 3.1940 |
| NCI-H520 | Lung | 5.2445 | 8.3699 |
| CFPAC-1 | Pancreas | 1.9512 | 7.3967 |
| PANC-1 | Pancreas | 5.4360 | 10.0000 |
| KATOIII | Stomach | 7.0455 | 8.0240 |

Compound 1 was shown to inhibit the proliferation of multiple cancer cell lines derived from CRC, melanoma, gastric cancer, HCC, lung cancer, pancreatic cancer, leukemia, and multiple myeloma.

Anti-Proliferative and Apoptotic Activity in BRAF Mutant and Beta-Catenin Mutant or Active Cancer Cell Lines.

The mutation status of BRAF, CTNNB1, KRAS, and EGFR in five cell lines evaluated was based on public data (COSMIC and CCLE) and confirmed internally. β-catenin status was evaluated using TOP Flash reporter system by transient transfection. A cell line was defined as β-catenin active if a ratio of Top Flash reporter over Fop Flash reporter is greater than 2. N/A: Not available. Transfection efficiency in Colo 205 (BRAF V600E) was too low to access its β-catenin activity using this approach. Antiproliferative and apoptotic activity of Compound 1 in the five cell lines were measured as described above.

TABLE 6

Antiproliferative and apoptosis activity of Compound 1 in BRAF mutant and beta-catenin mutant and active cell lines.

| Cell lines | Tumor type | Mutation status of key genes | β-catenin status | Proliferation IC$_{50}$ (μM) | Apoptosis induction CalX2 (μM) |
|---|---|---|---|---|---|
| Colo 205 | CRC | BRAF (V600E) | N/A | 0.036 +/− 0.023 | 0.053 +/− 0.039 |
| LOX-IMVI | Melanoma | BRAF (V600E) | Inactive | 0.025 +/− 0.008 | 0.034 +/− 0.028 |
| SW48 | CRC | CTNNB1 (S33Y); EGFR (G179S) | Active | 0.009 +/− 0.007 | 0.005 +/− 0.001 |
| AGS | Gastric | CTNNB1 (G43E); KRAS (G12D) | Active | 0.028 +/− 0.021 | 0.004 +/− 0.002 |
| Hep3B | HCC | — | Active | 0.014 +/− 0.006 | 0.002 +/− 0.002 |

Compound 1 potently inhibits proliferation and induces apoptosis in both BRAF mutant and beta-catenin mutant or active cancer cell lines, including BRAF mutant CRC, BRAF mutant melanoma, beta-catenin mutant/EGFR mutant CRC (i.e. beta-catenin active/EGFR mutant CRC), beta-catenin mutant/KRAS mutant gastric cancer (i.e. beta-catenin active/KRAS mutant gastric cancer), and HCC.

Oncogenic Pathway Inhibition. Effect on MAPK Signaling.

Cancer cells were seeded at a density of 25,000 cells per well in 96-well tissue culture plates and incubated at 37° C. in a CO$_2$ incubator overnight. After treatment with Compound 1 at 37° C. for 2 h, the cells were lysed with Mesoscale lysis buffer and pRSK S380 levels in each lysate were measured via Mesoscale ELISA technology.

Conclusion.

Compound 1 potently inhibited pRSK1 in multiple cancer cell lines (Table 7).

TABLE 7

Compound 1 pRSK1 S380 IC$_{50}$ Values in BRAF Mutant LOX-IMVI and Colo 205 Cancer Cell Lines

| Cell line (n = 3) | pRSK1 S380 IC$_{50}$ (μM) |
|---|---|
| LOX-IMVI | 0.038 +/− 0.009 |
| Colo 205 | 0.047 +/− 0.01 |
| SW48 | 0.021 +/− 0.001 |
| AGS | 0.020 +/− 0.001 |

Figure 1:
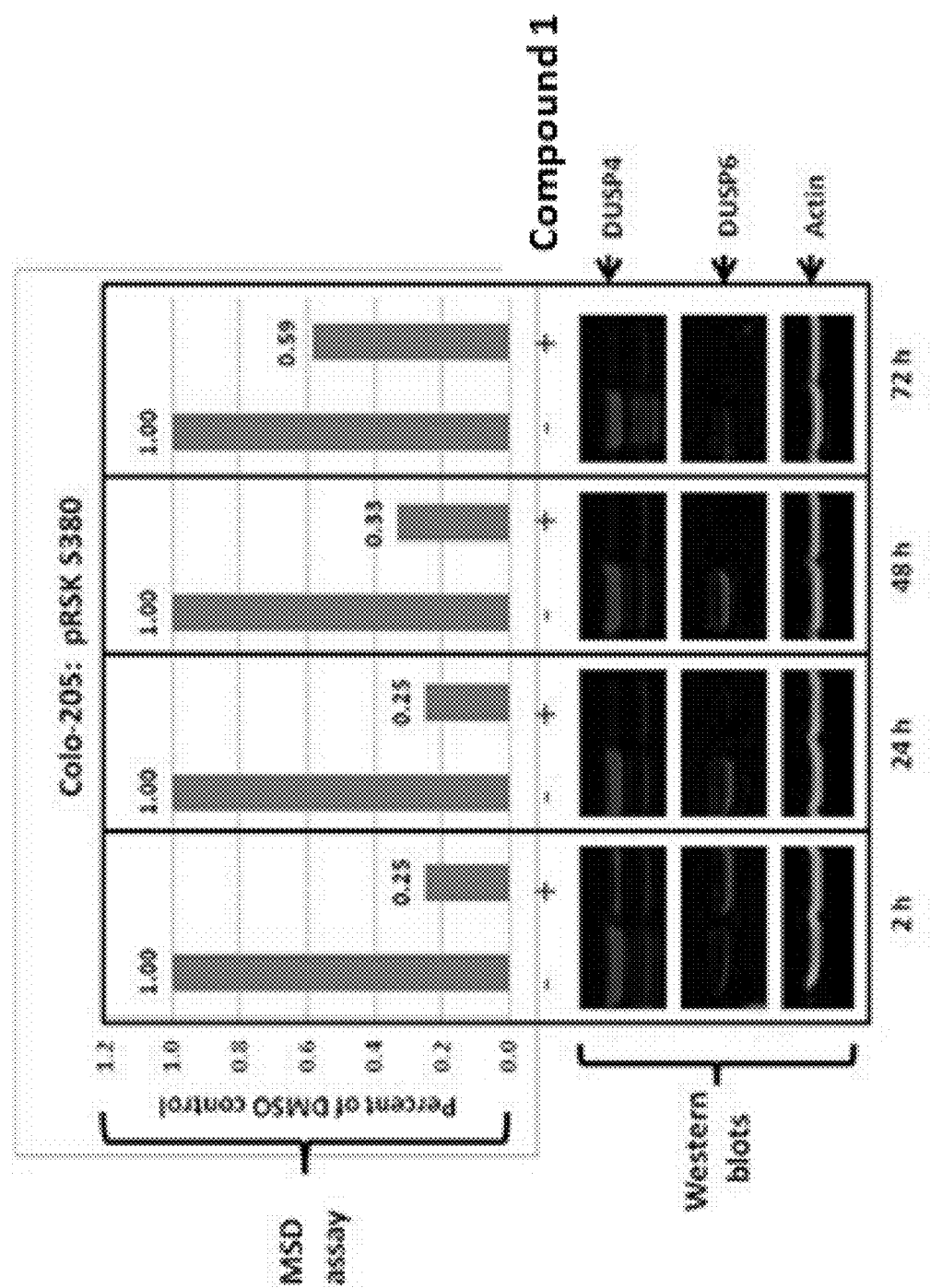
FIG. 1 illustrates Compound 1 Treatment Causes Sustained Inhibition of the ERK Substrate pRSK1 S380 in Colo 205 (mut BRAFV600E) Cells. Colo 205 cells were treated with DMSO or 0.5 µM Compound 1 for indicated time. pRSK1 S380 was measured by MSD assay (Top). DUSP4 and DUSP6 were detected by Western blotting (Bottom).

In a time course experiment, Colo-205 cancer cells were treated with 0.5 μM Compound 1 for various time periods. The effect of Compound 1 on pRSK S380 was measured as described. The effect of Compound 1 on other MAPK pathway markers (DUSP4 and DUSP6) was measured via Western blotting with specific antibodies. The time course data in FIG. 1 indicates Compound 1 causes sustained inhibition (up to 72 hr) of the following ERK targets: pRSK1, DUSP4 and DUSP6. BRAF inhibitors (BRAFi) do not cause sustained ERK inhibition in BRAF mutant CRC lines (Corcoran et al., Cancer Discov. 2012, 2:227-35). Sufficient and sustained inhibition of ERK seems to be critical for clinical efficacy of BRAFi and MEK inhibitors (MEKi) in BRAF mutant melanoma (Bollag et al., Nat Rev Drug Disc. 2012; 11, 873-886) and CRC patients (Corcoran et al., Cancer Discov. 2012, 2:227-35). Lack of sustained inhibition of ERK by BRAFi may contribute to the lack of clinical activity of BRAFi in BRAF mutant CRC patients. The sustained inhibition of ERK by Compound 1 may provide an advantage over BRAFi in BRAF mutant CRC patients.

The ability of Compound 1 to inhibit MAPK signaling was assessed by determining the DUSP4 and DUSP6 protein expression. Colon cancer cell line Colo 205 (BRAF V600E) cultures were treated with DMSO or increasing concentrations of Compound 1 for 2, 8 or 24 h. Proteins were extracted from treated cells and analyzed by Western blot using antibodies against DUSP4, DUSP6, cyclin D1, c-Myc, YAP or β-actin. RNAs were extracted using Cell-To-CT kit and quantitative PCR was performed with probes specific for DUSP4, DUSP6, SPRY2, c-Myc and cyclin D1. Specific probes for β-actin were used for normalization.

Figure 2A:
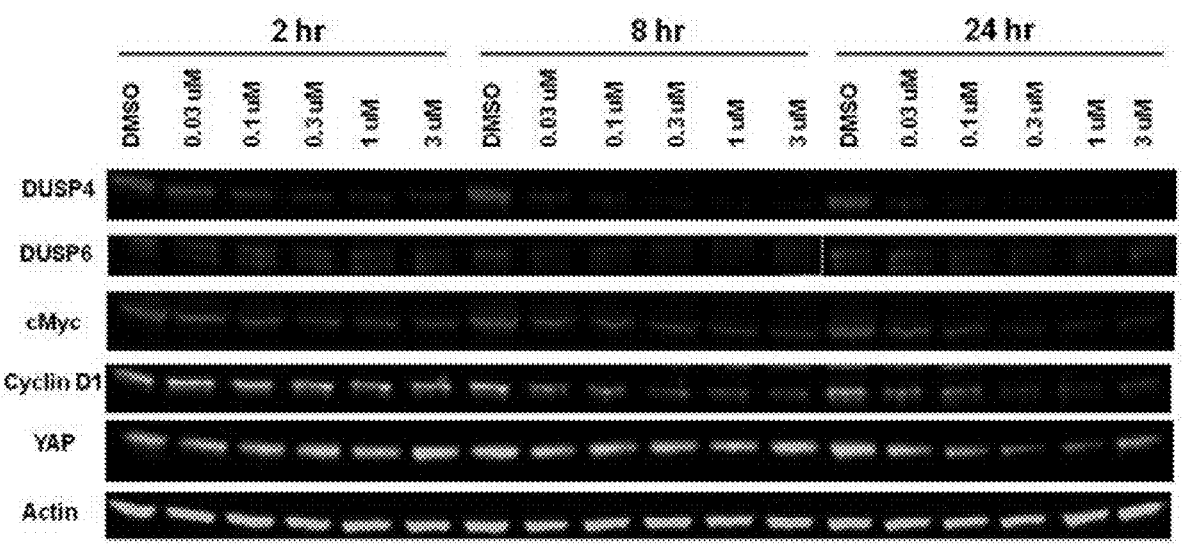
FIGS. 2A-2I illustrates Compound 1 potently inhibits MAP kinase signaling and downstream target genes in Colo 205. Colon cancer cell line Colo 205 (BRAF V600E) cultures were treated with DMSO or increasing concentrations of Compound 1 for 2, 8 or 24 h.
Figure 2B:
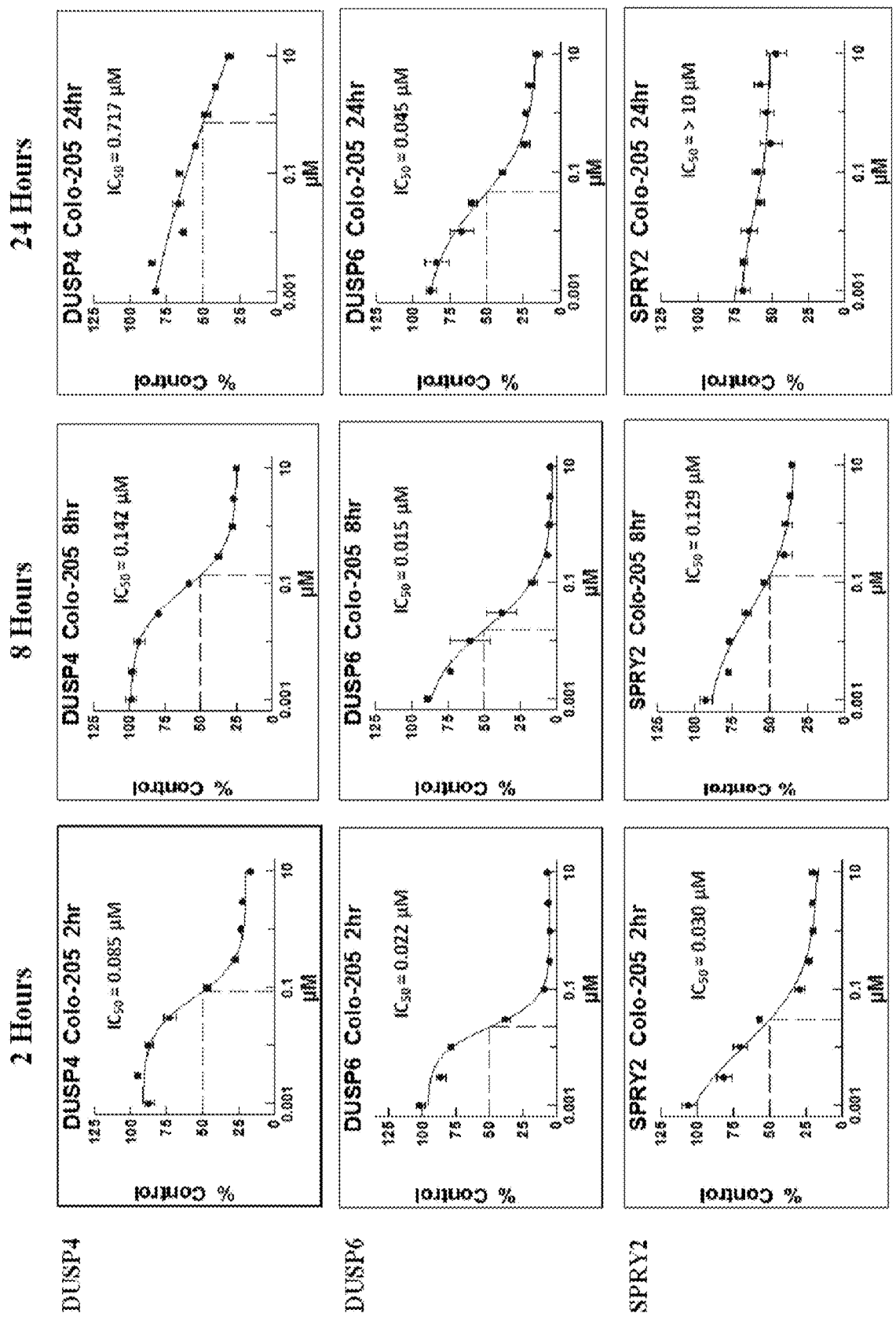
Figure 2C:
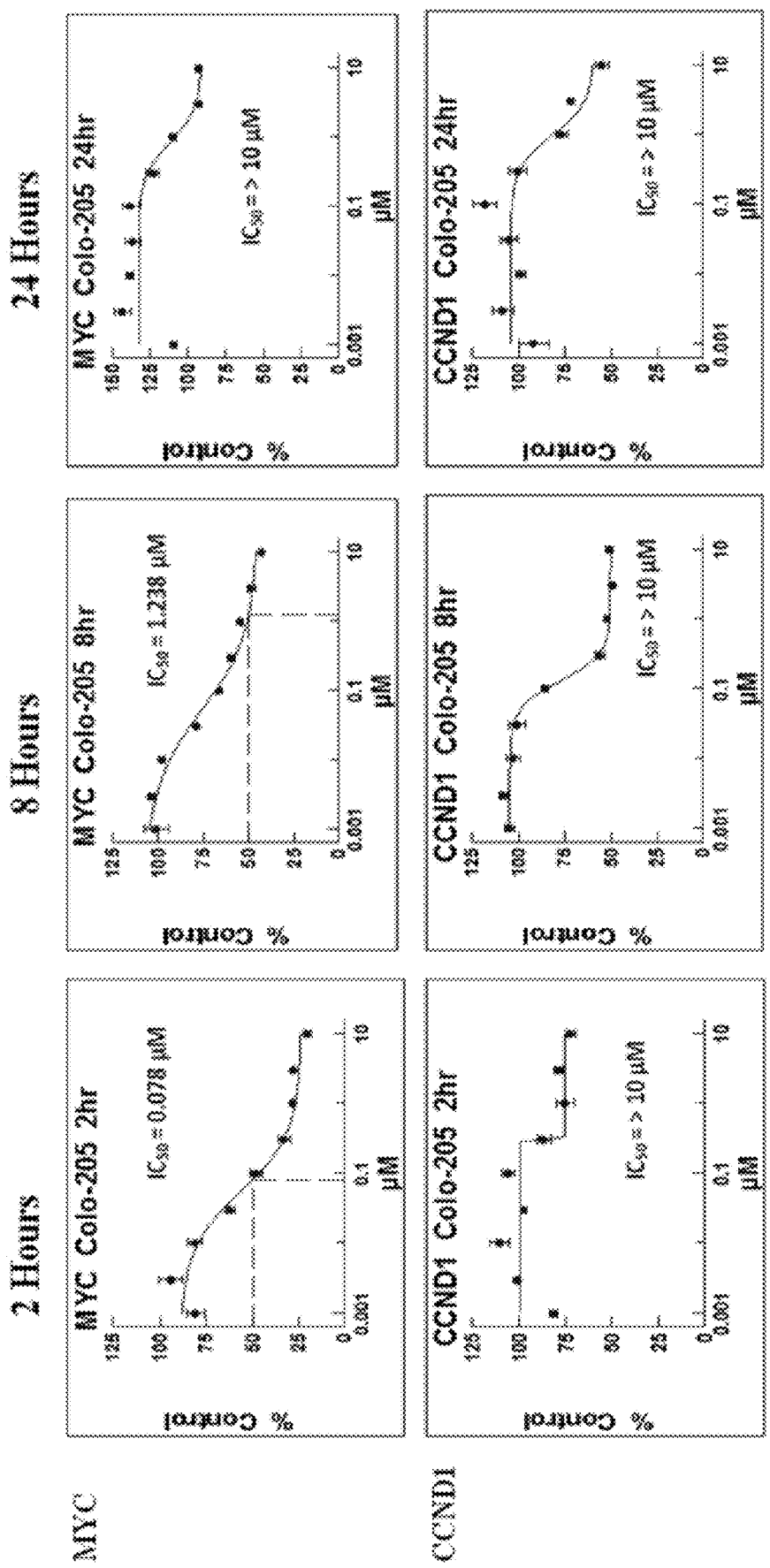
Figure 2D:
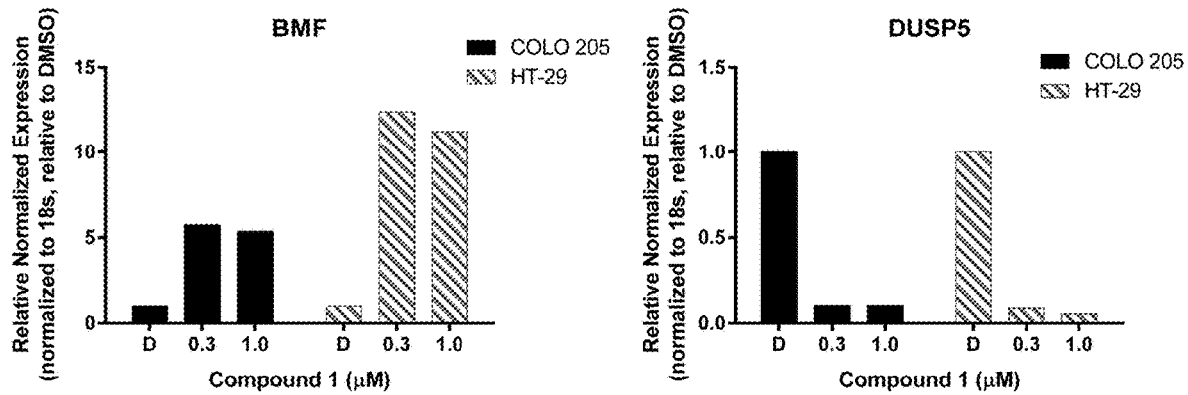
Figure 2E:
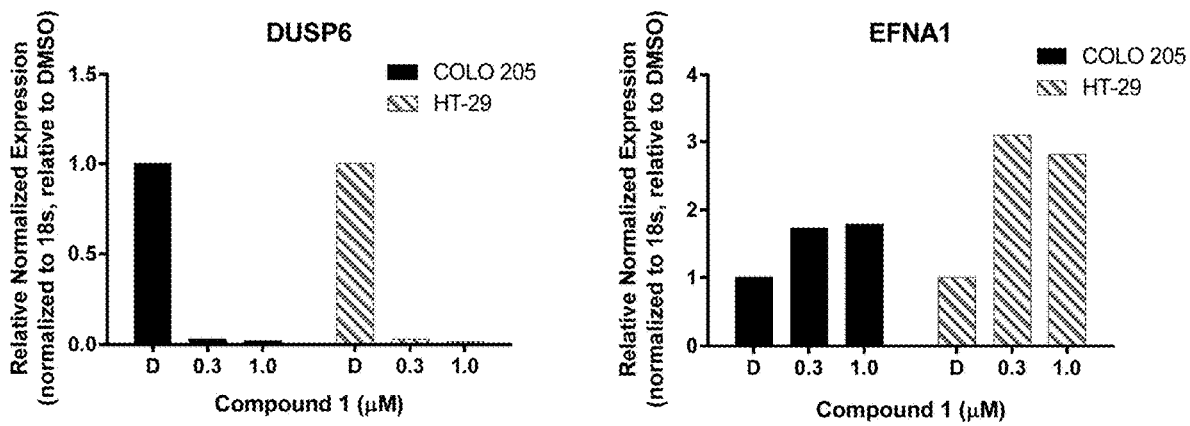
Figure 2F:
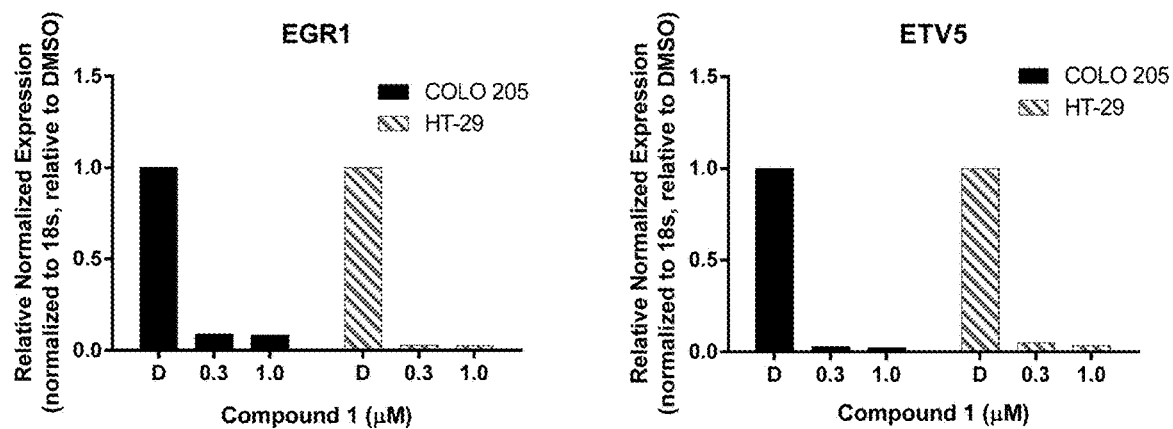
Figure 2G:
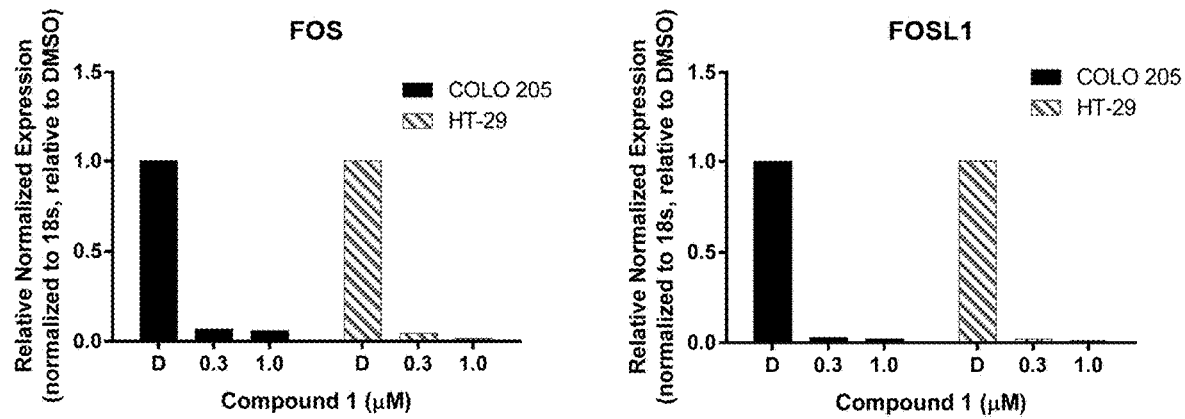
Figure 2H:
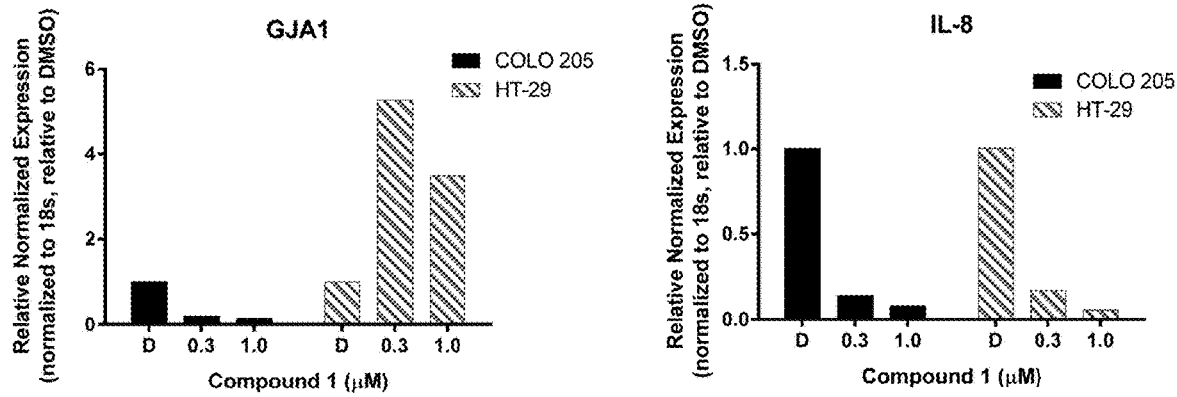
Figure 2I:
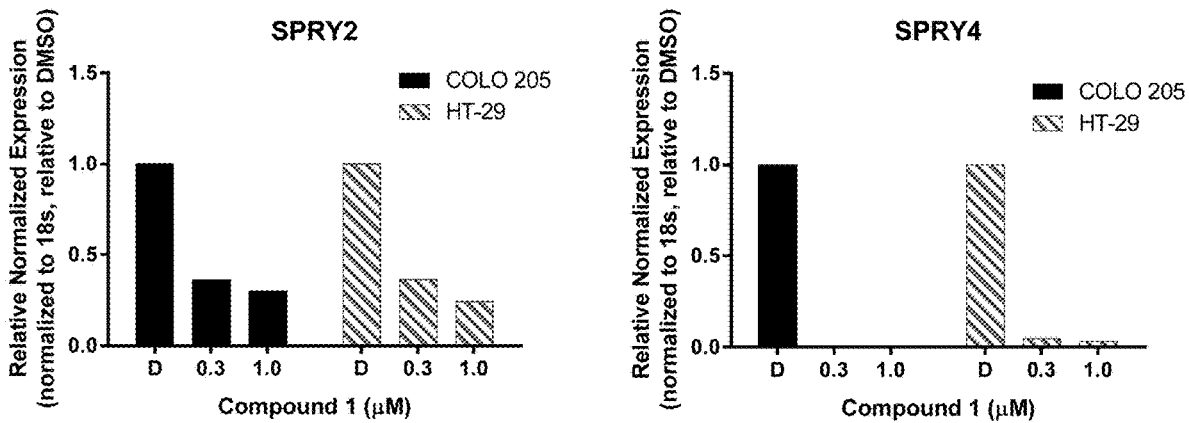

In Colo 205 (BRAF V600E), DUSP4 and DUSP6 were significantly reduced by Compound 1 as early as 2 h and the reduction was sustained through 24 h (FIG. 2A). Compound 1 treatment led to the reduction of SPRY2 transcription in a concentration-dependent manner in Colo 205 (FIG. 2B), consistent with potent ERK inhibition. Levels of cyclin D1 and c-Myc, which are downstream of both canonical Wnt and MAPK signaling, were assessed. Compound 1 significantly decreased cyclin D1 and c-Myc RNA and protein levels in Colo 205 cells (FIG. 2A-2C). Compound 1 treatment resulted in decreased YAP protein at 24 h in Colo 205 (FIG. 2A). Taken together, our cellular data is consistent with strong, sustained MAPK pathway inhibition.

To further evaluate the ability of Compound 1 to inhibit MAPK signaling, RNA expression was assessed of additional MAPK targets (BMF, DUSP5, DUSP6, EFNA1, EGR1, ETV5, FOS, FOSL1, GJA1, IL-8, SPRY2, and SPRY4). Cultures of the colon cancer cell lines Colo 205 (characterized by a BRAF V600E mutation) and HT-29 (characterized by a BRAF V600E mutation) were treated with DMSO or Compound 1 at 0.3 or 1 μM for 6 h. RNAs were extracted using MagMAX Total RNA Isolation kit and quantitative PCR was performed with probes specific for BMF, DUSP5, DUSP6, EFNA1, EGR1, ETV5, FOS, FOSL1, GJA1, IL-8, SPRY2, SPRY4. Specific probes for 18S rRNA were used for normalization.

In both cell lines, mRNA levels of DUSP5, DUSP6, EGR1, ETV5, FOS, FOSL1, IL-8, SPRY2, SPRY4 were reduced by Compound 1 (FIGS. 2D-2I), consistent with ERK inhibition. The finding that mRNA levels of GJA1 are reduced in Colo205 cells and increased in HT29 may be related to our finding that Compound 1 is cytotoxic in Colo205 and cytostatic in HT29. Compound 1 treatment resulted in increased mRNA levels of BMF and EFNA1 at 6 h in Colo 205 and HT-29. Taken together, our cellular data is consistent with MAPK pathway inhibition.

Effect on Beta-Catenin and YAP Signaling.

Cellular activity against beta-catenin and YAP target genes by Compound 1 was evaluated. Colon cancer cell line Colo 205 (BRAF V600E) cultures were treated with DMSO or increasing concentrations of Compound 1 for 2, 8 or 24 h. RNAs were extracted using Cell-To-CT kit and quantitative PCR was performed with probes specific for Axin2, CTGF, and AREG. Specific probes for β-actin were used for normalization.

Figure 3A:
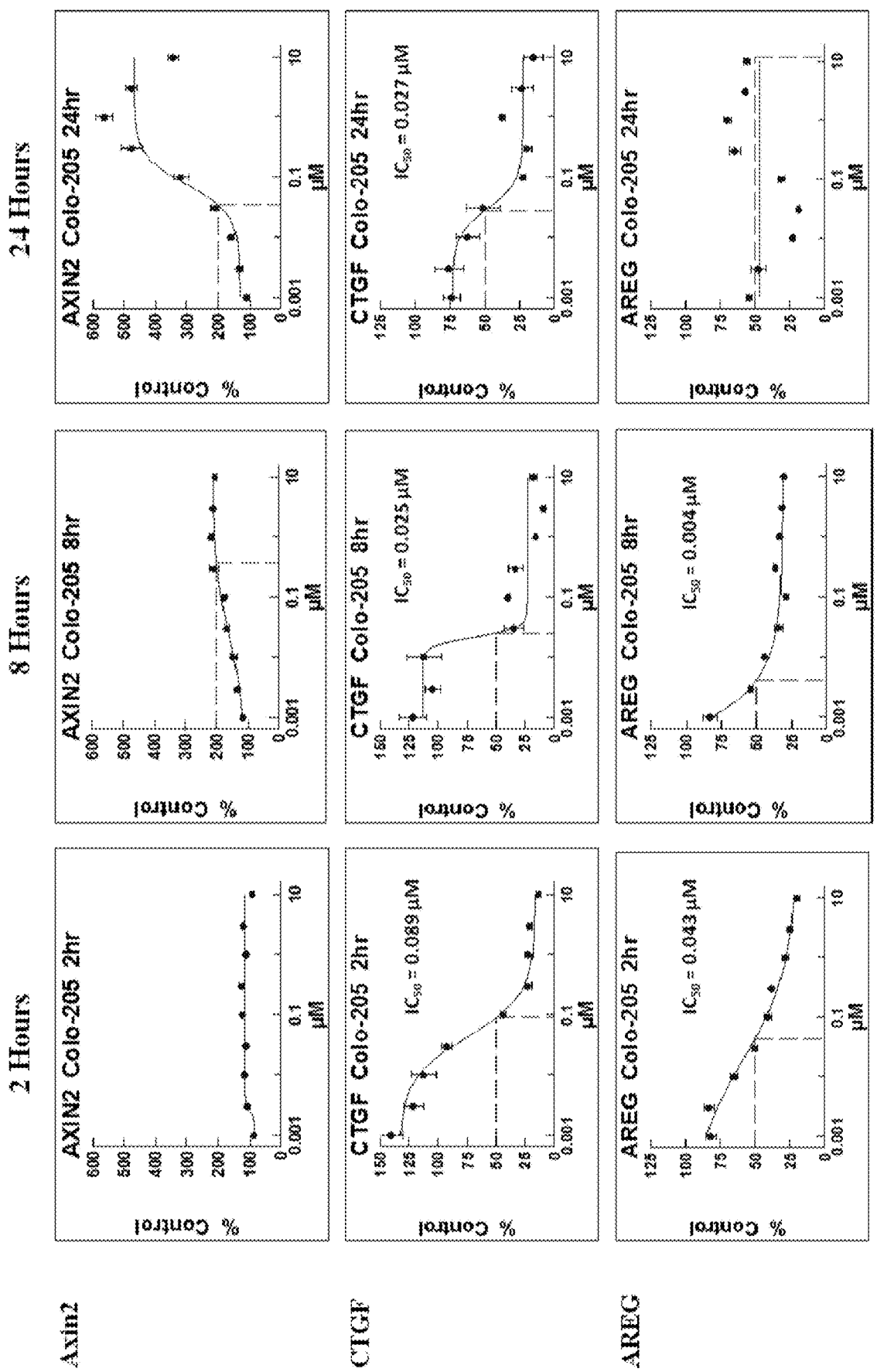
FIG. 3A illustrates Compound 1 effects on WNT/beta-catenin and HIPPO/YAP signaling pathway target genes in Colo 205. Colon cancer cell line Colo 205 (BRAF V600E) cultures were treated with DMSO or increasing concentrations of Compound 1 for 2, 8 or 24 h. RNAs were extracted using Cell-To-CT kit and quantitative PCR was performed with probes specific for Axin2, CTGF, and AREG. Specific probes for β-actin were used for normalization.
Figure 3B:
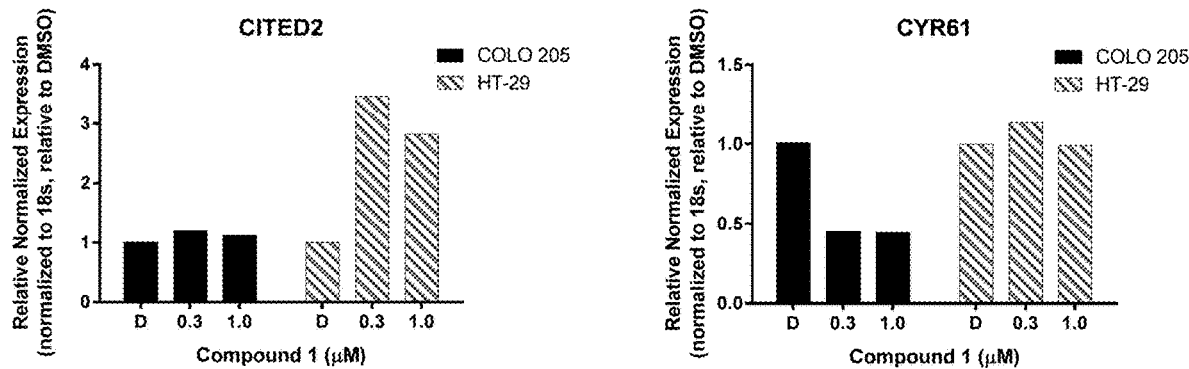
FIGS. 3B-3E illustrate Compound 1 treatment regulates YAP-driven mRNA levels in Colo 205 (mut BRAFV600E) and HT-29 (mut BRAFV600E) Cells. Colo 205 or HT-29 cells were treated with DMSO or 0.3 or 1 µM Compound 1 for 6 h. RNAs were extracted using MagMAX Total RNA Isolation kit and quantitative PCR was performed.
Figure 3C:
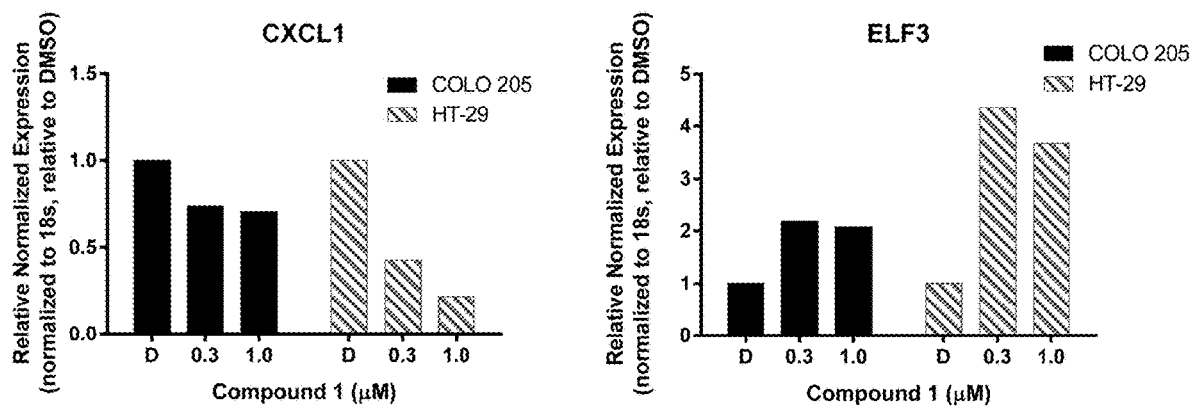
Figure 3D:
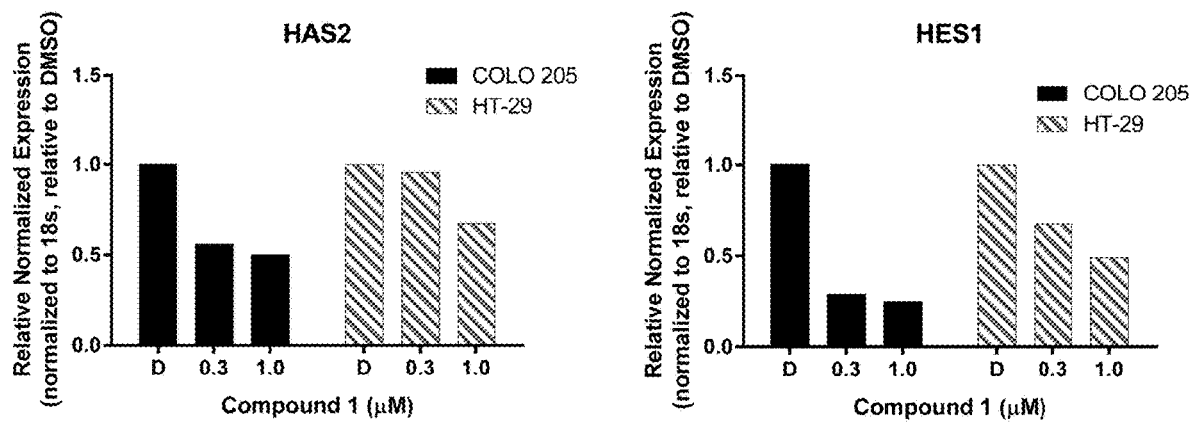
Figure 3E:
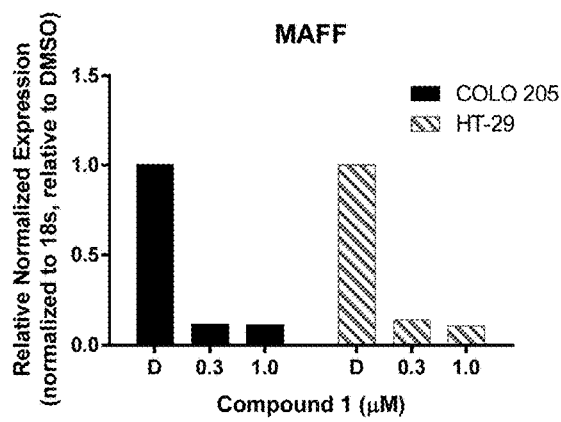

Compound 1 treatment led to increased Axin2 RNA (FIG. 3A). Compound 1 significantly reduced the expression of Hippo/YAP target genes (CTGF, AREG) in Colo 205 (BRAF V600E) at 2, 8 and 24 hr (FIG. 3A). Taken together, these data suggest that Compound 1 impacts Wnt signaling and blocks Hippo signaling in Colo 205 cancer cells.

Cellular activity against additional YAP target genes by Compound 1 was evaluated (FIGS. 3B-3E). Cultures of the colon cancer cell lines Colo 205 and HT-29 were treated with DMSO or Compound 1 at 0.3 or 1 μM for 6 h. RNAs were extracted using MagMAX Total RNA Isolation kit and quantitative PCR was performed with probes specific for CYR61, CITED2, CXCL1, ELF3, HAS2, HES1, and MAFF. Specific probes for 18S rRNA were used for normalization.

In both cell lines, mRNA levels of CYR61, CXCL1, HAS2, HES1 and MAFF were reduced by Compound 1. The finding that CYR61 mRNA levels are reduced in Colo205 cells but not in HT29 and that mRNA levels of CITED2 are increased in HT29, but not in Colo205, may be related to our finding that Compound 1 is cytotoxic in Colo205 and cytostatic in HT29. Compound 1 treatment resulted in increased mRNA levels for CITED2 and ELF3 mRNA at 6 h in Colo 205 and HT-29. (FIG. 3B) Taken together, our cellular data is consistent with YAP pathway inhibition.

Evaluation of Sensitivity in Cell Lines Having Beta-Catenin Mutations.

The effect of Compound 1 on cell lines having β-catenin mutations was evaluated. (FIG. 18 and FIGS. 19A-19B). Compound 1 showed efficacy against cell lines with mutated β-catenin. Such cell lines demonstrate that cancers characterized by mutated β-catenin are more sensitive to treatment with Compound 1. Compound 1 was further shown to modulate β-catenin, and YAP in BRAF and CTNNB1 mutant cell lines as shown in FIG. 20. Compound 1 also modulates target gene expression controlled by MAPK, β-catenin, and YAP in BRAF and CTNNB1 mutant cell lines as provided in FIG. 21A and FIG. 21B.

Western Blot.

Compound 1 modulation of MAPK, WNT/β-catenin, and Hippo/YAP pathway markers was evaluated by standard Western blotting. LOX-IMVI, SW48, and Colo-205 cells were plated in 6-well plates at a density of 250,000 cells per well and were allowed to attach overnight. Compound 1 was added to cells at concentrations of 0.03, 0.1, 0.3, 1, and 3 μM for durations of 2, 8, and 24 hours. Cells were harvested and lysed in RIPA buffer (50 mM Tris-HCl, pH 7.4, 150 mM sodium chloride [NaCl], 0.25% deoxycholic acid, 1% Non-idet P-40, 1 mM ethylenediaminetetraacetic acid [EDTA], protease and phosphatase inhibitors). The cell lysates were heated in sodium dodecyl sulfate (SDS)-sample buffer and 40 μg of cell lysate per condition were loaded onto gels and separated using SDS polyacrylamide gel electrophoresis (PAGE). Protein was transferred to nitrocellulose membrane, and immunoblotted with anti DUSP4, DUSP6, cMyc, Cyclin D1, YAP, AXIN2, HDACS (phospho S498), and β-actin antibodies. Membranes were scanned on the Licor Odyssey system.

Quantitative Polymerase Chain Reaction.

Compound 1 modulation of MAPK, WNT/β-catenin, and Hippo/YAP pathway genes was evaluated by real-time (RT)-qPCR. Lysyl oxidase IMVI, SW48, and Colo-205 cells were plated in 96-well plates at a density of 20,000 cells per well and were allowed to attach overnight. Compound 1 was added to cells at half log concentrations from 1 nM to 10 μM for durations of 2, 8, and 24 hours. Cells were harvested using the TaqMan Gene Expression Cells-to-CT Kit according to the product manual. Next, RT-PCR was performed and the resulting cDNA was used in qPCR reactions on the ViiA7 Real-Time PCR System (Thermo Fisher Scientific). TaqMan probes were used to monitor changes in DUSP4, DUSP6, SPRY2, MYC, CCND1, AXIN2, CTGF, Cyr61, AREG, and ACTB genes. All genes were normalized to ACTB expression and reported as percentage of DMSO-only control.

Gene Expression Analysis:

Human bronchial epithelial cells were cultured in T-150 flasks in BEpiCM growth medium and allowed to reach 80% confluency. Cells were plated in 12-well plastic culture plates at 150,000 cells per well in BEpiCM medium for 24 hours. After a 24-hour incubation, cells were treated with dimethyl sulfoxide (DMSO) as a control, Compound 1 at 0.1, 1, 10 uM, for 30 minutes. Cells were then stimulated with 100 ng/ml recombinant Wnt3a (formulated in phosphate buffered saline [PBS]), 350 pM RSPO3 (formulated in PBS) or a combination of Wnt3 and RSPO3 for 24 hours. Ribonucleic acid (RNA) was isolated using a Qiagen Rneasy Mini Kit according to manufacturer's instruction. Axin2 and gene expression was determined using reverse transcription polymerase chain reaction (RT-PCR) Taq-Man assays. Quantitative PCR (qPCR) was performed using SuperScript® III One-Step RT-PCR System and ran on a Viia 7 Real-Time PCR System. Data was normalized to glyceraldehyde 3-phosphate dehydrogenase. Compound 1 inhibits Axin2 expression in human bronchial epithelial cells. Gene expression was measured at 24 hours. From these results it was shown that Compound 1 inhibits Axin2 expression in human bronchial epithelial cells. (FIG. 22).

Long Term Colony Assay.

Compound 1 was assessed for its ability to inhibit the colony formation of cancer cells via a long-term colony forming assay. Cells and compounds were added to 96-well plates and were monitored for up to 8 weeks for the formation of colonies. Compound and media were replenished every 1 week throughout the course of the assay. Colony formation was detected via imaging at 4× on the IncuCyte ZOOM System. Compound 1 demonstrated inhibition of colony formation of β-catenin mutant cells at a level greater than MEK inhibitors (trametinib) and ERK inhibitors (GDC0994). SW48 (colo) cells, HCT-116 (colo) cells, AGS (gastric) cells, and Hep3B (HCC) cells were treated with Compound 1 and showed greater levels of inhibition than seen with treatment with MEK inhibitors or ERK inhibitors. (FIG. 23A-23D). Compound 1 was further shown to surprisingly inhibit colony formation of AGS cells that are resistant to MEK inhibitor treatment with trametinib. Such results suggest Aminopurine Compounds described herein, such as Compound 1, can be useful in treating cancers resistant to other treatments.

Evaluation of Immunomodulatory Effects.

The effect of Compound 1 was evaluated on PD-L1 expression levels. Cells were cultured in presence or absence of Compound 1 for indicated time before expression levels of PD-L1, DUSP4 and α-tubulin or α-actin were measured by Western blot. To detect surface levels of PD-L1, cells were treated with DMSO or Compound 1 at indicated concentrations for 48 h and cell surface expression of PD-L1 was detected using flow cytometry analysis (FACS) with an APC-labeled antibody to PD-L1 (clone 29E.1A3; BioLegend, San Diego, Calif.). Geometric mean of PD-L1 positive cells was determined by FlowJo 10 (Treestar, Ashland, Oreg.).

Conclusion.

Compound 1 directly inhibits PD-L1 expression in multiple cancer cells including HOP62, KARPAS-299, and LOX-IMVI (BRAF V600E) (FIG. 4A). FACS analysis indicates that surface PD-L1 levels are also inhibited by Compound 1 in multiple cancer cell lines (FIG. 4B).

To determine if Compound 1 down-regulation of PD-L1 enhances T cell activation, compound-treated KARPAS-299 cancer cells were co-cultured with PBMC-derived T cells stimulated with low concentrations of super antigen (SEB). KARPAS-299 cells were treated with DMSO (D) or Compound 1 at indicated concentrations for 48 h. PBMC from healthy donors were treated with or without 20 ng/ml SEB for 48 h. After wash with PBS, the PBMCs were incubated with the cancer cells for 24 h and the supernatants were collected to measure IL-2 and IFNγ using Mesoscale assays.

Figure 5B:
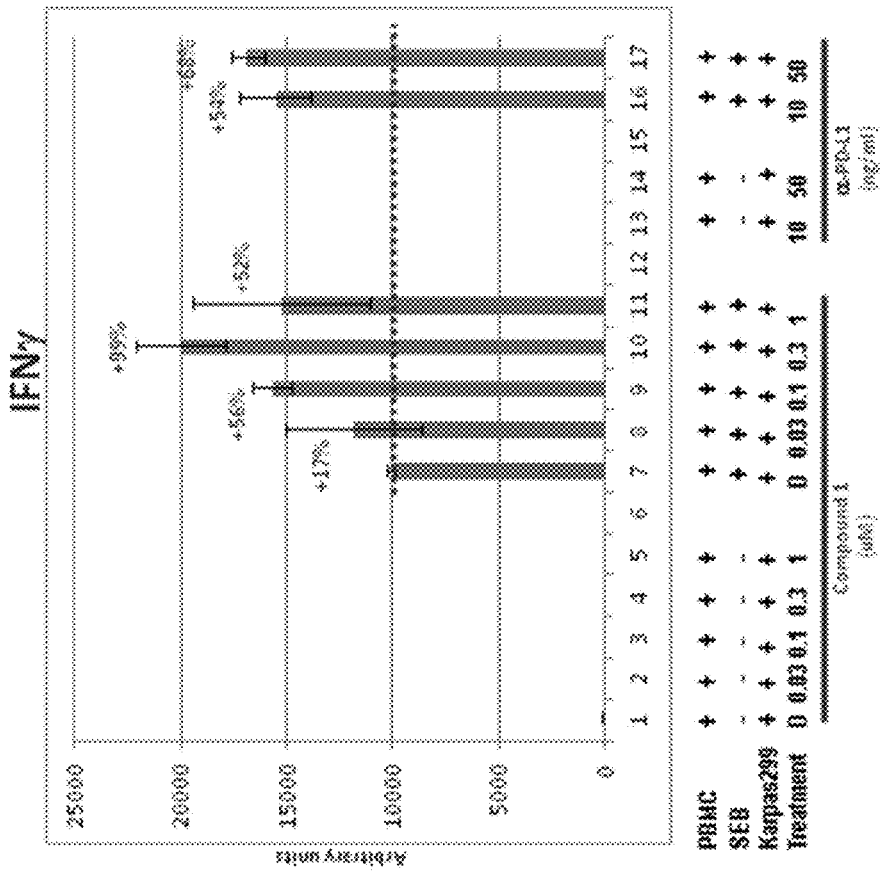
FIGS. 5A-5B illustrate Compound 1-treated KARPAS-299 cells increase production of IL-2 (FIG. 5A) and IFNγ (FIG. 5B) by PBMC-derived T cells stimulated with superantigen (SEB) in vitro. KARPAS-299 cells were treated with DMSO (D) or Compound 1 at indicated concentrations for 48 h. PBMC from healthy donors were treated with or without 20 ng/ml SEB for 48 h. After wash with PBS, the PBMCs were incubated with the cancer cells for 24 h and the supernatants were collected to measure IL-2 and IFNγ using MSD assays.
Figure 5A:
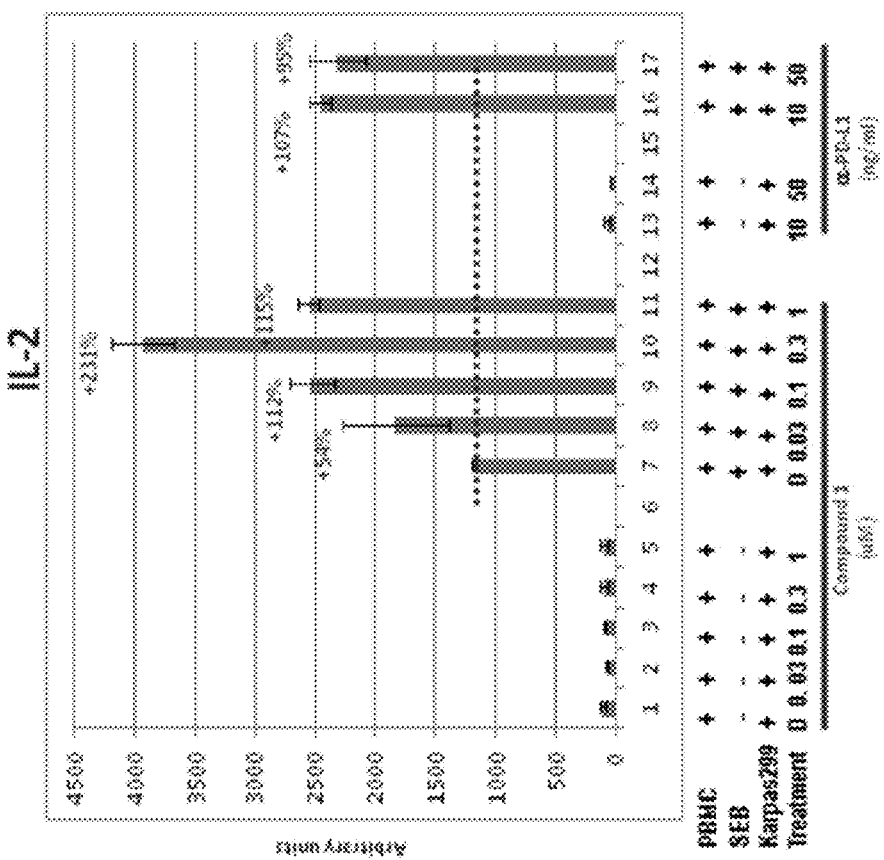

Supernatant levels of IL-2 and IFNγ were used as functional markers of T cell activation. In the absence of SEB, PBMC co-cultured with Compound-1-treated KARPAS-299 cells produced little IL-2 or IFNγ. In the presence of low concentrations of SEB (20 ng/ml), Compound 1-treated cancer cells co-cultured with PBMC demonstrated increased levels of both IL-2 and IFNγ production (FIGS. 5A-5B). The increased levels of IL-2 and IFNγ in Compound 1-treated cancer cells were similar to the levels observed with treatment of anti-PD-L1 (Ultra-LEAF™ from Biolegend).

Figure 5C:
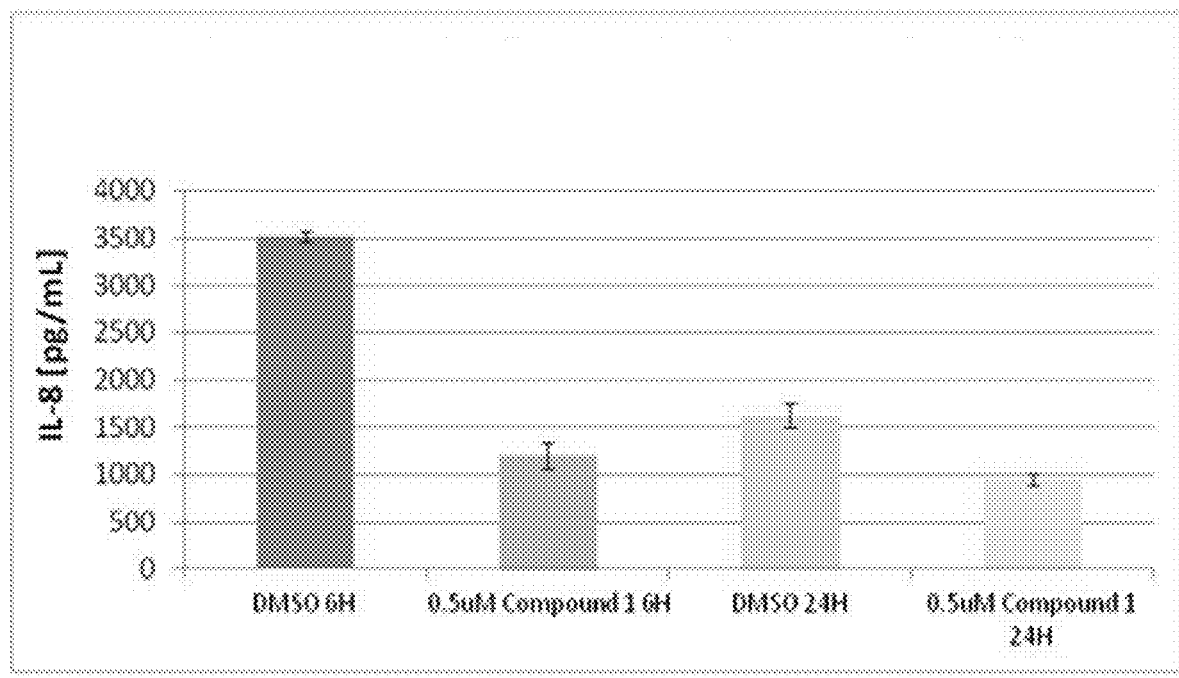
FIG. 5C illustrates the effect of Compound 1 treatment on levels of IL-8 were determined in PBMC culture media. PBMCs were isolated from whole blood and cultured in RPMI media plus 10% FBS. PBMCs were plated at $1 \times 10^6$ per milliliter in 10 cm$^2$ dishes. The PBMCs were treated with 0.1% DMSO or 0.5 µM Compound 1. Treatments were taken down at designated time points. PBMCs were pelleted and used for Western blot analysis and 1 mL of culture media was taken for IL-8 analysis. The IL-8 analysis was performed with a Mesoscale V-Plex Human IL-8 kit according to the manufacturer's instructions. Compound 1 was shown to inhibit IL-8 levels at different time-points.

The effect of Compound 1 treatment on levels of IL-8 was determined in PBMC culture media. PBMCs were isolated from whole blood and cultured in RPMI media plus 10% FBS. PBMCs were plated at $1\times10^6$ per milliliter in 10 cm$^2$ dishes. The PBMCs were treated with 0.1% DMSO or 0.5 μM Compound 1. Treatments were taken down at the designated time points. The culture media (1 mL) was used for IL-8 analysis. The IL-8 analysis was performed with a Mesoscale V-Plex Human IL-8 kit according to the manufacturer's instructions. Compound 1 was shown to inhibit IL-8 levels at different time-points (FIG. 5C).

TEAD Reporter Assay.

TEAD reporter activity was analyzed using WI38 VA13 cells stably expressing a YAP/TAZ responsive synthetic promoter driving luciferase expression (8×GTIIC-luciferase). 10,000 cells per well were seeded on a white-walled 96-well plate and left overnight. After 16-20 hours, cells were treated with compound and TEAD reporter activity was measured 24 or 72 hours later using Bright Glo luciferase assay (Promega) according to the manufacturers instructions. This assay was performed 3 times for Compound 1 and twice for Trametinib. See FIG. 25.

Viability Assay.

In parallel 10,000 WI38 VA13 cells expressing 8×GTIIC-luciferase were seeded in each well of a black-walled 96-well plate. After 16-20 hours cells were treated with compound for 24 or 72 hours. At this time the serum and compound containing media was removed and replaced with 100 μl serum free media and 100 μl Cell Titer Fluor (Promega). The plate was incubated for 2 hours at 37° C. before reading fluorescence output. This assay is based on measurement of live-cell protease activity. The viability assay was performed to confirm that any effects of compounds on TEAD reporter were not the result of compound effects on viability. This assay was performed 3 times for Compound 1 and twice for Trametinib.

Conclusion.

These data provide an additional therapeutic hypothesis suggesting that treatment with Compound 1 will potentiate T cell activation. The in vitro data suggests that Compound 1 may enhance T cell immunity against cancer cells by inhibiting key oncogenic pathways such as the MAPK pathway and down-regulating the immune checkpoint molecule PD-L1 expression in tumor microenvironment. Cancer types that express high levels of PD-L1 (for example, melanoma, lung, RCC, or HCC) may therefore be sensitive to Compound 1.

Animal Models

Xenograft Models.

For xenograft model studies human cancer cell lines were injected into SCID (severe combined immunodeficiency) mice. Cancer cell lines were propagated in culture in vitro. Tumor bearing animals were generated by injecting precisely determined numbers of cells into mice. Following inoculation of animals, the tumors were allowed to grow to a certain size prior to randomization. The mice bearing xenograft tumors ranging between pre-determined sizes were pooled together and randomized into various treatment groups. A typical efficacy study design involved administering one or more compounds at various dose levels to tumor-bearing mice. Additionally, reference chemotherapeutic agents (positive control) and negative controls were similarly administered and maintained. Tumor measurements and body weights were taken over the course of the study.

Mice were anesthetized with inhaled isoflurane and then inoculated with LOX-IMVI tumor cells subcutaneously above the right hind leg with 0.1 mL of a single cell suspension in PBS using a sterile 1 mL syringe fitted with a 26-gauge needle. Following inoculation of the animals, tumors were allowed to grow to approximately 75-125 mm$^3$ or in some cases 250-400 mm$^3$ prior to randomization of the mice. The tumor of each animal was measured and animals with tumors in the appropriate range were included in the study. Animals from the study pool were then distributed randomly into various cages and the cages were randomly assigned to vehicle, positive control, or test article groups. All of the mice were tagged with metal ear tags on the right ear. A typical group consisted of 8-10 animals. For a typical xenograft study, SCID mice bearing tumors were randomized and dosed with compounds ranging from, for example, 100 mg/kg to 0.1 mg/kg with different dose scheduling, including, but not limited to, qd, q2d, q3d, q5d, q7d and bid. The mice were dosed for 1-4 weeks. Tumors were measured twice a week using calipers and tumor volumes were calculated using the formula of $W^2 \times L/2$.

The purpose of these studies was to test the efficacy of Compound 1 in the cell line-derived xenograft models, LOX-IMVI (melanoma) and Colo205 (colorectal) and the PDX1994060146 (patient-derived xenograft [PDX146]) colorectal xenograft model. These models were chosen because they harbor the V600E BRAF mutation. Additional PK/PD analysis was performed to examine the Compound 1-mediated inhibition of pathway biomarkers in the PDX146 xenograft model.

LOX-IMVI Subcutaneous Melanoma Xenograft Model.

Figure 6:
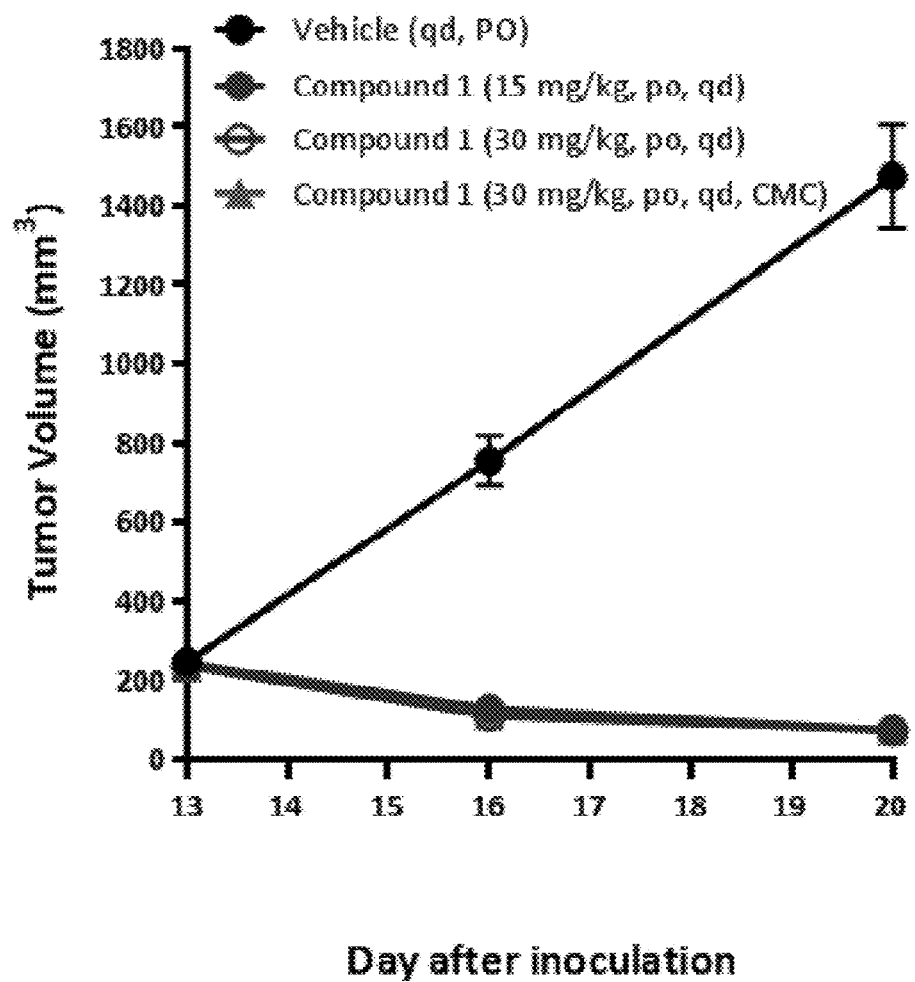
FIG. 6 illustrates antitumor activity of Compound 1 in the LOX-IMVI Xenograft Model. Female SCID mice were inoculated with $1 \times 10^6$ LOX-IMVI tumor cells into the right flank. Mice were randomized into treatment groups (n=9/group) at the time of treatment initiation. Test article treatment started on Day 13 when the tumors were approximately 240 mm$^3$.

The purpose of this study was to confirm the efficacy of Compound 1 in the LOX-IMVI melanoma xenograft model. One study (FIG. 6) in the LOX-IMVI xenograft model testing two dose levels of Compound 1 (15 and 30 mg/kg) demonstrated significant tumor volume reduction compared to the vehicle control (p<0.001 for both dose levels). Tumor regression was observed in 9 out of 9 animals for both dose levels and 1 out of 9 animals from each group was tumor free at study end.

Figure 7:
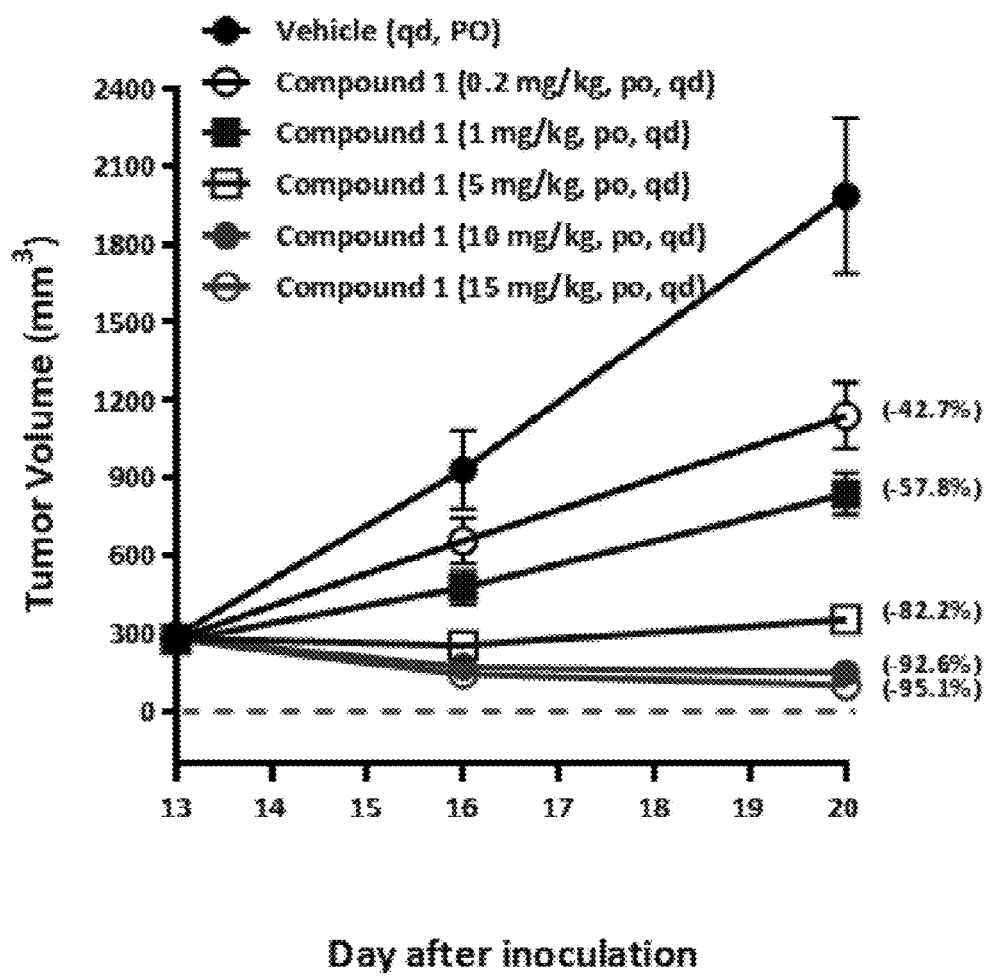
FIG. 7 illustrates antitumor activity of Compound 1 in the LOX IMVI Xenograft Model. Female severe-combined immunodeficient (SCID) mice were inoculated with $1 \times 10^6$ LOX-IMVI tumor cells into the right flank. Mice were randomized into treatment groups (n=10/group) at the time of treatment initiation. Test article treatment started on Day 13 when the tumors were approximately 300 mm$^3$. Percent inhibition is calculated relative to the vehicle control on the last study day and is in parentheses next to the respective tumor volume for the treatment groups. Dotted line is the tumor volume at the initiation of dosing.

In a separate experiment, Compound 1 was administered orally, QD for 8 days at 0.2, 1, 5, 10, and 15 mg/kg. Dose-dependent antitumor activity was observed with Compound 1 treatment in the LOX-IMVI xenograft model (FIG. 7). Tumor regression was observed at the 10 and 15 mg/kg dose levels.

Colo 205 Subcutaneous Colorectal Xenograft Model.

Figure 8:
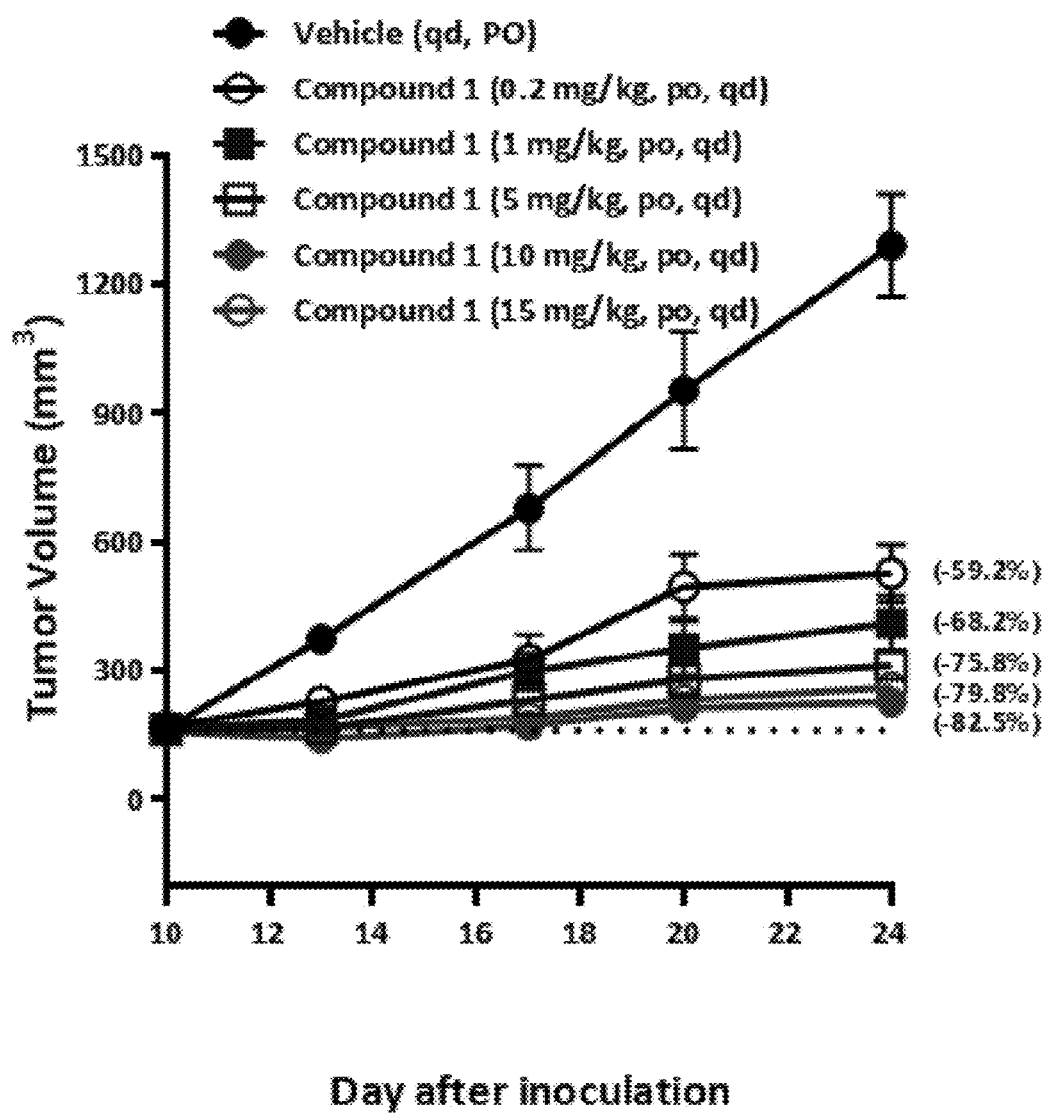
FIG. 8 illustrates antitumor activity of Compound 1 in the Colo 205 Xenograft Model. Female SCID mice were inoculated with $2 \times 10^6$ Colo 205 tumor cells into the right flank. Mice were randomized into treatment groups (n=10/group) at the time of treatment initiation. Test article treatment started on Day 10 when the tumors were approximately 160 mm$^3$. Percent inhibition is calculated relative to the vehicle control on the last study day and is in parentheses next to the respective tumor volume for the treatment groups. Dotted line is the tumor volume at the initiation of dosing.
Figure 9:
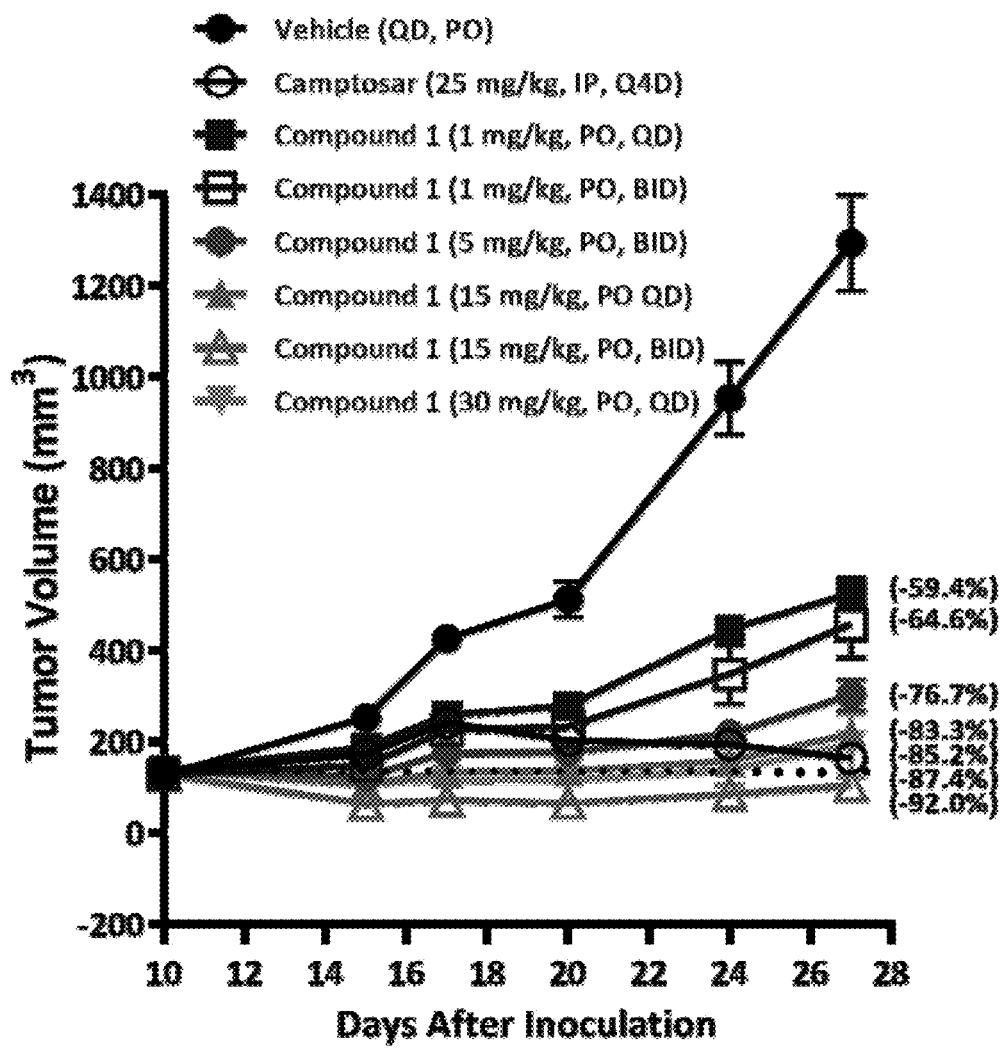
FIG. 9 illustrates antitumor activity of Compound 1 in the Colo 205 Xenograft Model. Female SCID mice were inoculated with $2 \times 10^6$ Colo 205 tumor cells into the right flank. Mice were randomized into treatment groups (n=10/group) at the time of treatment initiation. Test article treatment started on Day 10 when the tumors were approximately 130 or 160 mm³. Percent inhibition is calculated relative to the vehicle control on the last study day and is in parentheses next to the respective tumor volume for the treatment groups. Dotted line is the tumor volume at the initiation of dosing.

The purpose of these studies was to test the efficacy of Compound 1 in the Colo 205 colorectal cancer xenograft model, and determine whether twice daily dosing (BID) had an impact on antitumor activity. In the first experiment Compound 1 was administered orally, QD for 15 days at 0.2, 1, 5, 10, and 15 mg/kg. Dose-dependent antitumor activity was observed with Compound 1 treatment in the Colo 205 xenograft model (FIG. 8). A scheduling study was conducted to determine whether BID dosing increased the antitumor activity of Compound 1. Dose-dependent antitumor activity was observed with Compound 1 treatment in the Colo 205 xenograft model (FIG. 9).

PDX1994060146 Subcutaneous Colorectal Patient-Derived Xenograft Model.

The purpose of these studies was to test the efficacy of Compound 1 in the PDX1994060146 (PDX146) colorectal cancer xenograft model and determine whether BID dosing had an impact on antitumor activity. A time to progression (TTP) study was performed to determine the effect of longer treatment duration on tumor growth.

In the first experiment Compound 1 was administered orally, QD at 1, 5, and 15 mg/kg or 5 and 15 mg/kg BID for 22 days. Dose-dependent antitumor activity was observed with Compound 1 treatment in the PDX146 xenograft model (FIGS. 10A-10B). Dosing 15 mg/kg BID appeared to increase the antitumor activity of Compound 1 compared to the administration of 15 mg/kg QD.

In the TTP study, Compound 1 was administered orally, 1, 5, and 15 mg/kg BID for 49-77 days. Compound 1 treatment groups were dosed throughout the duration of the study until the group mean reached the predetermined endpoint of approximately 1200 $mm^3$ or study termination. Tumor growth delay (TGD) was calculated as the time between the termination of the vehicle control group (on day 43) and the Compound 1 treatment groups. The TGD was 8, 12 and >37 days for the 1, 5 and 15 mg/kg treatment groups, respectively. (FIG. 11)

Biomarkers representing the activity of three different pathways, MAPK, Wnt, and Hippo, were inhibited in the PDX146 xenograft model. Sustained inhibition of these pathway biomarkers was observed through 24 h.

Antitumor Activity of Compound 1 in the β-Catenin Mutant SW48 Colorectal Xenograft Model.

Female SCID mice were inoculated with $2\times10^6$ SW48 tumor cells into the right flank. Mice were randomized into treatment groups (n=10/group) at the time of treatment initiation. Test article treatment started on Day 10 when the tumors were approximately 110 and 105 $mm^3$. (See FIGS. 15A-15B.) Black dotted line is the tumor volume at the initiation of dosing. Graph on the left is a dose-response study. Graph on the right is a time to progression study where animals were maintained on drug during the course of the study. Dotted line is the tumor volume on Day 28 when the vehicle control group was terminated.

Antitumor Activity in the Orthotopic Hep3B2.1-7 Hepatocellular Carcinoma Xenograft.

Female SCID mice were orthotopically inoculated with $2\times10^6$ Hep3B2.1-7 tumor cells per animal. Seven days post-inoculation the animals were randomized into treatment groups based on body weight and the treatment commenced (Study day 0). Take rate assessment of a satellite group confirmed the presence of tumor in the liver in 100% of the animals. Treatment with Compound 1 was started and Compound 1 was dosed orally, QD for 21 days. Significant mean body weight loss expected with this model was observed in the vehicle control group. Animals treated with 15 mg/kg Compound 1 showed minimal body weight loss and a significant mean body weight gain was observed in the 30 mg/kg Compound 1 treatment group. On the day of study termination, the tumors were removed and weighed. Individual tumor weights and the mean tumor weight±SEM of each group was plotted (FIG. 16). Percent inhibition was calculated relative to the vehicle control. P values were derived from a one-way ANOVA with a Dunnet's post-hoc analysis. ***=p<0.001.

Antitumor Activity of Compound 1 in the C-Met Amplified Hepatocellular Carcinoma Patient-Derived Xenograft Model, LI0612.

Female SCID mice were inoculated with hepatocellular carcinoma PDX model LI0612 tumor fragments (2-4 mm in diameter) into the right flank. The mice were randomized into treatment groups (n=10/group) at the time of treatment initiation. Test article treatment started on Day 18 when the tumors were approximately 150 $mm^3$ in size. Tumor growth progressed in the vehicle control and Compound 1 treatment groups over the dosing period. A change in the growth kinetics was noted with Compound 1 administration resulting in significant tumor growth inhibition (TGI) with 30 mg/kg treatment (p=0.038, compared to the vehicle control). See FIG. 17.

Pharmacokinetic/Pharmacodynamic Data in a BRAF Mutant Patient-Derived Xenograft Model.

Based on the known kinases (ERK 1/2, NLK and SIK) that are inhibited by Compound 1, the impact of compound treatment was evaluated on MAPK, β-catenin and Hippo pathway biomarkers in PDX146 tumors from xenografted mice. Tumor-bearing mice (tumors were ~400 $mm^3$) were treated with a single dose of 1 or 5 mg/kg Compound 1. Tumor tissue was collected at 1, 2, 4, 8, and 24 h post-dose.

Figure 12A:
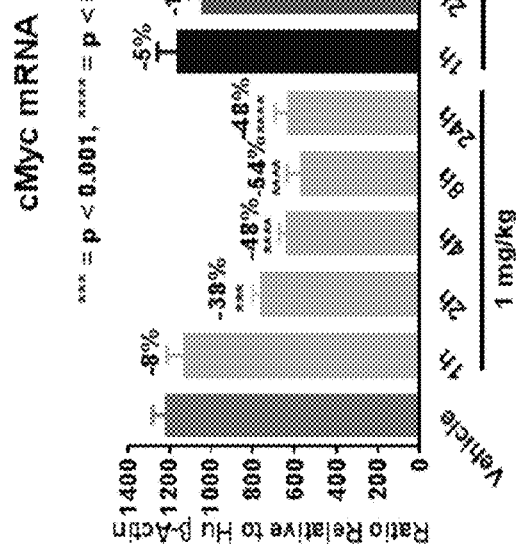
Figure 12B:
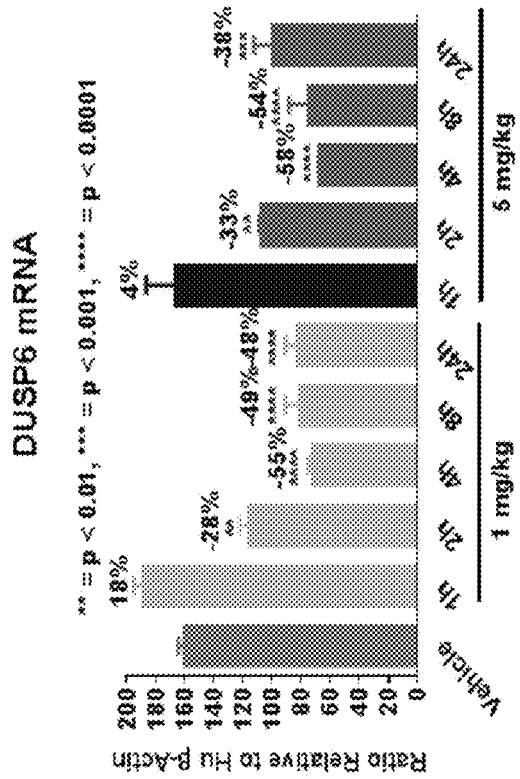
Figure 12C:
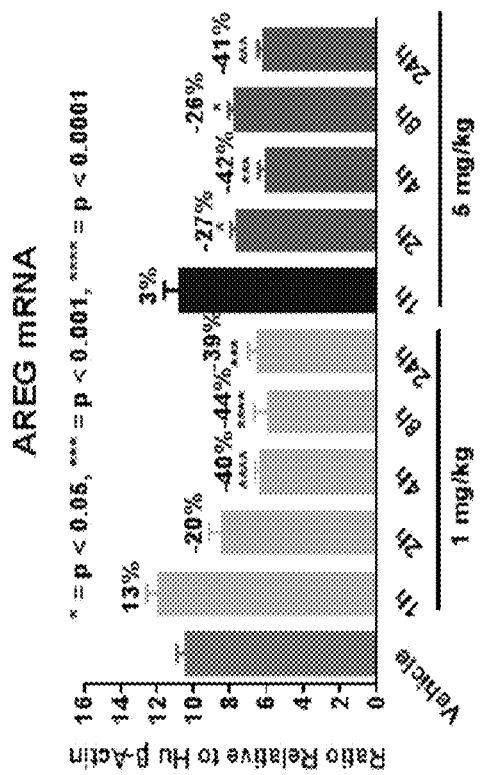
Figure 12D:
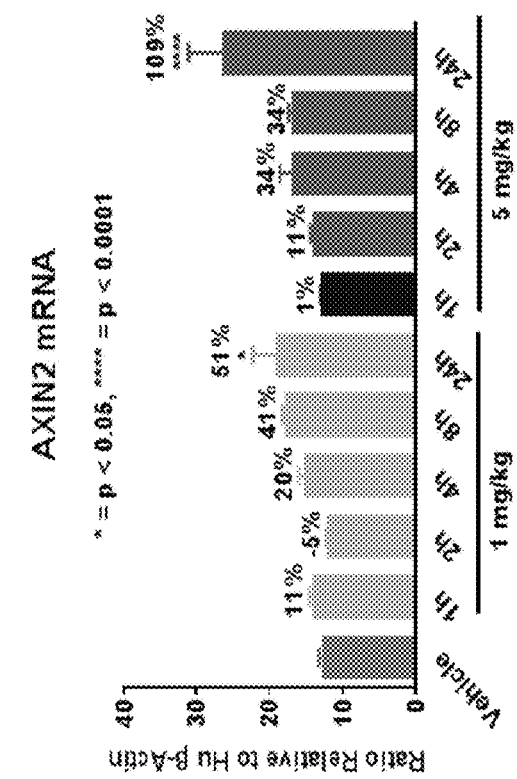
Figure 13A:
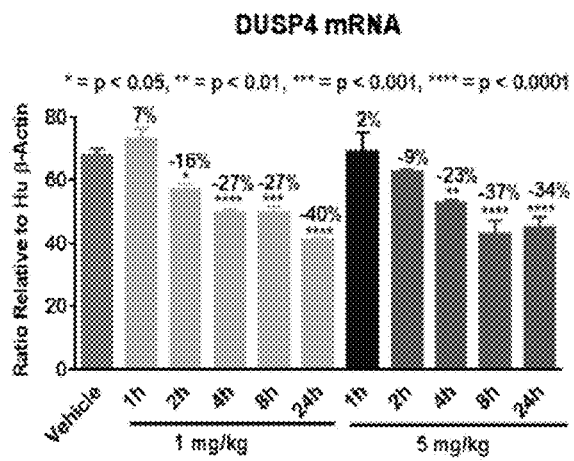
Figure 13B:
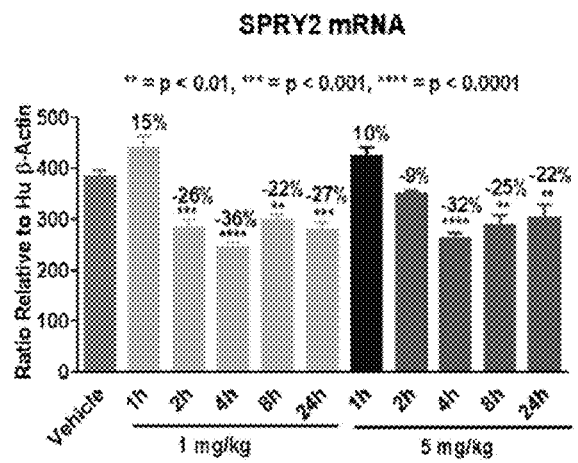
Figure 13C:
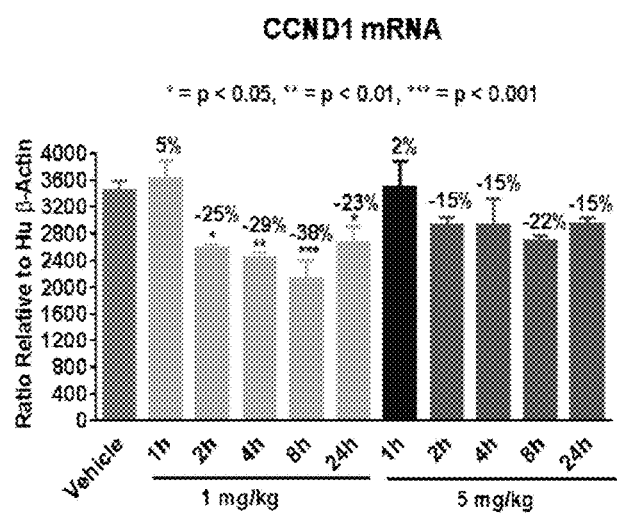
Figure 13D:
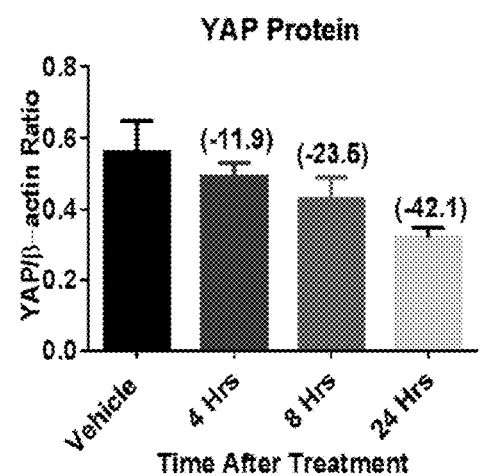
Figure 14A:
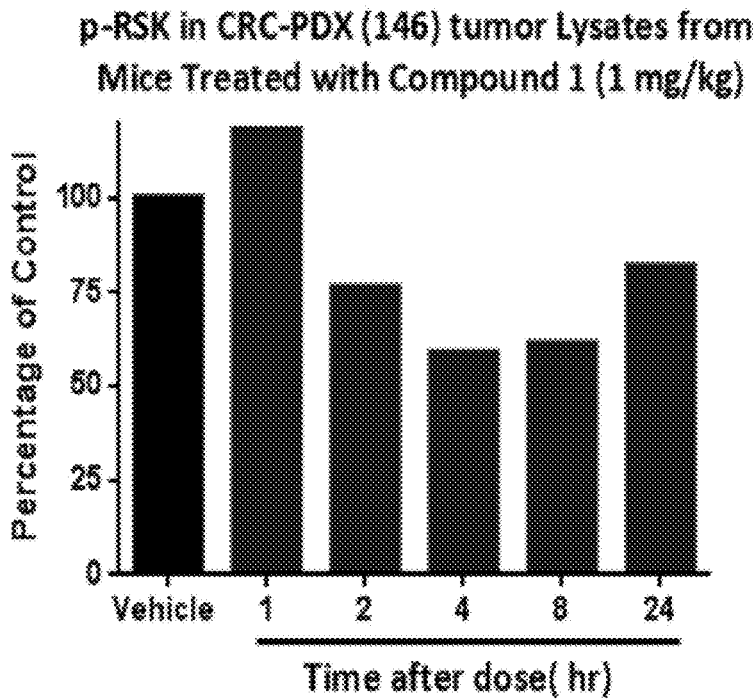
Figure 14B:
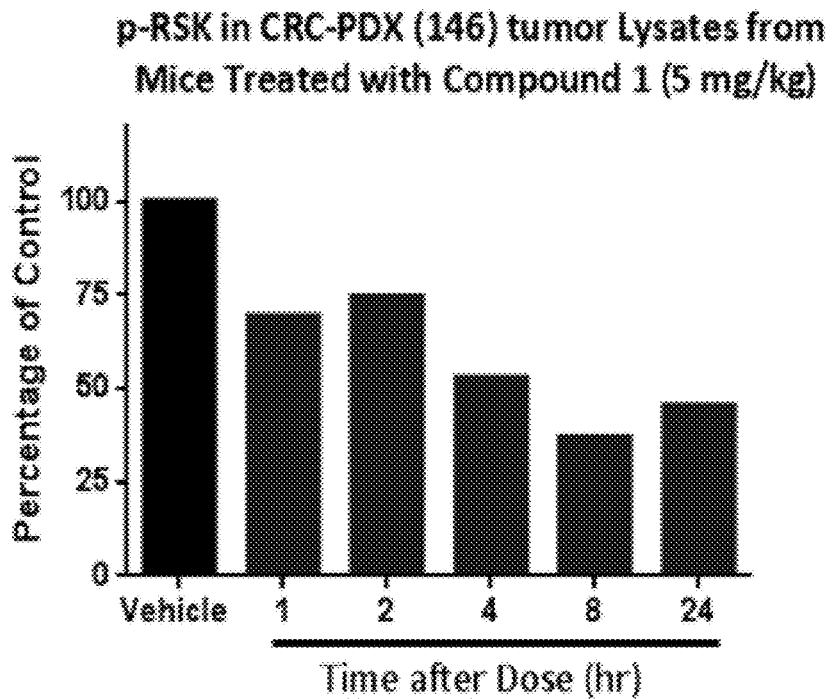
Figure 14C:
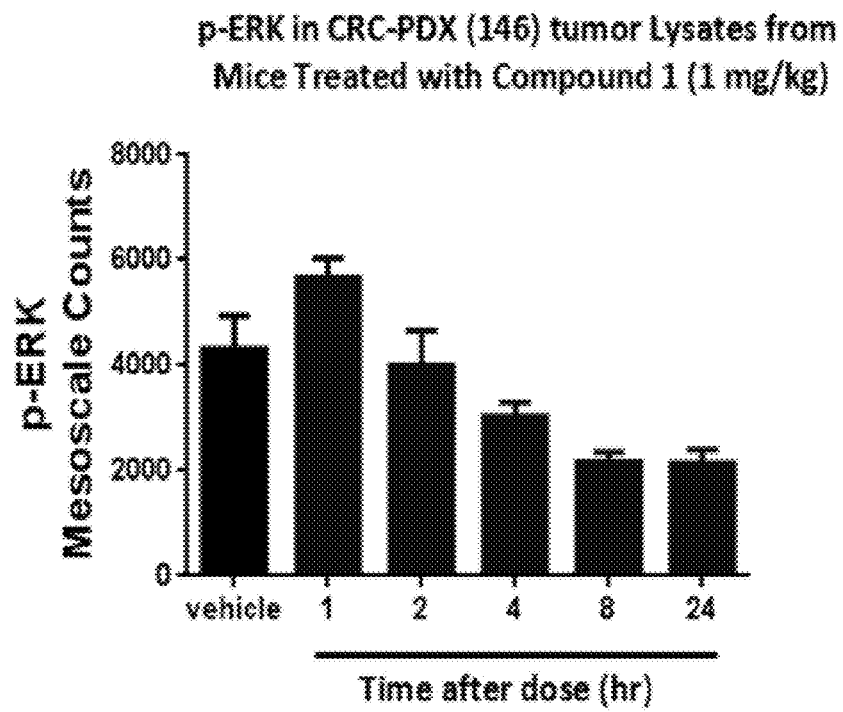
Figure 14D:
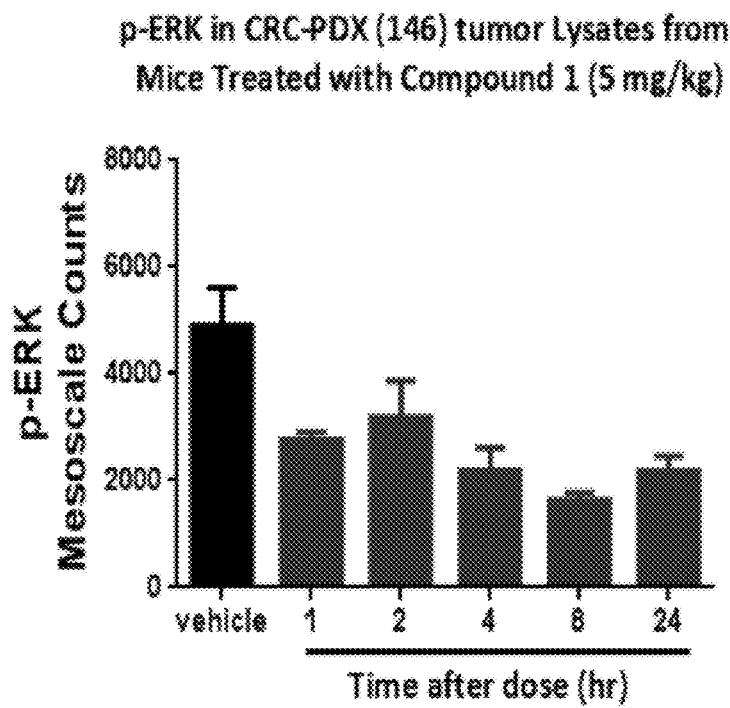

The modulation of the MAPK pathway was evaluated by examination of tumor DUSP4, DUSP6 and Sprouty (SPRY2) mRNA levels and pRSK and pERK protein levels. DUSP6 mRNA levels were significantly decreased with compound treatment starting 2 hr post-dose and remained suppressed through 24 h at both dose levels (FIG. 12A). A similar pattern was observed with DUSP4 and SPRY2 mRNA levels (FIGS. 13A-13B). Phospho-RSK (pRSK) and phospho-ERK (pERK) protein levels were modulated by Compound 1 treatment in a dose- and time-dependent manner (FIGS. 14A-14D). Levels of cMyc (FIG. 12B) and cyclin D1 (FIG. 13C), which are downstream of both the MAPK and Wnt signaling pathways, were inhibited with Compound 1 treatment. Compound 1 treatment upregulated the Wnt target gene, Axin2. Treatment with Compound 1 at both dose levels demonstrated a significant increase in Axin2 mRNA levels 24 h post-dose. Sustained inhibition of AREG (a downstream target gene in the Hippo pathway) mRNA levels was observed through 24 h. Additionally Compound 1 inhibited YAP protein levels in a time-dependent manner (not statistically significant (see FIG. 13D), which could be due to SIK inhibition and Hippo pathway regulation or an indirect effect as a result of MAPK inhibition.

These data suggest that Compound 1 impacts three different pathways, MAPK, Wnt and Hippo, in this BRAF mutant colorectal PDX model following a single dose administration.

Conclusion:

Significant dose-dependent antitumor activity was observed in all three BRAF mutant xenograft models (See FIGS. 15A-15B, FIG. 16, and FIG. 17). Tumor regression was observed with Compound 1 treatment across the models and there was a significant growth delay with long term treatment in the PDX146 model.

Patient Enrichment and Tumor Indications.

Based upon the in vitro and in vivo data of Compound 1, the patient enrichment hypotheses and tumor indications are outlined in Table 8 and Table 9.

TABLE 8

Patient enrichment biomarkers and tumor indications

| Patient Enrichment Biomarkers | Tumor indications |
|---|---|
| BRAF mutant | CRC, Thyroid, Melanoma, Lung |
| NRAS mutant | Melanoma |
| KRAS mutant | Lung, CRC, Pancreas |
| CTNNB1 (β-catenin mutant and/or active) | CRC, Stomach, HCC, Sarcoma |

TABLE 9

| Molecular Alterations | Pathways | Clinical Indications |
|---|---|---|
| CTNNB1 mutant, YAP amplification | Wnt/b-catenin//Hippo | HCC |
| BRAF mutant, CTNNB1 | MAPK//Wnt/b-catenin | CRC |
| CTNNB1 mutant | Wnt/b-catenin | Gastric |
| BRAF mutant, NRAS mutant | MAPK | Melanoma |

A number of references have been cited, the disclosures of which are incorporated herein by reference in their entirety.

Although the invention has been described with reference to the disclosed embodiments, those skilled in the art will readily appreciate that the specific examples and studies detailed above are only illustrative of the invention. It should be understood that various modifications can be made without departing from the spirit of the invention. Accordingly, the invention is limited only by the following claims.

What is claimed is:

1. A method for treating a cancer, the method comprising administering to a subject having the cancer an effective amount of an Aminopurine Compound of formula (I):

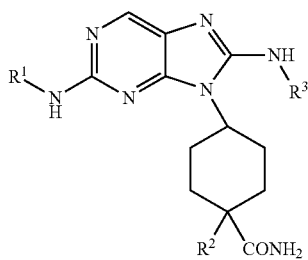

(I)

or a pharmaceutically acceptable salt, tautomer, stereoisomer, enantiomer, or isotopologue thereof, wherein:

$R^1$ is substituted or unsubstituted non-aromatic heterocyclyl;

$R^2$ is H or substituted or unsubstituted $C_{1-3}$ alkyl; and $R^3$ is phenyl, substituted with one or more halogen, optionally further substituted with one or more substituents independently selected from substituted or unsubstituted $C_{1-3}$ alkyl, CN, and —OR', wherein each R' is independently substituted or unsubstituted $C_{1-3}$ alkyl;

wherein when a $C_{1-3}$ alkyl group is substituted, the $C_{1-3}$ alkyl group is substituted with halogen, alkyl, hydroxyl, alkoxy, alkoxyalkyl, amino, alkylamino, carboxy, nitro, cyano, thiol, thioether, imine, imide, amidine, guanidine, enamine, aminocarbonyl, acylamino, phosphonate, phosphine, thiocarbonyl, sulfinyl, sulfone, sulfonamide, ketone, aldehyde, ester, urea, urethane, oxime, hydroxyl amine, alkoxyamine, aryloxyamine, aralkoxyamine, N-oxide, hydrazine, hydrazide, hydrazone, azide, isocyanate, isothiocyanate, cyanate, thiocyanate, $B(OH)_2$, or O(alkyl)aminocarbonyl;

wherein when a group, other than a $C_{1-3}$ alkyl group, is substituted, the group is substituted with halogen, alkyl, hydroxyl, alkoxy, alkoxyalkyl, amino, alkylamino, carboxy, nitro, cyano, thiol, thioether, imine, imide, amidine, guanidine, enamine, aminocarbonyl, acylamino, phosphonate, phosphine, thiocarbonyl, sulfinyl, sulfone, sulfonamide, ketone, aldehyde, ester, urea, urethane, oxime, hydroxyl amine, alkoxyamine, aryloxyamine, aralkoxyamine, N-oxide, hydrazine, hydrazide, hydrazone, azide, isocyanate, isothiocyanate, cyanate, thiocyanate, oxygen (=O), $B(OH)_2$, O(alkyl)aminocarbonyl, cycloalkyl, heterocyclyl, aryl, heteroaryl, aryloxy, aralkyloxy, heterocyclyloxy, or heterocyclyl alkoxy; and wherein the cancer is colorectal cancer, colon cancer, renal cell carcinoma, gastric cancer, stomach cancer, hepatocellular carcinoma, liver cancer, lung cancer, pancreatic cancer, leukemia, or multiple myeloma.

2. A method for treating a cancer, the method comprising administering to a subject having the cancer an effective amount of an Aminopurine Compound, wherein the cancer is colorectal cancer, colon cancer, renal cell carcinoma, gastric cancer, stomach cancer, hepatocellular carcinoma, liver cancer, lung cancer, pancreatic cancer, leukemia, or multiple myeloma; and wherein the Aminopurine compound is (1s,4s)-4-(2-((3S,4R)-3-fluorotetrahydro-2H-pyran-4-ylamino)-8-(2,4,6-trichlorophenylamino)-9H-purin-9-yl)-1-methylcyclohexanecarboxamide;

(1s,4s)-4-(8-(3-chlorophenylamino)-2-(isopropylamino)-9H-purin-9-yl)cyclohexanecarboxamide;

(1s,4s)-4-(8-(3-chlorophenylamino)-2-(cyclopentylamino)-9H-purin-9-yl)cyclohexanecarboxamide;

(1s,4s)-4-(2-(cyclopentylamino)-8-(2,4-difluorophenylamino)-9H-purin-9-yl)cyclohexanecarboxamide;

(1s,4s)-4-(8-(3-chlorophenylamino)-2-(4-methyltetrahydro-2H-pyran-4-ylamino)-9H-purin-9-yl)cyclohexanecarboxamide;

(1s,4s)-4-(8-(2,4-difluorophenylamino)-2-(3-methyltetrahydro-2H-pyran-4-ylamino)-9H-purin-9-yl)cyclohexanecarboxamide;

(1s,4s)-4-(8-(2,4-difluorophenylamino)-2-(1-methylcyclobutylamino)-9H-purin-9-yl)cyclohexanecarboxamide;

(1s,4s)-4-(2-(tert-butylamino)-8-(2,4,6-trifluorophenylamino)-9H-purin-9-yl)cyclohexanecarboxamide;
(1s,4s)-4-(8-(2,4-difluorophenylamino)-2-((3R,4R)-3-methyltetrahydro-2H-pyran-4-ylamino)-9H-purin-9-yl)cyclohexanecarboxamide;
(1s,4s)-4-(2-(4-methyltetrahydro-2H-pyran-4-ylamino)-8-(2,4,6-trifluorophenylamino)-9H-purin-9-yl)cyclohexanecarboxamide;
(1s,4s)-4-(8-(3-chloro-2-fluorophenylamino)-2-(4-methyltetrahydro-2H-pyran-4-ylamino)-9H-purin-9-yl)cyclohexanecarboxamide;
(1s,4s)-4-(2-(tetrahydro-2H-pyran-4-ylamino)-8-(2,4,6-trifluorophenylamino)-9H-purin-9-yl)cyclohexanecarboxamide;
(1s,4s)-4-(8-(2,6-difluorophenylamino)-2-(tetrahydro-2H-pyran-4-ylamino)-9H-purin-9-yl)cyclohexanecarboxamide;
(1s,4s)-4-(8-(2-fluorophenylamino)-2-(tetrahydro-2H-pyran-4-ylamino)-9H-purin-9-yl)cyclohexanecarboxamide;
(1s,4s)-4-(2-((3R,4R)-3-methyltetrahydro-2H-pyran-4-ylamino)-8-(2,4,6-trifluorophenylamino)-9H-purin-9-yl)cyclohexanecarboxamide;
(1s,4s)-4-(8-(2,6-difluorophenylamino)-2-((3R,4R)-3-methyltetrahydro-2H-pyran-4-ylamino)-9H-purin-9-yl)cyclohexanecarboxamide;
(1s,4s)-4-(8-(2-chloro-6-methylphenylamino)-2-(tetrahydro-2H-pyran-4-ylamino)-9H-purin-9-yl)cyclohexanecarboxamide;
(1s,4s)-4-(8-(2,6-dichlorophenylamino)-2-(tetrahydro-2H-pyran-4-ylamino)-9H-purin-9-yl)cyclohexanecarboxamide;
(1s,4s)-4-(8-(3-chlorophenylamino)-2-(tetrahydro-2H-pyran-4-ylamino)-9H-purin-9-yl)cyclohexanecarboxamide;
(1s,4s)-4-(8-(2,4-difluorophenylamino)-2-(tetrahydro-2H-pyran-4-ylamino)-9H-purin-9-yl)cyclohexanecarboxamide;
(1s,4s)-4-(8-(3,4-dichlorophenylamino)-2-(tetrahydro-2H-pyran-4-ylamino)-9H-purin-9-yl)cyclohexanecarboxamide;
(1s,4s)-4-(8-(5-chloro-2-fluorophenylamino)-2-(tetrahydro-2H-pyran-4-ylamino)-9H-purin-9-yl)cyclohexanecarboxamide;
(1s,4s)-4-(8-(3-chloro-2-fluorophenylamino)-2-(tetrahydro-2H-pyran-4-ylamino)-9H-purin-9-yl)cyclohexanecarboxamide;
(1s,4s)-4-(8-(2,5-difluorophenylamino)-2-(tetrahydro-2H-pyran-4-ylamino)-9H-purin-9-yl)cyclohexanecarboxamide;
(1s,4s)-4-(8-(3-chloro-2-methylphenylamino)-2-(tetrahydro-2H-pyran-4-ylamino)-9H-purin-9-yl)cyclohexanecarboxamide;
(1s,4s)-4-(2-(tetrahydro-2H-pyran-4-ylamino)-8-(2,4,6-trichlorophenylamino)-9H-purin-9-yl)cyclohexanecarboxamide;
(1s,4s)-4-(8-(2,3-difluorophenylamino)-2-(tetrahydro-2H-pyran-4-ylamino)-9H-purin-9-yl)cyclohexanecarboxamide;
(1s,4s)-4-(8-(2,4-dichlorophenylamino)-2-(tetrahydro-2H-pyran-4-ylamino)-9H-purin-9-yl)cyclohexanecarboxamide;
(1s,4s)-4-(8-(2-chloro-5-fluorophenylamino)-2-(tetrahydro-2H-pyran-4-ylamino)-9H-purin-9-yl)cyclohexanecarboxamide;
(1s,4s)-4-(8-(2-chloro-4-fluorophenylamino)-2-(tetrahydro-2H-pyran-4-ylamino)-9H-purin-9-yl)cyclohexanecarboxamide;
(1s,4s)-4-(8-(2-chloro-4-methylphenylamino)-2-(tetrahydro-2H-pyran-4-ylamino)-9H-purin-9-yl)cyclohexanecarboxamide;
(1s,4s)-4-(8-(3-fluoro-2-methylphenylamino)-2-(tetrahydro-2H-pyran-4-ylamino)-9H-purin-9-yl)cyclohexanecarboxamide;
(1s,4s)-4-(8-(4-bromo-2-fluorophenylamino)-2-(tetrahydro-2H-pyran-4-ylamino)-9H-purin-9-yl)cyclohexanecarboxamide;
(1s,4s)-4-(8-(2-fluoro-4-methylphenylamino)-2-(tetrahydro-2H-pyran-4-ylamino)-9H-purin-9-yl)cyclohexanecarboxamide;
(1s,4s)-4-(8-(2-chloro-4-(trifluoromethyl)phenylamino)-2-(tetrahydro-2H-pyran-4-ylamino)-9H-purin-9-yl)cyclohexanecarboxamide;
(1s,4s)-4-(8-(2,6-difluorophenylamino)-2-(tetrahydro-2H-pyran-4-ylamino)-9H-purin-9-yl)-1-methylcyclohexanecarboxamide;
(1s,4s)-4-(8-(2-chloro-6-fluorophenylamino)-2-(tetrahydro-2H-pyran-4-ylamino)-9H-purin-9-yl)cyclohexanecarboxamide;
(1s,4s)-4-(8-(4-fluoro-2-methylphenylamino)-2-(tetrahydro-2H-pyran-4-ylamino)-9H-purin-9-yl)cyclohexanecarboxamide;
(1s,4s)-4-(2-(tetrahydro-2H-pyran-4-ylamino)-8-(2,3,6-trifluorophenylamino)-9H-purin-9-yl)cyclohexanecarboxamide;
(1s,4s)-1-methyl-4-(2-(tetrahydro-2H-pyran-4-ylamino)-8-(2,4,6-trifluorophenylamino)-9H-purin-9-yl)cyclohexanecarboxamide;
(1s,4s)-4-(8-(2,4-dichloro-6-fluorophenylamino)-2-(tetrahydro-2H-pyran-4-ylamino)-9H-purin-9-yl)cyclohexanecarboxamide;
(1s,4s)-4-(2-(cyclobutylamino)-8-(2,4,6-trifluorophenylamino)-9H-purin-9-yl)cyclohexanecarboxamide;
(1s,4s)-4-(2-(cyclobutylamino)-8-(2,6-difluorophenylamino)-9H-purin-9-yl)cyclohexanecarboxamide;
(1s,4s)-4-(8-(2-chloro-6-fluorophenylamino)-2-(cyclobutylamino)-9H-purin-9-yl)cyclohexanecarboxamide;
(1s,4s)-4-(2-(cyclopentylamino)-8-(2,4,6-trifluorophenylamino)-9H-purin-9-yl)cyclohexanecarboxamide;
(1s,4s)-4-(2-(cyclopentylamino)-8-(2,6-difluorophenylamino)-9H-purin-9-yl)cyclohexanecarboxamide;
(1s,4s)-4-(8-(2-chloro-6-fluorophenylamino)-2-(cyclopentylamino)-9H-purin-9-yl)cyclohexanecarboxamide;
(1s,4s)-4-(8-(2,6-difluorophenylamino)-2-(isopropylamino)-9H-purin-9-yl)cyclohexanecarboxamide;
(1s,4s)-4-(8-(2-chloro-6-fluorophenylamino)-2-(isopropylamino)-9H-purin-9-yl)cyclohexanecarboxamide;
(1s,4s)-4-(8-(4-chloro-2,6-difluorophenylamino)-2-(tetrahydro-2H-pyran-4-ylamino)-9H-purin-9-yl)cyclohexanecarboxamide;
(1s,4s)-4-(8-(2,6-dichloro-4-fluorophenylamino)-2-(tetrahydro-2H-pyran-4-ylamino)-9H-purin-9-yl)cyclohexanecarboxamide;
(1s,4s)-4-(2-(cyclobutylamino)-8-(2,6-dichlorophenylamino)-9H-purin-9-yl)cyclohexanecarboxamide;
(1s,4s)-4-(8-(2,6-dichlorophenylamino)-2-(isopropylamino)-9H-purin-9-yl)cyclohexanecarboxamide;
(1s,4s)-4-(8-(2-chloro-4,6-difluorophenylamino)-2-(tetrahydro-2H-pyran-4-ylamino)-9H-purin-9-yl)cyclohexanecarboxamide;

(1s,4s)-4-(2-(cyclopentylamino)-8-(2,6-dichlorophe-nylamino)-9H-purin-9-yl)cyclohexanecarboxamide;
(1s,4s)-4-(2-(oxetan-3-ylamino)-8-(2,4,6-trifluorophe-nylamino)-9H-purin-9-yl)cyclohexanecarboxamide;
(1s,4s)-4-(8-(2,6-dichlorophenylamino)-2-(oxetan-3-ylamino)-9H-purin-9-yl)cyclohexanecarboxamide;
(1s,4s)-4-(8-(2-chloro-6-fluorophenylamino)-2-(oxetan-3-ylamino)-9H-purin-9-yl)cyclohexanecarboxamide;
(1s,4s)-4-(2-(tetrahydro-2H-pyran-4-ylamino)-8-(2,4,5-trifluorophenylamino)-9H-purin-9-yl)cyclohexanecarboxamide;
(1s,4s)-4-(2-(isopropylamino)-8-(2,4,6-trichlorophe-nylamino)-9H-purin-9-yl)cyclohexanecarboxamide;
(1s,4s)-4-(8-(4-chloro-2-fluorophenylamino)-2-(tetra-hydro-2H-pyran-4-ylamino)-9H-purin-9-yl)cyclo-hexanecarboxamide;
(1s,4s)-4-(8-(2-chloro-3-fluorophenylamino)-2-(tetra-hydro-2H-pyran-4-ylamino)-9H-purin-9-yl)cyclo-hexanecarboxamide;
(1s,4s)-4-(8-(2,3-dichlorophenylamino)-2-(tetrahydro-2H-pyran-4-ylamino)-9H-purin-9-yl)cyclohexanecar-boxamide;
(1s,4s)-4-(8-(2-fluoro-6-methylphenylamino)-2-(tetra-hydro-2H-pyran-4-ylamino)-9H-purin-9-yl)cyclo-hexanecarboxamide;
(1s,4s)-4-(8-(5-chloro-2,4-difluorophenylamino)-2-(tet-rahydro-2H-pyran-4-ylamino)-9H-purin-9-yl)cyclo-hexanecarboxamide;
(1s,4s)-4-(2-(tetrahydro-2H-pyran-4-ylamino)-8-(2,4,5-trichlorophenylamino)-9H-purin-9-yl)cyclohexanecar-boxamide;
(1s,4s)-4-(2-(tetrahydro-2H-pyran-4-ylamino)-8-(2,3,4-trifluorophenylamino)-9H-purin-9-yl)cyclohexanecar-boxamide;
(1s,4s)-4-(8-(3-chloro-2,6-difluorophenylamino)-2-(tet-rahydro-2H-pyran-4-ylamino)-9H-purin-9-yl)cyclo-hexanecarboxamide;
(1s,4s)-4-(2-(cyclopentylamino)-8-(2,4,6-trichlorophe-nylamino)-9H-purin-9-yl)cyclohexanecarboxamide;
(1s,4s)-4-(8-(2-chloro-3-methylphenylamino)-2-(tetra-hydro-2H-pyran-4-ylamino)-9H-purin-9-yl)cyclo-hexanecarboxamide;
(1s,4s)-4-(8-(4-chloro-2,5-difluorophenylamino)-2-(tet-rahydro-2H-pyran-4-ylamino)-9H-purin-9-yl)cyclo-hexanecarboxamide;
(1s,4s)-4-(8-(4-chloro-2-fluoro-5-methylphenylamino)-2-(tetrahydro-2H-pyran-4-ylamino)-9H-purin-9-yl)cy-clohexanecarboxamide;
(1s,4s)-4-(8-(4-chloro-2,3-difluorophenylamino)-2-(tet-rahydro-2H-pyran-4-ylamino)-9H-purin-9-yl)cyclo-hexanecarboxamide;
(1s,4s)-4-(2-(tetrahydro-2H-pyran-4-ylamino)-8-(2,3,4-trichlorophenylamino)-9H-purin-9-yl)cyclohexanecar-boxamide;
(1s,4s)-4-(8-(2-chloro-4-fluoro-6-methylphenylamino)-2-(tetrahydro-2H-pyran-4-ylamino)-9H-purin-9-yl)cy-clohexanecarboxamide;
(1s,4s)-4-(8-(4-chloro-2-fluoro-6-methylphenylamino)-2-(tetrahydro-2H-pyran-4-ylamino)-9H-purin-9-yl)cy-clohexanecarboxamide;
(1s,4s)-4-(2-((R)-tetrahydrofuran-3-ylamino)-8-(2,4,6-trichlorophenylamino)-9H-purin-9-yl)cyclohexanecar-boxamide;
(1s,4s)-4-(2-((1r,4r)-4-methoxycyclohexylamino)-8-(2,4,6-trichlorophenylamino)-9H-purin-9-yl)cyclohexan-ecarboxamide;

(1s,4s)-4-(2-((1r,4r)-4-hydroxycyclohexylamino)-8-(2,4,6-trichlorophenylamino)-9H-purin-9-yl)cyclohexan-ecarboxamide;
(1s,4s)-4-(8-(3-chloro-6-fluoro-2-methylphenylamino)-2-(tetrahydro-2H-pyran-4-ylamino)-9H-purin-9-yl)cy-clohexanecarboxamide;
(1s,4s)-4-(8-(2,5-dichloro-4-methylphenylamino)-2-(tet-rahydro-2H-pyran-4-ylamino)-9H-purin-9-yl)cyclo-hexanecarboxamide;
(1s,4s)-4-(8-(2,3-dichloro-4-fluorophenylamino)-2-(tet-rahydro-2H-pyran-4-ylamino)-9H-purin-9-yl)cyclo-hexanecarboxamide;
(1s,4s)-4-(8-(2,4-dichloro-3-fluorophenylamino)-2-(tet-rahydro-2H-pyran-4-ylamino)-9H-purin-9-yl)cyclo-hexanecarboxamide;
(1s,4s)-4-(8-(2,3-difluoro-4-methylphenylamino)-2-(tet-rahydro-2H-pyran-4-ylamino)-9H-purin-9-yl)cyclo-hexanecarboxamide;
(1s,4s)-4-(8-(2-chloro-3-fluoro-4-methylphenylamino)-2-(tetrahydro-2H-pyran-4-ylamino)-9H-purin-9-yl)cy-clohexanecarboxamide;
(1s,4s)-4-(8-(2,3-dichloro-4-methylphenylamino)-2-(tet-rahydro-2H-pyran-4-ylamino)-9H-purin-9-yl)cyclo-hexanecarboxamide;
(1s,4s)-4-(8-(2,4-difluoro-6-methylphenylamino)-2-(tet-rahydro-2H-pyran-4-ylamino)-9H-purin-9-yl)cyclo-hexanecarboxamide;
(1r,4s)-4-(2-((S)-tetrahydrofuran-3-ylamino)-8-(2,4,6-trichlorophenylamino)-9H-purin-9-yl)cyclohexanecar-boxamide;
(1s,4s)-4-(2-(4,4-difluorocyclohexylamino)-8-(2,4,6-trichlorophenylamino)-9H-purin-9-yl)cyclohexanecar-boxamide;
(1s,4s)-4-(8-(4-chloro-3-fluoro-2-methylphenylamino)-2-(tetrahydro-2H-pyran-4-ylamino)-9H-purin-9-yl)cy-clohexanecarboxamide;
(1s,4s)-4-(8-(2-chloro-3,6-difluorophenylamino)-2-(tet-rahydro-2H-pyran-4-ylamino)-9H-purin-9-yl)cyclo-hexanecarboxamide;
(1s,4s)-4-(8-(2-chloro-6-fluoro-3-methylphenylamino)-2-(tetrahydro-2H-pyran-4-ylamino)-9H-purin-9-yl)cy-clohexanecarboxamide;
(1s,4s)-4-(2-((1,1-dioxidotetrahydro-2H-thiopyran-4-yl)amino)-8-((2,4,6-trichlorophenyl)amino)-9H-purin-9-yl)cyclohexane-1-carboxamide;
(1s,4s)-4-(8-(2-chlorophenylamino)-2-(cyclopenty-lamino)-9H-purin-9-yl)cyclohexanecarboxamide;
(1s,4s)-4-(2-(cyclopentylamino)-8-(2,4-dichlorophe-nylamino)-9H-purin-9-yl)cyclohexanecarboxamide;
(1s,4s)-4-(8-(4-chloro-2-fluorophenylamino)-2-(cyclo-pentylamino)-9H-purin-9-yl)cyclohexanecarboxam-ide;
(1s,4s)-4-(8-(2,4-dichlorophenylamino)-2-(isopropy-lamino)-9H-purin-9-yl)cyclohexanecarboxamide;
(1s,4s)-4-(8-(2-chloro-4-fluorophenylamino)-2-(isopro-pylamino)-9H-purin-9-yl)cyclohexanecarboxamide;
(1s,4s)-4-(8-(2,4-dichloro-6-fluorophenylamino)-2-(iso-propylamino)-9H-purin-9-yl)cyclohexanecarboxam-ide;
(1s,4s)-4-(8-(2-chloro-4,5-difluorophenylamino)-2-(tet-rahydro-2H-pyran-4-ylamino)-9H-purin-9-yl)cyclo-hexanecarboxamide;
(1s,4s)-4-(8-(2-chloro-4,5-dimethylphenylamino)-2-(tet-rahydro-2H-pyran-4-ylamino)-9H-purin-9-yl)cyclo-hexanecarboxamide;

(1s,4s)-4-(8-(4-chloro-2-fluoro-3-methylphenylamino)-2-(tetrahydro-2H-pyran-4-ylamino)-9H-purin-9-yl)cyclohexanecarboxamide;
(1s,4s)-4-(8-(2,4-dichloro-6-methylphenylamino)-2-(tetrahydro-2H-pyran-4-ylamino)-9H-purin-9-yl)cyclohexanecarboxamide;
(1s,4s)-4-(8-(2,3-dichloro-6-fluorophenylamino)-2-(tetrahydro-2H-pyran-4-ylamino)-9H-purin-9-yl)cyclohexanecarboxamide;
(1s,4s)-4-(8-(2,4-dichloro-5-fluorophenylamino)-2-(tetrahydro-2H-pyran-4-ylamino)-9H-purin-9-yl)cyclohexanecarboxamide;
(1s,4s)-4-(8-(2,5-difluoro-4-methylphenylamino)-2-(tetrahydro-2H-pyran-4-ylamino)-9H-purin-9-yl)cyclohexanecarboxamide;
(1s,4s)-4-(8-(2-chloro-6-fluorophenylamino)-2-(1-(pyridin-3-yl)piperidin-4-ylamino)-9H-purin-9-yl)cyclohexanecarboxamide;
(1s,4s)-4-(8-(2-chloro-6-fluorophenylamino)-2-(1-phenylpiperidin-4-ylamino)-9H-purin-9-yl)cyclohexanecarboxamide;
(1s,4s)-4-(8-(2,4,6-trichlorophenylamino)-2-(2,2,2-trifluoroethylamino)-9H-purin-9-yl)cyclohexanecarboxamide;
(1s,4s)-4-(2-(cyclobutylmethylamino)-8-(2,4,6-trichlorophenylamino)-9H-purin-9-yl)cyclohexanecarboxamide;
(1s,4s)-4-(2-((R)-tetrahydro-2H-pyran-3-ylamino)-8-(2,4,6-trichlorophenylamino)-9H-purin-9-yl)cyclohexanecarboxamide;
(1s,4s)-4-(8-(3,4-dichloro-2-fluorophenylamino)-2-(tetrahydro-2H-pyran-4-ylamino)-9H-purin-9-yl)cyclohexanecarboxamide;
(1s,4s)-4-(8-(6-chloro-2,3-difluorophenylamino)-2-(tetrahydro-2H-pyran-4-ylamino)-9H-purin-9-yl)cyclohexanecarboxamide;
(1s,4s)-4-(8-(2-chloro-6-fluorophenylamino)-2-(1-(methylsulfonyl)piperidin-4-ylamino)-9H-purin-9-yl)cyclohexanecarboxamide;
(1s,4s)-4-(8-(2,6-difluoro-4-methylphenylamino)-2-(tetrahydro-2H-pyran-4-ylamino)-9H-purin-9-yl)cyclohexanecarboxamide;
(1s,4s)-4-(8-(2,6-dichloro-4-methylphenylamino)-2-(tetrahydro-2H-pyran-4-ylamino)-9H-purin-9-yl)cyclohexanecarboxamide;
(1s,4s)-4-(8-(2-chloro-4,6-difluorophenylamino)-2-(cyclobutylamino)-9H-purin-9-yl)cyclohexanecarboxamide;
(1s,4s)-4-(2-(cyclobutylamino)-8-(2,6-dichloro-4-fluorophenylamino)-9H-purin-9-yl)cyclohexanecarboxamide;
(1s,4s)-4-(8-(2-chloro-4,6-difluorophenylamino)-2-(cyclopentylamino)-9H-purin-9-yl)cyclohexanecarboxamide;
(1s,4s)-4-(8-(4-chloro-2,6-difluorophenylamino)-2-(cyclopentylamino)-9H-purin-9-yl)cyclohexanecarboxamide;
(1s,4s)-4-(2-(cyclopentylamino)-8-(2,6-dichloro-4-fluorophenylamino)-9H-purin-9-yl)cyclohexanecarboxamide;
(1s,4s)-4-(2-(cyclopentylamino)-8-(2,4-dichloro-6-fluorophenylamino)-9H-purin-9-yl)cyclohexanecarboxamide;
(1s,4s)-4-(8-(2,6-dichloro-4-fluorophenylamino)-2-(isopropylamino)-9H-purin-9-yl)cyclohexanecarboxamide;
(1s,4s)-4-(8-(4-chloro-2,6-difluorophenylamino)-2-(isopropylamino)-9H-purin-9-yl)cyclohexanecarboxamide;
(1s,4s)-4-(8-(2-chloro-4,6-difluorophenylamino)-2-(isopropylamino)-9H-purin-9-yl)cyclohexanecarboxamide;
(1s,4s)-4-(8-(2,6-dichloro-4-fluorophenylamino)-2-((R)-1-hydroxybutan-2-ylamino)-9H-purin-9-yl)cyclohexanecarboxamide;
(3R,4S)-tert-butyl 4-(9-((1s,4r)-4-carbamoylcyclohexyl)-8-(2,4,6-trifluorophenylamino)-9H-purin-2-ylamino)-3-fluoropiperidine-1-carboxylate;
(3R,4S)-tert-butyl 4-(9-((1s,4r)-4-carbamoylcyclohexyl)-8-(2,6-difluorophenylamino)-9H-purin-2-ylamino)-3-fluoropiperidine-1-carboxylate;
(1s,4s)-4-(8-(4-chloro-2,6-difluorophenylamino)-2-(cyclobutylamino)-9H-purin-9-yl)cyclohexanecarboxamide;
(1s,4s)-4-(2-(cyclobutylamino)-8-(2,4-dichloro-6-fluorophenylamino)-9H-purin-9-yl)cyclohexanecarboxamide;
(1s,4s)-4-(8-(2,6-dichloro-4-fluorophenylamino)-2-((R)-1-hydroxypropan-2-ylamino)-9H-purin-9-yl)cyclohexanecarboxamide;
(1s,4s)-4-(8-(4-chloro-2,6-difluorophenylamino)-2-((R)-1-hydroxypropan-2-ylamino)-9H-purin-9-yl)cyclohexanecarboxamide;
(1s,4s)-4-(8-(2,4-dichloro-6-fluorophenylamino)-2-((R)-1-hydroxypropan-2-ylamino)-9H-purin-9-yl)cyclohexanecarboxamide;
(1s,4s)-4-(8-(2-chloro-4,6-difluorophenylamino)-2-((R)-1-hydroxypropan-2-ylamino)-9H-purin-9-yl)cyclohexanecarboxamide;
(1r,4s)-4-(8-(2,4-dichloro-6-fluorophenylamino)-2-((S)-1-hydroxypropan-2-ylamino)-9H-purin-9-yl)cyclohexanecarboxamide;
(1r,4s)-4-(8-(2-chloro-4,6-difluorophenylamino)-2-((S)-1-hydroxypropan-2-ylamino)-9H-purin-9-yl)cyclohexanecarboxamide;
(1s,4s)-4-(2-((R)-1-hydroxybutan-2-ylamino)-8-(2,4,6-trichlorophenylamino)-9H-purin-9-yl)cyclohexanecarboxamide;
(1r,4s)-4-(2-((3R,4S)-3-fluoropiperidin-4-ylamino)-8-(2,4,6-trichlorophenylamino)-9H-purin-9-yl)cyclohexanecarboxamide;
(1s,4s)-4-(2-(cyclopentylamino)-8-(2,3-difluorophenylamino)-9H-purin-9-yl)cyclohexanecarboxamide;
(1s,4s)-4-(8-(3-chloro-2-fluorophenylamino)-2-(cyclopentylamino)-9H-purin-9-yl)cyclohexanecarboxamide;
(1s,4s)-4-(2-(cyclopentylamino)-8-(2,3,6-trifluorophenylamino)-9H-purin-9-yl)cyclohexanecarboxamide;
(1r,4s)-4-(2-((S)-1-methoxypropan-2-ylamino)-8-(2,4,6-trichlorophenylamino)-9H-purin-9-yl)cyclohexanecarboxamide;
(1r,4s)-4-(2-((S)-1-hydroxybutan-2-ylamino)-8-(2,4,6-trifluorophenylamino)-9H-purin-9-yl)cyclohexanecarboxamide;
(1r,4s)-4-(8-(2-chloro-6-fluorophenylamino)-2-((S)-1-hydroxybutan-2-ylamino)-9H-purin-9-yl)cyclohexanecarboxamide;
(1r,4s)-4-(8-(2,6-dichloro-4-fluorophenylamino)-2-((S)-1-hydroxybutan-2-ylamino)-9H-purin-9-yl)cyclohexanecarboxamide;
(1r,4s)-4-(8-(4-chloro-2,6-difluorophenylamino)-2-((S)-1-hydroxybutan-2-ylamino)-9H-purin-9-yl)cyclohexanecarboxamide;

(1r,4s)-4-(8-(2-chloro-4,6-difluorophenylamino)-2-((S)-1-hydroxybutan-2-ylamino)-9H-purin-9-yl)cyclohexanecarboxamide;

(1r,4s)-4-(2-((S)-1-hydroxybutan-2-ylamino)-8-(2,3,6-trifluorophenylamino)-9H-purin-9-yl)cyclohexanecarboxamide;

(1r,4s)-4-(8-(2,4-dichlorophenylamino)-2-((S)-1-hydroxybutan-2-ylamino)-9H-purin-9-yl)cyclohexanecarboxamide;

(1r,4s)-4-(8-(3-chloro-2-fluorophenylamino)-2-((S)-1-hydroxybutan-2-ylamino)-9H-purin-9-yl)cyclohexanecarboxamide;

(1r,4s)-4-(2-((S)-1-hydroxybutan-2-ylamino)-8-(2,3,4-trifluorophenylamino)-9H-purin-9-yl)cyclohexanecarboxamide;

(1s,4s)-4-(2-((R)-2-hydroxypropylamino)-8-(2,4,6-trichlorophenylamino)-9H-purin-9-yl)cyclohexanecarboxamide;

(1r,4s)-4-(8-(2,6-dichlorophenylamino)-2-((S)-1-hydroxybutan-2-ylamino)-9H-purin-9-yl)cyclohexanecarboxamide;

(1r,4s)-4-(2-((S)-1-hydroxybutan-2-ylamino)-8-(2,4,6-trichlorophenylamino)-9H-purin-9-yl)cyclohexanecarboxamide;

(3R,4S)-tert-butyl 4-(9-((1s,4r)-4-carbamoylcyclohexyl)-8-(4-chloro-2,6-difluorophenylamino)-9H-purin-2-ylamino)-3-fluoropiperidine-1-carboxylate;

(1s,4s)-4-(8-((4-chloro-2,6-difluorophenyl)amino)-2-((1,1-dioxidotetrahydro-2H-thiopyran-4-yl)amino)-9H-purin-9-yl)cyclohexane-1-carboxamide;

(1s,4s)-4-(8-(2,4-dichloro-6-fluorophenyl)amino)-2-((1,1-dioxidotetrahydro-2H-thiopyran-4-yl)amino)-9H-purin-9-yl)cyclohexane-1-carboxamide;

(R)-tert-butyl 3-(9-((1s,4s)-4-carbamoylcyclohexyl)-8-(2,4,6-trifluorophenylamino)-9H-purin-2-ylamino)piperidine-1-carboxylate;

(R)-tert-butyl 3-(9-((1s,4s)-4-carbamoylcyclohexyl)-8-(2,6-difluorophenylamino)-9H-purin-2-ylamino)piperidine-1-carboxylate;

(R)-tert-butyl 3-(9-((1s,4s)-4-carbamoylcyclohexyl)-8-(2,6-dichlorophenylamino)-9H-purin-2-ylamino)piperidine-1-carboxylate;

(R)-tert-butyl 3-(9-((1s,4s)-4-carbamoylcyclohexyl)-8-(2-chloro-4,6-difluorophenylamino)-9H-purin-2-ylamino)piperidine-1-carboxylate;

(R)-tert-butyl 3-(9-((1s,4s)-4-carbamoylcyclohexyl)-8-(4-chloro-2,6-difluorophenylamino)-9H-purin-2-ylamino)piperidine-1-carboxylate;

(R)-tert-butyl 3-(9-((1s,4s)-4-carbamoylcyclohexyl)-8-(2,4,6-trichlorophenylamino)-9H-purin-2-ylamino)piperidine-1-carboxylate;

(1r,4s)-4-(2-((S)-1-hydroxypropan-2-ylamino)-8-(2,4,6-trifluorophenylamino)-9H-purin-9-yl)cyclohexanecarboxamide;

(1r,4s)-4-(2-((S)-1-hydroxypropan-2-ylamino)-8-(2,4,6-trichlorophenylamino)-9H-purin-9-yl)cyclohexanecarboxamide;

(1r,4s)-4-(8-(2,6-dichloro-4-fluorophenylamino)-2-((S)-1-hydroxypropan-2-ylamino)-9H-purin-9-yl)cyclohexanecarboxamide;

(1r,4s)-4-(8-(2,6-difluorophenylamino)-2-((S)-1-hydroxypropan-2-ylamino)-9H-purin-9-yl)cyclohexanecarboxamide;

(1r,4s)-4-(8-(2,6-dichlorophenylamino)-2-((S)-1-hydroxypropan-2-ylamino)-9H-purin-9-yl)cyclohexanecarboxamide;

(1r,4s)-4-(8-(4-chloro-2,6-difluorophenylamino)-2-((S)-1-hydroxypropan-2-ylamino)-9H-purin-9-yl)cyclohexanecarboxamide;

(1r,4s)-4-(8-(2,4-dichlorophenylamino)-2-((S)-1-hydroxypropan-2-ylamino)-9H-purin-9-yl)cyclohexanecarboxamide;

(1r,4s)-4-(8-(5-chloro-2-fluorophenylamino)-2-((S)-1-hydroxypropan-2-ylamino)-9H-purin-9-yl)cyclohexanecarboxamide;

(1r,4s)-4-(8-(3-chloro-2-fluorophenylamino)-2-((S)-1-hydroxypropan-2-ylamino)-9H-purin-9-yl)cyclohexanecarboxamide;

(1s,4s)-4-(2-(2-oxaspiro[3.3]heptan-6-ylamino)-8-(2,6-difluorophenylamino)-9H-purin-9-yl)cyclohexanecarboxamide;

(1s,4s)-4-(2-(2-oxaspiro[3.3]heptan-6-ylamino)-8-(2,6-dichlorophenylamino)-9H-purin-9-yl)cyclohexanecarboxamide;

(1s,4s)-4-(2-(2-oxaspiro[3.3]heptan-6-ylamino)-8-(2-chloro-4,6-difluorophenylamino)-9H-purin-9-yl)cyclohexanecarboxamide;

(1s,4s)-4-(2-(2-oxaspiro[3.3]heptan-6-ylamino)-8-(4-chloro-2,6-difluorophenylamino)-9H-purin-9-yl)cyclohexanecarboxamide;

(1s,4s)-4-(2-(2-oxaspiro[3.3]heptan-6-ylamino)-8-(2,4,6-trichlorophenylamino)-9H-purin-9-yl)cyclohexanecarboxamide;

(1s,4s)-4-(2-(4-hydroxytetrahydrofuran-3-ylamino)-8-(2,4,6-trifluorophenylamino)-9H-purin-9-yl)cyclohexanecarboxamide;

(1s,4s)-4-(8-(2-chloro-4,6-difluorophenylamino)-2-(4-hydroxytetrahydrofuran-3-ylamino)-9H-purin-9-yl)cyclohexanecarboxamide;

(1s,4s)-4-(8-(2,6-dichlorophenylamino)-2-(4-hydroxytetrahydrofuran-3-ylamino)-9H-purin-9-yl)cyclohexanecarboxamide;

(1s,4s)-4-(2-(4-hydroxytetrahydrofuran-3-ylamino)-8-(2,4,6-trichlorophenylamino)-9H-purin-9-yl)cyclohexanecarboxamide;

(1s,4s)-4-(8-(2,4-dichloro-6-fluorophenylamino)-2-(4-hydroxytetrahydrofuran-3-ylamino)-9H-purin-9-yl)cyclohexanecarboxamide;

(1s,4s)-4-(8-(2,6-dichloro-4-fluorophenylamino)-2-(4-hydroxytetrahydrofuran-3-ylamino)-9H-purin-9-yl)cyclohexanecarboxamide;

(1s,4s)-4-(8-(4-chloro-2,6-difluorophenylamino)-2-(4-hydroxytetrahydrofuran-3-ylamino)-9H-purin-9-yl)cyclohexanecarboxamide;

(1s,4s)-4-(8-(2-chloro-4,6-difluorophenylamino)-2-(4,4-difluorocyclohexylamino)-9H-purin-9-yl)cyclohexanecarboxamide;

(1s,4s)-4-(8-(2,4-dichloro-6-fluorophenylamino)-2-(4,4-difluorocyclohexylamino)-9H-purin-9-yl)cyclohexanecarboxamide;

(1s,4s)-4-(8-(2-chloro-4,6-difluorophenylamino)-2-((R)-tetrahydro-2H-pyran-3-ylamino)-9H-purin-9-yl)cyclohexanecarboxamide;

(1s,4s)-4-(8-(4-chloro-2,6-difluorophenylamino)-2-((R)-tetrahydro-2H-pyran-3-ylamino)-9H-purin-9-yl)cyclohexanecarboxamide;

(1s,4s)-4-(8-(2,6-dichloro-4-fluorophenylamino)-2-((R)-tetrahydro-2H-pyran-3-ylamino)-9H-purin-9-yl)cyclohexanecarboxamide;

(1s,4s)-4-(8-(2,4-dichloro-6-fluorophenylamino)-2-((R)-tetrahydro-2H-pyran-3-ylamino)-9H-purin-9-yl)cyclohexanecarboxamide;

(1s,4s)-4-(8-(2,4-dichlorophenylamino)-2-(4-hydroxytetrahydrofuran-3-ylamino)-9H-purin-9-yl)cyclohexanecarboxamide;

(1s,4s)-4-(8-(3-chloro-2-fluorophenylamino)-2-(4-hydroxytetrahydrofuran-3-ylamino)-9H-purin-9-yl)cyclohexanecarboxamide;

(1s,4s)-4-(2-(2-oxaspiro[3.3]heptan-6-ylamino)-8-(2,6-dichloro-4-fluorophenylamino)-9H-purin-9-yl)cyclohexanecarboxamide;

(1s,4s)-4-(2-(2-oxaspiro[3.3]heptan-6-ylamino)-8-(4-chloro-2,3-difluorophenylamino)-9H-purin-9-yl)cyclohexanecarboxamide;

(1s,4s)-4-(2-(2-oxaspiro[3.3]heptan-6-ylamino)-8-(2,4-dichloro-6-fluorophenylamino)-9H-purin-9-yl)cyclohexanecarboxamide;

(1s,4s)-4-(2-(2-oxaspiro[3.3]heptan-6-ylamino)-8-(3-chloro-2,6-difluorophenylamino)-9H-purin-9-yl)cyclohexanecarboxamide;

(1s,4s)-4-(2-(1-acetylpiperidin-4-ylamino)-8-(2,4,6-trichlorophenylamino)-9H-purin-9-yl)cyclohexanecarboxamide;

(1s,4s)-4-(2-(1-acetylpiperidin-4-ylamino)-8-(2,4-dichloro-6-fluorophenylamino)-9H-purin-9-yl)cyclohexanecarboxamide;

(1s,4s)-4-(8-(2-chloro-4,6-difluorophenylamino)-2-((R)-tetrahydrofuran-3-ylamino)-9H-purin-9-yl)cyclohexanecarboxamide;

(1s,4s)-4-(8-(4-chloro-2,6-difluorophenylamino)-2-(4,4-difluorocyclohexylamino)-9H-purin-9-yl)cyclohexanecarboxamide;

(1s,4s)-4-(8-(2,6-dichloro-4-fluorophenylamino)-2-(4,4-difluorocyclohexylamino)-9H-purin-9-yl)cyclohexanecarboxamide;

(1r,4s)-4-(8-(2,6-dichloro-4-fluorophenylamino)-2-((S)-tetrahydro-2H-pyran-3-ylamino)-9H-purin-9-yl)cyclohexanecarboxamide;

(1r,4s)-4-(8-(4-chloro-2,6-difluorophenylamino)-2-((S)-tetrahydro-2H-pyran-3-ylamino)-9H-purin-9-yl)cyclohexanecarboxamide;

(1r,4s)-4-(8-(2,4-dichloro-6-fluorophenylamino)-2-((S)-tetrahydro-2H-pyran-3-ylamino)-9H-purin-9-yl)cyclohexanecarboxamide;

(1s,4s)-4-(2-((1-(hydroxymethyl)cyclopropyl)methylamino)-8-(2,4,6-trichlorophenylamino)-9H-purin-9-yl)cyclohexanecarboxamide;

(1s,4s)-4-(8-(2,4-dichloro-6-fluorophenylamino)-2-((1-(hydroxymethyl)cyclopropyl)methylamino)-9H-purin-9-yl)cyclohexanecarboxamide;

(1s,4s)-4-(2-((1R,3R)-3-hydroxycyclopentylamino)-8-(2,4,6-trifluorophenylamino)-9H-purin-9-yl)cyclohexanecarboxamide;

(1s,4s)-4-(8-(2-chloro-6-fluorophenylamino)-2-((1R,3R)-3-hydroxycyclopentylamino)-9H-purin-9-yl)cyclohexanecarboxamide;

(1s,4s)-4-(8-(2,6-difluorophenylamino)-2-((1R,3R)-3-hydroxycyclopentylamino)-9H-purin-9-yl)cyclohexanecarboxamide;

(1s,4s)-4-(8-(2-chloro-4,6-difluorophenylamino)-2-((1R,3R)-3-hydroxycyclopentylamino)-9H-purin-9-yl)cyclohexanecarboxamide;

(1s,4s)-4-(8-(2,6-dichlorophenylamino)-2-((1R,3R)-3-hydroxycyclopentylamino)-9H-purin-9-yl)cyclohexanecarboxamide;

(1s,4s)-4-(2-((1R,3R)-3-hydroxycyclopentylamino)-8-(2,4,6-trichlorophenylamino)-9H-purin-9-yl)cyclohexanecarboxamide;

(1s,4s)-4-(8-(2,4-dichloro-6-fluorophenylamino)-2-((1R,3R)-3-hydroxycyclopentylamino)-9H-purin-9-yl)cyclohexanecarboxamide;

(1s,4s)-4-(8-(2,6-dichloro-4-fluorophenylamino)-2-((1R,3R)-3-hydroxycyclopentylamino)-9H-purin-9-yl)cyclohexanecarboxamide;

(1s,4s)-4-(8-(4-chloro-2,6-difluorophenylamino)-2-((1R,3R)-3-hydroxycyclopentylamino)-9H-purin-9-yl)cyclohexanecarboxamide;

(1s,4s)-4-(8-(4-chloro-2,3-difluorophenylamino)-2-((1R,3R)-3-hydroxycyclopentylamino)-9H-purin-9-yl)cyclohexanecarboxamide;

(1s,4s)-4-(8-(3-chloro-2,6-difluorophenylamino)-2-((1R,3R)-3-hydroxycyclopentylamino)-9H-purin-9-yl)cyclohexanecarboxamide;

(1s,4s)-4-(2-((1R,3R)-3-hydroxycyclopentylamino)-8-(2,3,6-trifluorophenylamino)-9H-purin-9-yl)cyclohexanecarboxamide;

(1s,4s)-4-(8-(2,4-dichlorophenylamino)-2-((1R,3R)-3-hydroxycyclopentylamino)-9H-purin-9-yl)cyclohexanecarboxamide;

(1s,4s)-4-(2-((1R,3R)-3-hydroxycyclopentylamino)-8-(2,3,4-trifluorophenylamino)-9H-purin-9-yl)cyclohexanecarboxamide;

(1s,4s)-4-(8-(4-chloro-2,6-difluorophenylamino)-2-((R)-tetrahydrofuran-3-ylamino)-9H-purin-9-yl)cyclohexanecarboxamide;

(1s,4s)-4-(8-(2,6-dichloro-4-fluorophenylamino)-2-((R)-tetrahydrofuran-3-ylamino)-9H-purin-9-yl)cyclohexanecarboxamide;

(1s,4s)-4-(8-(2,4-dichloro-6-fluorophenylamino)-2-((R)-tetrahydrofuran-3-ylamino)-9H-purin-9-yl)cyclohexanecarboxamide;

(1s,4s)-4-(2-(3,3-difluorocyclobutylamino)-8-(2,4,6-trichlorophenylamino)-9H-purin-9-yl)cyclohexanecarboxamide;

(1s,4s)-4-(8-(2-chloro-6-fluorophenylamino)-2-(3,3-difluorocyclobutylamino)-9H-purin-9-yl)cyclohexanecarboxamide;

(1s,4s)-4-(2-(3,3-difluorocyclobutylamino)-8-(2,4,6-trifluorophenylamino)-9H-purin-9-yl)cyclohexanecarboxamide;

(1s,4s)-4-(2-(3,3-difluorocyclobutylamino)-8-(2,6-difluorophenylamino)-9H-purin-9-yl)cyclohexanecarboxamide;

(1s,4s)-4-(8-(2-chloro-4,6-difluorophenylamino)-2-(3,3-difluorocyclobutylamino)-9H-purin-9-yl)cyclohexanecarboxamide;

(1s,4s)-4-(8-(4-chloro-2,6-difluorophenylamino)-2-(3,3-difluorocyclobutylamino)-9H-purin-9-yl)cyclohexanecarboxamide;

(1s,4s)-4-(8-(2,4-dichloro-6-fluorophenylamino)-2-(3,3-difluorocyclobutylamino)-9H-purin-9-yl)cyclohexanecarboxamide;

(1s,4s)-4-(8-(2,6-dichloro-4-fluorophenylamino)-2-(3,3-difluorocyclobutylamino)-9H-purin-9-yl)cyclohexanecarboxamide;

(1s,4s)-4-(8-(4-chloro-2,3-difluorophenylamino)-2-(3,3-difluorocyclobutylamino)-9H-purin-9-yl)cyclohexanecarboxamide;

(1s,4s)-4-(2-(3,3-difluorocyclobutylamino)-8-(2,3,6-trifluorophenylamino)-9H-purin-9-yl)cyclohexanecarboxamide;

(1s,4s)-4-(8-(3-chloro-2,6-difluorophenylamino)-2-(3,3-difluorocyclobutylamino)-9H-purin-9-yl)cyclohexanecarboxamide;

(1s,4s)-4-(8-(2-chloro-6-fluorophenylamino)-2-(4,4-difluorocyclohexylamino)-9H-purin-9-yl)cyclohexanecarboxamide;

(1s,4s)-4-(8-(2,6-dichlorophenylamino)-2-(4,4-difluorocyclohexylamino)-9H-purin-9-yl)cyclohexanecarboxamide;

(1s,4s)-4-(8-(3-chloro-2-fluorophenylamino)-2-(4,4-difluorocyclohexylamino)-9H-purin-9-yl)cyclohexanecarboxamide;

(1s,4s)-4-(8-(4-chloro-2,5-difluorophenylamino)-2-(4,4-difluorocyclohexylamino)-9H-purin-9-yl)cyclohexanecarboxamide;

(1s,4s)-4-(2-(4,4-difluorocyclohexylamino)-8-(2,3,6-trifluorophenylamino)-9H-purin-9-yl)cyclohexanecarboxamide;

(1s,4s)-4-(8-(2,4-dichlorophenylamino)-2-(4,4-difluorocyclohexylamino)-9H-purin-9-yl)cyclohexanecarboxamide;

(1r,4s)-4-(8-(2-chloro-4,6-difluorophenylamino)-2-((S)-tetrahydrofuran-3-ylamino)-9H-purin-9-yl)cyclohexanecarboxamide;

(1r,4s)-4-(8-(4-chloro-2,6-difluorophenylamino)-2-((S)-tetrahydrofuran-3-ylamino)-9H-purin-9-yl)cyclohexanecarboxamide;

(1r,4s)-4-(8-(2,6-dichloro-4-fluorophenylamino)-2-((S)-tetrahydrofuran-3-ylamino)-9H-purin-9-yl)cyclohexanecarboxamide;

(1r,4s)-4-(8-(2,4-dichloro-6-fluorophenylamino)-2-((S)-tetrahydrofuran-3-ylamino)-9H-purin-9-yl)cyclohexanecarboxamide;

(1r,4s)-4-(8-(2-chloro-4,6-difluorophenylamino)-2-((S)-tetrahydro-2H-pyran-3-ylamino)-9H-purin-9-yl)cyclohexanecarboxamide;

(1r,4s)-4-(2-((3R,4S)-3-fluorotetrahydro-2H-pyran-4-ylamino)-8-(2,4,6-trichlorophenylamino)-9H-purin-9-yl)cyclohexanecarboxamide;

(1r,4s)-4-(8-(2,6-difluorophenylamino)-2-((3R,4S)-3-fluorotetrahydro-2H-pyran-4-ylamino)-9H-purin-9-yl)cyclohexanecarboxamide;

(1s,4s)-4-(8-(2-chloro-4-cyanophenylamino)-2-(tetrahydro-2H-pyran-4-ylamino)-9H-purin-9-yl)cyclohexanecarboxamide;

(1s,4s)-4-(2-((1R,2R)-2-hydroxycyclopentylamino)-8-(2,4,6-trifluorophenylamino)-9H-purin-9-yl)cyclohexanecarboxamide;

(1s,4s)-4-(8-(2-chloro-6-fluorophenylamino)-2-((1R,2R)-2-hydroxycyclopentylamino)-9H-purin-9-yl)cyclohexanecarboxamide;

(1s,4s)-4-(8-(2,6-difluorophenylamino)-2-((1R,2R)-2-hydroxycyclopentylamino)-9H-purin-9-yl)cyclohexanecarboxamide;

(1s,4s)-4-(8-(2-chloro-4,6-difluorophenylamino)-2-((1R,2R)-2-hydroxycyclopentylamino)-9H-purin-9-yl)cyclohexanecarboxamide;

(1s,4s)-4-(8-(2,6-dichlorophenylamino)-2-((1R,2R)-2-hydroxycyclopentylamino)-9H-purin-9-yl)cyclohexanecarboxamide;

(1s,4s)-4-(2-((1R,2R)-2-hydroxycyclopentylamino)-8-(2,4,6-trichlorophenylamino)-9H-purin-9-yl)cyclohexanecarboxamide;

(1s,4s)-4-(8-(2,4-dichloro-6-fluorophenylamino)-2-((1R,2R)-2-hydroxycyclopentylamino)-9H-purin-9-yl)cyclohexanecarboxamide;

(1s,4s)-4-(8-(2,6-dichloro-4-fluorophenylamino)-2-((1R,2R)-2-hydroxycyclopentylamino)-9H-purin-9-yl)cyclohexanecarboxamide;

(1s,4s)-4-(8-(4-chloro-2,6-difluorophenylamino)-2-((1R,2R)-2-hydroxycyclopentylamino)-9H-purin-9-yl)cyclohexanecarboxamide;

(1s,4s)-4-(8-(4-chloro-2,3-difluorophenylamino)-2-((1R,2R)-2-hydroxycyclopentylamino)-9H-purin-9-yl)cyclohexanecarboxamide;

(1s,4s)-4-(8-(3-chloro-2,6-difluorophenylamino)-2-((1R,2R)-2-hydroxycyclopentylamino)-9H-purin-9-yl)cyclohexanecarboxamide;

(1s,4s)-4-(2-((1R,2R)-2-hydroxycyclopentylamino)-8-(2,3,6-trifluorophenylamino)-9H-purin-9-yl)cyclohexanecarboxamide;

(1s,4s)-4-(8-(2,4-dichlorophenylamino)-2-((1R,2R)-2-hydroxycyclopentylamino)-9H-purin-9-yl)cyclohexanecarboxamide;

(1s,4s)-4-(8-(5-chloro-2-fluorophenylamino)-2-((1R,2R)-2-hydroxycyclopentylamino)-9H-purin-9-yl)cyclohexanecarboxamide;

(1s,4s)-4-(8-(3-chloro-2-fluorophenylamino)-2-((1R,2R)-2-hydroxycyclopentylamino)-9H-purin-9-yl)cyclohexanecarboxamide;

(1s,4s)-4-(2-((1R,2R)-2-hydroxycyclopentylamino)-8-(2,3,4-trifluorophenylamino)-9H-purin-9-yl)cyclohexanecarboxamide;

(1s,4s)-4-(8-(4-chloro-2,5-difluorophenylamino)-2-((1R,2R)-2-hydroxycyclopentylamino)-9H-purin-9-yl)cyclohexanecarboxamide;

(1r,4s)-4-(2-((1S,2S)-2-hydroxycyclopentylamino)-8-(2,4,6-trichlorophenylamino)-9H-purin-9-yl)cyclohexanecarboxamide;

(1r,4s)-4-(8-(2,6-difluorophenylamino)-2-((1S,2S)-2-hydroxycyclopentylamino)-9H-purin-9-yl)cyclohexanecarboxamide;

(1r,4s)-4-(8-(2,6-dichlorophenylamino)-2-((1S,2S)-2-hydroxycyclopentylamino)-9H-purin-9-yl)cyclohexanecarboxamide;

(1r,4s)-4-(8-(4-chloro-2,6-difluorophenylamino)-2-((1S,2S)-2-hydroxycyclopentylamino)-9H-purin-9-yl)cyclohexanecarboxamide;

(1r,4s)-4-(2-((1S,2S)-2-hydroxycyclopentylamino)-8-(2,4,6-trichlorophenylamino)-9H-purin-9-yl)cyclohexanecarboxamide;

(1r,4s)-4-(8-(2,4-dichloro-6-fluorophenylamino)-2-((1S,2S)-2-hydroxycyclopentylamino)-9H-purin-9-yl)cyclohexanecarboxamide;

(1r,4s)-4-(8-(2,6-dichloro-4-fluorophenylamino)-2-((1S,2S)-2-hydroxycyclopentylamino)-9H-purin-9-yl)cyclohexanecarboxamide;

(1r,4s)-4-(8-(3-chloro-2,6-difluorophenylamino)-2-((1S,2S)-2-hydroxycyclopentylamino)-9H-purin-9-yl)cyclohexanecarboxamide;

(1s,4s)-4-(2-((3S,4R)-3-fluorotetrahydro-2H-pyran-4-ylamino)-8-(2,4,6-trichlorophenylamino)-9H-purin-9-yl)cyclohexanecarboxamide;

(1s,4s)-4-(8-(2,6-difluorophenylamino)-2-((3S,4R)-3-fluorotetrahydro-2H-pyran-4-ylamino)-9H-purin-9-yl)cyclohexanecarboxamide;

(1s,4s)-4-(2-((3S,4R)-3-fluorotetrahydro-2H-pyran-4-ylamino)-8-(2,4,6-trifluorophenylamino)-9H-purin-9-yl)cyclohexanecarboxamide;

(1r,4s)-4-(2-((3R,4S)-3-fluorotetrahydro-2H-pyran-4-ylamino)-8-(2,4,6-trifluorophenylamino)-9H-purin-9-yl)cyclohexanecarboxamide;

(1s,4s)-4-(8-(2,6-dichloro-4-cyanophenylamino)-2-(tetrahydro-2H-pyran-4-ylamino)-9H-purin-9-yl)cyclohexanecarboxamide;

(1s,4s)-4-(2-((1r,3r)-3-hydroxycyclobutylamino)-8-(2,4,6-trifluorophenylamino)-9H-purin-9-yl)cyclohexanecarboxamide;
(1s,4s)-4-(8-(2,6-dichlorophenylamino)-2-((1r,3r)-3-hydroxycyclobutylamino)-9H-purin-9-yl)cyclohexanecarboxamide;
(1s,4s)-4-(8-(2-chloro-6-fluorophenylamino)-2-((1r,3r)-3-hydroxycyclobutylamino)-9H-purin-9-yl)cyclohexanecarboxamide;
(1s,4s)-4-(8-(2-chloro-4,6-difluorophenylamino)-2-((1r,3r)-3-hydroxycyclobutylamino)-9H-purin-9-yl)cyclohexanecarboxamide;
(1s,4s)-4-(8-(4-chloro-2,6-difluorophenylamino)-2-((1r,3r)-3-hydroxycyclobutylamino)-9H-purin-9-yl)cyclohexanecarboxamide;
(1s,4s)-4-(8-(2,6-dichloro-4-fluorophenylamino)-2-((1r,3r)-3-hydroxycyclobutylamino)-9H-purin-9-yl)cyclohexanecarboxamide;
(1s,4s)-4-(8-(4-chloro-2,3-difluorophenylamino)-2-((1r,3r)-3-hydroxycyclobutylamino)-9H-purin-9-yl)cyclohexanecarboxamide;
(1s,4s)-4-(8-(3-chloro-2,6-difluorophenylamino)-2-((1r,3r)-3-hydroxycyclobutylamino)-9H-purin-9-yl)cyclohexanecarboxamide;
(1s,4s)-4-(8-(3-chloro-2,5-difluorophenylamino)-2-((1r,3r)-3-hydroxycyclobutylamino)-9H-purin-9-yl)cyclohexanecarboxamide;
(1s,4s)-4-(2-(4,4-difluorocyclohexylamino)-8-(2,4,6-trifluorophenylamino)-9H-purin-9-yl)cyclohexanecarboxamide;
(1s,4s)-4-(2-(4,4-difluorocyclohexylamino)-8-(2,6-difluorophenylamino)-9H-purin-9-yl)cyclohexanecarboxamide;
(1s,4s)-4-(8-(4-chloro-2,3-difluorophenylamino)-2-(4,4-difluorocyclohexylamino)-9H-purin-9-yl)cyclohexanecarboxamide;
(1s,4s)-4-(8-(3-chloro-2,6-difluorophenylamino)-2-(4,4-difluorocyclohexylamino)-9H-purin-9-yl)cyclohexanecarboxamide;
(1s,4s)-4-(2-(1-(methylsulfonyl)piperidin-4-ylamino)-8-(2,4,6-trichlorophenylamino)-9H-purin-9-yl)cyclohexanecarboxamide;
(1s,4s)-4-(8-(2,6-dichlorophenylamino)-2-(1-(methylsulfonyl)piperidin-4-ylamino)-9H-purin-9-yl)cyclohexanecarboxamide;
(1s,4s)-4-(8-(2-chloro-4,6-difluorophenylamino)-2-(1-(methylsulfonyl)piperidin-4-ylamino)-9H-purin-9-yl)cyclohexanecarboxamide;
(1s,4s)-4-(8-(4-chloro-2,6-difluorophenylamino)-2-(1-(methylsulfonyl)piperidin-4-ylamino)-9H-purin-9-yl)cyclohexanecarboxamide;
(1s,4s)-4-(8-(2,4-dichloro-6-fluorophenylamino)-2-(1-(methylsulfonyl)piperidin-4-ylamino)-9H-purin-9-yl)cyclohexanecarboxamide;
(1s,4s)-4-(8-(2,6-dichloro-4-fluorophenylamino)-2-(1-(methylsulfonyl)piperidin-4-ylamino)-9H-purin-9-yl)cyclohexanecarboxamide;
(1s,4s)-4-(8-(4-chloro-2,3-difluorophenylamino)-2-(1-(methylsulfonyl)piperidin-4-ylamino)-9H-purin-9-yl)cyclohexanecarboxamide;
(1s,4s)-4-(8-(2,4-dichlorophenylamino)-2-(1-(methylsulfonyl)piperidin-4-ylamino)-9H-purin-9-yl)cyclohexanecarboxamide;
(1s,4s)-4-(2-((1r,3r)-3-hydroxycyclobutylamino)-8-(2,4,6-trichlorophenylamino)-9H-purin-9-yl)cyclohexanecarboxamide;
(1s,4s)-4-(8-(2,4-dichloro-6-fluorophenylamino)-2-((1r,3r)-3-hydroxycyclobutylamino)-9H-purin-9-yl)cyclohexanecarboxamide;
(1s,4s)-4-(2-((3R,4R)-3-fluorotetrahydro-2H-pyran-4-ylamino)-8-(2,4,6-trichlorophenylamino)-9H-purin-9-yl)cyclohexanecarboxamide;
(1r,4s)-4-(2-((3S,4S)-3-fluorotetrahydro-2H-pyran-4-ylamino)-8-(2,4,6-trichlorophenylamino)-9H-purin-9-yl)cyclohexanecarboxamide;
(1s,4s)-4-(8-(2,6-difluorophenylamino)-2-((3R,4R)-3-fluorotetrahydro-2H-pyran-4-ylamino)-9H-purin-9-yl)cyclohexanecarboxamide;
(1r,4s)-4-(8-(2,6-difluorophenylamino)-2-((3S,4S)-3-fluorotetrahydro-2H-pyran-4-ylamino)-9H-purin-9-yl)cyclohexanecarboxamide;
(1r,4s)-4-(2-((3S,4S)-3-fluorotetrahydro-2H-pyran-4-ylamino)-8-(2,4,6-trifluorophenylamino)-9H-purin-9-yl)cyclohexanecarboxamide;
(1s,4s)-4-(2-((3R,4R)-3-fluorotetrahydro-2H-pyran-4-ylamino)-8-(2,4,6-trifluorophenylamino)-9H-purin-9-yl)cyclohexanecarboxamide;
(1s,4s)-4-(8-(2-chloro-4-cyano-6-fluorophenylamino)-2-(tetrahydro-2H-pyran-4-ylamino)-9H-purin-9-yl)cyclohexanecarboxamide;
(1s,4s)-4-(8-(4-cyano-2,6-difluorophenylamino)-2-(tetrahydro-2H-pyran-4-ylamino)-9H-purin-9-yl)cyclohexanecarboxamide;
(1s,4s)-4-(8-(4-chloro-2,3-difluorophenylamino)-2-((1s,3s)-3-hydroxycyclobutylamino)-9H-purin-9-yl)cyclohexanecarboxamide;
(1r,4s)-4-(2-((3S,4R)-4-hydroxytetrahydrofuran-3-ylamino)-8-(2,4,6-trifluorophenylamino)-9H-purin-9-yl)cyclohexanecarboxamide;
(1r,4s)-4-(8-(2-chloro-4,6-difluorophenylamino)-2-((3S,4R)-4-hydroxytetrahydrofuran-3-ylamino)-9H-purin-9-yl)cyclohexanecarboxamide;
(1r,4s)-4-(2-((3S,4R)-4-hydroxytetrahydrofuran-3-ylamino)-8-(2,4,6-trichlorophenylamino)-9H-purin-9-yl)cyclohexanecarboxamide;
(1s,4s)-4-(8-(2,4-dichloro-6-fluorophenylamino)-2-((3R,4S)-4-hydroxytetrahydrofuran-3-ylamino)-9H-purin-9-yl)cyclohexanecarboxamide;
(1s,4s)-4-(8-(2,6-dichloro-4-fluorophenylamino)-2-((3R,4S)-4-hydroxytetrahydrofuran-3-ylamino)-9H-purin-9-yl)cyclohexanecarboxamide;
(1s,4s)-4-(8-(4-chloro-2,6-difluorophenylamino)-2-((3R,4S)-4-hydroxytetrahydrofuran-3-ylamino)-9H-purin-9-yl)cyclohexanecarboxamide;
(1r,4s)-4-(8-(4-chloro-2,3-difluorophenylamino)-2-((3S,4R)-4-hydroxytetrahydrofuran-3-ylamino)-9H-purin-9-yl)cyclohexanecarboxamide;
(1r,4s)-4-(8-(3-chloro-2,6-difluorophenylamino)-2-((3S,4R)-4-hydroxytetrahydrofuran-3-ylamino)-9H-purin-9-yl)cyclohexanecarboxamide;
(1r,4s)-4-(8-(2,4-dichlorophenylamino)-2-((3S,4R)-4-hydroxytetrahydrofuran-3-ylamino)-9H-purin-9-yl)cyclohexanecarboxamide;
(1r,4s)-4-(8-(5-chloro-2-fluorophenylamino)-2-((3S,4R)-4-hydroxytetrahydrofuran-3-ylamino)-9H-purin-9-yl)cyclohexanecarboxamide;
(1s,4s)-4-(8-(4-chloro-2,5-difluorophenylamino)-2-((3R,4S)-4-hydroxytetrahydrofuran-3-ylamino)-9H-purin-9-yl)cyclohexanecarboxamide;
(1s,4s)-4-(8-(4-chloro-2,6-difluorophenylamino)-2-((1s,3s)-3-hydroxycyclobutylamino)-9H-purin-9-yl)cyclohexanecarboxamide;

(1s,4s)-4-(2-((1s,3s)-3-hydroxycyclobutylamino)-8-(2,4,6-trichlorophenylamino)-9H-purin-9-yl)cyclohexanecarboxamide;

(1s,4s)-4-(8-(2,4-dichloro-6-fluorophenylamino)-2-((1s,3s)-3-hydroxycyclobutylamino)-9H-purin-9-yl)cyclohexanecarboxamide;

(1r,4s)-4-(8-(2-chloro-6-fluorophenylamino)-2-((1S,3S)-3-hydroxycyclopentylamino)-9H-purin-9-yl)cyclohexanecarboxamide;

(1r,4s)-4-(8-(2,6-difluorophenylamino)-2-((1S,3S)-3-hydroxycyclopentylamino)-9H-purin-9-yl)cyclohexanecarboxamide;

(1r,4s)-4-(8-(2,6-dichlorophenylamino)-2-((1S,3S)-3-hydroxycyclopentylamino)-9H-purin-9-yl)cyclohexanecarboxamide;

(1s,4s)-4-(8-(4-chloro-2,6-difluorophenylamino)-2-((1R,3S)-3-hydroxycyclopentylamino)-9H-purin-9-yl)cyclohexanecarboxamide;

(1r,4s)-4-(8-(4-chloro-2,6-difluorophenylamino)-2-((1S,3S)-3-hydroxycyclopentylamino)-9H-purin-9-yl)cyclohexanecarboxamide;

(1r,4s)-4-(2-((1S,3S)-3-hydroxycyclopentylamino)-8-(2,4,6-trichlorophenylamino)-9H-purin-9-yl)cyclohexanecarboxamide;

(1r,4s)-4-(2-((1S,3S)-3-hydroxycyclopentylamino)-8-(2,4,6-trifluorophenylamino)-9H-purin-9-yl)cyclohexanecarboxamide;

(1s,4s)-4-(2-((1R,3S)-3-hydroxycyclopentylamino)-8-(2,4,6-trifluorophenylamino)-9H-purin-9-yl)cyclohexanecarboxamide;

(1s,4s)-4-(2-((1R,3S)-3-hydroxycyclopentylamino)-8-(2,4,6-trichlorophenylamino)-9H-purin-9-yl)cyclohexanecarboxamide;

(1r,4s)-4-(2-(sec-butylamino)-8-(2,4,6-trifluorophenylamino)-9H-purin-9-yl)cyclohexanecarboxamide;

(1r,4s)-4-(2-(sec-butylamino)-8-(2,6-difluorophenylamino)-9H-purin-9-yl)cyclohexanecarboxamide;

(1r,4s)-4-(2-(sec-butylamino)-8-(2,6-dichlorophenylamino)-9H-purin-9-yl)cyclohexanecarboxamide;

(1r,4s)-4-(2-(sec-butylamino)-8-(2-chloro-6-fluorophenylamino)-9H-purin-9-yl)cyclohexanecarboxamide;

(1r,4s)-4-(2-(sec-butylamino)-8-(2-chloro-4,6-difluorophenylamino)-9H-purin-9-yl)cyclohexanecarboxamide;

(1r,4s)-4-(2-(sec-butylamino)-8-(2,4-dichloro-6-fluorophenylamino)-9H-purin-9-yl)cyclohexanecarboxamide;

(1r,4s)-4-(2-(sec-butylamino)-8-(3-chloro-2,6-difluorophenylamino)-9H-purin-9-yl)cyclohexanecarboxamide;

(1s,4s)-4-(2-((1R,3R,4R)-3-hydroxy-4-methylcyclohexylamino)-8-(2,4,6-trifluorophenylamino)-9H-purin-9-yl)cyclohexanecarboxamide;

(1s,4s)-4-(8-(2-chloro-6-fluorophenylamino)-2-((1R,3R,4R)-3-hydroxy-4-methylcyclohexylamino)-9H-purin-9-yl)cyclohexanecarboxamide;

(1s,4s)-4-(8-(2,6-difluorophenylamino)-2-((1R,3R,4R)-3-hydroxy-4-methylcyclohexylamino)-9H-purin-9-yl)cyclohexanecarboxamide;

(1s,4s)-4-(8-(2-chloro-4,6-difluorophenylamino)-2-((1R,3R,4R)-3-hydroxy-4-methylcyclohexylamino)-9H-purin-9-yl)cyclohexanecarboxamide;

(1s,4s)-4-(8-(2,6-dichlorophenylamino)-2-((1R,3R,4R)-3-hydroxy-4-methylcyclohexylamino)-9H-purin-9-yl)cyclohexanecarboxamide;

(1s,4s)-4-(8-(2,4-dichloro-6-fluorophenylamino)-2-((1R,3R,4R)-3-hydroxy-4-methylcyclohexylamino)-9H-purin-9-yl)cyclohexanecarboxamide;

(1s,4s)-4-(2-((1R,3S)-3-hydroxycyclohexylamino)-8-(2,4,6-trifluorophenylamino)-9H-purin-9-yl)cyclohexanecarboxamide;

(1s,4s)-4-(8-(2,6-difluorophenylamino)-2-((1R,3S)-3-hydroxycyclohexylamino)-9H-purin-9-yl)cyclohexanecarboxamide;

(1s,4s)-4-(8-(2,6-dichlorophenylamino)-2-((1R,3S)-3-hydroxycyclohexylamino)-9H-purin-9-yl)cyclohexanecarboxamide;

(1s,4s)-4-(8-(2-chloro-6-fluorophenylamino)-2-((1R,3S)-3-hydroxycyclohexylamino)-9H-purin-9-yl)cyclohexanecarboxamide;

(1s,4s)-4-(8-(2-chloro-4,6-difluorophenylamino)-2-((1R,3S)-3-hydroxycyclohexylamino)-9H-purin-9-yl)cyclohexanecarboxamide;

(1s,4s)-4-(8-(4-chloro-2,6-difluorophenylamino)-2-((1R,3S)-3-hydroxycyclohexylamino)-9H-purin-9-yl)cyclohexanecarboxamide;

(1s,4s)-4-(2-((1R,3S)-3-hydroxycyclohexylamino)-8-(2,4,6-trichlorophenylamino)-9H-purin-9-yl)cyclohexanecarboxamide;

(1s,4s)-4-(8-(2,6-dichloro-4-fluorophenylamino)-2-((1R,3S)-3-hydroxycyclohexylamino)-9H-purin-9-yl)cyclohexanecarboxamide;

(1s,4s)-4-(8-(2,6-dichloro-4-fluorophenylamino)-2-((1R,3R,4R)-3-hydroxy-4-methylcyclohexylamino)-9H-purin-9-yl)cyclohexanecarboxamide;

(1s,4s)-4-(8-(4-chloro-2,6-difluorophenylamino)-2-((1R,3R,4R)-3-hydroxy-4-methylcyclohexylamino)-9H-purin-9-yl)cyclohexanecarboxamide;

(1s,4s)-4-(8-(4-chloro-2,3-difluorophenylamino)-2-((1R,3R,4R)-3-hydroxy-4-methylcyclohexylamino)-9H-purin-9-yl)cyclohexanecarboxamide;

(1s,4s)-4-(8-(3-chloro-2,6-difluorophenylamino)-2-((1R,3R,4R)-3-hydroxy-4-methylcyclohexylamino)-9H-purin-9-yl)cyclohexanecarboxamide;

(1s,4s)-4-(2-((1R,3R,4R)-3-hydroxy-4-methylcyclohexylamino)-8-(2,3,6-trifluorophenylamino)-9H-purin-9-yl)cyclohexanecarboxamide;

(1s,4s)-4-(8-(4-chloro-2,3-difluorophenylamino)-2-((1R,3S)-3-hydroxycyclohexylamino)-9H-purin-9-yl)cyclohexanecarboxamide;

(1s,4s)-4-(8-(2,4-dichloro-6-fluorophenylamino)-2-((1R,3S)-3-hydroxycyclohexylamino)-9H-purin-9-yl)cyclohexanecarboxamide;

(1s,4s)-4-(8-(3-chloro-2,6-difluorophenylamino)-2-((1R,3S)-3-hydroxycyclohexylamino)-9H-purin-9-yl)cyclohexanecarboxamide;

(1s,4s)-4-(8-(4-chloro-2,5-difluorophenylamino)-2-((1R,3S)-3-hydroxycyclohexylamino)-9H-purin-9-yl)cyclohexanecarboxamide;

(1s,4s)-4-(2-((1R,3S)-3-hydroxycyclohexylamino)-8-(2,3,4-trifluorophenylamino)-9H-purin-9-yl)cyclohexanecarboxamide;

(1s,4s)-4-(8-(2,6-dichloro-4-(trifluoromethoxy)phenylamino)-2-(tetrahydro-2H-pyran-4-ylamino)-9H-purin-9-yl)cyclohexanecarboxamide;

(1r,4s)-4-(8-(2,6-dichloro-4-cyanophenylamino)-2-((S)-1-hydroxypropan-2-ylamino)-9H-purin-9-yl)cyclohexanecarboxamide;

(1s,4s)-4-(2-(cyclopentylamino)-8-(2,6-dichloro-4-cyanophenylamino)-9H-purin-9-yl)cyclohexanecarboxamide;

(1s,4s)-4-(8-(4-cyano-2,6-difluorophenylamino)-2-(cyclobutylamino)-9H-purin-9-yl)cyclohexanecarboxamide;

(1s,4s)-4-(8-(2-chloro-4-cyano-6-fluorophenylamino)-2-(cyclopentylamino)-9H-purin-9-yl)cyclohexanecarboxamide;

(1r,4s)-4-(8-(2,6-dichlorophenylamino)-2-((1S,3R)-3-hydroxycyclohexylamino)-9H-purin-9-yl)cyclohexanecarboxamide;

(1r,4s)-4-(8-(2-chloro-4,6-difluorophenylamino)-2-((1S,3R)-3-hydroxycyclohexylamino)-9H-purin-9-yl)cyclohexanecarboxamide;

(1r,4s)-4-(8-(4-chloro-2,6-difluorophenylamino)-2-((1S,3R)-3-hydroxycyclohexylamino)-9H-purin-9-yl)cyclohexanecarboxamide;

(1r,4s)-4-(2-((1S,3R)-3-hydroxycyclohexylamino)-8-(2,4,6-trichlorophenylamino)-9H-purin-9-yl)cyclohexanecarboxamide;

(1r,4s)-4-(8-(2,6-dichloro-4-fluorophenylamino)-2-((1S,3R)-3-hydroxycyclohexylamino)-9H-purin-9-yl)cyclohexanecarboxamide;

(1r,4s)-4-(8-(4-chloro-2,3-difluorophenylamino)-2-((1S,3R)-3-hydroxycyclohexylamino)-9H-purin-9-yl)cyclohexanecarboxamide;

(1r,4s)-4-(8-(2,4-dichloro-6-fluorophenylamino)-2-((1S,3R)-3-hydroxycyclohexylamino)-9H-purin-9-yl)cyclohexanecarboxamide;

(1r,4s)-4-(8-(3-chloro-2,6-difluorophenylamino)-2-((1S,3R)-3-hydroxycyclohexylamino)-9H-purin-9-yl)cyclohexanecarboxamide;

(1s,4s)-4-(8-(2-chloro-4-cyano-6-fluorophenylamino)-2-(4,4-difluorocyclohexylamino)-9H-purin-9-yl)cyclohexanecarboxamide;

(1s,4s)-4-(8-(4-cyano-2,3-difluorophenylamino)-2-(tetrahydro-2H-pyran-4-ylamino)-9H-purin-9-yl)cyclohexanecarboxamide;

(1s,4s)-4-(8-(2,3-difluoro-4-methoxyphenylamino)-2-(tetrahydro-2H-pyran-4-ylamino)-9H-purin-9-yl)cyclohexanecarboxamide;

(1s,4s)-4-(2-((1R,3R)-3-hydroxy-4,4-dimethylcyclohexylamino)-8-(2,4,6-trifluorophenylamino)-9H-purin-9-yl)cyclohexanecarboxamide;

(1s,4s)-4-(8-(2,6-difluorophenylamino)-2-((1R,3R)-3-hydroxy-4,4-dimethylcyclohexylamino)-9H-purin-9-yl)cyclohexanecarboxamide;

(1s,4s)-4-(8-(2,6-dichlorophenylamino)-2-((1R,3R)-3-hydroxy-4,4-dimethylcyclohexylamino)-9H-purin-9-yl)cyclohexanecarboxamide;

(1s,4s)-4-(8-(2-chloro-6-fluorophenylamino)-2-((1R,3R)-3-hydroxy-4,4-dimethylcyclohexylamino)-9H-purin-9-yl)cyclohexanecarboxamide;

(1s,4s)-4-(8-(2-chloro-4,6-difluorophenylamino)-2-((1R,3R)-3-hydroxy-4,4-dimethylcyclohexylamino)-9H-purin-9-yl)cyclohexanecarboxamide;

(1s,4s)-4-(8-(4-chloro-2,6-difluorophenylamino)-2-((1R,3R)-3-hydroxy-4,4-dimethylcyclohexylamino)-9H-purin-9-yl)cyclohexanecarboxamide;

(1s,4s)-4-(2-((1R,3R)-3-hydroxy-4,4-dimethylcyclohexylamino)-8-(2,4,6-trichlorophenylamino)-9H-purin-9-yl)cyclohexanecarboxamide;

(1s,4s)-4-(8-(2,6-dichloro-4-fluorophenylamino)-2-((1R,3R)-3-hydroxy-4,4-dimethylcyclohexylamino)-9H-purin-9-yl)cyclohexanecarboxamide;

(1s,4s)-4-(8-(2,4-dichloro-6-fluorophenylamino)-2-((1R,3R)-3-hydroxy-4,4-dimethylcyclohexylamino)-9H-purin-9-yl)cyclohexanecarboxamide;

(1s,4s)-4-(8-(3-chloro-2,6-difluorophenylamino)-2-((1R,3R)-3-hydroxy-4,4-dimethylcyclohexylamino)-9H-purin-9-yl)cyclohexanecarboxamide;

(1s,4s)-4-(8-(2,4-dichlorophenylamino)-2-((1R,3R,4R)-3-hydroxy-4-methylcyclohexylamino)-9H-purin-9-yl)cyclohexanecarboxamide;

(1s,4s)-4-(2-(cyclobutylamino)-8-(2,6-dichloro-4-cyanophenylamino)-9H-purin-9-yl)cyclohexanecarboxamide;

(1s,4s)-4-(8-(2-chloro-4-cyano-6-fluorophenylamino)-2-(cyclobutylamino)-9H-purin-9-yl)cyclohexanecarboxamide;

(1r,4s)-4-(8-(4-cyano-2,6-difluorophenylamino)-2-((S)-1-hydroxypropan-2-ylamino)-9H-purin-9-yl)cyclohexanecarboxamide;

(1r,4s)-4-(8-(2-chloro-4-cyano-6-fluorophenylamino)-2-((S)-1-hydroxypropan-2-ylamino)-9H-purin-9-yl)cyclohexanecarboxamide;

(1s,4s)-4-(8-(4-cyano-2,6-difluorophenylamino)-2-(4,4-difluorocyclohexylamino)-9H-purin-9-yl)cyclohexanecarboxamide;

(1s,4s)-4-(8-(2,6-dichloro-4-cyanophenylamino)-2-(4,4-difluorocyclohexylamino)-9H-purin-9-yl)cyclohexanecarboxamide;

(1s,4s)-4-(8-(2-chloro-6-fluoro-4-(trifluoromethyl)phenylamino)-2-(tetrahydro-2H-pyran-4-ylamino)-9H-purin-9-yl)cyclohexanecarboxamide;

(1s,4s)-4-(8-(2,6-dichloro-4-cyanophenylamino)-2-(3,3-difluorocyclobutylamino)-9H-purin-9-yl)cyclohexanecarboxamide;

(1s,4s)-4-(8-(2-chloro-4-cyano-6-fluorophenylamino)-2-(3,3-difluorocyclobutylamino)-9H-purin-9-yl)cyclohexanecarboxamide;

(1s,4s)-4-(8-(4-cyano-2,6-difluorophenylamino)-2-(3,3-difluorocyclobutylamino)-9H-purin-9-yl)cyclohexanecarboxamide;

(1r,4s)-4-(8-(4-cyano-2,6-difluorophenylamino)-2-((S)-1-hydroxybutan-2-ylamino)-9H-purin-9-yl)cyclohexanecarboxamide;

(R)-methyl 3-(9-((1s,4s)-4-carbamoylcyclohexyl)-8-(2,4,6-trifluorophenylamino)-9H-purin-2-ylamino)piperidine-1-carboxylate;

(R)-methyl 3-(9-((1s,4s)-4-carbamoylcyclohexyl)-8-(2,6-difluorophenylamino)-9H-purin-2-ylamino)piperidine-1-carboxylate;

(R)-methyl 3-(9-((1s,4s)-4-carbamoylcyclohexyl)-8-(2,6-dichlorophenylamino)-9H-purin-2-ylamino)piperidine-1-carboxylate;

(R)-methyl 3-(9-((1s,4s)-4-carbamoylcyclohexyl)-8-(2-chloro-6-fluorophenylamino)-9H-purin-2-ylamino)piperidine-1-carboxylate;

(R)-methyl 3-(9-((1s,4s)-4-carbamoylcyclohexyl)-8-(2-chloro-4,6-difluorophenylamino)-9H-purin-2-ylamino)piperidine-1-carboxylate;

(R)-methyl 3-(9-((1s,4s)-4-carbamoylcyclohexyl)-8-(4-chloro-2,6-difluorophenylamino)-9H-purin-2-ylamino)piperidine-1-carboxylate;

(R)-methyl 3-(9-((1s,4s)-4-carbamoylcyclohexyl)-8-(2,4,6-trichlorophenylamino)-9H-purin-2-ylamino)piperidine-1-carboxylate;

(R)-methyl 3-(9-((1s,4s)-4-carbamoylcyclohexyl)-8-(2,6-dichloro-4-fluorophenylamino)-9H-purin-2-ylamino)piperidine-1-carboxylate;

(R)-methyl 3-(9-((1s,4s)-4-carbamoylcyclohexyl)-8-(4-chloro-2,3-difluorophenylamino)-9H-purin-2-ylamino)piperidine-1-carboxylate;

(R)-methyl 3-(9-((1s,4s)-4-carbamoylcyclohexyl)-8-(2,4-dichloro-6-fluorophenylamino)-9H-purin-2-ylamino)piperidine-1-carboxylate;

(R)-methyl 3-(9-((1s,4s)-4-carbamoylcyclohexyl)-8-(3-chloro-2,6-difluorophenylamino)-9H-purin-2-ylamino)piperidine-1-carboxylate;

(R)-methyl 3-(9-((1s,4s)-4-carbamoylcyclohexyl)-8-(2,3,4-trifluorophenylamino)-9H-purin-2-ylamino)piperidine-1-carboxylate;

(1s,4s)-4-(2-((1R,3R)-3-hydroxycyclohexylamino)-8-(2,4,6-trichlorophenylamino)-9H-purin-9-yl)cyclohexanecarboxamide;

(1s,4s)-4-(8-(2-chloro-6-fluorophenylamino)-2-((1R,3R)-3-hydroxycyclohexylamino)-9H-purin-9-yl)cyclohexanecarboxamide;

(1s,4s)-4-(8-(2,6-dichlorophenylamino)-2-((1R,3R)-3-hydroxycyclohexylamino)-9H-purin-9-yl)cyclohexanecarboxamide;

(1s,4s)-4-(2-((1R,3R)-3-hydroxycyclohexylamino)-8-(2,4,6-trifluorophenylamino)-9H-purin-9-yl)cyclohexanecarboxamide;

(1s,4s)-4-(8-(2,6-difluorophenylamino)-2-((1R,3R)-3-hydroxycyclohexylamino)-9H-purin-9-yl)cyclohexanecarboxamide;

(1s,4s)-4-(8-(2-chloro-4,6-difluorophenylamino)-2-((1R,3R)-3-hydroxycyclohexylamino)-9H-purin-9-yl)cyclohexanecarboxamide;

(1s,4s)-4-(8-(4-chloro-2,6-difluorophenylamino)-2-((1R,3R)-3-hydroxycyclohexylamino)-9H-purin-9-yl)cyclohexanecarboxamide;

(1s,4s)-4-(8-(2,4-dichloro-6-fluorophenylamino)-2-((1R,3R)-3-hydroxycyclohexylamino)-9H-purin-9-yl)cyclohexanecarboxamide;

(1s,4s)-4-(8-(2,6-dichloro-4-fluorophenylamino)-2-((1R,3R)-3-hydroxycyclohexylamino)-9H-purin-9-yl)cyclohexanecarboxamide;

(1s,4s)-4-(8-(2,6-dichlorophenylamino)-2-((1R,3S)-3-hydroxy-3-methylcyclohexylamino)-9H-purin-9-yl)cyclohexanecarboxamide;

(1s,4s)-4-(8-(2-chloro-4,6-difluorophenylamino)-2-((1R,3S)-3-hydroxy-3-methylcyclohexylamino)-9H-purin-9-yl)cyclohexanecarboxamide;

(1s,4s)-4-(8-(4-chloro-2,6-difluorophenylamino)-2-((1R,3S)-3-hydroxy-3-methylcyclohexylamino)-9H-purin-9-yl)cyclohexanecarboxamide;

(1s,4s)-4-(8-(2,4-dichloro-6-fluorophenylamino)-2-((1R,3S)-3-hydroxy-3-methylcyclohexylamino)-9H-purin-9-yl)cyclohexanecarboxamide;

(1s,4s)-4-(8-(2,6-dichloro-4-fluorophenylamino)-2-((1R,3S)-3-hydroxy-3-methylcyclohexylamino)-9H-purin-9-yl)cyclohexanecarboxamide;

(1s,4s)-4-(8-(2-chloro-4-fluorophenylamino)-2-((1R,3S)-3-hydroxy-3-methylcyclohexylamino)-9H-purin-9-yl)cyclohexanecarboxamide;

(1s,4s)-4-(8-(2-chloro-4-cyano-6-fluorophenylamino)-2-(isopropylamino)-9H-purin-9-yl)cyclohexanecarboxamide;

(1s,4s)-4-(8-(2,6-dichloro-4-cyanophenylamino)-2-(isopropylamino)-9H-purin-9-yl)cyclohexanecarboxamide;

(1r,4s)-4-(8-(2,6-dichloro-4-cyanophenylamino)-2-((S)-1-hydroxybutan-2-ylamino)-9H-purin-9-yl)cyclohexanecarboxamide;

(1r,4s)-4-(8-(2-chloro-4-cyano-6-fluorophenylamino)-2-((S)-1-hydroxybutan-2-ylamino)-9H-purin-9-yl)cyclohexanecarboxamide;

(1s,4s)-4-(2-((1R,3S)-3-hydroxycycloheptylamino)-8-(2,4,6-trifluorophenylamino)-9H-purin-9-yl)cyclohexanecarboxamide;

(1s,4s)-4-(8-(2,6-dichlorophenylamino)-2-((1R,3S)-3-hydroxycycloheptylamino)-9H-purin-9-yl)cyclohexanecarboxamide;

(1s,4s)-4-(8-(2-chloro-6-fluorophenylamino)-2-((1R,3S)-3-hydroxycycloheptylamino)-9H-purin-9-yl)cyclohexanecarboxamide;

(1s,4s)-4-(8-(2-chloro-4,6-difluorophenylamino)-2-((1R,3S)-3-hydroxycycloheptylamino)-9H-purin-9-yl)cyclohexanecarboxamide;

(1s,4s)-4-(8-(4-chloro-2,6-difluorophenylamino)-2-((1R,3S)-3-hydroxycycloheptylamino)-9H-purin-9-yl)cyclohexanecarboxamide;

(1s,4s)-4-(2-((1R,3S)-3-hydroxycycloheptylamino)-8-(2,4,6-trichlorophenylamino)-9H-purin-9-yl)cyclohexanecarboxamide;

(1s,4s)-4-(8-(4-chloro-2,3-difluorophenylamino)-2-((1R,3S)-3-hydroxycycloheptylamino)-9H-purin-9-yl)cyclohexanecarboxamide;

(1s,4s)-4-(8-(4-cyano-2,6-difluorophenylamino)-2-(isopropylamino)-9H-purin-9-yl)cyclohexanecarboxamide;

(1s,4s)-4-(8-(2,6-dichloro-4-(trifluoromethyl)phenylamino)-2-(tetrahydro-2H-pyran-4-ylamino)-9H-purin-9-yl)cyclohexanecarboxamide;

(1s,4s)-4-(8-(2,6-dichloro-3-cyanophenylamino)-2-(tetrahydro-2H-pyran-4-ylamino)-9H-purin-9-yl)cyclohexanecarboxamide;

(1r,4s)-4-(2-((1S,3R)-3-hydroxycycloheptylamino)-8-(2,4,6-trichlorophenylamino)-9H-purin-9-yl)cyclohexanecarboxamide;

(1s,4s)-4-(8-(4-chloro-2,6-difluorophenylamino)-2-((2S,4R)-2-(hydroxymethyl)tetrahydro-2H-pyran-4-ylamino)-9H-purin-9-yl)cyclohexanecarboxamide;

(1s,4s)-4-(2-((2 S,4R)-2-(hydroxymethyl)tetrahydro-2H-pyran-4-ylamino)-8-(2,4,6-trifluorophenylamino)-9H-purin-9-yl)cyclohexanecarboxamide;

(1s,4s)-4-(8-(3-cyano-2,6-difluorophenylamino)-2-(tetrahydro-2H-pyran-4-ylamino)-9H-purin-9-yl)cyclohexanecarboxamide;

(1r,4s)-4-(8-(2-chloro-4-cyano-6-fluorophenylamino)-2-((1S,3S)-3-hydroxycycloheptylamino)-9H-purin-9-yl)cyclohexanecarboxamide;

(1r,4s)-4-(8-(2,6-dichloro-4-cyanophenylamino)-2-((1S,3S)-3-hydroxycycloheptylamino)-9H-purin-9-yl)cyclohexanecarboxamide;

(1s,4s)-4-(2-(2,2-difluoro-3-hydroxypropylamino)-8-(2,4,6-trichlorophenylamino)-9H-purin-9-yl)cyclohexanecarboxamide;

(1s,4s)-4-(8-(2,4-dichloro-6-fluorophenylamino)-2-(2,2-difluoro-3-hydroxypropylamino)-9H-purin-9-yl)cyclohexanecarboxamide;

(1s,4s)-4-(8-(2,6-dichloro-4-fluorophenylamino)-2-(2,2-difluoro-3-hydroxypropylamino)-9H-purin-9-yl)cyclohexanecarboxamide;

(1s,4s)-4-(8-(4-chloro-2,6-difluorophenylamino)-2-(2,2-difluoro-3-hydroxypropylamino)-9H-purin-9-yl)cyclohexanecarboxamide;

(1s,4s)-4-(8-(2,6-dichloro-4-(trifluoromethyl)phenylamino)-2-((1R,3S)-3-hydroxycyclohexylamino)-9H-purin-9-yl)cyclohexanecarboxamide;

(1s,4s)-4-(8-(2,6-dichloro-4-cyanophenylamino)-2-((1R,3S)-3-hydroxycyclohexylamino)-9H-purin-9-yl)cyclohexanecarboxamide;

(1s,4s)-4-(8-(2-chloro-4-cyano-6-fluorophenylamino)-2-((1R,3S)-3-hydroxycyclohexylamino)-9H-purin-9-yl)cyclohexanecarboxamide;

(1s,4s)-4-(8-(4-cyano-2,6-difluorophenylamino)-2-((1R,3S)-3-hydroxycyclohexylamino)-9H-purin-9-yl)cyclohexanecarboxamide;

(1r,4s)-4-(2-((1S,3S)-3-hydroxycyclohexylamino)-8-(2,4,6-trifluorophenylamino)-9H-purin-9-yl)cyclohexanecarboxamide;

(1r,4s)-4-(8-(2-chloro-4,6-difluorophenylamino)-2-((1S,3S)-3-hydroxycyclohexylamino)-9H-purin-9-yl)cyclohexanecarboxamide;

(1r,4s)-4-(8-(4-chloro-2,6-difluorophenylamino)-2-((1S,3S)-3-hydroxycyclohexylamino)-9H-purin-9-yl)cyclohexanecarboxamide;

(1r,4s)-4-(2-((1S,3S)-3-hydroxycyclohexylamino)-8-(2,4,6-trichlorophenylamino)-9H-purin-9-yl)cyclohexanecarboxamide;

(1r,4s)-4-(8-(2,6-dichloro-4-fluorophenylamino)-2-((1S,3S)-3-hydroxycyclohexylamino)-9H-purin-9-yl)cyclohexanecarboxamide;

(1r,4s)-4-(8-(4-chloro-2,3-difluorophenylamino)-2-((1S,3S)-3-hydroxycyclohexylamino)-9H-purin-9-yl)cyclohexanecarboxamide;

(1r,4s)-4-(8-(2,4-dichloro-6-fluorophenylamino)-2-((1S,3S)-3-hydroxycyclohexylamino)-9H-purin-9-yl)cyclohexanecarboxamide;

(1r,4s)-4-(8-(4-chloro-2,5-difluorophenylamino)-2-((1S,3S)-3-hydroxycyclohexylamino)-9H-purin-9-yl)cyclohexanecarboxamide;

(1s,4s)-4-(8-(2-chloro-4,6-difluorophenylamino)-2-((1R,2R)-2-hydroxycyclohexylamino)-9H-purin-9-yl)cyclohexanecarboxamide;

(1s,4s)-4-(8-(4-chloro-2,6-difluorophenylamino)-2-((1R,2R)-2-hydroxycyclohexylamino)-9H-purin-9-yl)cyclohexanecarboxamide;

(1s,4s)-4-(2-((1R,2R)-2-hydroxycyclohexylamino)-8-(2,4,6-trichlorophenylamino)-9H-purin-9-yl)cyclohexanecarboxamide;

(1s,4s)-4-(8-(2,6-dichloro-4-fluorophenylamino)-2-((1R,2R)-2-hydroxycyclohexylamino)-9H-purin-9-yl)cyclohexanecarboxamide;

(1s,4s)-4-(8-(2,4-dichloro-6-fluorophenylamino)-2-((1R,2R)-2-hydroxycyclohexylamino)-9H-purin-9-yl)cyclohexanecarboxamide;

(1s,4s)-4-(8-(2,4-dichloro-6-fluorophenylamino)-2-((R)-1,1,1-trifluoro-3-hydroxypropan-2-ylamino)-9H-purin-9-yl)cyclohexanecarboxamide;

(1s,4s)-4-(8-(2,6-dichloro-4-cyanophenylamino)-2-((R)-1,1,1-trifluoro-3-hydroxypropan-2-ylamino)-9H-purin-9-yl)cyclohexanecarboxamide;

(1r,4r)-4-(8-(4-chloro-2,6-difluorophenylamino)-2-(tetrahydro-2H-pyran-4-ylamino)-9H-purin-9-yl)-1-methylcyclohexanecarboxamide;

(1r,4r)-1-methyl-4-(2-(tetrahydro-2H-pyran-4-ylamino)-8-(2,4,6-trichlorophenylamino)-9H-purin-9-yl)cyclohexanecarboxamide;

(1r,4r)-4-(8-(2,6-dichloro-4-cyanophenylamino)-2-(tetrahydro-2H-pyran-4-ylamino)-9H-purin-9-yl)-1-methylcyclohexanecarboxamide;

(1r,4r)-4-(8-(2,6-dichloro-4-fluorophenylamino)-2-(4,4-difluorocyclohexylamino)-9H-purin-9-yl)-1-methylcyclohexanecarboxamide;

(1r,4r)-4-(8-(2-chloro-4,6-difluorophenylamino)-2-(4,4-difluorocyclohexylamino)-9H-purin-9-yl)-1-methylcyclohexanecarboxamide;

(1r,4r)-4-(8-(2,4-dichloro-6-fluorophenylamino)-2-(4,4-difluorocyclohexylamino)-9H-purin-9-yl)-1-methylcyclohexanecarboxamide;

(1r,4r)-4-(8-(2,6-dichloro-4-cyanophenylamino)-2-(4,4-difluorocyclohexylamino)-9H-purin-9-yl)-1-methylcyclohexanecarboxamide;

(1S,4r)-4-(8-(2,6-dichloro-4-(trifluoromethyl)phenylamino)-2-((S)-1-hydroxypropan-2-ylamino)-9H-purin-9-yl)-1-methylcyclohexanecarboxamide;

(1S,4r)-4-(2-((S)-1-hydroxypropan-2-ylamino)-8-(2,4,6-trichlorophenylamino)-9H-purin-9-yl)-1-methylcyclohexanecarboxamide;

(1s,4s)-4-(8-(2,6-dichloro-4-cyanophenylamino)-2-(3-hydroxy-2,2-dimethylpropylamino)-9H-purin-9-yl)cyclohexanecarboxamide;

(1s,4s)-4-(2-((1R,2S)-2-hydroxycyclohexylamino)-8-(2,4,6-trichlorophenylamino)-9H-purin-9-yl)cyclohexanecarboxamide;

(1R,4r)-4-(8-(2,4-dichloro-6-fluorophenylamino)-2-((1R,3S)-3-hydroxycyclohexylamino)-9H-purin-9-yl)-1-methylcyclohexanecarboxamide;

(1r,4r)-4-(2-(cyclopentylamino)-8-(2,6-dichloro-4-cyanophenylamino)-9H-purin-9-yl)-1-methylcyclohexanecarboxamide;

(1r,4r)-4-(8-(2-chloro-4-cyano-6-fluorophenylamino)-2-(cyclopentylamino)-9H-purin-9-yl)-1-methylcyclohexanecarboxamide;

(1r,4r)-4-(8-(4-cyano-2,6-difluorophenylamino)-2-(cyclopentylamino)-9H-purin-9-yl)-1-methylcyclohexanecarboxamide;

(1r,4r)-4-(2-(cyclopentylamino)-8-(2,6-dichloro-4-(trifluoromethyl)phenylamino)-9H-purin-9-yl)-1-methylcyclohexanecarboxamide;

(1r,4r)-4-(8-(4-chloro-2,6-difluorophenylamino)-2-(cyclopentylamino)-9H-purin-9-yl)-1-methylcyclohexanecarboxamide;

(1r,4r)-4-(2-(cyclopentylamino)-8-(2,4,6-trichlorophenylamino)-9H-purin-9-yl)-1-methylcyclohexanecarboxamide;

(1r,4r)-4-(8-(2-chloro-4,6-difluorophenylamino)-2-(cyclopentylamino)-9H-purin-9-yl)-1-methylcyclohexanecarboxamide;

(1r,4r)-4-(2-(cyclopentylamino)-8-(2,4-dichloro-6-fluorophenylamino)-9H-purin-9-yl)-1-methylcyclohexanecarboxamide;

(1r,4r)-4-(2-(cyclopentylamino)-8-(2,6-dichloro-4-fluorophenylamino)-9H-purin-9-yl)-1-methylcyclohexanecarboxamide;

(1r,4r)-4-(2-(cyclopentylamino)-8-(2,4,6-trifluorophenylamino)-9H-purin-9-yl)-1-methylcyclohexanecarboxamide;

(1s,4s)-4-(8-(2,6-dichloro-4-cyanophenylamino)-2-((3S,4R)-3-methyltetrahydro-2H-pyran-4-ylamino)-9H-purin-9-yl)cyclohexanecarboxamide;

(1s,4s)-4-(8-(2,6-dichloro-4-cyanophenylamino)-2-((3R,4S)-3-methyltetrahydro-2H-pyran-4-ylamino)-9H-purin-9-yl)cyclohexanecarboxamide;

(1s,4s)-4-(8-(2,6-dichloro-4-cyanophenylamino)-2-((3R,4R)-3-methyltetrahydro-2H-pyran-4-ylamino)-9H-purin-9-yl)cyclohexanecarboxamide;

(1r,4s)-4-(8-(2,6-dichloro-4-cyanophenylamino)-2-((3S,4S)-3-methyltetrahydro-2H-pyran-4-ylamino)-9H-purin-9-yl)cyclohexanecarboxamide;

(1s,4s)-4-(2-((3S,4R)-3-methyltetrahydro-2H-pyran-4-ylamino)-8-(2,4,6-trichlorophenylamino)-9H-purin-9-yl)cyclohexanecarboxamide;

(1r,4s)-4-(2-((3R,4S)-3-methyltetrahydro-2H-pyran-4-ylamino)-8-(2,4,6-trichlorophenylamino)-9H-purin-9-yl)cyclohexanecarboxamide;

(1s,4s)-4-(2-((3R,4R)-3-methyltetrahydro-2H-pyran-4-ylamino)-8-(2,4,6-trichlorophenylamino)-9H-purin-9-yl)cyclohexanecarboxamide;

(1r,4s)-4-(2-((3S,4S)-3-methyltetrahydro-2H-pyran-4-ylamino)-8-(2,4,6-trichlorophenylamino)-9H-purin-9-yl)cyclohexanecarboxamide;

(1s,4s)-4-(8-(2,4-dichloro-6-fluorophenylamino)-2-((3S,4R)-3-methyltetrahydro-2H-pyran-4-ylamino)-9H-purin-9-yl)cyclohexanecarboxamide;

(1r,4s)-4-(8-(2,4-dichloro-6-fluorophenylamino)-2-((3R,4S)-3-methyltetrahydro-2H-pyran-4-ylamino)-9H-purin-9-yl)cyclohexanecarboxamide;

(1s,4s)-4-(8-(2,4-dichloro-6-fluorophenylamino)-2-((3R,4R)-3-methyltetrahydro-2H-pyran-4-ylamino)-9H-purin-9-yl)cyclohexanecarboxamide;

(1r,4s)-4-(8-(2,4-dichloro-6-fluorophenylamino)-2-((3S,4S)-3-methyltetrahydro-2H-pyran-4-ylamino)-9H-purin-9-yl)cyclohexanecarboxamide;

(1r,4s)-4-(8-(4-chloro-2,6-difluorophenylamino)-2-((3R,4 S)-3-methyltetrahydro-2H-pyran-4-ylamino)-9H-purin-9-yl)cyclohexanecarboxamide;

(1s,4s)-4-(8-(4-chloro-2,6-difluorophenylamino)-2-((3R,4R)-3-methyltetrahydro-2H-pyran-4-ylamino)-9H-purin-9-yl)cyclohexanecarboxamide;

(1r,4s)-4-(8-(4-chloro-2,6-difluorophenylamino)-2-((3S,4S)-3-methyltetrahydro-2H-pyran-4-ylamino)-9H-purin-9-yl)cyclohexanecarboxamide;

(1r,4s)-4-(2-((3R,4S)-3-methyltetrahydro-2H-pyran-4-ylamino)-8-(2,4,6-trifluorophenylamino)-9H-purin-9-yl)cyclohexanecarboxamide;

(1r,4s)-4-(2-((3S,4S)-3-methyltetrahydro-2H-pyran-4-ylamino)-8-(2,4,6-trifluorophenylamino)-9H-purin-9-yl)cyclohexanecarboxamide;

(1r,4s)-4-(2-((1S,2R)-2-hydroxycyclohexylamino)-8-(2,4,6-trifluorophenylamino)-9H-purin-9-yl)cyclohexanecarboxamide;

(1r,4s)-4-(8-(2,4-dichloro-6-fluorophenylamino)-2-((1S,2R)-2-hydroxycyclohexylamino)-9H-purin-9-yl)cyclohexanecarboxamide;

(1r,4s)-4-(2-((1S,2R)-2-hydroxycyclohexylamino)-8-(2,4,6-trichlorophenylamino)-9H-purin-9-yl)cyclohexanecarboxamide;

(1r,4s)-4-(8-(4-chloro-2,6-difluorophenylamino)-2-((1S,2R)-2-hydroxycyclohexylamino)-9H-purin-9-yl)cyclohexanecarboxamide;

(1r,4s)-4-(8-(2,6-dichloro-4-fluorophenylamino)-2-((1S,2R)-2-hydroxycyclohexylamino)-9H-purin-9-yl)cyclohexanecarboxamide;

(1r,4s)-4-(8-(2-chloro-4-cyano-6-fluorophenylamino)-2-((1S,2R)-2-hydroxycyclohexylamino)-9H-purin-9-yl)cyclohexanecarboxamide;

(1s,4s)-4-(8-(2,6-dichloro-4-cyanophenylamino)-2-((R)-tetrahydrofuran-3-ylamino)-9H-purin-9-yl)cyclohexanecarboxamide;

(1r,4s)-4-(8-(2,6-dichloro-4-cyanophenylamino)-2-((1S,2R)-2-hydroxycyclohexylamino)-9H-purin-9-yl)cyclohexanecarboxamide;

(1s,4s)-4-(8-(2-chloro-4-cyano-6-fluorophenylamino)-2-((R)-tetrahydrofuran-3-ylamino)-9H-purin-9-yl)cyclohexanecarboxamide;

(1s,4s)-4-(8-(4-chloro-2,6-difluorophenylamino)-2-(tetrahydro-2H-pyran-4-ylamino)-9H-purin-9-yl)-1-methylcyclohexanecarboxamide;

(1s,4s)-1-methyl-4-(2-(tetrahydro-2H-pyran-4-ylamino)-8-(2,4,6-trichlorophenylamino)-9H-purin-9-yl)cyclohexanecarboxamide;

(1s,4s)-4-(8-(2,6-dichloro-4-(trifluoromethyl)phenylamino)-2-((R)-tetrahydrofuran-3-ylamino)-9H-purin-9-yl)cyclohexanecarboxamide;

(1s,4s)-4-(8-(4-cyano-2,6-difluorophenylamino)-2-(tetrahydro-2H-pyran-4-ylamino)-9H-purin-9-yl)-1-methylcyclohexanecarboxamide;

(1s,4s)-4-(8-(2-chloro-4-cyano-6-fluorophenylamino)-2-(tetrahydro-2H-pyran-4-ylamino)-9H-purin-9-yl)-1-methylcyclohexanecarboxamide;

(1s,4s)-4-(8-(2,6-dichloro-4-fluorophenylamino)-2-(4,4-difluorocyclohexylamino)-9H-purin-9-yl)-1-methylcyclohexanecarboxamide;

(1s,4s)-4-(8-(2-chloro-4,6-difluorophenylamino)-2-(4,4-difluorocyclohexylamino)-9H-purin-9-yl)-1-methylcyclohexanecarboxamide;

(1s,4s)-4-(8-(2,4-dichloro-6-fluorophenylamino)-2-(4,4-difluorocyclohexylamino)-9H-purin-9-yl)-1-methylcyclohexanecarboxamide;

(1s,4s)-4-(8-(4-cyano-2,6-difluorophenylamino)-2-((R)-tetrahydrofuran-3-ylamino)-9H-purin-9-yl)cyclohexanecarboxamide;

(1s,4s)-4-(2-((R)-tetrahydrofuran-3-ylamino)-8-(2,4,6-trifluorophenylamino)-9H-purin-9-yl)cyclohexanecarboxamide;

(1s,4s)-4-(2-(1-morpholinopropan-2-ylamino)-8-(2,4,6-trichlorophenylamino)-9H-purin-9-yl)cyclohexanecarboxamide;

(1s,4s)-4-(8-(4-chloro-2,6-difluorophenylamino)-2-((3S,4R)-3-methyltetrahydro-2H-pyran-4-ylamino)-9H-purin-9-yl)cyclohexanecarboxamide;

(1s,4s)-4-(2-((3S,4R)-3-methyltetrahydro-2H-pyran-4-ylamino)-8-(2,4,6-trifluorophenylamino)-9H-purin-9-yl)cyclohexanecarboxamide;

(1s,4s)-4-(8-(2,6-dichloro-4-cyanophenylamino)-2-(4,4-difluorocyclohexylamino)-9H-purin-9-yl)-1-methylcyclohexanecarboxamide;

(1s,4s)-4-(8-(2,6-dichloro-4-cyanophenylamino)-2-(tetrahydro-2H-pyran-4-ylamino)-9H-purin-9-yl)-1-methylcyclohexanecarboxamide;

(1s,4s)-4-(2-(oxepan-4-ylamino)-8-(2,4,6-trifluorophenylamino)-9H-purin-9-yl)cyclohexanecarboxamide;

(1s,4s)-4-(8-(2,4-dichloro-6-fluorophenylamino)-2-(oxepan-4-ylamino)-9H-purin-9-yl)cyclohexanecarboxamide;

(1s,4s)-4-(8-(2-chloro-4,6-difluorophenylamino)-2-(oxepan-4-ylamino)-9H-purin-9-yl)cyclohexanecarboxamide;

(1s,4s)-4-(2-(oxepan-4-ylamino)-8-(2,4,6-trichlorophenylamino)-9H-purin-9-yl)cyclohexanecarboxamide;

(1s,4s)-4-(8-(4-chloro-2,6-difluorophenylamino)-2-(oxepan-4-ylamino)-9H-purin-9-yl)cyclohexanecarboxamide;

(1s,4s)-4-(8-(2,6-dichloro-4-fluorophenylamino)-2-(oxepan-4-ylamino)-9H-purin-9-yl)cyclohexanecarboxamide;

(1s,4s)-4-(8-(4-cyano-2,6-difluorophenylamino)-2-(oxepan-4-ylamino)-9H-purin-9-yl)cyclohexanecarboxamide;

(1s,4s)-4-(8-(2-chloro-4-cyano-6-fluorophenylamino)-2-(oxepan-4-ylamino)-9H-purin-9-yl)cyclohexanecarboxamide;

(1s,4s)-4-(8-(2,6-dichloro-4-(trifluoromethyl)phenylamino)-2-(oxepan-4-ylamino)-9H-purin-9-yl)cyclohexanecarboxamide;

(1s,4s)-4-(2-((R)-3,3-difluorocyclopentylamino)-8-(2,4,6-trifluorophenylamino)-9H-purin-9-yl)cyclohexanecarboxamide;

(1r,4s)-4-(2-((S)-1-hydroxypropan-2-ylamino)-8-(2,4,6-trifluorophenylamino)-9H-purin-9-yl)-1-methylcyclohexanecarboxamide;

(1r,4s)-4-(8-(2,4-dichloro-6-fluorophenylamino)-2-((S)-1-hydroxypropan-2-ylamino)-9H-purin-9-yl)-1-methylcyclohexanecarboxamide;

(1r,4s)-4-(8-(2-chloro-4,6-difluorophenylamino)-2-((S)-1-hydroxypropan-2-ylamino)-9H-purin-9-yl)-1-methylcyclohexanecarboxamide;

(1r,4s)-4-(2-((S)-1-hydroxypropan-2-ylamino)-8-(2,4,6-trichlorophenylamino)-9H-purin-9-yl)-1-methylcyclohexanecarboxamide;

(1r,4s)-4-(8-(4-chloro-2,6-difluorophenylamino)-2-((S)-1-hydroxypropan-2-ylamino)-9H-purin-9-yl)-1-methylcyclohexanecarboxamide;

(1r,4s)-4-(8-(2,6-dichloro-4-fluorophenylamino)-2-((S)-1-hydroxypropan-2-ylamino)-9H-purin-9-yl)-1-methylcyclohexanecarboxamide;

(1r,4s)-4-(8-(2-chloro-4-cyano-6-fluorophenylamino)-2-((S)-1-hydroxypropan-2-ylamino)-9H-purin-9-yl)-1-methylcyclohexanecarboxamide;

(1r,4s)-4-(8-(2,6-dichloro-4-cyanophenylamino)-2-((S)-1-hydroxypropan-2-ylamino)-9H-purin-9-yl)-1-methylcyclohexanecarboxamide;

(1r,4s)-4-(8-(2,6-dichloro-4-(trifluoromethyl)phenylamino)-2-((S)-1-hydroxypropan-2-ylamino)-9H-purin-9-yl)-1-methylcyclohexanecarboxamide;

(1s,4s)-4-(8-(2,6-dichloro-4-cyanophenylamino)-2-(oxepan-4-ylamino)-9H-purin-9-yl)cyclohexanecarboxamide;

(1s,4s)-4-(2-(cyclopentylamino)-8-(2,4,6-trifluorophenylamino)-9H-purin-9-yl)-1-methylcyclohexanecarboxamide;

(1s,4s)-4-(2-(cyclopentylamino)-8-(2,4-dichloro-6-fluorophenylamino)-9H-purin-9-yl)-1-methylcyclohexanecarboxamide;

(1s,4s)-4-(8-(2-chloro-4,6-difluorophenylamino)-2-(cyclopentylamino)-9H-purin-9-yl)-1-methylcyclohexanecarboxamide;

(1s,4s)-4-(8-(4-chloro-2,6-difluorophenylamino)-2-(cyclopentylamino)-9H-purin-9-yl)-1-methylcyclohexanecarboxamide;

(1s,4s)-4-(2-(cyclopentylamino)-8-(2,6-dichloro-4-fluorophenylamino)-9H-purin-9-yl)-1-methylcyclohexanecarboxamide;

(1s,4s)-4-(2-(cyclopentylamino)-8-(2,6-dichloro-4-cyanophenylamino)-9H-purin-9-yl)-1-methylcyclohexanecarboxamide;

(1s,4s)-4-(2-(cyclopentylamino)-8-(2,6-dichloro-4-(trifluoromethyl)phenylamino)-9H-purin-9-yl)-1-methylcyclohexanecarboxamide;

(1s,4s)-4-(2-((1R,3S)-3-hydroxycyclohexylamino)-8-(2,4,6-trifluorophenylamino)-9H-purin-9-yl)-1-methylcyclohexanecarboxamide;

(1s,4s)-4-(8-(2,4-dichloro-6-fluorophenylamino)-2-((1R,3S)-3-hydroxycyclohexylamino)-9H-purin-9-yl)-1-methylcyclohexanecarboxamide;

(1s,4s)-4-(2-((1R,3S)-3-hydroxycyclohexylamino)-8-(2,4,6-trichlorophenylamino)-9H-purin-9-yl)-1-methylcyclohexanecarboxamide;

(1s,4s)-4-(8-(4-chloro-2,6-difluorophenylamino)-2-((1R,3S)-3-hydroxycyclohexylamino)-9H-purin-9-yl)-1-methylcyclohexanecarboxamide;

(1s,4s)-4-(8-(2,6-dichloro-4-fluorophenylamino)-2-((1R,3S)-3-hydroxycyclohexylamino)-9H-purin-9-yl)-1-methylcyclohexanecarboxamide;

(1s,4s)-4-(8-(2-chloro-4-cyano-6-fluorophenylamino)-2-((1R,3S)-3-hydroxycyclohexylamino)-9H-purin-9-yl)-1-methylcyclohexanecarboxamide;

(1s,4s)-4-(8-(2,6-dichloro-4-cyanophenylamino)-2-((1R,3S)-3-hydroxycyclohexylamino)-9H-purin-9-yl)-1-methylcyclohexanecarboxamide;

(1s,4s)-4-(2-(2-oxaspiro[3.3]heptan-6-ylamino)-8-(2,6-dichloro-4-(trifluoromethyl)phenylamino)-9H-purin-9-yl)cyclohexanecarboxamide;

(1s,4s)-4-(2-(2-oxaspiro[3.3]heptan-6-ylamino)-8-(2,6-dichloro-4-cyanophenylamino)-9H-purin-9-yl)cyclohexanecarboxamide;

(1s,4s)-4-(2-(2-oxaspiro[3.3]heptan-6-ylamino)-8-(2-chloro-4-cyano-6-fluorophenylamino)-9H-purin-9-yl)cyclohexanecarboxamide;

(1s,4s)-4-(2-(2-oxaspiro[3.3]heptan-6-ylamino)-8-(4-cyano-2,6-difluorophenylamino)-9H-purin-9-yl)cyclohexanecarboxamide;

(1s,4s)-4-(2-(cyclopentylamino)-8-(2,4,6-trichlorophenylamino)-9H-purin-9-yl)-1-methylcyclohexanecarboxamide;

(1s,4s)-4-(8-(2-chloro-4-cyano-6-fluorophenylamino)-2-(cyclopentylamino)-9H-purin-9-yl)-1-methylcyclohexanecarboxamide;

(1s,4s)-4-(8-(2-chloro-4,6-difluorophenylamino)-2-((1R,3S)-3-hydroxycyclohexylamino)-9H-purin-9-yl)-1-methylcyclohexanecarboxamide;

(1s,4s)-4-(8-(2,6-dichloro-4-(trifluoromethyl)phenylamino)-2-((1R,3S)-3-hydroxycyclohexylamino)-9H-purin-9-yl)-1-methylcyclohexanecarboxamide;

(1s,4s)-4-(2-(3,3-difluorocyclobutylamino)-8-(2,4,6-trifluorophenylamino)-9H-purin-9-yl)-1-methylcyclohexanecarboxamide;

(1s,4s)-4-(8-(2-chloro-4,6-difluorophenylamino)-2-(3,3-difluorocyclobutylamino)-9H-purin-9-yl)-1-methylcyclohexanecarboxamide;

(1s,4s)-4-(2-(3,3-difluorocyclobutylamino)-8-(2,4,6-trichlorophenylamino)-9H-purin-9-yl)-1-methylcyclohexanecarboxamide;

(1s,4s)-4-(8-(4-chloro-2,6-difluorophenylamino)-2-(3,3-difluorocyclobutylamino)-9H-purin-9-yl)-1-methylcyclohexanecarboxamide;

(1s,4s)-4-(8-(2,6-dichloro-4-fluorophenylamino)-2-(3,3-difluorocyclobutylamino)-9H-purin-9-yl)-1-methylcyclohexanecarboxamide;

(1s,4s)-4-(8-(2-chloro-4-cyano-6-fluorophenylamino)-2-(3,3-difluorocyclobutylamino)-9H-purin-9-yl)-1-methylcyclohexanecarboxamide;

(1s,4s)-4-(8-(2,6-dichloro-4-(trifluoromethyl)phenylamino)-2-(3,3-difluorocyclobutylamino)-9H-purin-9-yl)-1-methylcyclohexanecarboxamide;

(1r,4s)-4-(8-(2,6-dichloro-4-fluorophenylamino)-2-((S)-3,3-difluorocyclopentylamino)-9H-purin-9-yl)cyclohexanecarboxamide;

(1s,4s)-4-(8-(2,6-dichloro-4-fluorophenylamino)-2-((R)-3,3-difluorocyclopentylamino)-9H-purin-9-yl)cyclohexanecarboxamide;

(1r,4s)-4-(8-(4-chloro-2,6-difluorophenylamino)-2-((S)-3,3-difluorocyclopentylamino)-9H-purin-9-yl)cyclohexanecarboxamide;

(1s,4s)-4-(8-(4-chloro-2,6-difluorophenylamino)-2-((R)-3,3-difluorocyclopentylamino)-9H-purin-9-yl)cyclohexanecarboxamide;

(1r,4s)-4-(8-(2-chloro-4,6-difluorophenylamino)-2-((S)-3,3-difluorocyclopentylamino)-9H-purin-9-yl)cyclohexanecarboxamide;

(1s,4s)-4-(8-(2-chloro-4,6-difluorophenylamino)-2-((R)-3,3-difluorocyclopentylamino)-9H-purin-9-yl)cyclohexanecarboxamide;

(1r,4s)-4-(8-(2,4-dichloro-6-fluorophenylamino)-2-((S)-3,3-difluorocyclopentylamino)-9H-purin-9-yl)cyclohexanecarboxamide;

(1s,4s)-4-(8-(2,4-dichloro-6-fluorophenylamino)-2-((R)-3,3-difluorocyclopentylamino)-9H-purin-9-yl)cyclohexanecarboxamide;

(1r,4s)-4-(2-((S)-3,3-difluorocyclopentylamino)-8-(2,4,6-trifluorophenylamino)-9H-purin-9-yl)cyclohexanecarboxamide;

(1r,4s)-4-(2-((S)-3,3-difluorocyclopentylamino)-8-(2,4,6-trichlorophenylamino)-9H-purin-9-yl)cyclohexanecarboxamide;

(1s,4s)-4-(8-(2,6-dichloro-4-(trifluoromethoxy)phenylamino)-2-((1R,3S)-3-hydroxycyclohexylamino)-9H-purin-9-yl)cyclohexanecarboxamide;

(1s,4s)-4-(8-(2,6-dichloro-4-(trifluoromethoxy)phenylamino)-2-(4,4-difluorocyclohexylamino)-9H-purin-9-yl)cyclohexanecarboxamide;

(1s,4s)-4-(2-(cyclopentylamino)-8-(2,6-dichloro-4-(trifluoromethoxy)phenylamino)-9H-purin-9-yl)cyclohexanecarboxamide;

(1s,4s)-4-(2-(cyclobutylamino)-8-(2,6-dichloro-4-(trifluoromethoxy)phenylamino)-9H-purin-9-yl)-1-methylcyclohexanecarboxamide;

(1s,4s)-4-(2-(cyclobutylamino)-8-(2,6-dichloro-4-cyanophenylamino)-9H-purin-9-yl)-1-methylcyclohexanecarboxamide;

(1s,4s)-4-(8-(2-chloro-4-cyano-6-fluorophenylamino)-2-(cyclobutylamino)-9H-purin-9-yl)-1-methylcyclohexanecarboxamide;

(1s,4s)-4-(8-(4-cyano-2,6-difluorophenylamino)-2-(cyclobutylamino)-9H-purin-9-yl)-1-methylcyclohexanecarboxamide;

(1s,4s)-4-(2-(cyclobutylamino)-8-(2,6-dichloro-4-(trifluoromethyl)phenylamino)-9H-purin-9-yl)-1-methylcyclohexanecarboxamide;

(1s,4s)-4-(2-(cyclobutylamino)-8-(2,4,6-trichlorophenylamino)-9H-purin-9-yl)-1-methylcyclohexanecarboxamide;

(1s,4s)-4-(8-(2-chloro-4,6-difluorophenylamino)-2-(cyclobutylamino)-9H-purin-9-yl)-1-methylcyclohexanecarboxamide;

(1s,4s)-4-(2-(cyclobutylamino)-8-(2,4-dichloro-6-fluorophenylamino)-9H-purin-9-yl)-1-methylcyclohexanecarboxamide;

(1s,4s)-4-(2-(cyclobutylamino)-8-(2,6-dichloro-4-fluorophenylamino)-9H-purin-9-yl)-1-methylcyclohexanecarboxamide;

(1s,4s)-4-(2-(cyclobutylamino)-8-(2,4,6-trifluorophenylamino)-9H-purin-9-yl)-1-methylcyclohexanecarboxamide;

(1s,4s)-4-(8-(4-chloro-2,6-difluorophenylamino)-2-(cyclobutylamino)-9H-purin-9-yl)-1-methylcyclohexanecarboxamide;

(1r,4s)-4-(2-((1S,3S)-3-hydroxycyclohexylamino)-8-(2,4,6-trifluorophenylamino)-9H-purin-9-yl)-1-methylcyclohexanecarboxamide;

(1r,4s)-4-(8-(2-chloro-4,6-difluorophenylamino)-2-((1S,3S)-3-hydroxycyclohexylamino)-9H-purin-9-yl)-1-methylcyclohexanecarboxamide;

(1r,4s)-4-(2-((1S,3S)-3-hydroxycyclohexylamino)-8-(2,4,6-trichlorophenylamino)-9H-purin-9-yl)-1-methylcyclohexanecarboxamide;

(1r,4s)-4-(8-(2,4-dichloro-6-fluorophenylamino)-2-((1S,3S)-3-hydroxycyclohexylamino)-9H-purin-9-yl)-1-methylcyclohexanecarboxamide;

(1r,4s)-4-(8-(2,6-dichloro-4-fluorophenylamino)-2-((1S,3S)-3-hydroxycyclohexylamino)-9H-purin-9-yl)-1-methylcyclohexanecarboxamide;

(1r,4s)-4-(8-(4-chloro-2,6-difluorophenylamino)-2-((1S,3S)-3-hydroxycyclohexylamino)-9H-purin-9-yl)-1-methylcyclohexanecarboxamide;

(1r,4s)-4-(8-(2-chloro-4-cyano-6-fluorophenylamino)-2-((1S,3S)-3-hydroxycyclohexylamino)-9H-purin-9-yl)-1-methylcyclohexanecarboxamide;

(1r,4s)-4-(8-(2,6-dichloro-4-cyanophenylamino)-2-((1S,3S)-3-hydroxycyclohexylamino)-9H-purin-9-yl)-1-methylcyclohexanecarboxamide;

(1s,4s)-4-(2-((1R,3R)-3-hydroxycyclohexylamino)-8-(2,4,6-trifluorophenylamino)-9H-purin-9-yl)-1-methylcyclohexanecarboxamide;

(1s,4s)-4-(8-(2-chloro-4,6-difluorophenylamino)-2-((1R,3R)-3-hydroxycyclohexylamino)-9H-purin-9-yl)-1-methylcyclohexanecarboxamide;

(1s,4s)-4-(2-((1R,3R)-3-hydroxycyclohexylamino)-8-(2,4,6-trichlorophenylamino)-9H-purin-9-yl)-1-methylcyclohexanecarboxamide;

(1s,4s)-4-(8-(2,4-dichloro-6-fluorophenylamino)-2-((1R,3R)-3-hydroxycyclohexylamino)-9H-purin-9-yl)-1-methylcyclohexanecarboxamide;

(1s,4s)-4-(8-(2,6-dichloro-4-fluorophenylamino)-2-((1R,3R)-3-hydroxycyclohexylamino)-9H-purin-9-yl)-1-methylcyclohexanecarboxamide;

(1s,4s)-4-(8-(4-chloro-2,6-difluorophenylamino)-2-((1R,3R)-3-hydroxycyclohexylamino)-9H-purin-9-yl)-1-methylcyclohexanecarboxamide;

(1s,4s)-4-(8-(2-chloro-4-cyano-6-fluorophenylamino)-2-((1R,3R)-3-hydroxycyclohexylamino)-9H-purin-9-yl)-1-methylcyclohexanecarboxamide;

(1s,4s)-4-(8-(2,6-dichloro-4-cyanophenylamino)-2-((1R,3R)-3-hydroxycyclohexylamino)-9H-purin-9-yl)-1-methylcyclohexanecarboxamide;

(1r,4s)-4-(2-((1S,3R)-3-hydroxycyclohexylamino)-8-(2,4,6-trifluorophenylamino)-9H-purin-9-yl)-1-methylcyclohexanecarboxamide;

(1r,4s)-4-(8-(2-chloro-4,6-difluorophenylamino)-2-((1S,3R)-3-hydroxycyclohexylamino)-9H-purin-9-yl)-1-methylcyclohexanecarboxamide;

(1r,4s)-4-(2-((1S,3R)-3-hydroxycyclohexylamino)-8-(2,4,6-trichlorophenylamino)-9H-purin-9-yl)-1-methylcyclohexanecarboxamide;

(1r,4s)-4-(8-(2,4-dichloro-6-fluorophenylamino)-2-((1S,3R)-3-hydroxycyclohexylamino)-9H-purin-9-yl)-1-methylcyclohexanecarboxamide;

(1s,4s)-4-(8-(2-chloro-4-cyano-6-fluorophenylamino)-2-((3S,4R)-3-fluorotetrahydro-2H-pyran-4-ylamino)-9H-purin-9-yl)cyclohexanecarboxamide;

(1s,4s)-4-(8-(2-chloro-4,6-difluorophenylamino)-2-((3S,4R)-3-fluorotetrahydro-2H-pyran-4-ylamino)-9H-purin-9-yl)cyclohexanecarboxamide;

(1r,4s)-4-(8-(2,6-dichloro-4-fluorophenylamino)-2-((1S,3R)-3-hydroxycyclohexylamino)-9H-purin-9-yl)-1-methylcyclohexanecarboxamide;

(1r,4s)-4-(8-(4-chloro-2,6-difluorophenylamino)-2-((1S,3R)-3-hydroxycyclohexylamino)-9H-purin-9-yl)-1-methylcyclohexanecarboxamide;

(1r,4s)-4-(8-(2-chloro-4-cyano-6-fluorophenylamino)-2-((1S,3R)-3-hydroxycyclohexylamino)-9H-purin-9-yl)-1-methylcyclohexanecarboxamide;

(1s,4s)-4-(2-((1R,3R)-3-hydroxycyclopentylamino)-8-(2,4,6-trifluorophenylamino)-9H-purin-9-yl)-1-methylcyclohexanecarboxamide;

(1s,4s)-4-(8-(2-chloro-4,6-difluorophenylamino)-2-((1R,3R)-3-hydroxycyclopentylamino)-9H-purin-9-yl)-1-methylcyclohexanecarboxamide;

(1s,4s)-4-(2-((1R,3R)-3-hydroxycyclopentylamino)-8-(2,4,6-trichlorophenylamino)-9H-purin-9-yl)-1-methylcyclohexanecarboxamide;

(1s,4s)-4-(8-(2,4-dichloro-6-fluorophenylamino)-2-((1R,3R)-3-hydroxycyclopentylamino)-9H-purin-9-yl)-1-methylcyclohexanecarboxamide;

(1s,4s)-4-(8-(2,6-dichloro-4-fluorophenylamino)-2-((1R,3R)-3-hydroxycyclopentylamino)-9H-purin-9-yl)-1-methylcyclohexanecarboxamide;

(1s,4s)-4-(8-(4-chloro-2,6-difluorophenylamino)-2-((1R,3R)-3-hydroxycyclopentylamino)-9H-purin-9-yl)-1-methylcyclohexanecarboxamide;

(1s,4s)-4-(8-(2-chloro-4-cyano-6-fluorophenylamino)-2-((1R,3R)-3-hydroxycyclopentylamino)-9H-purin-9-yl)-1-methylcyclohexanecarboxamide;

(1s,4s)-4-(8-(2,6-dichloro-4-cyanophenylamino)-2-((1R,3R)-3-hydroxycyclopentylamino)-9H-purin-9-yl)-1-methylcyclohexanecarboxamide;

(1s,4s)-4-(8-(4-cyano-2,6-difluorophenylamino)-2-((1R,3R)-3-hydroxycyclohexylamino)-9H-purin-9-yl)-1-methylcyclohexanecarboxamide;

(1r,4s)-4-(2-((1S,3S)-3-hydroxycyclopentylamino)-8-(2,4,6-trifluorophenylamino)-9H-purin-9-yl)-1-methylcyclohexanecarboxamide;

(1r,4s)-4-(8-(2-chloro-4,6-difluorophenylamino)-2-((1S,3S)-3-hydroxycyclopentylamino)-9H-purin-9-yl)-1-methylcyclohexanecarboxamide;

(1r,4s)-4-(2-((1S,3S)-3-hydroxycyclopentylamino)-8-(2,4,6-trichlorophenylamino)-9H-purin-9-yl)-1-methylcyclohexanecarboxamide;

(1r,4s)-4-(8-(2,4-dichloro-6-fluorophenylamino)-2-((1S,3S)-3-hydroxycyclopentylamino)-9H-purin-9-yl)-1-methylcyclohexanecarboxamide;

(1r,4s)-4-(8-(2,6-dichloro-4-fluorophenylamino)-2-((1S,3S)-3-hydroxycyclopentylamino)-9H-purin-9-yl)-1-methylcyclohexanecarboxamide;

(1r,4s)-4-(8-(4-chloro-2,6-difluorophenylamino)-2-((1S,3S)-3-hydroxycyclopentylamino)-9H-purin-9-yl)-1-methylcyclohexanecarboxamide;

(1r,4s)-4-(8-(2-chloro-4-cyano-6-fluorophenylamino)-2-((1S,3S)-3-hydroxycyclopentylamino)-9H-purin-9-yl)-1-methylcyclohexanecarboxamide;

(1r,4s)-4-(8-(2,6-dichloro-4-cyanophenylamino)-2-((1S,3S)-3-hydroxycyclopentylamino)-9H-purin-9-yl)-1-methylcyclohexanecarboxamide;

(1s,4s)-4-(8-(2,4-dichloro-6-fluorophenylamino)-2-(3,3-difluorocyclobutylamino)-9H-purin-9-yl)-1-methylcyclohexanecarboxamide;

(1r,4s)-4-(2-(((1S,2S)-2-hydroxycyclohexyl)methylamino)-8-(2,4,6-trifluorophenylamino)-9H-purin-9-yl)cyclohexanecarboxamide;

(1r,4s)-4-(8-(2-chloro-4,6-difluorophenylamino)-2-(((1S,2S)-2-hydroxycyclohexyl)methylamino)-9H-purin-9-yl)cyclohexanecarboxamide;

(1r,4s)-4-(2-(((1S,2S)-2-hydroxycyclohexyl)methylamino)-8-(2,4,6-trichlorophenylamino)-9H-purin-9-yl)cyclohexanecarboxamide;

(1r,4s)-4-(8-(2,4-dichloro-6-fluorophenylamino)-2-(((1S,2S)-2-hydroxycyclohexyl)methylamino)-9H-purin-9-yl)cyclohexanecarboxamide;

(1r,4s)-4-(8-(2,6-dichloro-4-fluorophenylamino)-2-(((1S,2S)-2-hydroxycyclohexyl)methylamino)-9H-purin-9-yl)cyclohexanecarboxamide;

(1r,4s)-4-(8-(4-chloro-2,6-difluorophenylamino)-2-(((1S,2S)-2-hydroxycyclohexyl)methylamino)-9H-purin-9-yl)cyclohexanecarboxamide;

(1r,4s)-4-(8-(2-chloro-4-cyano-6-fluorophenylamino)-2-(((1S,2S)-2-hydroxycyclohexyl)methylamino)-9H-purin-9-yl)cyclohexanecarboxamide;

(1r,4s)-4-(8-(2,6-dichloro-4-cyanophenylamino)-2-(((1S,2S)-2-hydroxycyclohexyl)methylamino)-9H-purin-9-yl)cyclohexanecarboxamide;

(1r,4s)-4-(8-(2-chloro-4,6-difluorophenylamino)-2-(((1S,2R)-2-hydroxycyclohexyl)methylamino)-9H-purin-9-yl)cyclohexanecarboxamide;

(1r,4s)-4-(2-(((1S,2R)-2-hydroxycyclohexyl)methylamino)-8-(2,4,6-trichlorophenylamino)-9H-purin-9-yl)cyclohexanecarboxamide;

(1r,4s)-4-(8-(2,4-dichloro-6-fluorophenylamino)-2-(((1S,2R)-2-hydroxycyclohexyl)methylamino)-9H-purin-9-yl)cyclohexanecarboxamide;

(1r,4s)-4-(8-(4-chloro-2,6-difluorophenylamino)-2-(((1S,2R)-2-hydroxycyclohexyl)methylamino)-9H-purin-9-yl)cyclohexanecarboxamide;

(1r,4s)-4-(8-(2-chloro-4-cyano-6-fluorophenylamino)-2-(((1S,2R)-2-hydroxycyclohexyl)methylamino)-9H-purin-9-yl)cyclohexanecarboxamide;

(1r,4s)-4-(8-(2,6-dichloro-4-cyanophenylamino)-2-(((1S,2R)-2-hydroxycyclohexyl)methylamino)-9H-purin-9-yl)cyclohexanecarboxamide;

(1s,4s)-4-(8-(2,6-dichloro-4-cyanophenylamino)-2-(3,3-difluorocyclobutylamino)-9H-purin-9-yl)-1-methylcyclohexanecarboxamide;

(1s,4s)-4-(8-(2,4-dichloro-6-fluorophenylamino)-2-(4-(2,5-dioxopyrrolidin-1-yl)cyclohexylamino)-9H-purin-9-yl)cyclohexanecarboxamide;

(1s,4s)-4-(8-(2,6-dichloro-4-cyanophenylamino)-2-(4-(2,5-dioxopyrrolidin-1-yl)cyclohexylamino)-9H-purin-9-yl)cyclohexanecarboxamide;

(1r,4s)-4-(8-(4-cyano-2,6-difluorophenylamino)-2-((3S,4S)-3-fluorotetrahydro-2H-pyran-4-ylamino)-9H-purin-9-yl)cyclohexanecarboxamide;

(1r,4s)-4-(8-(2-chloro-4-cyano-6-fluorophenylamino)-2-((3S,4S)-3-fluorotetrahydro-2H-pyran-4-ylamino)-9H-purin-9-yl)cyclohexanecarboxamide;

(1s,4s)-4-(8-(4-chloro-2,6-difluorophenylamino)-2-((3S,4R)-3-fluorotetrahydro-2H-pyran-4-ylamino)-9H-purin-9-yl)cyclohexanecarboxamide;

(1r,4s)-4-(8-(4-chloro-2,6-difluorophenylamino)-2-((3S,4S)-3-fluorotetrahydro-2H-pyran-4-ylamino)-9H-purin-9-yl)cyclohexanecarboxamide;

(1s,4s)-4-(8-(2-chloro-4,6-difluorophenylamino)-2-(tetrahydro-2H-pyran-4-ylamino)-9H-purin-9-yl)-1-methylcyclohexanecarboxamide;

(1s,4s)-4-(8-(2,4-dichloro-6-fluorophenylamino)-2-(tetrahydro-2H-pyran-4-ylamino)-9H-purin-9-yl)-1-methylcyclohexanecarboxamide;

(1s,4s)-4-(8-(2,6-dichloro-4-fluorophenylamino)-2-(tetrahydro-2H-pyran-4-ylamino)-9H-purin-9-yl)-1-methylcyclohexanecarboxamide;

(1s,4s)-4-(2-(4-(1,2,4-oxadiazol-5-yl)cyclohexylamino)-8-(2,4-dichloro-6-fluorophenylamino)-9H-purin-9-yl)cyclohexanecarboxamide;

(1s,4s)-4-(2-(4-(1,2,4-oxadiazol-5-yl)cyclohexylamino)-8-(2-chloro-4,6-difluorophenylamino)-9H-purin-9-yl)cyclohexanecarboxamide;
(1s,4s)-4-(2-(4-(1,2,4-oxadiazol-5-yl)cyclohexylamino)-8-(2,4,6-trichlorophenylamino)-9H-purin-9-yl)cyclohexanecarboxamide;
(1s,4s)-4-(2-(4-(1,2,4-oxadiazol-5-yl)cyclohexylamino)-8-(2,6-dichloro-4-fluorophenylamino)-9H-purin-9-yl)cyclohexanecarboxamide;
(1s,4s)-4-(2-(4-(1,2,4-oxadiazol-5-yl)cyclohexylamino)-8-(2-chloro-4-cyano-6-fluorophenylamino)-9H-purin-9-yl)cyclohexanecarboxamide;
(1s,4s)-4-(2-(4-(1,2,4-oxadiazol-5-yl)cyclohexylamino)-8-(2,6-dichloro-4-cyanophenylamino)-9H-purin-9-yl)cyclohexanecarboxamide;
(1s,4s)-4-(8-(2-chloro-4-cyano-6-fluorophenylamino)-2-((1R,3R)-3-hydroxycyclopentylamino)-9H-purin-9-yl)cyclohexanecarboxamide;
(1s,4s)-4-(8-(2,6-dichloro-4-cyanophenylamino)-2-((1R,3R)-3-hydroxycyclopentylamino)-9H-purin-9-yl)cyclohexanecarboxamide;
(1s,4s)-4-(8-(2,6-dichloro-4-cyanophenylamino)-2-((1R,3R)-3-hydroxycyclohexylamino)-9H-purin-9-yl)cyclohexanecarboxamide;
(1s,4s)-4-(8-(2-chloro-4-cyano-6-fluorophenylamino)-2-((1R,3R)-3-hydroxycyclohexylamino)-9H-purin-9-yl)cyclohexanecarboxamide;
(1r,4s)-4-(8-(2,6-dichloro-4-cyanophenylamino)-2-((1S,3R)-3-hydroxycyclohexylamino)-9H-purin-9-yl)cyclohexanecarboxamide;
(1r,4s)-4-(8-(2-chloro-4-cyano-6-fluorophenylamino)-2-((1S,3R)-3-hydroxycyclohexylamino)-9H-purin-9-yl)cyclohexanecarboxamide;
(1r,4s)-4-(8-(2,6-dichloro-4-cyanophenylamino)-2-((1S,3S)-3-hydroxycyclohexylamino)-9H-purin-9-yl)cyclohexanecarboxamide;
(1r,4s)-4-(8-(2-chloro-4-cyano-6-fluorophenylamino)-2-((1S,3S)-3-hydroxycyclohexylamino)-9H-purin-9-yl)cyclohexanecarboxamide;
(1s,4s)-4-(8-(4-bromo-2,6-dichlorophenylamino)-2-(tetrahydro-2H-pyran-4-ylamino)-9H-purin-9-yl)cyclohexanecarboxamide;
(1s,4s)-4-(8-(4-bromo-2,6-dichlorophenylamino)-2-(4,4-difluorocyclohexylamino)-9H-purin-9-yl)cyclohexanecarboxamide;
(1r,4s)-4-(8-(2-chloro-4,6-difluorophenylamino)-2-((3S,4S)-3-fluorotetrahydro-2H-pyran-4-ylamino)-9H-purin-9-yl)cyclohexanecarboxamide;
(1s,4s)-4-(2-(cyclopentylamino)-8-(2,3-dichloro-4-cyanophenylamino)-9H-purin-9-yl)cyclohexanecarboxamide;
(1r,4s)-4-(8-(2,3-dichloro-4-cyanophenylamino)-2-((S)-1-hydroxypropan-2-ylamino)-9H-purin-9-yl)cyclohexanecarboxamide;
(1s,4s)-4-(8-(2,3-dichloro-4-cyanophenylamino)-2-(4,4-difluorocyclohexylamino)-9H-purin-9-yl)cyclohexanecarboxamide;
(1s,4s)-4-(8-(2,3-dichloro-4-cyanophenylamino)-2-(tetrahydro-2H-pyran-4-ylamino)-9H-purin-9-yl)cyclohexanecarboxamide;
(1s,4s)-4-(8-(4-cyano-2,6-difluorophenylamino)-2-((R)-3,3-difluorocyclopentylamino)-9H-purin-9-yl)cyclohexanecarboxamide;
(1s,4s)-4-(8-(2-chloro-4-cyano-6-fluorophenylamino)-2-((R)-3,3-difluorocyclopentylamino)-9H-purin-9-yl)cyclohexanecarboxamide;
(1s,4s)-4-(8-(2,6-dichloro-4-cyanophenylamino)-2-((R)-3,3-difluorocyclopentylamino)-9H-purin-9-yl)cyclohexanecarboxamide;
(1s,4s)-4-(2-((R)-1-(methylsulfonyl)piperidin-3-ylamino)-8-(2,4,6-trichlorophenylamino)-9H-purin-9-yl)cyclohexanecarboxamide;
(1s,4s)-4-(8-(2,4-dichloro-6-fluorophenylamino)-2-((R)-1-(methylsulfonyl)piperidin-3-ylamino)-9H-purin-9-yl)cyclohexanecarboxamide;
(1s,4s)-4-(8-(2,6-dichloro-4-cyanophenylamino)-2-((R)-1-(methylsulfonyl)piperidin-3-ylamino)-9H-purin-9-yl)cyclohexanecarboxamide;
(1s,4s)-4-(8-(4-chloro-2,6-difluorophenylamino)-2-((R)-1-(methylsulfonyl)piperidin-3-ylamino)-9H-purin-9-yl)cyclohexanecarboxamide;
(1s,4s)-4-(8-(2-chloro-4-cyano-6-fluorophenylamino)-2-((R)-1-(methylsulfonyl)piperidin-3-ylamino)-9H-purin-9-yl)cyclohexanecarboxamide;
(R)-3-(9-((1s,4s)-4-carbamoylcyclohexyl)-8-(2,4,6-trichlorophenylamino)-9H-purin-2-ylamino)-N-methylpiperidine-1-carboxamide;
(R)-3-(9-((1s,4s)-4-carbamoylcyclohexyl)-8-(2,4-dichloro-6-fluorophenylamino)-9H-purin-2-ylamino)-N-methylpiperidine-1-carboxamide;
(R)-3-(9-((1s,4s)-4-carbamoylcyclohexyl)-8-(2,6-dichloro-4-cyanophenylamino)-9H-purin-2-ylamino)-N-methylpiperidine-1-carboxamide;
(R)-methyl 3-(9-((1s,4s)-4-carbamoylcyclohexyl)-8-(2,6-dichloro-4-cyanophenylamino)-9H-purin-2-ylamino)piperidine-1-carboxylate;
(R)-methyl 3-(9-((1s,4s)-4-carbamoylcyclohexyl)-8-(2-chloro-4-cyano-6-fluorophenylamino)-9H-purin-2-ylamino)piperidine-1-carboxylate;
(1s,4s)-4-(2-((R)-1-acetylpiperidin-3-ylamino)-8-(2,4,6-trichlorophenylamino)-9H-purin-9-yl)cyclohexanecarboxamide;
(1s,4s)-4-(2-((R)-1-acetylpiperidin-3-ylamino)-8-(2,4-dichloro-6-fluorophenylamino)-9H-purin-9-yl)cyclohexanecarboxamide;
(1s,4s)-4-(2-((R)-1-acetylpiperidin-3-ylamino)-8-(2,6-dichloro-4-cyanophenylamino)-9H-purin-9-yl)cyclohexanecarboxamide;
(1s,4s)-4-(2-((R)-1-acetylpiperidin-3-ylamino)-8-(4-chloro-2,6-difluorophenylamino)-9H-purin-9-yl)cyclohexanecarboxamide;
(1r,4s)-4-(8-(2,4-dichloro-6-fluorophenylamino)-2-((3S,4S)-3-fluorotetrahydro-2H-pyran-4-ylamino)-9H-purin-9-yl)cyclohexanecarboxamide;
(1s,4s)-4-(8-(2-chloro-4,6-difluorophenylamino)-2-((3S,4R)-3-fluorotetrahydro-2H-pyran-4-ylamino)-9H-purin-9-yl)-1-methylcyclohexanecarboxamide;
(1r,4s)-4-(8-(2,4-dichloro-6-fluorophenylamino)-2-((3S,4S)-3-fluorotetrahydro-2H-pyran-4-ylamino)-9H-purin-9-yl)-1-methylcyclohexanecarboxamide;
(1s,4s)-4-(8-(2,4-dichloro-6-fluorophenylamino)-2-((3S,4R)-3-methyltetrahydro-2H-pyran-4-ylamino)-9H-purin-9-yl)-1-methylcyclohexanecarboxamide;
(1r,4s)-4-(2-((3S,4S)-3-fluorotetrahydro-2H-pyran-4-ylamino)-8-(2,4,6-trichlorophenylamino)-9H-purin-9-yl)-1-methylcyclohexanecarboxamide;
(1s,4s)-4-(8-(4-chloro-2,6-difluorophenylamino)-2-((3S,4R)-3-fluorotetrahydro-2H-pyran-4-ylamino)-9H-purin-9-yl)-1-methylcyclohexanecarboxamide;
(1r,4s)-4-(8-(4-chloro-2,6-difluorophenylamino)-2-((3S,4S)-3-fluorotetrahydro-2H-pyran-4-ylamino)-9H-purin-9-yl)-1-methylcyclohexanecarboxamide;

(1s,4s)-4-(8-(4-chloro-2,6-difluorophenylamino)-2-((3S,4R)-3-methyltetrahydro-2H-pyran-4-ylamino)-9H-purin-9-yl)-1-methylcyclohexanecarboxamide;

(1s,4s)-4-(8-(2-chloro-4,6-difluorophenylamino)-2-((3S,4R)-3-methyltetrahydro-2H-pyran-4-ylamino)-9H-purin-9-yl)cyclohexanecarboxamide;

(1r,4s)-4-(8-(2-chloro-4,6-difluorophenylamino)-2-((3S,4S)-3-fluorotetrahydro-2H-pyran-4-ylamino)-9H-purin-9-yl)-1-methylcyclohexanecarboxamide;

(1s,4s)-4-(8-(2-chloro-4,6-difluorophenylamino)-2-((3S,4R)-3-methyltetrahydro-2H-pyran-4-ylamino)-9H-purin-9-yl)-1-methylcyclohexanecarboxamide;

(1s,4s)-4-(8-(2,4-dichloro-6-fluorophenylamino)-2-((3S,4R)-3-fluorotetrahydro-2H-pyran-4-ylamino)-9H-purin-9-yl)-1-methylcyclohexanecarboxamide;

(1s,4s)-1-methyl-4-(2-((3S,4R)-3-methyltetrahydro-2H-pyran-4-ylamino)-8-(2,4,6-trichlorophenylamino)-9H-purin-9-yl)cyclohexanecarboxamide;

(1s,4s)-4-(8-(2,4-dichloro-6-fluorophenylamino)-2-((3S,4R)-3-fluorotetrahydro-2H-pyran-4-ylamino)-9H-purin-9-yl)cyclohexanecarboxamide;

(1s,4s)-4-(2-(3-(methylsulfonyl)cyclobutylamino)-8-(2,4,6-trichlorophenylamino)-9H-purin-9-yl)cyclohexanecarboxamide;

(1s,4s)-4-(8-(2,6-dichloro-4-cyanophenylamino)-2-(3-(methylsulfonyl)cyclobutylamino)-9H-purin-9-yl)cyclohexanecarboxamide;

(1s,4s)-4-(8-(2,4-dichloro-6-fluorophenylamino)-2-(3-(methylsulfonyl)cyclobutylamino)-9H-purin-9-yl)cyclohexanecarboxamide;

(1s,4s)-4-(2-((R)-1-ethylpiperidin-3-ylamino)-8-(2,4,6-trichlorophenylamino)-9H-purin-9-yl)cyclohexanecarboxamide;

(1s,4s)-4-(8-(2,6-dichloro-4-cyanophenylamino)-2-((R)-1-ethylpiperidin-3-ylamino)-9H-purin-9-yl)cyclohexanecarboxamide;

(1s,4s)-4-(8-(2,4-dichloro-6-fluorophenylamino)-2-((R)-1-ethylpiperidin-3-ylamino)-9H-purin-9-yl)cyclohexanecarboxamide;

(1s,4s)-4-(8-(2,6-dichloro-4-(trifluoromethyl)phenylamino)-2-(3-(methylsulfonyl)cyclobutylamino)-9H-purin-9-yl)cyclohexanecarboxamide;

(1s,4s)-4-(8-(4-chloro-2,6-difluorophenylamino)-2-(3-(methylsulfonyl)cyclobutylamino)-9H-purin-9-yl)cyclohexanecarboxamide;

(1s,4s)-4-(8-(2,6-dichloro-4-(trifluoromethyl)phenylamino)-2-((R)-1-ethylpiperidin-3-ylamino)-9H-purin-9-yl)cyclohexanecarboxamide;

(1s,4s)-4-(2-((R)-1-isopropylpiperidin-3-ylamino)-8-(2,4,6-trichlorophenylamino)-9H-purin-9-yl)cyclohexanecarboxamide;

(1s,4s)-4-(8-(2,6-dichloro-4-cyanophenylamino)-2-((R)-1-isopropylpiperidin-3-ylamino)-9H-purin-9-yl)cyclohexanecarboxamide;

(1s,4s)-4-(8-(4-chloro-2,6-difluorophenylamino)-2-((R)-1-isopropylpiperidin-3-ylamino)-9H-purin-9-yl)cyclohexanecarboxamide;

(1s,4s)-4-(8-(2,4-dichloro-6-fluorophenylamino)-2-((R)-1-isopropylpiperidin-3-ylamino)-9H-purin-9-yl)cyclohexanecarboxamide;

(1s,4s)-4-(8-(2-chloro-4,6-difluorophenylamino)-2-((R)-1-phenylpiperidin-3-ylamino)-9H-purin-9-yl)cyclohexanecarboxamide;

(1s,4s)-4-(2-((R)-1-phenylpiperidin-3-ylamino)-8-(2,4,6-trichlorophenylamino)-9H-purin-9-yl)cyclohexanecarboxamide;

(1s,4s)-4-(8-(2,6-dichloro-4-cyanophenylamino)-2-((R)-1-phenylpiperidin-3-ylamino)-9H-purin-9-yl)cyclohexanecarboxamide;

(1s,4s)-4-(8-(4-cyano-2,6-difluorophenylamino)-2-((R)-1-phenylpiperidin-3-ylamino)-9H-purin-9-yl)cyclohexanecarboxamide;

(1s,4s)-4-(2-((R)-1-phenylpiperidin-3-ylamino)-8-(2,4,6-trifluorophenylamino)-9H-purin-9-yl)cyclohexanecarboxamide;

(1s,4s)-4-(8-(4-chloro-2,6-difluorophenylamino)-2-((R)-1-phenylpiperidin-3-ylamino)-9H-purin-9-yl)cyclohexanecarboxamide;

(1s,4s)-4-(8-(2,4-dichloro-6-fluorophenylamino)-2-((R)-1-phenylpiperidin-3-ylamino)-9H-purin-9-yl)cyclohexanecarboxamide;

(1s,4s)-4-(8-(2,6-dichloro-4-fluorophenylamino)-2-((R)-1-phenylpiperidin-3-ylamino)-9H-purin-9-yl)cyclohexanecarboxamide;

(1s,4s)-4-(8-(2-chloro-4-cyano-6-fluorophenylamino)-2-((R)-1-phenylpiperidin-3-ylamino)-9H-purin-9-yl)cyclohexanecarboxamide;

(1s,4s)-4-(2-((R)-1-benzylpiperidin-3-ylamino)-8-(2-chloro-4,6-difluorophenylamino)-9H-purin-9-yl)cyclohexanecarboxamide;

(1s,4s)-4-(2-((R)-1-benzylpiperidin-3-ylamino)-8-(2,4,6-trichlorophenylamino)-9H-purin-9-yl)cyclohexanecarboxamide;

(1s,4s)-4-(2-((R)-1-benzylpiperidin-3-ylamino)-8-(2,6-dichloro-4-cyanophenylamino)-9H-purin-9-yl)cyclohexanecarboxamide;

(1s,4s)-4-(2-((R)-1-benzylpiperidin-3-ylamino)-8-(2,6-dichloro-4-(trifluoromethyl)phenylamino)-9H-purin-9-yl)cyclohexanecarboxamide;

(1s,4s)-4-(2-((R)-1-benzylpiperidin-3-ylamino)-8-(4-cyano-2,6-difluorophenylamino)-9H-purin-9-yl)cyclohexanecarboxamide;

(1s,4s)-4-(2-((R)-1-benzylpiperidin-3-ylamino)-8-(2,4,6-trifluorophenylamino)-9H-purin-9-yl)cyclohexanecarboxamide;

(1s,4s)-4-(2-((R)-1-benzylpiperidin-3-ylamino)-8-(4-chloro-2,6-difluorophenylamino)-9H-purin-9-yl)cyclohexanecarboxamide;

(1s,4s)-4-(2-((R)-1-benzylpiperidin-3-ylamino)-8-(2,4-dichloro-6-fluorophenylamino)-9H-purin-9-yl)cyclohexanecarboxamide;

(1s,4s)-4-(2-((R)-1-benzylpiperidin-3-ylamino)-8-(2,6-dichloro-4-fluorophenylamino)-9H-purin-9-yl)cyclohexanecarboxamide;

(1s,4s)-4-(8-(2,6-dichloro-4-cyanophenylamino)-2-((3S,4R)-3-fluorotetrahydro-2H-pyran-4-ylamino)-9H-purin-9-yl)-1-methylcyclohexanecarboxamide;

(1r,4s)-4-(8-(2,6-dichloro-4-cyanophenylamino)-2-((3S,4S)-3-fluorotetrahydro-2H-pyran-4-ylamino)-9H-purin-9-yl)-1-methylcyclohexanecarboxamide;

(1s,4s)-4-(8-(2,6-dichloro-4-cyanophenylamino)-2-((3S,4R)-3-fluorotetrahydro-2H-pyran-4-ylamino)-9H-purin-9-yl)cyclohexanecarboxamide;

(1s,4s)-4-(8-(2,6-dichloro-4-cyanophenylamino)-2-((3S,4R)-3-methyltetrahydro-2H-pyran-4-ylamino)-9H-purin-9-yl)-1-methylcyclohexanecarboxamide;

(1s,4s)-4-(8-(2,4-dichloro-6-fluorophenylamino)-2-((R)-3,3-dimethyltetrahydro-2H-pyran-4-ylamino)-9H-purin-9-yl)cyclohexanecarboxamide;

(1r,4s)-4-(8-(2,6-dichloro-4-cyanophenylamino)-2-((3S,4S)-3-fluorotetrahydro-2H-pyran-4-ylamino)-9H-purin-9-yl)cyclohexanecarboxamide;

(1s,4s)-4-(2-((R)-3,3-dimethyltetrahydro-2H-pyran-4-ylamino)-8-(2,4,6-trichlorophenylamino)-9H-purin-9-yl)cyclohexanecarboxamide;

(R)-isopropyl 3-(9-((1s,4s)-4-carbamoylcyclohexyl)-8-(2-chloro-4,6-difluorophenylamino)-9H-purin-2-ylamino)piperidine-1-carboxylate;

(R)-isopropyl 3-(9-((1s,4s)-4-carbamoylcyclohexyl)-8-(2,4,6-trichlorophenylamino)-9H-purin-2-ylamino)piperidine-1-carboxylate;

(R)-isopropyl 3-(9-((1s,4s)-4-carbamoylcyclohexyl)-8-(2,6-dichloro-4-cyanophenylamino)-9H-purin-2-ylamino)piperidine-1-carboxylate;

(R)-isopropyl 3-(9-((1s,4s)-4-carbamoylcyclohexyl)-8-(2,6-dichloro-4-(trifluoromethyl)phenylamino)-9H-purin-2-ylamino)piperidine-1-carboxylate;

(R)-isopropyl 3-(9-((1s,4s)-4-carbamoylcyclohexyl)-8-(4-cyano-2,6-difluorophenylamino)-9H-purin-2-ylamino)piperidine-1-carboxylate;

(R)-isopropyl 3-(9-((1s,4s)-4-carbamoylcyclohexyl)-8-(2,4,6-trifluorophenylamino)-9H-purin-2-ylamino)piperidine-1-carboxylate;

(R)-isopropyl 3-(9-((1s,4s)-4-carbamoylcyclohexyl)-8-(4-chloro-2,6-difluorophenylamino)-9H-purin-2-ylamino)piperidine-1-carboxylate;

(R)-isopropyl 3-(9-((1s,4s)-4-carbamoylcyclohexyl)-8-(2,4-dichloro-6-fluorophenylamino)-9H-purin-2-ylamino)piperidine-1-carboxylate;

(R)-isopropyl 3-(9-((1s,4s)-4-carbamoylcyclohexyl)-8-(2,6-dichloro-4-fluorophenylamino)-9H-purin-2-ylamino)piperidine-1-carboxylate;

(R)-isopropyl 3-(9-((1s,4s)-4-carbamoylcyclohexyl)-8-(2-chloro-4-cyano-6-fluorophenylamino)-9H-purin-2-ylamino)piperidine-1-carboxylate;

(1s,4s)-4-(2-((R)-1-benzylpiperidin-3-ylamino)-8-(2-chloro-4-cyano-6-fluorophenylamino)-9H-purin-9-yl)cyclohexanecarboxamide;

(R)-3-(9-((1s,4s)-4-carbamoylcyclohexyl)-8-(2-chloro-4,6-difluorophenylamino)-9H-purin-2-ylamino)-N-phenylpiperidine-1-carboxamide;

(R)-3-(9-((1s,4s)-4-carbamoylcyclohexyl)-8-(2,4,6-trichlorophenylamino)-9H-purin-2-ylamino)-N-phenylpiperidine-1-carboxamide;

(R)-3-(9-((1s,4s)-4-carbamoylcyclohexyl)-8-(2,6-dichloro-4-cyanophenylamino)-9H-purin-2-ylamino)-N-phenylpiperidine-1-carboxamide;

(R)-3-(9-((1s,4s)-4-carbamoylcyclohexyl)-8-(2,4,6-trifluorophenylamino)-9H-purin-2-ylamino)-N-phenylpiperidine-1-carboxamide;

(R)-3-(9-((1s,4s)-4-carbamoylcyclohexyl)-8-(4-chloro-2,6-difluorophenylamino)-9H-purin-2-ylamino)-N-phenylpiperidine-1-carboxamide;

(R)-3-(9-((1s,4s)-4-carbamoylcyclohexyl)-8-(2,4-dichloro-6-fluorophenylamino)-9H-purin-2-ylamino)-N-phenylpiperidine-1-carboxamide;

(R)-3-(9-((1s,4s)-4-carbamoylcyclohexyl)-8-(2,6-dichloro-4-fluorophenylamino)-9H-purin-2-ylamino)-N-phenylpiperidine-1-carboxamide;

(R)-3-(9-((1s,4s)-4-carbamoylcyclohexyl)-8-(2-chloro-4-cyano-6-fluorophenylamino)-9H-purin-2-ylamino)-N-phenylpiperidine-1-carboxamide;

(1s,4s)-4-(8-(4-chloro-2,6-difluorophenylamino)-2-((R)-3,3-dimethyltetrahydro-2H-pyran-4-ylamino)-9H-purin-9-yl)cyclohexanecarboxamide;

(1s,4s)-4-(8-(2-chloro-4,6-difluorophenylamino)-2-((R)-1-tosylpiperidin-3-ylamino)-9H-purin-9-yl)cyclohexanecarboxamide;

(1s,4s)-4-(2-((R)-1-tosylpiperidin-3-ylamino)-8-(2,4,6-trichlorophenylamino)-9H-purin-9-yl)cyclohexanecarboxamide;

(1s,4s)-4-(8-(2,6-dichloro-4-cyanophenylamino)-2-((R)-1-tosylpiperidin-3-ylamino)-9H-purin-9-yl)cyclohexanecarboxamide;

(1s,4s)-4-(8-(4-cyano-2,6-difluorophenylamino)-2-((R)-1-tosylpiperidin-3-ylamino)-9H-purin-9-yl)cyclohexanecarboxamide;

(1s,4s)-4-(2-((R)-1-tosylpiperidin-3-ylamino)-8-(2,4,6-trifluorophenylamino)-9H-purin-9-yl)cyclohexanecarboxamide;

(1s,4s)-4-(8-(4-chloro-2,6-difluorophenylamino)-2-((R)-1-tosylpiperidin-3-ylamino)-9H-purin-9-yl)cyclohexanecarboxamide;

(1s,4s)-4-(8-(2,4-dichloro-6-fluorophenylamino)-2-((R)-1-tosylpiperidin-3-ylamino)-9H-purin-9-yl)cyclohexanecarboxamide;

(1s,4s)-4-(8-(2,6-dichloro-4-fluorophenylamino)-2-((R)-1-tosylpiperidin-3-ylamino)-9H-purin-9-yl)cyclohexanecarboxamide;

(1s,4s)-4-(8-(2-chloro-4-cyano-6-fluorophenylamino)-2-((R)-1-tosylpiperidin-3-ylamino)-9H-purin-9-yl)cyclohexanecarboxamide;

(R)-3-(9-((1s,4s)-4-carbamoylcyclohexyl)-8-(2,6-dichloro-4-(trifluoromethyl)phenylamino)-9H-purin-2-ylamino)-N-methylpiperidine-1-carboxamide;

(1s,4s)-4-(2-((R)-1-acetylpiperidin-3-ylamino)-8-(2-chloro-4,6-difluorophenylamino)-9H-purin-9-yl)cyclohexanecarboxamide;

(1s,4s)-4-(2-((R)-1-acetylpiperidin-3-ylamino)-8-(2,6-dichloro-4-(trifluoromethyl)phenylamino)-9H-purin-9-yl)cyclohexanecarboxamide;

(1s,4s)-4-(2-((R)-1-acetylpiperidin-3-ylamino)-8-(2,6-dichloro-4-fluorophenylamino)-9H-purin-9-yl)cyclohexanecarboxamide;

(1s,4s)-4-(2-((R)-1-acetylpiperidin-3-ylamino)-8-(2,6-dichlorophenylamino)-9H-purin-9-yl)cyclohexanecarboxamide;

(1s,4s)-4-(8-(4-cyano-2,6-difluorophenylamino)-2-((3S,4R)-3-fluorotetrahydro-2H-pyran-4-ylamino)-9H-purin-9-yl)cyclohexanecarboxamide; or (1r,4s)-4-(2-(((3R,4S)-3-fluorotetrahydro-2H-pyran-4-yl)amino)-8-((2,4,6-trichlorophenyl)amino)-9H-purin-9-yl)-1-methylcyclohexane-1-carboxamide or a pharmaceutically acceptable salt thereof.

3. The method of claim 1, wherein the cancer is colorectal cancer, stomach cancer, colon cancer, or gastric cancer.

4. The method of claim 1, wherein the cancer is liver cancer, lung cancer, or pancreatic cancer.

5. The method of claim 1, wherein the cancer is leukemia, or multiple myeloma.

6. The method of claim 1, wherein the cancer is hepatocellular carcinoma.

7. The method of claim 1, wherein the cancer is a cancer expressing PD-L1.

8. The method of claim 7, wherein the PD-L1 expressing cancer is lung cancer, renal cell carcinoma, or hepatocellular carcinoma.

9. The method of claim 1, wherein the cancer is characterized by a BRAF mutation.

10. The method of claim 9, wherein the cancer characterized by a BRAF mutation is colorectal cancer, or lung cancer.

11. The method of claim 9, wherein the BRAF mutation is BRAF V600E.

12. The method of claim 1, wherein the cancer is characterized by an NRAS mutation.

13. The method of claim 1, wherein the cancer is characterized by a KRAS mutation.

14. The method of claim 13, wherein the cancer characterized by a KRAS mutation is colorectal cancer, pancreatic cancer or lung cancer.

15. The method of claim 1, wherein the cancer is characterized by an activated beta-catenin pathway.

16. The method of claim 15, wherein the cancer is colorectal cancer, stomach cancer, or hepatocellular carcinoma.

17. The method of claim 1, wherein the Aminopurine Compound is administered as a pharmaceutical composition comprising at least one pharmaceutically acceptable excipient.

18. The method of claim 15, wherein the cancer is hepatocellular carcinoma, gastric cancer, or melanoma.

19. The method of claim 15, wherein the cancer is further characterized by an EGFR mutation or increased EGFR activity.

20. The method of claim 19, wherein the EGFR mutation is one or more of EGFR E282K, G719S, P753S, or V1011M.

21. The method of claim 15, wherein the cancer is further characterized by a BRAF mutation.

22. The method of claim 21, wherein the BRAF mutation comprises a BRAF V600E, BRAF T119S, or BRAF G596R mutation.

* * * * *